(12) United States Patent
Muhsin et al.

(10) Patent No.: US 11,024,064 B2
(45) Date of Patent: Jun. 1, 2021

(54) AUGMENTED REALITY SYSTEM FOR DISPLAYING PATIENT DATA

(71) Applicant: Masimo Corporation, Irvine, CA (US)

(72) Inventors: Bilal Muhsin, San Clemente, CA (US); Omar Ahmed, Mission Viejo, CA (US); Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/902,955

(22) Filed: Feb. 22, 2018

(65) Prior Publication Data

US 2018/0300919 A1      Oct. 18, 2018

Related U.S. Application Data

(60) Provisional application No. 62/463,452, filed on Feb. 24, 2017, provisional application No. 62/463,517, filed on Feb. 24, 2017.

(51) Int. Cl.
 *G06T 11/60* (2006.01)
 *G16H 40/63* (2018.01)
 (Continued)

(52) U.S. Cl.
 CPC ............ *G06T 11/60* (2013.01); *A61B 5/0002* (2013.01); *A61B 5/743* (2013.01); *A61B 5/744* (2013.01);
 (Continued)

(58) Field of Classification Search
 CPC ....... A61B 5/00; A61B 5/0002; A61B 5/0004; A61B 5/0006; A61B 5/002; A61B 5/0022; A61B 5/0024; A61B 5/7435; A61B 5/743; A61B 5/744; G06T 2207/30196; G06T 2200/24; G06T 11/60; G06T 7/90; G06T 2207/10024; G06T 2210/41; G06F 9/451; G06F 3/011; G06F 3/012; G06F 3/013; G06F 3/017; H04L 63/083; G16H 50/00; G16H 50/20; G16H 50/30; G16H 50/50; G16H 50/80; G16H 40/20; G16H 30/00;
 (Continued)

(56) References Cited

U.S. PATENT DOCUMENTS 4,960,128 A    10/1990  Gordon et al.
4,964,408 A    10/1990  Hink et al.
(Continued)

*Primary Examiner* — Charles L Beard
(74) *Attorney, Agent, or Firm* — Knobbe, Martens, Olson & Bear, LLP

(57) ABSTRACT

System and methods are provided for augmented reality displays for medical and physiological monitoring. Augmented reality user interfaces are virtually pinned to a physical device, a location, or to a patient. An augmented reality position determination process determines the presentation of user interfaces relative to reference positions and reference objects. Detection of gestures causes the augmented reality users interfaces to be updated, such as pinning a user interface to a device, location, or patient. Looking away from an augmented reality user interface causes the user interface to minimize or disappear in an augmented reality display. An augmented reality gesture detection process determines gestures based on captured image data and computer vision techniques performed on the image data.

22 Claims, 112 Drawing Sheets

(51) Int. Cl.
  *A61B 5/00* (2006.01)
  *H04L 29/06* (2006.01)
  *G16H 50/50* (2018.01)
  *G06F 3/01* (2006.01)
  *G06F 9/451* (2018.01)
  *G06T 7/90* (2017.01)

(52) U.S. Cl.
  CPC ............ *A61B 5/7435* (2013.01); *G06F 3/012* (2013.01); *G06F 3/017* (2013.01); *G06F 9/451* (2018.02); *G16H 40/63* (2018.01); *G16H 50/50* (2018.01); *H04L 63/083* (2013.01); *G06T 7/90* (2017.01); *G06T 2200/24* (2013.01); *G06T 2207/10024* (2013.01); *G06T 2210/41* (2013.01)

(58) Field of Classification Search
  CPC ........ G16H 15/00; G16H 10/60; G16H 10/20; G16H 10/00; G16H 40/63
  See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |

(56) References Cited

U.S. PATENT DOCUMENTS

| | | |
|---|---|---|
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,858,012 B2* | 2/2005 | Burns ............... A61B 5/0205 600/483 |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,306,560 B2* | 12/2007 | Iliff ............... G16H 20/10 600/300 |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |

(56) References Cited

U.S. PATENT DOCUMENTS

| | | |
|---|---|---|
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,177,704 B1* | 5/2012 | Mohl ............... A61B 5/6859 600/16 |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1* | 4/2013 | Al-Ali ............... A61B 5/7221 600/301 |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,521,558 B2* | 8/2013 | Malave ............... G16H 40/63 705/2 |
| 8,523,781 B2* | 9/2013 | Al-Ali ............... A61B 5/08 600/529 |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2* | 4/2014 | Telfort ............... A61B 7/003 600/586 |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,743,148 B2* | 6/2014 | Gegner ............... G16H 40/63 345/660 |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |

(56) References Cited

U.S. PATENT DOCUMENTS

| | | |
|---|---|---|
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 * | 8/2014 | Al-Ali ............... A61B 5/14551 600/438 |
| 8,821,397 B2 | 9/2014 | Al-Ali et al. |
| 8,821,415 B2 * | 9/2014 | Al-Ali .................. A61B 7/003 600/586 |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 * | 10/2014 | Al-Ali .................. A61B 5/742 600/586 |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 * | 12/2015 | Al-Ali .................. A61B 5/1455 |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 * | 7/2016 | Al-Ali .................. A61B 7/003 |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 * | 9/2016 | Al-Ali ................. G06F 13/4081 |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,501,613 B1 * | 11/2016 | Hanson ............... G06F 19/3418 |
| 9,510,779 B2 | 12/2016 | Poeze et al. |
| 9,517,024 B2 * | 12/2016 | Kiani .................. A61B 5/0205 |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| 9,629,570 B2 * | 4/2017 | Bar-Tal .................. A61B 5/062 |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,700,218 B2 * | 7/2017 | Boyer ................ A61B 5/02416 |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |

(56) References Cited

U.S. PATENT DOCUMENTS

| | | | |
|---|---|---|---|
| 9,750,443 B2 | 9/2017 | Smith et al. | |
| 9,750,461 B1 | 9/2017 | Telfort | |
| 9,757,020 B1* | 9/2017 | Elazar | A61B 1/00045 |
| 9,770,203 B1* | 9/2017 | Berme | G01B 11/00 |
| 9,775,545 B2 | 10/2017 | Al-Ali et al. | |
| 9,775,546 B2 | 10/2017 | Diab et al. | |
| 9,775,570 B2 | 10/2017 | Al-Ali | |
| 9,778,079 B1 | 10/2017 | Al-Ali et al. | |
| 9,782,077 B2 | 10/2017 | Lamego et al. | |
| 9,782,110 B2 | 10/2017 | Kiani | |
| 9,787,568 B2 | 10/2017 | Lamego et al. | |
| 9,788,735 B2 | 10/2017 | Al-Ali | |
| 9,788,768 B2 | 10/2017 | Al-Ali et al. | |
| 9,795,300 B2 | 10/2017 | Al-Ali | |
| 9,795,310 B2 | 10/2017 | Al-Ali | |
| 9,795,358 B2 | 10/2017 | Telfort et al. | |
| 9,795,739 B2 | 10/2017 | Al-Ali et al. | |
| 9,801,556 B2 | 10/2017 | Kiani | |
| 9,801,588 B2 | 10/2017 | Weber et al. | |
| 9,808,188 B1 | 11/2017 | Perea et al. | |
| 9,814,418 B2 | 11/2017 | Weber et al. | |
| 9,820,691 B2 | 11/2017 | Kiani | |
| 9,833,152 B2 | 12/2017 | Kiani et al. | |
| 9,833,180 B2 | 12/2017 | Shakespeare et al. | |
| 9,839,379 B2 | 12/2017 | Al-Ali et al. | |
| 9,839,381 B1 | 12/2017 | Weber et al. | |
| 9,847,002 B2 | 12/2017 | Kiani et al. | |
| 9,847,749 B2 | 12/2017 | Kiani et al. | |
| 9,848,800 B1 | 12/2017 | Lee et al. | |
| 9,848,806 B2 | 12/2017 | Al-Ali et al. | |
| 9,848,807 B2 | 12/2017 | Lamego | |
| 9,861,298 B2 | 1/2018 | Eckerbom et al. | |
| 9,861,304 B2 | 1/2018 | Al-Ali et al. | |
| 9,861,305 B1 | 1/2018 | Weber et al. | |
| 9,867,578 B2 | 1/2018 | Al-Ali et al. | |
| 9,872,623 B2 | 1/2018 | Al-Ali | |
| 9,876,320 B2 | 1/2018 | Coverston et al. | |
| 9,877,650 B2 | 1/2018 | Muhsin et al. | |
| 9,877,686 B2 | 1/2018 | Al-Ali et al. | |
| 9,891,079 B2 | 2/2018 | Dalvi | |
| 9,892,564 B1* | 2/2018 | Cvetko | A61B 5/0071 |
| 9,895,107 B2 | 2/2018 | Al-Ali et al. | |
| 9,924,893 B2 | 3/2018 | Schurman et al. | |
| 9,924,897 B1 | 3/2018 | Abdul-Hafiz | |
| 9,958,681 B2* | 5/2018 | Ko | G02B 26/004 |
| 9,959,620 B2* | 5/2018 | Merlet | G06T 11/60 |
| 10,010,379 B1* | 7/2018 | Gibby | A61B 90/36 |
| 10,080,530 B2* | 9/2018 | Cheng | A61B 5/746 |
| 10,092,213 B2* | 10/2018 | Gossler | G16H 70/60 |
| 10,255,690 B2* | 4/2019 | Bhuruth | G06F 3/013 |
| 10,304,206 B2* | 5/2019 | Nakazato | G06T 7/73 |
| 10,304,251 B2* | 5/2019 | Pahud | G06F 3/1454 |
| 10,318,811 B1* | 6/2019 | Gold | G06F 3/0304 |
| 10,332,292 B1* | 6/2019 | Arnicar | G06T 5/005 |
| 10,403,047 B1* | 9/2019 | Comer | G06F 3/012 |
| 10,413,666 B2* | 9/2019 | Al-Ali | A61B 5/1455 |
| 10,803,608 B1* | 10/2020 | Na | G06T 19/006 |
| 10,856,796 B1* | 12/2020 | Berme | A61B 5/7445 |
| 10,885,530 B2* | 1/2021 | Mercury | G06F 21/316 |
| 10,888,402 B2* | 1/2021 | Kim | G06T 7/33 |
| 2002/0120310 A1* | 8/2002 | Linden | G16H 10/60 607/60 |
| 2002/0140675 A1* | 10/2002 | Ali | A61B 5/0002 345/158 |
| 2004/0102683 A1* | 5/2004 | Khanuja | A61B 5/0002 600/300 |
| 2005/0254134 A1* | 11/2005 | Yamamoto | G02B 27/017 359/630 |
| 2006/0241792 A1* | 10/2006 | Pretlove | G06F 3/011 700/83 |
| 2008/0081982 A1* | 4/2008 | Simon | A61B 34/25 600/407 |
| 2008/0183074 A1* | 7/2008 | Carls | A61B 5/0488 600/429 |
| 2008/0183190 A1* | 7/2008 | Adcox | A61B 34/20 606/130 |
| 2008/0270188 A1* | 10/2008 | Garg | A61N 1/37247 705/3 |
| 2009/0275844 A1 | 11/2009 | Al-Ali | |
| 2009/0311655 A1* | 12/2009 | Karkanias | G09B 23/28 434/262 |
| 2009/0312660 A1* | 12/2009 | Guarino | A61B 5/08 600/529 |
| 2010/0004518 A1 | 1/2010 | Vo et al. | |
| 2010/0030040 A1* | 2/2010 | Poeze | A61B 5/6829 600/316 |
| 2010/0199232 A1* | 8/2010 | Mistry | G06F 3/0425 715/863 |
| 2010/0249540 A1* | 9/2010 | Lisogurski | A61B 5/0002 600/301 |
| 2010/0298656 A1* | 11/2010 | McCombie | G16H 50/50 600/301 |
| 2011/0066007 A1* | 3/2011 | Banet | A61B 5/0402 600/301 |
| 2011/0082711 A1 | 4/2011 | Poeze et al. | |
| 2011/0105854 A1 | 5/2011 | Kiani et al. | |
| 2011/0124996 A1* | 5/2011 | Reinke | A61M 5/14248 600/365 |
| 2011/0125060 A1 | 5/2011 | Telfort et al. | |
| 2011/0202084 A1* | 8/2011 | Hoem | A61M 29/02 606/194 |
| 2011/0208015 A1 | 8/2011 | Welch et al. | |
| 2011/0213273 A1* | 9/2011 | Telfort | A61B 7/003 600/586 |
| 2011/0230733 A1 | 9/2011 | Al-Ali | |
| 2011/0257552 A1* | 10/2011 | Banet | A61B 5/0816 600/534 |
| 2011/0295301 A1* | 12/2011 | Hoem | A61B 5/0215 606/194 |
| 2011/0295302 A1* | 12/2011 | Mohl | A61B 17/1204 606/194 |
| 2012/0003933 A1* | 1/2012 | Baker | H04W 76/38 455/41.2 |
| 2012/0005624 A1* | 1/2012 | Vesely | G06F 3/012 715/808 |
| 2012/0054691 A1* | 3/2012 | Nurmi | G06F 16/951 715/854 |
| 2012/0109676 A1* | 5/2012 | Landau | G06Q 50/22 705/2 |
| 2012/0113140 A1* | 5/2012 | Hilliges | G06F 3/011 345/633 |
| 2012/0124506 A1* | 5/2012 | Stuebe | G06F 19/00 715/777 |
| 2012/0157806 A1* | 6/2012 | Steiger | G06F 19/3456 600/365 |
| 2012/0165629 A1 | 6/2012 | Merritt et al. | |
| 2012/0209082 A1 | 8/2012 | Al-Ali | |
| 2012/0209084 A1 | 8/2012 | Olsen et al. | |
| 2012/0226117 A1* | 9/2012 | Lamego | A61B 5/14532 600/316 |
| 2012/0249741 A1* | 10/2012 | Maciocci | G06F 3/011 348/46 |
| 2012/0283524 A1 | 11/2012 | Kiani et al. | |
| 2012/0319816 A1 | 12/2012 | Al-Ali | |
| 2013/0009993 A1* | 1/2013 | Horseman | G16H 40/63 345/633 |
| 2013/0017791 A1* | 1/2013 | Wang | H04W 16/14 455/41.2 |
| 2013/0023214 A1* | 1/2013 | Wang | A61B 5/0002 455/41.2 |
| 2013/0023215 A1* | 1/2013 | Wang | H04W 16/14 455/41.2 |
| 2013/0023775 A1 | 1/2013 | Lamego et al. | |
| 2013/0041591 A1 | 2/2013 | Lamego | |
| 2013/0050258 A1* | 2/2013 | Liu | G06F 3/005 345/633 |
| 2013/0050432 A1* | 2/2013 | Perez | G02B 27/017 348/47 |
| 2013/0060147 A1 | 3/2013 | Welch et al. | |

(56) References Cited

U.S. PATENT DOCUMENTS

| | | | |
|---|---|---|---|
| 2013/0078977 A1* | 3/2013 | Anderson | H04B 1/005 455/418 |
| 2013/0096405 A1 | 4/2013 | Garfio | |
| 2013/0096936 A1 | 4/2013 | Sampath et al. | |
| 2013/0147838 A1* | 6/2013 | Small | G06F 3/013 345/633 |
| 2013/0149684 A1* | 6/2013 | Ezzell | G09B 23/28 434/272 |
| 2013/0162632 A1* | 6/2013 | Varga | G06T 19/20 345/419 |
| 2013/0234934 A1* | 9/2013 | Champion | G06F 3/012 345/156 |
| 2013/0243021 A1 | 9/2013 | Siskavich | |
| 2013/0253334 A1* | 9/2013 | Al-Ali | A61B 5/002 600/476 |
| 2013/0262730 A1* | 10/2013 | Al-Ali | A61B 5/0002 710/303 |
| 2013/0267792 A1* | 10/2013 | Petersen | G06F 19/3418 600/301 |
| 2013/0293530 A1* | 11/2013 | Perez | G06K 9/00671 345/418 |
| 2013/0296672 A1 | 11/2013 | O'Neil et al. | |
| 2013/0296713 A1 | 11/2013 | Al-Ali et al. | |
| 2013/0316652 A1* | 11/2013 | Wang | H04W 48/06 455/41.2 |
| 2013/0324808 A1 | 12/2013 | Al-Ali et al. | |
| 2013/0331660 A1 | 12/2013 | Al-Ali et al. | |
| 2013/0337842 A1* | 12/2013 | Wang | A61B 5/0024 455/456.4 |
| 2014/0012100 A1 | 1/2014 | Al-Ali et al. | |
| 2014/0012509 A1* | 1/2014 | Barber | G06F 3/015 702/19 |
| 2014/0035925 A1* | 2/2014 | Muranjan | G06T 11/60 345/440.1 |
| 2014/0051953 A1 | 2/2014 | Lamego et al. | |
| 2014/0065972 A1* | 3/2014 | Wang | A61B 5/002 455/41.2 |
| 2014/0081175 A1 | 3/2014 | Telfort | |
| 2014/0120564 A1 | 5/2014 | Workman et al. | |
| 2014/0121482 A1 | 5/2014 | Merritt et al. | |
| 2014/0127137 A1 | 5/2014 | Bellott et al. | |
| 2014/0129493 A1* | 5/2014 | Leopold | G06F 19/32 706/12 |
| 2014/0135588 A1 | 5/2014 | Al-Ali et al. | |
| 2014/0163344 A1 | 6/2014 | Al-Ali | |
| 2014/0163376 A1* | 6/2014 | Caluser | A61B 8/483 600/443 |
| 2014/0163402 A1 | 6/2014 | Lamego et al. | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0180160 A1 | 6/2014 | Brown et al. | |
| 2014/0187973 A1 | 7/2014 | Brown et al. | |
| 2014/0207489 A1* | 7/2014 | Wartena | G06F 19/00 705/3 |
| 2014/0213864 A1 | 7/2014 | Abdul-Hafiz et al. | |
| 2014/0222462 A1* | 8/2014 | Shakil | G06Q 10/0631 705/3 |
| 2014/0225918 A1* | 8/2014 | Mittal | G02B 27/017 345/633 |
| 2014/0232747 A1* | 8/2014 | Sugimoto | G06F 3/011 345/633 |
| 2014/0249431 A1* | 9/2014 | Banet | A61B 5/01 600/485 |
| 2014/0266790 A1 | 9/2014 | Al-Ali et al. | |
| 2014/0266983 A1* | 9/2014 | Christensen | A61M 1/3609 345/8 |
| 2014/0267419 A1* | 9/2014 | Ballard | G06T 11/00 345/633 |
| 2014/0275808 A1 | 9/2014 | Poeze et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0276115 A1 | 9/2014 | Dalvi et al. | |
| 2014/0285521 A1* | 9/2014 | Kimura | G06F 3/011 345/633 |
| 2014/0288400 A1 | 9/2014 | Diab et al. | |
| 2014/0316217 A1 | 10/2014 | Purdon et al. | |
| 2014/0316218 A1 | 10/2014 | Purdon et al. | |
| 2014/0316228 A1 | 10/2014 | Blank et al. | |
| 2014/0323818 A1* | 10/2014 | Axelgaard | A61B 5/0022 600/301 |
| 2014/0323825 A1 | 10/2014 | Al-Ali et al. | |
| 2014/0323897 A1 | 10/2014 | Brown et al. | |
| 2014/0323898 A1 | 10/2014 | Purdon et al. | |
| 2014/0330092 A1 | 11/2014 | Al-Ali et al. | |
| 2014/0330098 A1 | 11/2014 | Merritt et al. | |
| 2014/0342766 A1* | 11/2014 | Wang | H04W 16/14 455/509 |
| 2014/0357966 A1 | 12/2014 | Al-Ali et al. | |
| 2014/0368539 A1* | 12/2014 | Yeh | G02B 27/017 345/633 |
| 2015/0005600 A1 | 1/2015 | Blank et al. | |
| 2015/0011907 A1 | 1/2015 | Purdon et al. | |
| 2015/0012231 A1 | 1/2015 | Poeze et al. | |
| 2015/0032029 A1 | 1/2015 | Al-Ali et al. | |
| 2015/0038859 A1 | 2/2015 | Dalvi et al. | |
| 2015/0067516 A1* | 3/2015 | Park | G06F 3/167 715/728 |
| 2015/0067580 A1* | 3/2015 | Um | G06F 3/017 715/781 |
| 2015/0080754 A1 | 3/2015 | Purdon et al. | |
| 2015/0087936 A1 | 3/2015 | Al-Ali et al. | |
| 2015/0088546 A1* | 3/2015 | Balram | G06F 21/32 705/3 |
| 2015/0091943 A1* | 4/2015 | Lee | G02B 27/0172 345/633 |
| 2015/0094546 A1 | 4/2015 | Al-Ali | |
| 2015/0097701 A1* | 4/2015 | Al-Ali | A61B 5/0002 340/870.07 |
| 2015/0099950 A1 | 4/2015 | Al-Ali et al. | |
| 2015/0099955 A1* | 4/2015 | Al-Ali | A61B 5/1455 600/364 |
| 2015/0101844 A1 | 4/2015 | Al-Ali et al. | |
| 2015/0106121 A1* | 4/2015 | Muhsin | G06F 19/3418 705/3 |
| 2015/0112151 A1 | 4/2015 | Muhsin et al. | |
| 2015/0116076 A1 | 4/2015 | Al-Ali et al. | |
| 2015/0119733 A1* | 4/2015 | Grubis | G06F 19/3418 600/509 |
| 2015/0125832 A1* | 5/2015 | Tran | G09B 19/0092 434/127 |
| 2015/0150518 A1* | 6/2015 | Cremades Peris | A61B 5/0402 600/301 |
| 2015/0153571 A1* | 6/2015 | Ballard | G02B 27/017 345/8 |
| 2015/0157326 A1* | 6/2015 | Schiemanck | A61B 17/1204 606/194 |
| 2015/0165312 A1 | 6/2015 | Kiani | |
| 2015/0186602 A1* | 7/2015 | Pipke | A61B 5/743 705/3 |
| 2015/0196249 A1 | 7/2015 | Brown et al. | |
| 2015/0205931 A1* | 7/2015 | Wang | G16H 40/63 702/19 |
| 2015/0212576 A1* | 7/2015 | Ambrus | G06F 3/013 345/156 |
| 2015/0215925 A1* | 7/2015 | Wang | A61B 5/0024 370/329 |
| 2015/0216459 A1 | 8/2015 | Al-Ali et al. | |
| 2015/0238722 A1 | 8/2015 | Al-Ali | |
| 2015/0245773 A1 | 9/2015 | Lamego et al. | |
| 2015/0245794 A1 | 9/2015 | Al-Ali | |
| 2015/0257689 A1 | 9/2015 | Al-Ali et al. | |
| 2015/0261291 A1* | 9/2015 | Mikhailov | G06F 3/012 345/156 |
| 2015/0272514 A1 | 10/2015 | Kiani et al. | |
| 2015/0277699 A1* | 10/2015 | Algreatly | G06F 3/04815 715/850 |

(56) References Cited

U.S. PATENT DOCUMENTS

| | | | |
|---|---|---|---|
| 2015/0286515 A1* | 10/2015 | Monk | G06F 11/079 714/57 |
| 2015/0301597 A1* | 10/2015 | Rogers | G06Q 30/00 345/156 |
| 2015/0351697 A1 | 12/2015 | Weber et al. | |
| 2015/0356263 A1* | 12/2015 | Chatterjee | G16H 50/20 705/3 |
| 2015/0359429 A1 | 12/2015 | Al-Ali et al. | |
| 2015/0366507 A1 | 12/2015 | Blank | |
| 2016/0019352 A1* | 1/2016 | Cohen | G06F 3/0482 705/3 |
| 2016/0027216 A1* | 1/2016 | da Veiga | G02B 27/0172 345/419 |
| 2016/0029906 A1* | 2/2016 | Tompkins | A61B 5/0205 600/301 |
| 2016/0029932 A1 | 2/2016 | Al-Ali | |
| 2016/0058347 A1 | 3/2016 | Reichgott et al. | |
| 2016/0066824 A1 | 3/2016 | Al-Ali et al. | |
| 2016/0081552 A1 | 3/2016 | Wojtczuk et al. | |
| 2016/0095543 A1 | 4/2016 | Telfort et al. | |
| 2016/0095548 A1 | 4/2016 | Al-Ali et al. | |
| 2016/0103598 A1 | 4/2016 | Al-Ali et al. | |
| 2016/0116979 A1* | 4/2016 | Border | G06F 3/013 345/156 |
| 2016/0124501 A1* | 5/2016 | Lam | G06F 3/011 345/156 |
| 2016/0135516 A1* | 5/2016 | Cobbett | A61B 5/0205 2/170 |
| 2016/0143548 A1 | 5/2016 | Al-Ali | |
| 2016/0166182 A1 | 6/2016 | Al-Ali et al. | |
| 2016/0166183 A1 | 6/2016 | Poeze et al. | |
| 2016/0180044 A1* | 6/2016 | Delisle | G16H 10/60 705/3 |
| 2016/0183836 A1* | 6/2016 | Muuranto | A61B 5/04288 600/301 |
| 2016/0189082 A1* | 6/2016 | Garrish | G06Q 10/06393 705/7.39 |
| 2016/0192869 A1 | 7/2016 | Kiani et al. | |
| 2016/0196388 A1 | 7/2016 | Lamego | |
| 2016/0197436 A1 | 7/2016 | Barker et al. | |
| 2016/0213281 A1 | 7/2016 | Eckerbom et al. | |
| 2016/0225192 A1* | 8/2016 | Jones | A61B 34/10 |
| 2016/0228043 A1 | 8/2016 | O'Neil et al. | |
| 2016/0228640 A1* | 8/2016 | Pindado | A61N 1/36139 |
| 2016/0233632 A1 | 8/2016 | Scruggs et al. | |
| 2016/0234944 A1 | 8/2016 | Schmidt et al. | |
| 2016/0235323 A1* | 8/2016 | Tadi | A61B 5/7285 |
| 2016/0239252 A1* | 8/2016 | Nakagawa | G02B 27/0172 |
| 2016/0270735 A1 | 9/2016 | Diab et al. | |
| 2016/0274358 A1* | 9/2016 | Yajima | G02B 27/017 |
| 2016/0278644 A1* | 9/2016 | He | A61B 5/02125 |
| 2016/0283665 A1 | 9/2016 | Sampath et al. | |
| 2016/0287090 A1 | 10/2016 | Al-Ali et al. | |
| 2016/0287207 A1* | 10/2016 | Xue | A61B 7/04 |
| 2016/0287786 A1 | 10/2016 | Kiani | |
| 2016/0296169 A1 | 10/2016 | McHale et al. | |
| 2016/0310005 A1* | 10/2016 | Pekander | H04W 4/70 |
| 2016/0310047 A1* | 10/2016 | Pekander | A61B 5/002 |
| 2016/0310052 A1 | 10/2016 | Al-Ali et al. | |
| 2016/0314260 A1 | 10/2016 | Kiani | |
| 2016/0314624 A1* | 10/2016 | Li | G06F 1/163 |
| 2016/0324486 A1 | 11/2016 | Al-Ali et al. | |
| 2016/0324488 A1 | 11/2016 | Olsen | |
| 2016/0327984 A1 | 11/2016 | Al-Ali et al. | |
| 2016/0328528 A1 | 11/2016 | Al-Ali et al. | |
| 2016/0330573 A1* | 11/2016 | Masoud | H04W 4/90 |
| 2016/0331332 A1 | 11/2016 | Al-Ali | |
| 2016/0335403 A1 | 11/2016 | Mabotuwana | G06F 19/324 |
| 2016/0335800 A1* | 11/2016 | DeStories | G02B 27/0172 |
| 2016/0351776 A1* | 12/2016 | Schneider | H01L 35/30 |
| 2016/0357491 A1* | 12/2016 | Oya | G06F 3/0488 |
| 2016/0367173 A1 | 12/2016 | Dalvi et al. | |
| 2016/0371886 A1* | 12/2016 | Thompson | G02B 27/0172 |
| 2017/0000394 A1 | 1/2017 | Al-Ali et al. | |
| 2017/0000422 A1* | 1/2017 | Moturu | A61B 5/7275 |
| 2017/0004106 A1* | 1/2017 | Joshua | G06F 11/2289 |
| 2017/0007134 A1 | 1/2017 | Al-Ali et al. | |
| 2017/0007198 A1 | 1/2017 | Al-Ali et al. | |
| 2017/0010850 A1* | 1/2017 | Kobayashi | G06F 3/1454 |
| 2017/0014083 A1 | 1/2017 | Diab et al. | |
| 2017/0014084 A1 | 1/2017 | Al-Ali et al. | |
| 2017/0027456 A1 | 2/2017 | Kinast et al. | |
| 2017/0042488 A1* | 2/2017 | Muhsin | A61B 5/742 |
| 2017/0046872 A1* | 2/2017 | Geselowitz | G06T 11/206 |
| 2017/0055851 A1 | 3/2017 | Al-Ali | |
| 2017/0055882 A1 | 3/2017 | Al-Ali et al. | |
| 2017/0055887 A1 | 3/2017 | Al-Ali | |
| 2017/0055896 A1 | 3/2017 | Al-Ali et al. | |
| 2017/0065379 A1* | 3/2017 | Cowburn | A61C 19/04 |
| 2017/0079594 A1 | 3/2017 | Telfort et al. | |
| 2017/0083104 A1* | 3/2017 | Namba | G06T 19/006 |
| 2017/0086723 A1 | 3/2017 | Al-Ali et al. | |
| 2017/0092002 A1* | 3/2017 | Mullins | G06F 3/013 |
| 2017/0111824 A1* | 4/2017 | Wang | H04W 28/085 |
| 2017/0140101 A1* | 5/2017 | Anderson | G16H 10/60 |
| 2017/0143281 A1 | 5/2017 | Olsen | |
| 2017/0147774 A1 | 5/2017 | Kiani | |
| 2017/0156620 A1 | 6/2017 | Al-Ali et al. | |
| 2017/0161455 A1* | 6/2017 | Grady | A61B 5/4848 |
| 2017/0172415 A1* | 6/2017 | Wik | H04W 4/80 |
| 2017/0172515 A1* | 6/2017 | Banet | A61B 5/7275 |
| 2017/0172696 A1* | 6/2017 | Saget | A61B 90/37 |
| 2017/0173632 A1 | 6/2017 | Al-Ali | |
| 2017/0177816 A1* | 6/2017 | Ribble | A61G 7/05 |
| 2017/0178356 A1* | 6/2017 | Bhuruth | G06T 7/73 |
| 2017/0181645 A1* | 6/2017 | Mahalingam | A61B 5/0004 |
| 2017/0186157 A1* | 6/2017 | Boettger | G06T 7/70 |
| 2017/0187146 A1 | 6/2017 | Kiani et al. | |
| 2017/0188919 A1 | 7/2017 | Al-Ali et al. | |
| 2017/0196464 A1 | 7/2017 | Jansen et al. | |
| 2017/0196470 A1 | 7/2017 | Lamego et al. | |
| 2017/0200296 A1* | 7/2017 | Jones | G06T 11/60 |
| 2017/0202490 A1 | 7/2017 | Al-Ali et al. | |
| 2017/0206676 A1* | 7/2017 | Nakazato | G06T 7/73 |
| 2017/0215261 A1* | 7/2017 | Potucek | A61H 33/005 |
| 2017/0215388 A1* | 8/2017 | Delecroix | A01K 29/005 |
| 2017/0216524 A1* | 8/2017 | Haider | A61M 5/1723 |
| 2017/0224262 A1 | 8/2017 | Al-Ali | |
| 2017/0228516 A1 | 8/2017 | Sampath et al. | |
| 2017/0242480 A1* | 8/2017 | Dees | G02B 27/0179 |
| 2017/0244796 A1* | 8/2017 | Liu | G06F 3/0481 |
| 2017/0245790 A1 | 8/2017 | Al-Ali et al. | |
| 2017/0251974 A1 | 9/2017 | Shreim et al. | |
| 2017/0251975 A1 | 9/2017 | Shreim et al. | |
| 2017/0255838 A1* | 9/2017 | Norieda | G06K 9/00671 |
| 2017/0258403 A1 | 9/2017 | Abdul-Hafiz et al. | |
| 2017/0262064 A1* | 9/2017 | Ofir | G06F 3/00 |
| 2017/0300824 A1* | 10/2017 | Peng | G06F 16/26 |
| 2017/0311891 A1 | 11/2017 | Kiani et al. | |
| 2017/0315774 A1* | 11/2017 | Meerbeek | G06F 3/011 |
| 2017/0316561 A1* | 11/2017 | Helm | G06T 7/0012 |
| 2017/0323479 A1* | 11/2017 | Mokuya | G06T 19/00 |
| 2017/0325684 A1* | 11/2017 | Vartiovaara | A61B 5/0017 |
| 2017/0325728 A1 | 11/2017 | Al-Ali et al. | |
| 2017/0329480 A1* | 11/2017 | Ishikawa | G06F 3/0484 |
| 2017/0332976 A1 | 11/2017 | Al-Ali et al. | |
| 2017/0340293 A1 | 11/2017 | Al-Ali et al. | |
| 2017/0351909 A1* | 12/2017 | Kaehler | G06K 9/6257 |
| 2017/0357397 A1* | 12/2017 | Masumoto | G06F 3/0484 |
| 2017/0359467 A1* | 12/2017 | Norris | H04S 1/005 |
| 2017/0360310 A1 | 12/2017 | Kiani et al. | |
| 2017/0367632 A1 | 12/2017 | Al-Ali et al. | |
| 2017/0367771 A1* | 12/2017 | Tako | A61B 34/20 |
| 2018/0000415 A1* | 1/2018 | Gupta | A61B 5/743 |
| 2018/0005424 A1* | 1/2018 | Niinuma | G06T 11/60 |
| 2018/0008146 A1 | 1/2018 | Al-Ali et al. | |
| 2018/0014752 A1 | 1/2018 | Al-Ali et al. | |
| 2018/0024630 A1* | 1/2018 | Goossens | G06F 3/013 345/156 |
| 2018/0025116 A1* | 1/2018 | Carrington | G16H 50/30 705/3 |
| 2018/0028124 A1 | 2/2018 | Al-Ali et al. | |
| 2018/0055385 A1 | 3/2018 | Al-Ali | |

(56) References Cited

U.S. PATENT DOCUMENTS

| | | | |
|---|---|---|---|
| 2018/0055390 A1 | 3/2018 | Kiani et al. | |
| 2018/0055430 A1 | 3/2018 | Diab et al. | |
| 2018/0059812 A1* | 3/2018 | Inomata | G06F 3/0346 |
| 2018/0064381 A1 | 3/2018 | Shakespeare et al. | |
| 2018/0069776 A1 | 3/2018 | Lamego et al. | |
| 2018/0074332 A1* | 3/2018 | Li | G06F 1/163 |
| 2018/0075658 A1* | 3/2018 | Lanier | G06T 19/006 |
| 2018/0080774 A1* | 3/2018 | Sink | G06F 3/012 |
| 2018/0082480 A1* | 3/2018 | White | G06T 11/00 |
| 2018/0084224 A1* | 3/2018 | McNelley | G09G 3/002 |
| 2018/0088682 A1* | 3/2018 | Tsang | G06F 3/02 |
| 2018/0103874 A1 | 4/2018 | Lee et al. | |
| 2018/0116575 A1 | 5/2018 | Perea et al. | |
| 2018/0125368 A1 | 5/2018 | Lamego et al. | |
| 2018/0125430 A1 | 5/2018 | Al-Ali et al. | |
| 2018/0130325 A1 | 5/2018 | Kiani et al. | |
| 2018/0132769 A1 | 5/2018 | Weber et al. | |
| 2018/0132770 A1 | 5/2018 | Lamego | |
| 2018/0139203 A1* | 5/2018 | Dolan | G06F 21/32 |
| 2018/0140362 A1* | 5/2018 | Cal | A61B 34/25 |
| 2018/0144497 A1* | 5/2018 | Hirota | G06F 3/011 |
| 2018/0147024 A1* | 5/2018 | Kall | A61B 90/98 |
| 2018/0153445 A1* | 6/2018 | Noda | A61B 5/1124 |
| 2018/0157344 A1* | 6/2018 | Toff | G06F 3/0346 |
| 2018/0160881 A1* | 6/2018 | Okabe | G02B 23/243 |
| 2018/0181810 A1* | 6/2018 | Jhawar | G06K 9/00671 |
| 2018/0188807 A1* | 7/2018 | Cimenser | A61B 5/0022 |
| 2018/0188831 A1* | 7/2018 | Lyons | G06F 3/04815 |
| 2018/0189556 A1* | 7/2018 | Shamir | G06K 9/00355 |
| 2018/0200018 A1* | 7/2018 | Silva | A61B 34/20 |
| 2018/0217734 A1* | 8/2018 | Koenig | G06T 11/60 |
| 2018/0225993 A1* | 8/2018 | Buras | A61B 90/361 |
| 2018/0235478 A1* | 8/2018 | Khachaturian | A61B 5/01 |
| 2018/0242920 A1* | 8/2018 | Hresko | A61B 5/743 |
| 2018/0247024 A1* | 8/2018 | Divine | G06F 19/321 |
| 2018/0250510 A1* | 9/2018 | Ziv | A61N 1/36031 |
| 2018/0251230 A1* | 9/2018 | Chavez | B64C 1/066 |
| 2018/0253947 A1* | 9/2018 | Muhsin | G08B 3/10 |
| 2018/0261329 A1* | 9/2018 | Blander | G16H 50/30 |
| 2018/0264945 A1* | 9/2018 | Torii | B60K 35/00 |
| 2018/0275837 A1* | 9/2018 | Getz | G06F 3/017 |
| 2018/0279947 A1* | 10/2018 | Ummat | A61B 5/4818 |
| 2018/0285094 A1* | 10/2018 | Housel | G16H 30/20 |
| 2018/0286132 A1* | 10/2018 | Cvetko | G06T 19/006 |
| 2018/0300031 A1* | 10/2018 | Parkinson | G06F 3/017 |
| 2018/0303558 A1* | 10/2018 | Thomas | A61B 34/10 |
| 2018/0310822 A1* | 11/2018 | Indorf | A61B 5/0015 |
| 2018/0315490 A1* | 11/2018 | Jaruzel, II | G16H 10/20 |
| 2018/0317826 A1* | 11/2018 | Muhsin | G16H 40/40 |
| 2018/0333643 A1* | 11/2018 | Luisi | A63F 13/26 |
| 2018/0342079 A1* | 11/2018 | Yaguchi | A61B 1/00009 |
| 2018/0344308 A1* | 12/2018 | Nawana | A61B 34/25 |
| 2018/0365897 A1* | 12/2018 | Pahud | G06F 3/1454 |
| 2019/0005724 A1* | 1/2019 | Pahud | G06T 19/006 |
| 2019/0033989 A1* | 1/2019 | Wang | G06T 19/003 |
| 2019/0034076 A1* | 1/2019 | Vinayak | G06F 3/017 |
| 2019/0043259 A1* | 2/2019 | Wang | G06T 19/003 |
| 2019/0053855 A1* | 2/2019 | Siemionow | G06T 7/11 |
| 2019/0064520 A1* | 2/2019 | Christensen | A61M 1/34 |
| 2019/0066538 A1* | 2/2019 | Chao | G09B 23/288 |
| 2019/0079156 A1* | 3/2019 | Krellmann | G01R 33/56572 |
| 2019/0080515 A1* | 3/2019 | Geri | G06T 7/73 |
| 2019/0121522 A1* | 4/2019 | Davis | G06F 3/04817 |
| 2019/0138183 A1* | 5/2019 | Rosas | G06F 3/017 |
| 2019/0141291 A1* | 5/2019 | McNelley | H04N 5/272 |
| 2019/0146578 A1* | 5/2019 | Ikuta | G06F 3/04815 |
| 2019/0149797 A1* | 5/2019 | Casas | G06F 3/0304 |
| | | | 348/47 |
| 2019/0155382 A1* | 5/2019 | Ikuta | G02B 27/0172 |
| 2019/0183577 A1* | 6/2019 | Fahim | G02B 27/01 |
| 2019/0206104 A1* | 7/2019 | Rahman | H04L 67/141 |
| 2019/0231436 A1* | 8/2019 | Panse | A61B 6/032 |
| 2019/0240508 A1* | 8/2019 | Friman | A61N 5/1037 |
| 2019/0243138 A1* | 8/2019 | Peltola | G16H 40/63 |
| 2019/0250873 A1* | 8/2019 | Blume | G06F 3/1454 |
| 2019/0254754 A1* | 8/2019 | Johnson | G16H 50/50 |
| 2019/0298270 A1* | 10/2019 | Al-Ali | A61B 5/0205 |
| 2019/0333276 A1* | 10/2019 | Brown | A61B 90/36 |
| 2019/0340434 A1* | 11/2019 | Chiu | G16H 20/60 |
| 2019/0340827 A1* | 11/2019 | Abercrombie | G06F 3/167 |
| 2019/0348169 A1* | 11/2019 | Gibby | G06K 7/1417 |
| 2019/0355182 A1* | 11/2019 | Nozaki | G06T 19/20 |
| 2019/0380792 A1* | 12/2019 | Poltaretskyi | A61B 5/1122 |
| 2019/0387102 A1* | 12/2019 | Norris | H04M 3/568 |
| 2020/0004328 A1* | 1/2020 | Blume | G06F 3/017 |
| 2020/0005542 A1* | 1/2020 | Kocharlakota | G06T 19/006 |
| 2020/0046473 A1* | 2/2020 | Kim | G06T 19/20 |
| 2020/0074740 A1* | 3/2020 | Singh | G06K 9/00671 |
| 2020/0125322 A1* | 4/2020 | Wilde | G06F 1/163 |
| 2020/0210679 A1* | 7/2020 | Kusens | G16H 80/00 |
| 2020/0319770 A1* | 10/2020 | Varga | G16H 15/00 |
| 2020/0321099 A1* | 10/2020 | Holladay | G06T 7/0012 |
| 2020/0327670 A1* | 10/2020 | Connor | G06T 7/62 |
| 2020/0372714 A1* | 11/2020 | Soryal | G16H 30/20 |
| 2020/0405151 A1* | 12/2020 | Berger | A61B 5/4836 |

\* cited by examiner

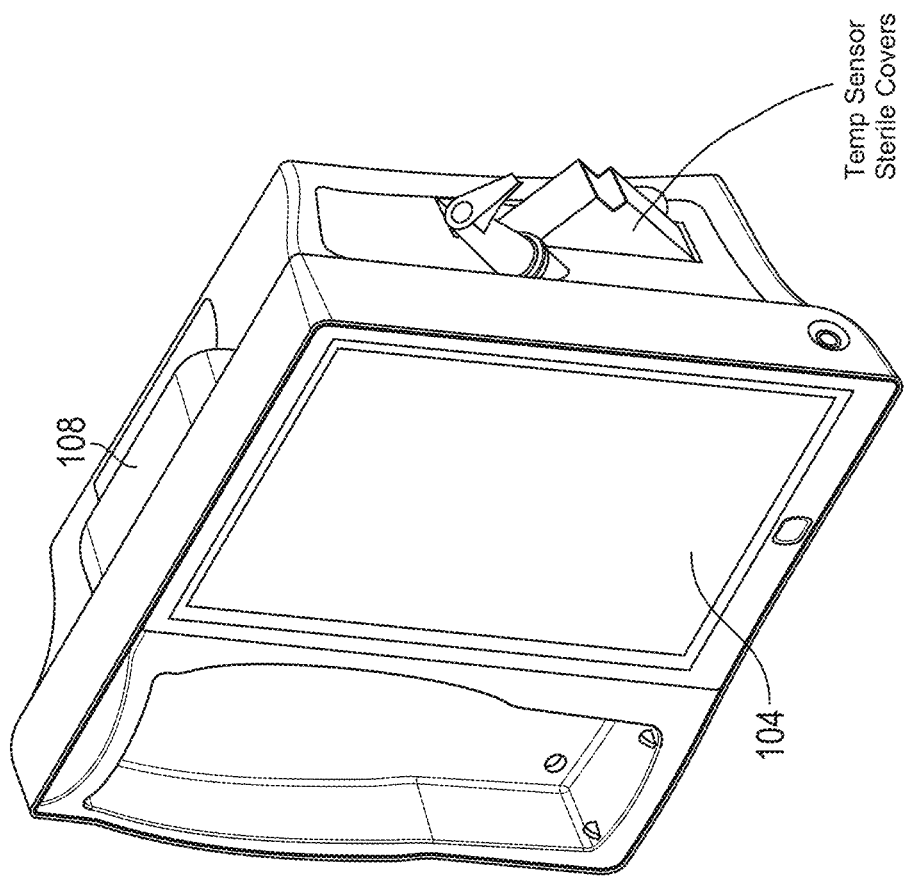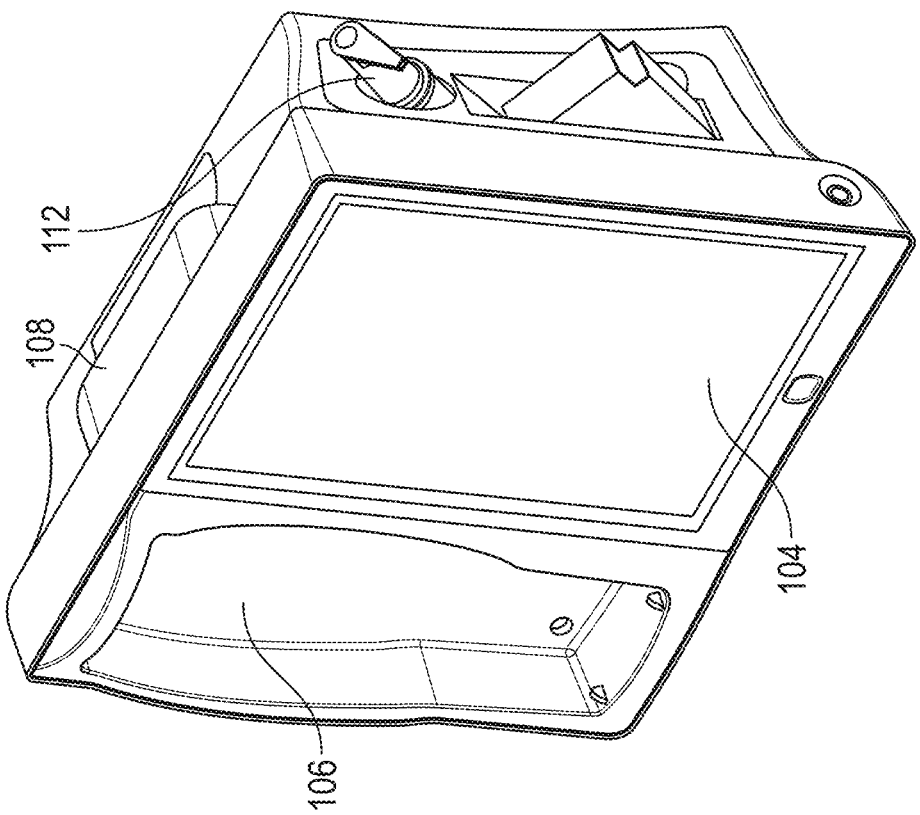
FIG. 1C

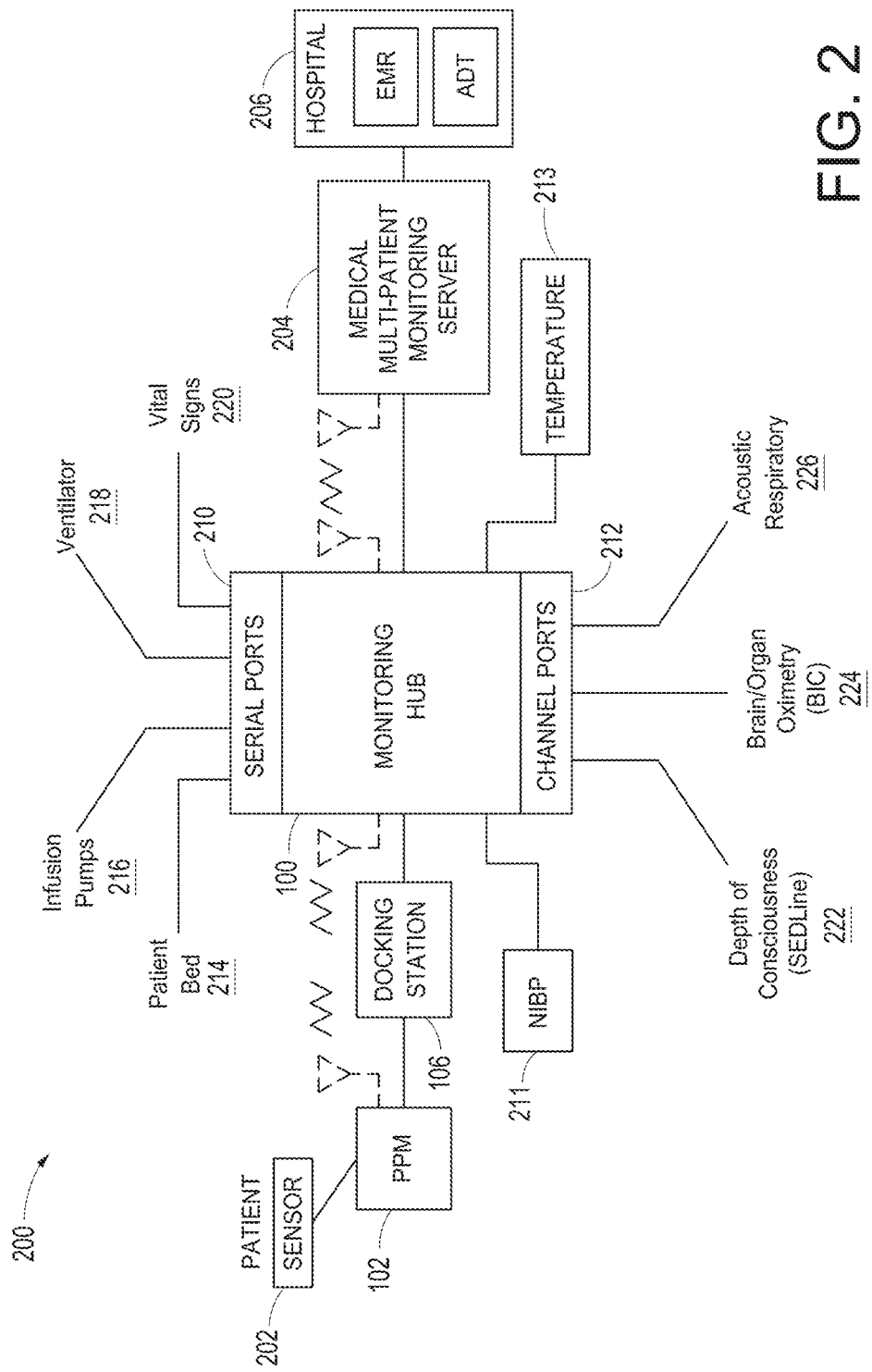

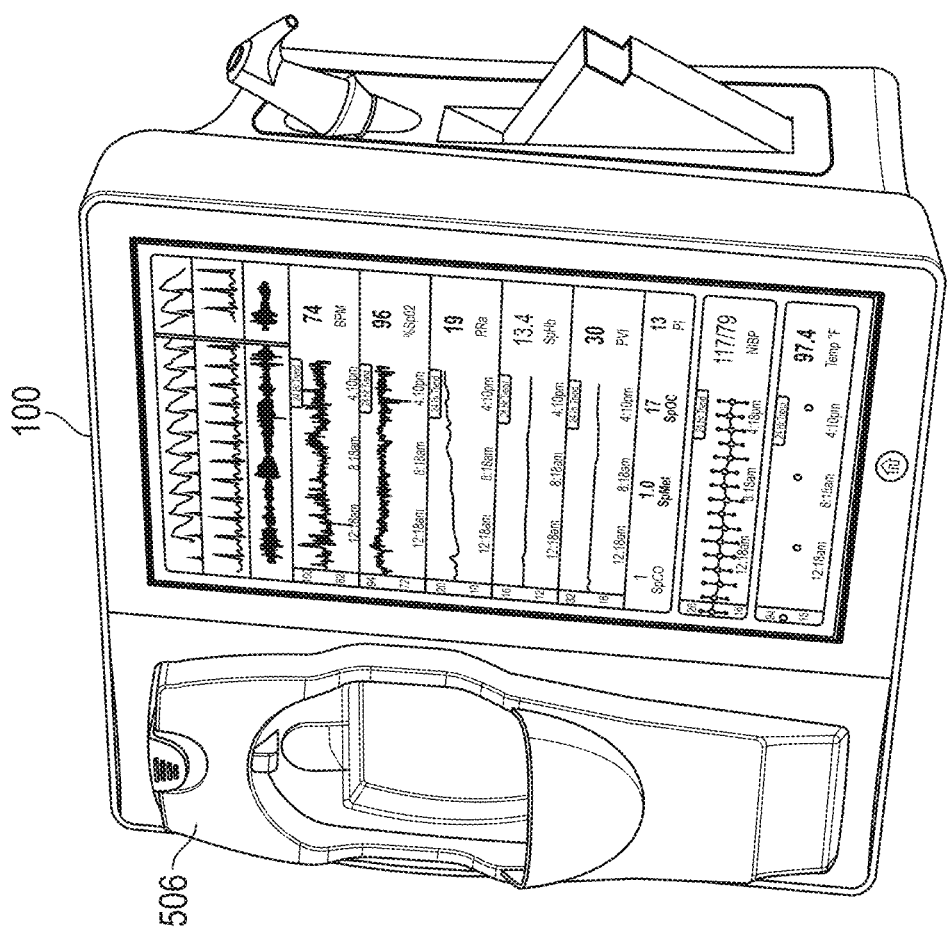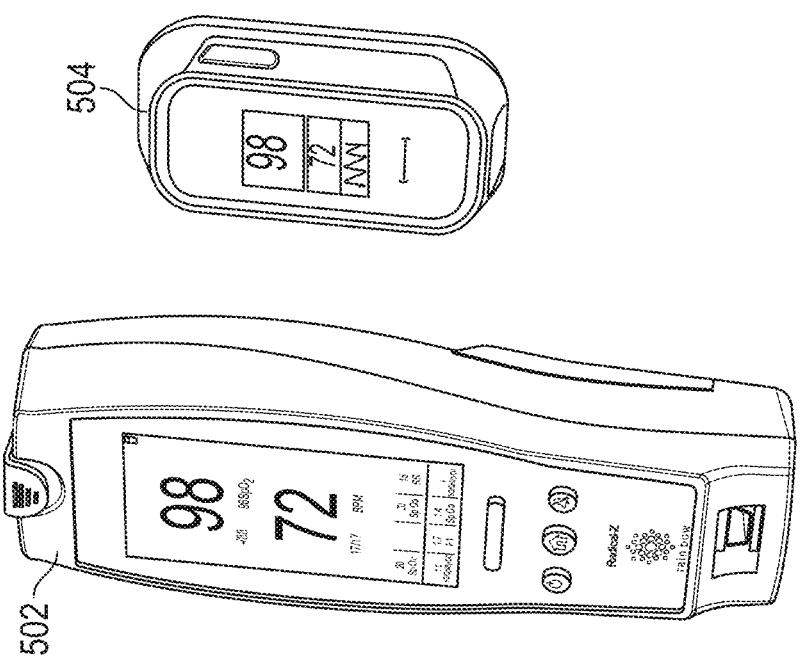
FIG. 5

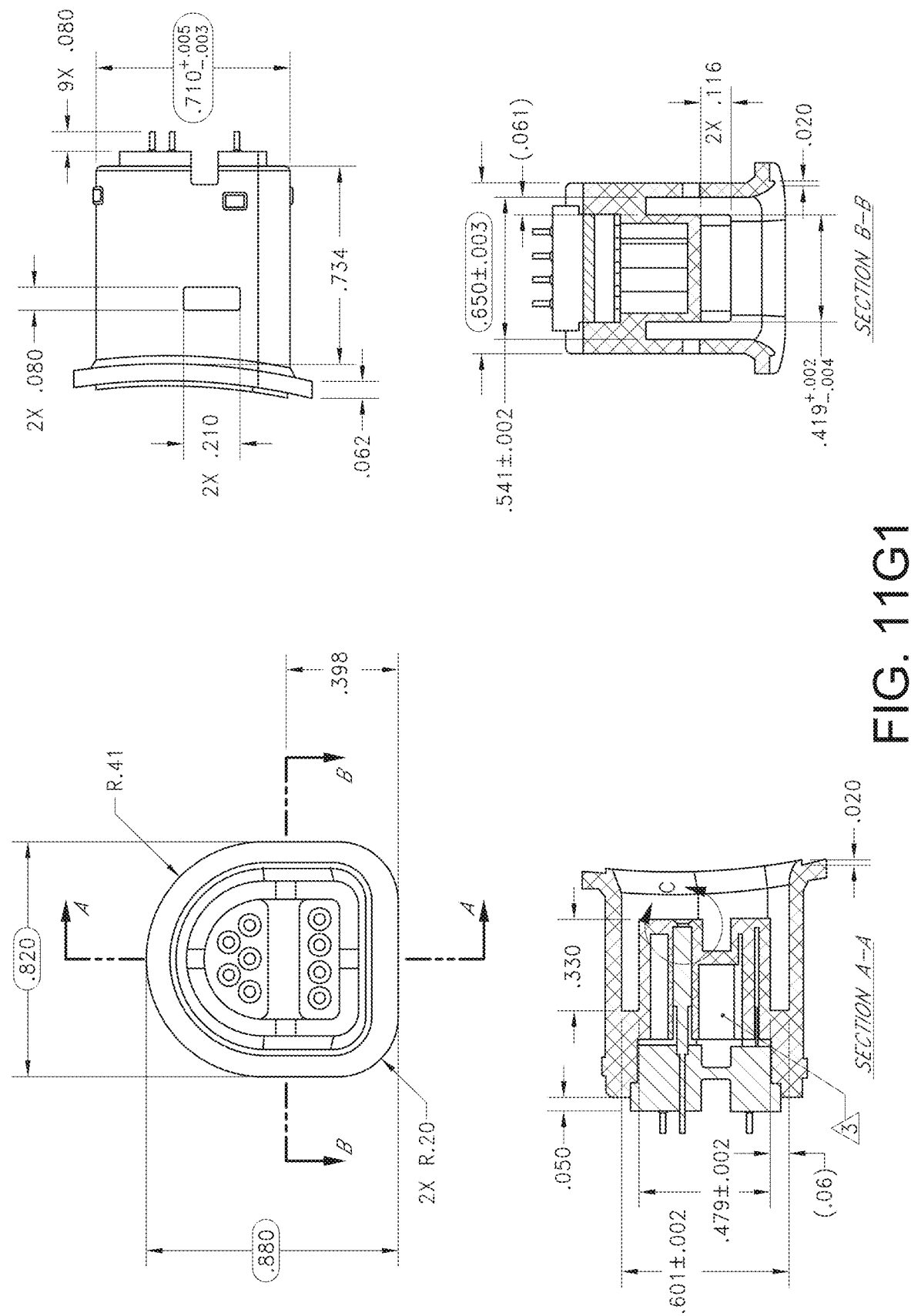
FIG. 11G1

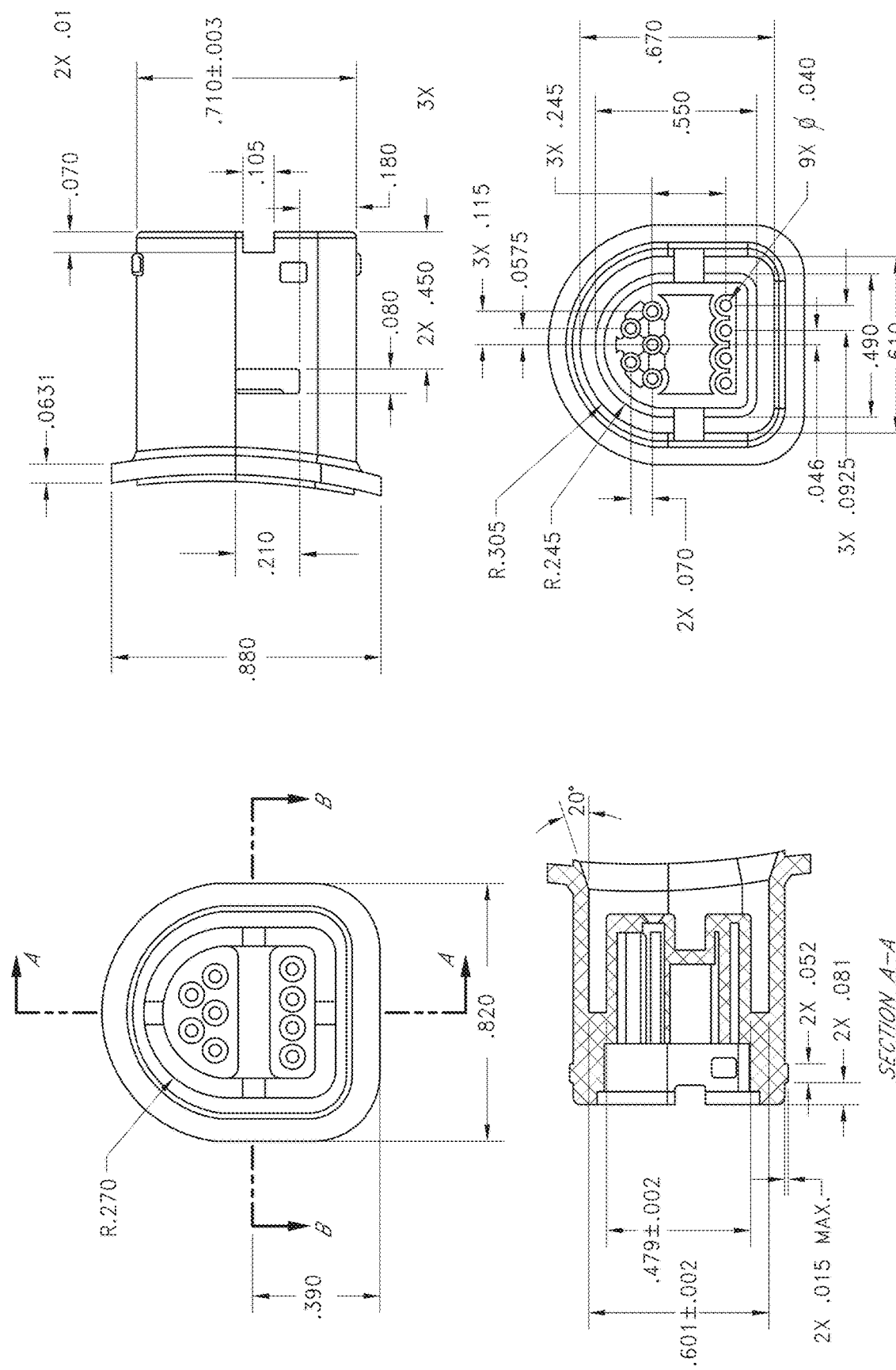
FIG. 11G2

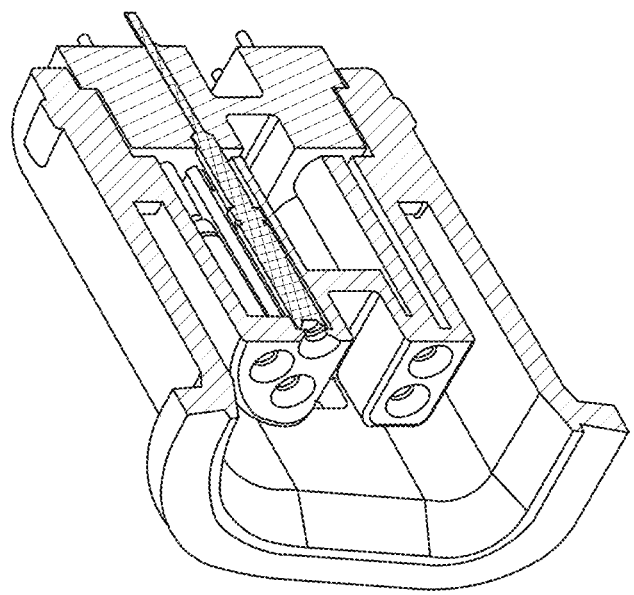
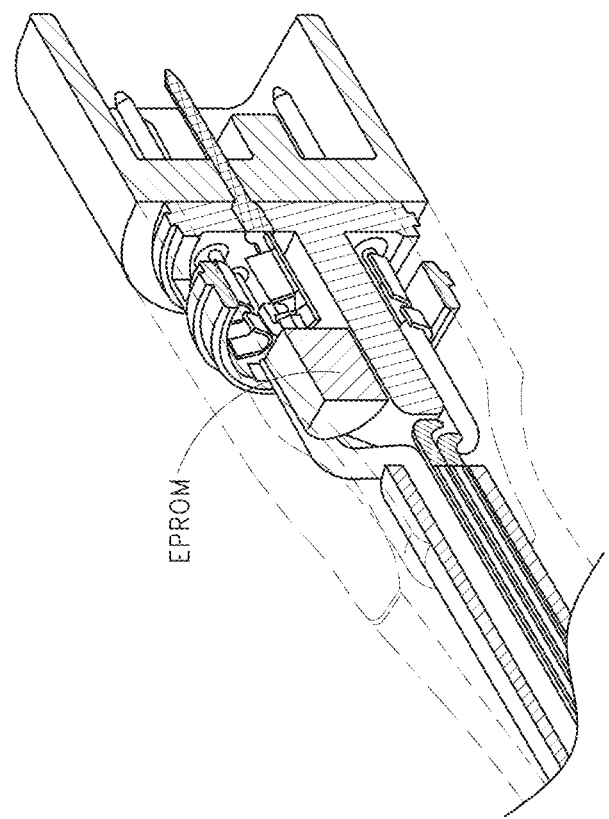
FIG. 11H

```
<SB>
MSH~|\&^VAFC PIMS^50^NPTF-508^200^20091120104609-0600^^ADT^A01^58103^P^^^^^USA<CR>
EVN^A01^20091120104517-0600^^05<CR>
PID^1^500000003V302090^11~7~M10^^LONG~BRIAN^^19800401^M^^^~""~""~""~CDC^^^~""~""~
""~""&""|""~""~""~""~VACE~""~""~""~""~""&""|""~""~""~""~VACAA~""~""~""~""~""&""|""~""~""~""~VACAC~""~""
~""&""|""~""~""~""~VACM~""~""~""~""~""&""|""~""~""~""~VACAO~""~""~""~""~""&""|""~""~""~""~29^^^^
^^^^~0189~""~""~CDC^ <CR>
PD1^^^SOFTWARE SERVICE~~050^""<CR>
ZPD^1^""^^^^^^~""^^^^^^^^^^^^^^^^^^^^^^~""^0^""^^^""^""<CR>
PV1^1^I^PSYCH~304~1^^^^^^~""^""~25~WESSELHOFT~MEGAN^""~""~""~""~""~""~""~""~""~""~SSA<CR>
(OTHER)^^^25^^^^^^^^^^^^^20091120104517-0600^^^^^^18<CR>
ROL^18-
25*1^CO^""^""~""~""~""~""~""~T^""~VA01^25&50~WESSELHOFT~MEGAN~""~""~""~""~""~""~""~""~""~""~VA200|""~""~""~""~""~""~""~""~""~""~SSA<CR>
ROL^18-
25*2^CO^""^""~""~""~""~""~""~A^""~VA01^25&50~WESSELHOFT~MEGAN~""~""~""~""~""~""~""~""~""~""~VA200|""~""~""~""~""~""~""~""~""~""~SSA<CR>
DG1^1^^^IBS<CR>
ZSP^1^0^""^N""~""^^^^^^^^^^^^^^<CR>
ZEL^1^8^---~""^""^""^^^^^^^^^^^^^^^~0^NON-VETERAN (OTHER)^^^^^^^^^^^^^^^^^^^^^^^^^^^<CR>
ZCT^1^1^^""^""^^^^^^^^^^^^^^^^^^<CR>
ZEM^1^^^^^^^^^^^^^^^^^^^;;<CR>
ZIR^<CR>
ZEN^1<CR>
<EB><CR>
```

FIG. 41A

```xml
<?xml version="1.0" encoding="UTF-8" standalone="no" ?>
  <ev7>
    <MSH>
      <MSH.1>^</MSH.1>
      <MSH.2>~|\&</MSH.2>
      <MSH.3>VAFC PIMS</MSH.3>
      <MSH.4>50</MSH.4>
      <MSH.5>NPTF-508</MSH.5>
      <MSH.6>200</MSH.6>
      <MSH.7>20091120104609-0600</MSH.7>
      <MSH.9>
        <component n="1">ADT</component>
        <component n="2">ADT</component>
      <MSH.9>
      <MSH.10>58103</MSH.10>
      <MSH.11>P</MSH.11>
      <MSH.17>USA</MSH.17>
    </MSH>
    <EVN>
      <EVN.1>A01</EVN.1>
      <EVN.2>20091120104517-0600</EVN.2>
      <EVN.4>05</EVN.4>
    </EVN>
    ...
  <ev7>
```

FIG. 41B

```xml
<?xml version="1.0" encoding="UTF-8"?>
<ADT_A01>
  <MSH>
    <MSH.1>^</MSH.1>
    <MSH.2>~|\&</MSH.2>
    <MSH.3>
      <HD.1>VAFC PIMS</HD.1>
    </MSH.3>
    <MSH.4>
      <HD.1>50</HD.1>
    </MSH.4>
    <MSH.5>
      <HD.1>NPTF-508</HD.1>
    </MSH.5>
    <MSH.6>
      <HD.1>200</HD.1>
    </MSH.6>
    <MSH.7>
      <TS.1>20091120104609-0600</TS.1>
    </MSH.7>
    <MSH.9>
      <MSG.1>ADT</MSG.1>
      <MSG.2>A01</MSG.2>
    </MSH.9>
    <MSH.10>58103</MSH.10>
    <MSH.11>
      <PT.1>P</PT.1>
    </MSH.11>
    <MSH.17>USA</MSH.17>
  </MSH>
```

FIG. 41C

```
<output-message>
  <ACK>
    <MSH>
      <MSH.1>^</MSH.1>
      <MSH.2>~|\&</MSH.2>
      <MSH.3>
        <HD.1>NPTF-508</HD.1>
      </MSH.3>
      <MSH.4>
        <HD.1>200</HD.1>
      </MSH.4>
      <MSH.5>
        <HD.1>VAFC PIMS</HD.1>
      </MSH.5>
      <MSH.6>
        <HD.1>50</HD.1>
      </MSH.6>
      <MSH.7>
        <TS.1>20091120104609-0600</TS.1>
      </MSH.7>
      <MSH.9>
        <MSG.1>ACK</MSG.1>
        <MSG.3>ACK</MSG.2>
      </MSH.9>
      <MSH.10>856bc9bd-97c8-4aa5-b411-3cd6fe2edd86</MSH.10>
    <MSH>
    <MSA>
      <MSA.1>AA</MSA.1>
      <MSA.2>58103</MSA.2>
    </MSA>
  </ACK>
</output-message>
```

AUGMENTED REALITY SYSTEM FOR DISPLAYING PATIENT DATA

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims benefit of U.S. Provisional Patent Application Ser. No. 62/463,517 entitled "System for Displaying and Controlling Medical Monitoring Data" filed Feb. 24, 2017, and U.S. Provisional Patent Application Ser. No. 62/463,452 entitled "Patient Monitor Communication Platform" filed Feb. 24, 2017, which are hereby incorporated by reference in their entireties.

FIELD OF THE DISCLOSURE

The present disclosure relates generally to patient monitoring devices and specifically to a patient monitor and medical data communication hub.

BACKGROUND OF THE DISCLOSURE

Today's patient monitoring environments are crowded with sophisticated and often electronic medical devices servicing a wide variety of monitoring and treatment endeavors for a given patient. Generally, many if not all of the devices are from differing manufacturers, and many may be portable devices. The devices may not communicate with one another and each may include its own control, display, alarms, configurations and the like. Complicating matters, caregivers often desire to associate all types of measurement and use data from these devices to a specific patient. Thus, patient information entry often occurs at each device. Sometimes, the disparity in devices leads to a need to simply print and store paper from each device in a patient's file for caregiver review.

The result of such device disparity is often a caregiver environment scattered with multiple displays and alarms leading to a potentially chaotic experience. Such chaos can be detrimental to the patient in many situations including surgical environments where caregiver distraction is unwanted, and including recovery or monitoring environments where patient distraction or disturbance may be unwanted.

Various manufacturers produce multi-monitor devices or devices that modularly expand to increase the variety of monitoring or treatment endeavors a particular system can accomplish. However, as medical device technology expands, such multi-monitor devices begin to be obsolete the moment they are installed.

SUMMARY

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

Some aspects of the disclosure describe a method for presenting augmented reality data from a medical monitoring device. Under control of a hardware processor, the method can include receiving physiological monitoring data comprising physiological parameter values associated with a patient from a monitoring hub. The method can further include accessing user interface configuration data. The method can further include generating, from the physiological monitoring data, a plurality of augmented reality objects according to the user interface configuration data. The method can further include receiving user interaction data from a user input device of an augmented reality device, wherein the user interaction data comprises an indication of an interaction to virtually pin the plurality of augmented reality objects to a reference object. The method can further include determining a reference position based at least in part the user interaction data. The method can further include causing presentation of the plurality of augmented reality objects in an augmented reality display, wherein the plurality of augmented reality objects are presented relative to the reference position.

The method can further include: identifying, from the user interaction data, the reference object; determining the reference position for the reference object; and calculating a positional offset from the reference position, wherein the plurality of augmented reality objects are presented relative to the reference position according to the positional offset.

The method can further include: determining, from the user interface configuration data, whether to present a direct overlay; identifying, from the user interface configuration data, the reference object; calculating the reference position for the reference object, wherein an overlay object of the plurality of augmented reality objects is presented at the reference position.

The method can further include: detecting a gesture from the user interaction data; and generating the user interface configuration data based at least in part on the gesture.

The plurality of augmented reality objects can be presented in a first arrangement. The method can further include: receiving second user interaction data from the user input device, the second user interaction data indicating a second arrangement of the plurality of augmented reality objects; generating second user interface configuration data from the second user interaction data; and causing presentation, in the augmented reality display, of the plurality of augmented reality objects in the second arrangement according to the second user interface configuration data.

A user interface of the augmented reality display can be configurable via a device different from an augmented reality device.

The method can further include: receiving hub user interaction data from the monitoring hub; determining a hub user interface configuration from the hub user interaction data, wherein the user interface configuration data is indicative of the hub user interface configuration; and causing presentation of a user interface on a display of the monitoring hub according to the hub user interface configuration.

The hub user interface configuration can include a plurality of user interface elements, wherein each element of the plurality of user interface elements comprises a physiological parameter value, and wherein each element of the plurality of user interface elements corresponds to an object from the plurality of augmented reality objects.

At least some of the plurality of augmented reality objects can correspond to the hub user interface configuration.

The hub user interaction data can be indicative of at least one addition, removal, or rearrangement of a user interface element.

An augmented reality device can be configured to present physiological data. The system can include a memory device configured to store instructions, and a hardware processor. The hardware processor can be configured to execute the instructions to receive physiological monitoring data comprising physiological parameter values associated with a patient from a patient monitor. The hardware processor can be further configured to access user interface configuration data. The hardware processor can be further configured to generate, from the physiological monitoring data, a plurality of augmented reality objects according to the user interface configuration data. The hardware processor can be further configured to determine that a clinician wearing the augmented reality device is looking toward the patient monitor. In response to said determination, the hardware processor can be further configured to cause presentation of the plurality of augmented reality objects in an augmented reality display in a vicinity of the patient monitor.

The hardware processor can be further configured to: receive user interaction data from a user input device of an augmented reality device; and generate the user interface configuration data from the user interaction data.

The hardware processor can be further configured to: receive user interaction data from a user input device of an augmented reality device; identify, from the user interaction data, a reference object; determine a reference position for the reference object; and calculate a positional offset from the reference position, wherein the plurality of augmented reality objects are presented relative to the reference position according to the positional offset.

The hardware processor can be further configured to: determine, from the user interface configuration data, whether to present a direct overlay; identify, from the user interface configuration data, a reference object; and calculating a reference position for the reference object, wherein an overlay object of the plurality of augmented reality objects is presented at the reference position.

The hardware processor can be further configured to: receive user input data from a user input device; detect a gesture from the user input data; and generate the user interface configuration data based at least in part on the gesture.

A user interface of the augmented reality device can be configurable via a device different from the augmented reality device.

The hardware processor can be further configured to: receive monitor user interaction data from the patient monitor; determine a monitor user interface configuration from the monitor user interaction data, wherein the user interface configuration data is indicative of the monitor user interface configuration; and cause presentation of a user interface on a display of the patient monitor according to the monitor user interface configuration.

At least some of the plurality of augmented reality objects can correspond to the monitor user interface configuration.

The monitor user interaction data can be indicative of at least one addition, removal, or rearrangement of a user interface element.

The user input data can include image data. Detecting the gesture from the user input data can further include: determining color histogram data from the image data; locating a search window in the image data according to the color histogram data; and identifying a plurality of positions of the search window in the image data.

The reference object can be the patient. The user input device can include a camera.

A system for presenting augmented reality data from a medical monitoring device can include: an augmented reality device comprising a hardware processor, memory, a display, and a wireless device configured to communicate with a medical monitoring device in communication with a patient. The hardware processor of the augmented reality device can be configured to identify a user interaction with the augmented reality device by a clinician wearing the augmented reality device, the user interaction comprising a gesture. The hardware processor can be further configured to determine that the user interaction is an instruction to virtually pin a user interface of the medical monitoring device to a virtual location separate from the medical monitoring device. The hardware processor can be further configured to wirelessly obtain patient data depicted in the user interface from the medical monitoring device. The hardware processor can be further configured to output for presentation to the clinician, in the augmented reality device, a display of the user interface pinned to the virtual location.

The instruction can be to virtually pin the user interface outside of and next to a hospital room of the patient so that the clinician can subsequently view the user interface while walking past the hospital room and without entering the hospital room.

The display of the user interface pinned to the virtual location can be viewable only when the display's field of view includes the virtual location, and wherein the virtual location does not obscure the patient.

The augmented reality device can be further operable to detect that the clinician has moved his or her head away from looking at the medical monitoring device and to reduce a size or content of the user interface at the virtual location.

The augmented reality device further can further include a camera or a movement sensor configured to detect that the clinician has moved his or her head away from looking at the medical monitoring device.

The user interface can be configurable via a device different from the augmented reality device.

BRIEF DESCRIPTION OF THE DRAWINGS

The following drawings and the associated descriptions are provided to illustrate embodiments of the present disclosure and do not limit the scope of the claims.

FIGS. 1A-1C illustrate perspective views of an example medical monitoring hub according. For example, FIG. 1A illustrates the hub with an example docked portable patient monitor, FIG. 1B illustrates the hub with a set of medical ports and a noninvasive blood pressure input, and FIG. 1C illustrates the hub with various example temperature sensors attached thereto.

FIG. 2 illustrates a simplified block diagram of an example monitoring environment including the hub of FIG. 1.

FIG. 5 illustrates a perspective view of example portable patient monitors undocked from the hub of FIG. 1. Moreover, FIG. 5 illustrates an example alternative docking station.

FIGS. 11A-11F, 11G1-11G2, and 11H-11K illustrate various views of example male and mating female universal medical connectors.

FIG. 41A illustrates an example input message received by the translation module.

FIG. 41B illustrates an example message header segment of an input message that has been parsed into fields.

FIG. 41C illustrates an example encoded version of the parsed message header segment of FIG. 41B.

FIG. 41D illustrates an example output message of the translation module based on the input message of FIG. 41A.

FIG. 44 illustrates an example screenshot from a messaging implementation tool for manually configuring translation rules to be used by the translation module.

Figure 1A:
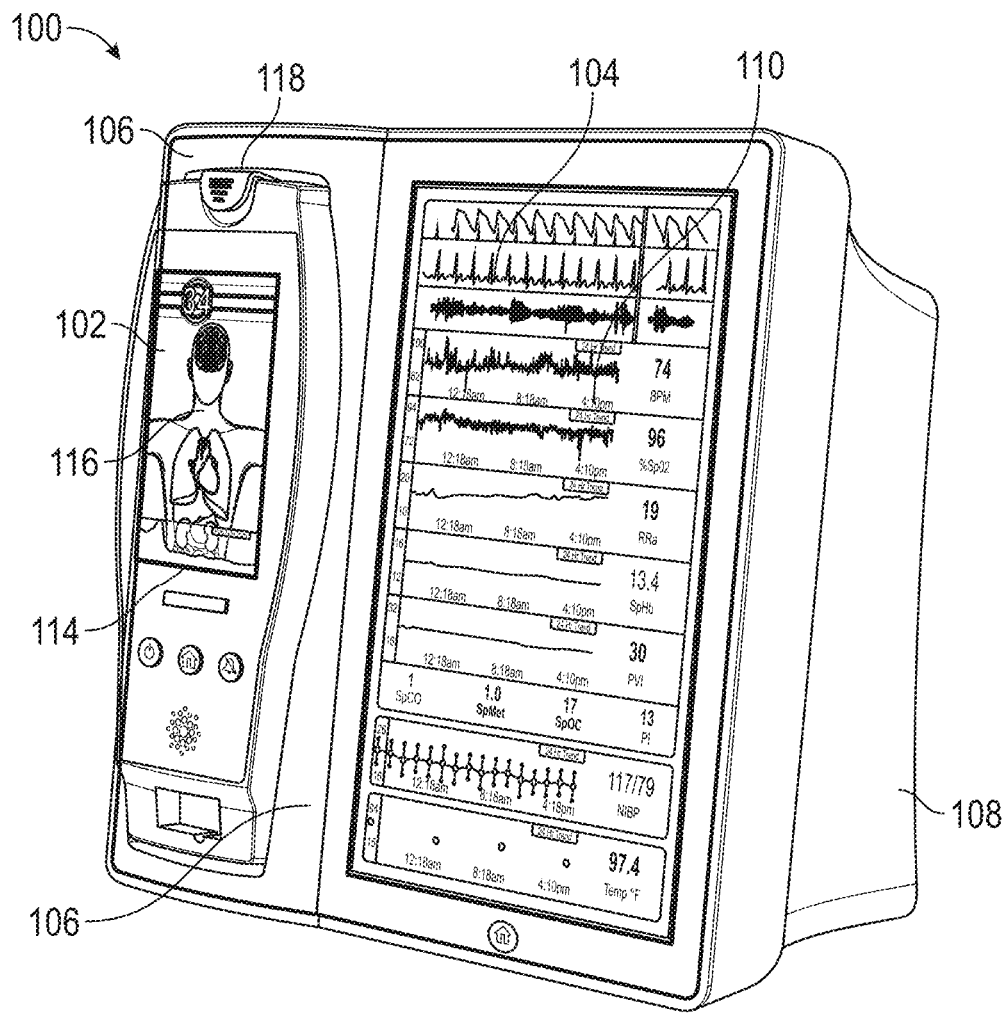

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

I. Introduction

Based on at least the foregoing, a solution is needed that coordinates the various medical devices treating or monitoring a patient. The solutions described herein can provide patient identification seamlessly across the device space and can expand for future technologies without necessarily requiring repeated software upgrades. In addition, such solutions can include patient electrical isolation where desired.

Therefore, the present disclosure relates to a patient monitoring hub that is the center of patient monitoring and treatment activities for a given patient. The patient monitoring hub can interface with legacy devices without necessitating legacy reprogramming, can provide flexibility for interfacing with future devices without necessitating software upgrades, and can offer optional patient electrical isolation. The hub can include a large display that can dynamically provide information to a caregiver about a wide variety of measurement or otherwise determined parameters. The hub can include a docking station for a portable patient monitor. The portable patient monitor may communicate with the hub through the docking station or through various wireless paradigms known to an artisan from the disclosure herein, including WiFi, Bluetooth, Zigbee, or the like.

The portable patient monitor can modify its screen when docked. The undocked display indicia is in part or in whole transferred to a large dynamic display of the hub and the docked display presents one or more anatomical graphics of monitored body parts. For example, the display may present a heart, lungs, a brain, kidneys, intestines, a stomach, other organs, digits, gastrointestinal systems or other body parts when it is docked. The anatomical graphics may advantageously be animated. The animation may generally follow the behavior of measured parameters, such as, for example, the lungs may inflate in approximate correlation to the measured respiration rate and/or the determined inspiration portion of a respiration cycle, and likewise deflate according to the expiration portion of the same. The heart may beat according to the pulse rate, may beat generally along understood actual heart contraction patterns, and the like. Moreover, when the measured parameters indicate a need to alert a caregiver, a changing severity in color may be associated with one or more displayed graphics, such as the heart, lungs, brain, or the like. The body portions may include animations on where, when or how to attach measurement devices to measurement sites on the patient. For example, the monitor may provide animated directions for CCHD screening procedures or glucose strip reading protocols, the application of a forehead sensor, a finger or toe sensor, one or more electrodes, an acoustic sensor, and ear sensor, a cannula sensor or the like.

The present disclosure relates to a medical monitoring hub configured to be the center of monitoring activity for a given patient. The hub can include a large easily readable display, such as an about ten (10) inch display dominating the majority of real estate on a front face of the hub. The display could be much larger or much smaller depending upon design constraints. However, for portability and current design goals, the preferred display is roughly sized proportional to the vertical footprint of one of the dockable portable patient monitors. Other considerations are recognizable from the disclosure herein by those in the art.

The display can provide measurement data for a wide variety of monitored parameters for the patient under observation in numerical or graphic form. The display can be automatically configured based on the type of data and information being received at the hub. The hub can be moveable, portable, or mountable so that it can be positioned to convenient areas within a caregiver environment. For example, the hub can be collected within a singular housing.

The hub may advantageously receive data from a portable patient monitor while docked or undocked from the hub. Typical portable patient monitors, such as oximeters or co-oximeters can provide measurement data for a large number of physiological parameters derived from signals output from optical and/or acoustic sensors, electrodes, or the like. The physiological parameters can include, but are not limited to oxygen saturation, carboxy hemoglobin, methemoglobin, total hemoglobin, glucose, pH, bilirubin, fractional saturation, pulse rate, respiration rate, components of a respiration cycle, indications of perfusion including perfusion index, signal quality and/or confidences, plethysmograph data, indications of wellness or wellness indexes or other combinations of measurement data, audio information responsive to respiration, ailment identification or diagnosis, blood pressure, patient and/or measurement site temperature, depth of sedation, organ or brain oxygenation, hydration, measurements responsive to metabolism, combinations of the same or the like, to name a few. The hub may also (or instead) output data sufficient to accomplish closed-loop drug administration in combination with infusion pumps or the like.

The hub can communicate with other devices in a monitoring environment that are interacting with the patient in a number of ways. For example, the hub advantageously can receive serial data from other devices without necessitating their reprogramming or that of the hub. Such other devices can include pumps, ventilators, all manner of monitors monitoring any combination of the foregoing parameters, ECG/EEG/EKG devices, electronic patient beds, and the like. Moreover, the hub advantageously can receive channel data from other medical devices without necessitating their reprogramming or that of the hub. When a device communicates through channel data, the hub may advantageously alter the large display to include measurement information from that device. Additionally, the hub can access nurse call systems to ensure that nurse call situations from the device are passed to the appropriate nurse call system.

The hub also can communicate with hospital systems to advantageously associate incoming patient measurement and treatment data with the patient being monitored. For example, the hub may communicate wirelessly or otherwise to a multi-patient monitoring system, such as a server or collection of servers, which in turn many communicate with a caregiver's data management systems, such as, for example, an Admit, Discharge, Transfer ("ADT") system and/or an Electronic Medical Records ("EMR") system. The hub advantageously can associate the data flowing through it with the patient being monitored thereby providing the electronic measurement and treatment information to be passed to the caregiver's data management systems without the caregiver associating each device in the environment with the patient.

The hub advantageously can include a reconfigurable and removable docking station. The docking station may dock additional layered docking stations to adapt to different patient monitoring devices. Additionally, the docking station itself can be modularized so that it may be removed if the primary dockable portable patient monitor changes its form factor. Thus, the hub can be flexible in how its docking station is configured.

The hub can include a large memory for storing some or all of the data it receives, processes, and/or associates with the patient, and/or communications it has with other devices and systems. Some or all of the memory may advantageously comprise removable SD memory.

The hub can communicate with other devices through at least (1) the docking station to acquire data from a portable monitor, (2) innovative universal medical connectors to acquire channel data, (3) serial data connectors, such as RJ ports to acquire output data, (4) Ethernet, USB, and nurse call ports, (5) Wireless devices to acquire data from a portable monitor, (6) other wired or wireless communication mechanisms known to an artisan. The universal medical connectors advantageously can provide optional electrically isolated power and communications, and can be designed to be smaller in cross section than isolation requirements. The connectors and the hub can communicate to advantageously translate or configure data from other devices to be usable and displayable for the hub. A software developers kit ("SDK") can be provided to a device manufacturer to establish or define the behavior and meaning of the data output from their device. When the output is defined, the definition can be programmed into a memory residing in the cable side of the universal medical connector and supplied as an original equipment manufacturer ("OEM") to the device provider. When the cable is connected between the device and the hub, the hub can understand the data and can use it for display and processing purposes without necessitating software upgrades to the device or the hub. The hub can negotiate the schema and can even add additional compression and/or encryption. Through the use of the universal medical connectors, the hub can organize the measurement and treatment data into a single display and alarm system effectively and efficiently bringing order to the monitoring environment.

As the hub can receive and track data from other devices according to a channel paradigm, the hub may advantageously provide processing to create virtual channels of patient measurement or treatment data. A virtual channel may comprise a non-measured parameter that is, for example, the result of processing data from various measured or other parameters. An example of such a parameter includes a wellness indicator derived from various measured parameters that give an overall indication of the wellbeing of the monitored patient. An example of a wellness parameter is disclosed in U.S. patent application Ser. Nos. 13/269,296, 13/371,767 and 12/904,925, by the assignee of the present disclosure and incorporated by reference herein. By organizing data into channels and virtual channels, the hub may advantageously time-wise synchronize incoming data and virtual channel data.

The hub can also receive serial data through serial communication ports, such as RJ connectors. The serial data can be associated with the monitored patient and passed on to the multi-patient server systems and/or caregiver backend systems discussed above. Through receiving the serial data, the caregiver advantageously can associate devices in the caregiver environment, often from varied manufactures, with a particular patient, avoiding a need to have each individual device associated with the patient and possible communicating with hospital systems. Such association can be vital as it reduces caregiver time spent entering biographic and demographic information into each device about the patient. Moreover, through the SDK the device manufacturer may advantageously provide information associated with any measurement delay of their device, thereby further allowing the hub to advantageously time-wise synchronize serial incoming data and other data associated with the patient.

When a portable patient monitor is docked, and it includes its own display, the hub can effectively increase its display real estate. For example, the portable patient monitor may simply continue to display its measurement and/or treatment data, which may be now duplicated on the hub display, or the docked display may alter its display to provide additional information. The docked display, when docked, presents anatomical graphical data of, for example, the heart, lungs, organs, the brain, or other body parts being measured and/or treated. The graphical data may advantageously animate similar to and in concert with the measurement data. For example, lungs may inflate in approximate correlation to the measured respiration rate and/or the determined inspiration/expiration portions of a respiration cycle, the heart may beat according to the pulse rate, may beat generally along understood actual heart contraction patterns, the brain may change color or activity based on varying depths of sedation, or the like. When the measured parameters indicate a need to alert a caregiver, a changing severity in color may be associated with one or more displayed graphics, such as the heart, lungs, brain, organs, circulatory system or portions thereof, respiratory system or portions thereof, other body parts or the like. The body portions may include animations on where, when or how to attach measurement devices.

The hub may also advantageously overlap parameter displays to provide additional visual information to the caregiver. Such overlapping may be user definable and configurable. The display may also incorporate analog-appearing icons or graphical indicia.

In the interest of clarity, not all features of an actual implementation are described in this specification. An artisan will of course be appreciate that in the development of any such actual implementation (as in any development project), numerous implementation-specific decisions must be made to achieve a developers' specific goals and sub-goals, such as compliance with system- and business-related constraints, which will vary from one implementation to another. Moreover, it will be appreciated that such a development effort might be complex and time-consuming, but would nevertheless be a routine undertaking of device engineering for those of ordinary skill having the benefit of this disclosure.

To facilitate a complete understanding of the disclosure, the remainder of the detailed description describes the disclosure with reference to the drawings, wherein like reference numbers are referenced with like numerals throughout.

II. Example Hubs

FIG. 1A illustrates a monitoring environment including a perspective view of an example medical monitoring hub 100 with an example docked portable patient monitor (PPM) 102. The hub 100 can include a display 104, and a docking station 106, which can be configured to mechanically and electrically mate with the portable patient monitor 102, each housed in a movable, mountable and portable housing 108. The housing 108 can include a generally upright inclined shape configured to rest on a horizontal flat surface, although the housing 108 can be affixed in a wide variety of positions and mountings and comprise a wide variety of shapes and sizes.

The display 104 may present a wide variety of measurement and/or treatment data in numerical, graphical, waveform, or other display indicia 110. The display 104 can occupy much of a front face of the housing 108, although an artisan will appreciate the display 104 may include a tablet or tabletop horizontal configuration, a laptop-like configuration or the like. Display information and data can be communicated to a table computer, smartphone, television, or any display system recognizable to an artisan. The upright inclined configuration of FIG. 1A presents display information to a caregiver in an easily viewable manner.

Figure 1B:
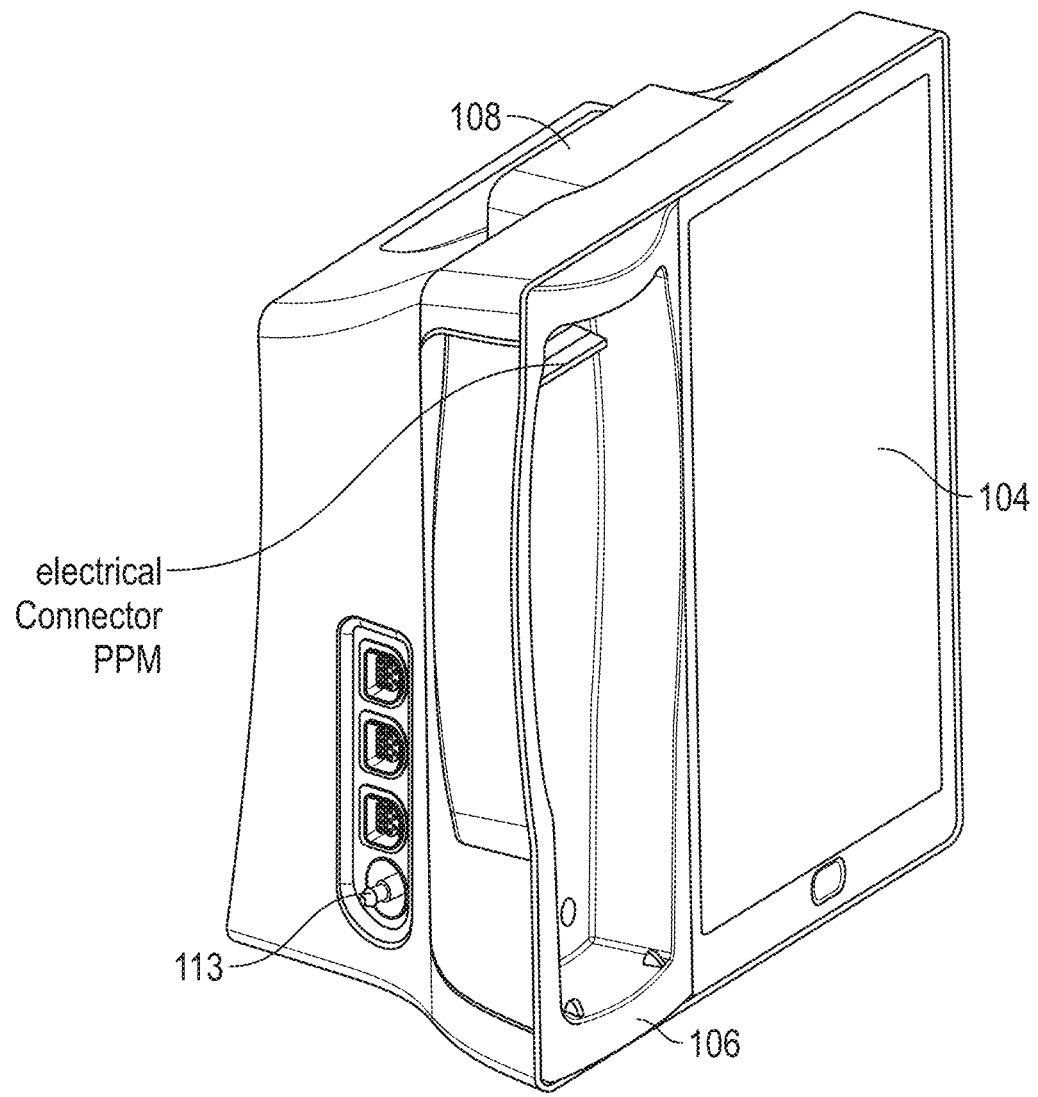

FIG. 1B shows a perspective side view of the hub 100 that can include the housing 108, the display 104, and the docking station 106 without a portable monitor docked. Also shown is a connector for noninvasive blood pressure.

The housing 108 may also include pockets or indentations to hold additional medical devices, such as, for example, a blood pressure monitor or temperature sensor 112, such as that shown in FIG. 1C.

The portable patient monitor 102 of FIG. 1A may advantageously comprise an oximeter, co-oximeter, respiratory monitor, depth of sedation monitor, noninvasive blood pressure monitor, vital signs monitor or the like, such as those commercially available from Masimo Corporation of Irvine, Calif., and/or disclosed in U.S. Pat. Pub. Nos. 2002/0140675, 2010/0274099, 2011/0213273, 2012/0226117, 2010/0030040; U.S. patent application Ser. Nos. 61/242,792, 61/387,457, 61/645,570, 13/554,908 and U.S. Pat. Nos. 6,157,850, 6,334,065, and the like. The monitor 102 may communicate with a variety of noninvasive and/or minimally invasive devices such as optical sensors with light emission and detection circuitry, acoustic sensors, devices that measure blood parameters from a finger prick, cuffs, ventilators, and the like. The monitor 102 may include its own display 114 presenting its own display indicia 116, discussed below with reference to FIGS. 19A-19J. The display indicia may advantageously change based on a docking state of the monitor 102. When undocked, the display indicia may include parameter information and may alter orientation based on, for example, a gravity sensor or accelerometer.

The docking station 106 of the hub 100 can include a mechanical latch 118, or mechanically releasable catch to ensure that movement of the hub 100 doesn't mechanically detach the monitor 102 in a manner that could damage the same.

Although disclosed with reference to particular portable patient monitors 102, an artisan will recognize from the disclosure herein a large number and wide variety of medical devices that may advantageously dock with the hub 100. Moreover, the docking station 106 may advantageously electrically and not mechanically connect with the monitor 102, and/or wirelessly communicate with the same.

FIG. 2 illustrates a simplified block diagram of an example monitoring environment 200 including the hub 100 of FIG. 1. As shown in FIG. 2, the environment may include the portable patient monitor 102 communicating with one or more patient sensors 202, such as, for example, oximetry optical sensors, acoustic sensors, blood pressure sensors, respiration sensors or the like. Additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

As disclosed herein, the portable patient monitor 102 can communicate with the hub 100 through the docking station 106 when docked and wirelessly when undocked; however, such undocked communication is not required. The hub 100 can communicate with one or more multi-patient monitoring servers 204 or server systems, such as, for example, those disclosed with in U.S. Pat. Pub. Nos. 2011/0105854, 2011/0169644, and 2007/0180140. In general, the server 204 can communicate with caregiver backend systems 206 such as EMR and/or ADT systems. The server 204 may advantageously obtain through push, pull or combination technologies patient information entered at patient admission, such as demographical information, billing information, and the like. The hub 100 can access this information to seamlessly associate the monitored patient with the caregiver backend systems 206. Communication between the server 204 and the monitoring hub 100 may be any recognizable to an artisan from the disclosure herein, including wireless, wired, over mobile or other computing networks, or the like.

FIG. 2 also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from SEDLine, brain or other organ oximeter devices 224, noninvasive blood pressure or acoustic devices 226, or the like. The channel device may include board-in-cable ("BIC") solutions where the processing algorithms and the signal processing devices that accomplish those algorithms are mounted to a board housed in a cable or cable connector, which may not include additional display technologies. The BIC solution can output its measured parameter data to the channel port 212 to be displayed on the display 104 of hub 100. The hub 100 may advantageously be entirely or partially formed as a BIC solution that communicates with other systems, such as, for example, tablets, smartphones, or other computing systems.

Although disclosed with reference to a single docking station 106, the environment 200 may include stacked docking stations where a subsequent docking station mechanically and electrically docks to a first docking station to change the form factor for a different portable patent monitor as discussed with reference to FIG. 5. Such stacking may include more than 2 docking stations, may reduce or increase the form fact for mechanical compliance with mating mechanical structures on a portable device.

Figure 3:
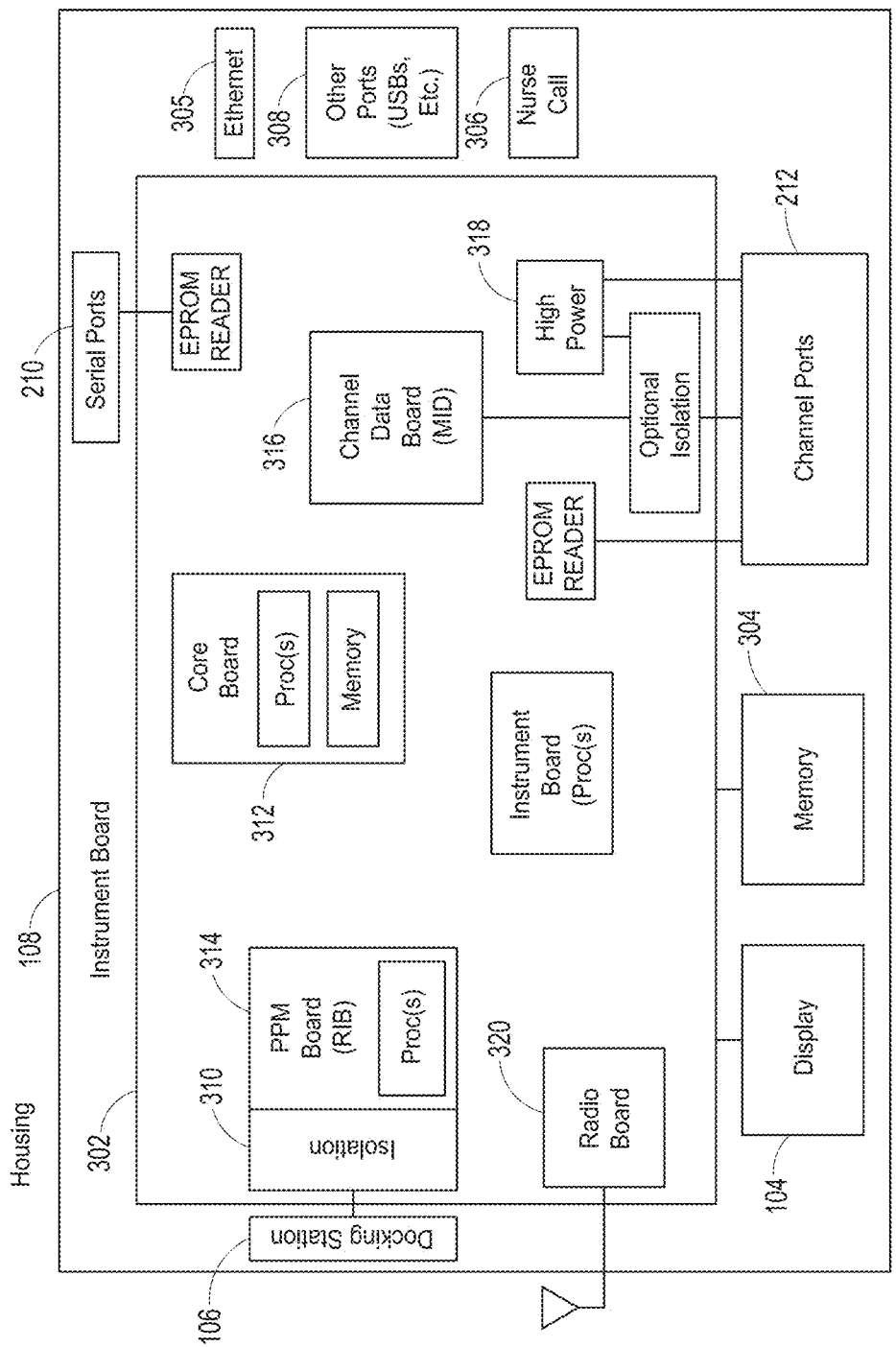
FIG. 3 illustrates a simplified example hardware block diagram of the hub of FIG. 1.

FIG. 3 illustrates a simplified example hardware block diagram of the hub 100 of FIG. 1. As shown in FIG. 3, the housing 108 of the hub 100 positions and/or encompasses an instrument board 302, the display 104, memory 304, and the various communication connections, including the serial ports 210, the channel ports 212, Ethernet ports 305, nurse call port 306, other communication ports 308 including standard USB or the like, and the docking station interface 310. The instrument board 302 comprises one or more substrates including communication interconnects, wiring, ports and the like to enable the communications and functions described herein, including inter-board communications. A core board 312 includes the main parameter, signal, and other processor(s) and memory, a portable monitor board ("RIB") 314 includes patient electrical isolation for the monitor 102 and one or more processors, a channel board ("MID") 316 controls the communication with the channel ports 212 including optional patient electrical isolation and power supply 318, and a radio board 320 includes components configured for wireless communications. Additionally, the instrument board 302 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 302 may comprise a large number of electronic components organized in a large number of ways. Using different boards such as those disclosed above advantageously provides organization and compartmentalization to the complex system.

Figure 4:
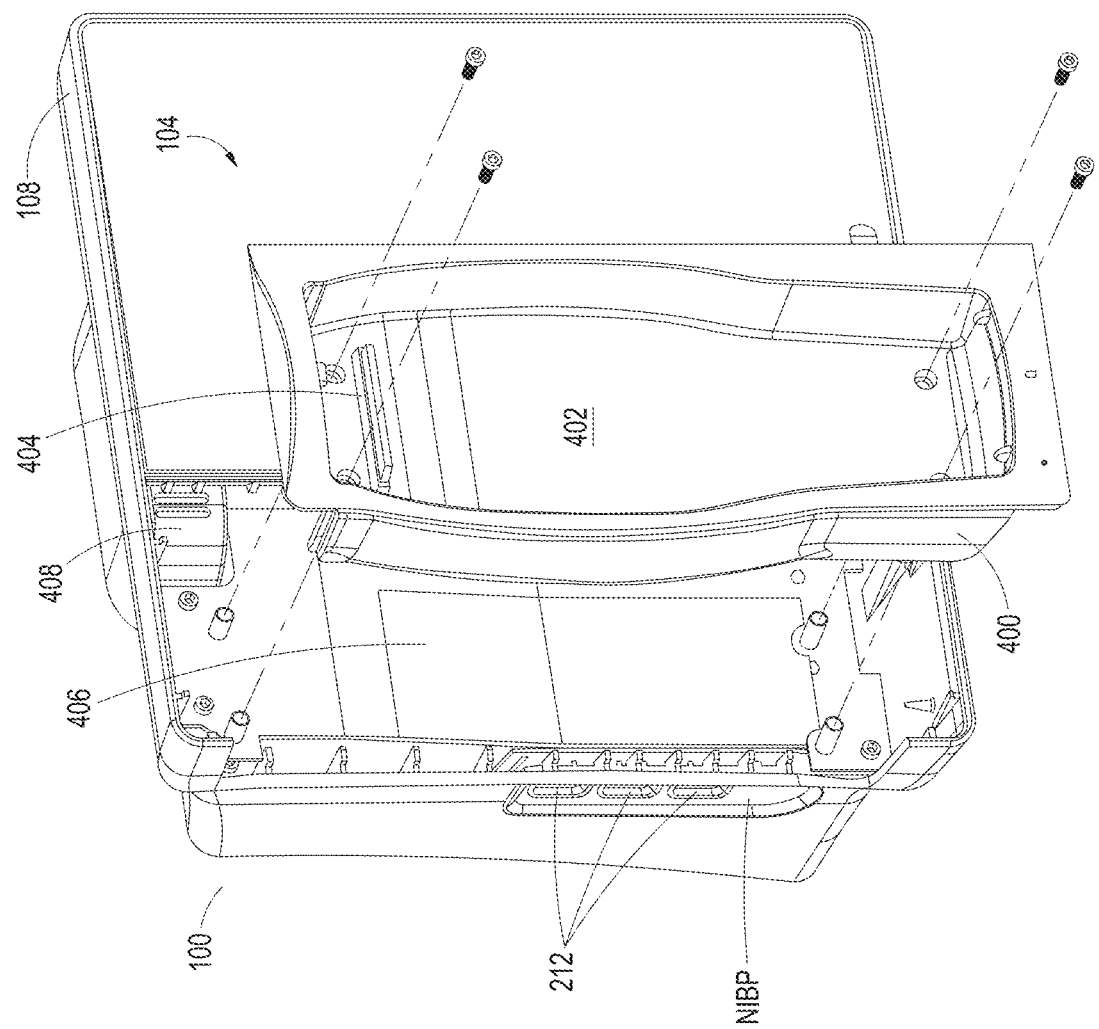
FIG. 4 illustrates a perspective view of an example removable docking station of the hub of FIG. 1.

FIG. 4 illustrates a perspective view of an example removable docking station 400 of the hub 100 of FIG. 1. As shown in FIG. 4, the docking station 400 can provide a mechanical mating to portable patient monitor 102 to provide secure mechanical support when the monitor 102 is docked. The docking station 400 can include a cavity 402 that is shaped similar to the periphery of a housing of the portable monitor 102. The station 400 can also include one or more electrical connectors 404 providing communication to the hub 100. Although shown as mounted with bolts, the docking station 400 may snap fit, may use movable tabs or catches, may magnetically attach, or may employ a wide variety or combination of attachment mechanisms know to an artisan from the disclosure herein. The attachment of the docking station 400 can be sufficiently secure that when docked, the monitor 102 and docking station cannot be accidentally detached in a manner that could damage the instruments, such as, for example, if the hub 100 was accidently bumped or the like, the monitor 102 and docking station 400 should remain intact.

The housing 108 of the hub 100 can also include a cavity 406 housing the docking station 400. To the extent a change to the form factor for the portable patient monitor 102 occurs, the docking station 400 can be advantageously removable and replaceable. Similar to the docking station 400, the hub 100 can include, within the cavity 406 of the housing 108, electrical connectors 408 providing electrical communication to the docking station 400. The docking station 400 can include its own microcontroller and processing capabilities, such as those disclosed in U.S. Pat. Pub. No. 2002/0140675. The docking station 400 can also (or instead) pass communications through to the electrical connector 408.

FIG. 4 also shows the housing 108 including openings for channel ports 212 as universal medical connectors discussed in detail below.

FIG. 5 illustrates a perspective view of the example portable patient monitors 502 and 504 undocked from the hub 100 of FIG. 1. As shown in FIG. 5, the monitor 502 may be removed and other monitors, like monitor 504 may be provided. The docking station 106 can include an additional docking station 506 that mechanically mates with the original docking station 106 and presents a form factor mechanically mateable with monitor 504. The monitor 504 can mechanically and electrically mate with the stacked docking stations 506 and 106 of hub 100. As can be readily appreciated by an artisan from the disclosure herein, the stackable function of the docking stations can provide the hub 100 with an extremely flexible mechanism for charging, communicating, and interfacing with a wide variety of patient monitoring devices. As noted above, the docking stations may be stacked, removed, or replaced.

Figure 6:
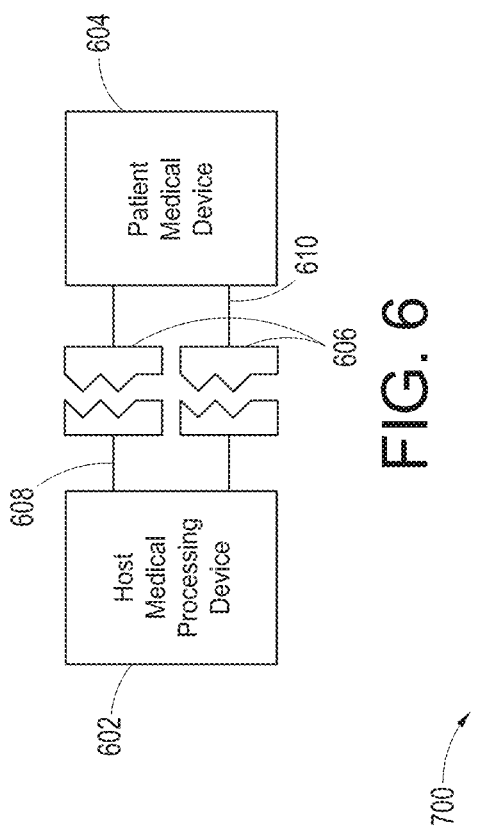
FIG. 6 illustrates a simplified block diagram of traditional patient device electrical isolation principles.

FIG. 6 illustrates a simplified block diagram of traditional patient electrical isolation principles. As shown in FIG. 6, a host device 602 can be generally associated with a patient device 604 through communication and power. As the patient device 604 often comprises electronics proximate or connected to a patient, such as sensors or the like, certain safety requirements dictate that electrical surges of energy from, for example, the power grid connected to the host device, should not find an electrical path to the patient. This is generally referred to a "patient isolation" which is a term known in the art and includes herein the removing of direct uninterrupted electrical paths between the host device 602 and the patient device 604. Such isolation can be accomplished through, for example, isolation devices 606 on power conductors 608 and communication conductors 610. Isolation devices 606 can include transformers, optical devices that emit and detect optical energy, and the like. Use of isolation devices, especially on power conductors, can be expensive component wise, expensive size wise, and drain power. Traditionally, the isolation devices were incorporated into the patient device 604; however, the patient devices 604 are trending smaller and smaller and not all devices incorporate isolation.

Figure 7B:
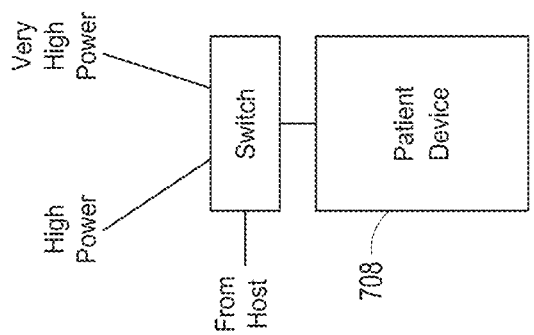
FIG. 7A illustrates a simplified block diagram of an example optional patient device isolation system, while FIG. 7B adds example optional non-isolation power levels for the system of FIG. 7A.
Figure 7A:
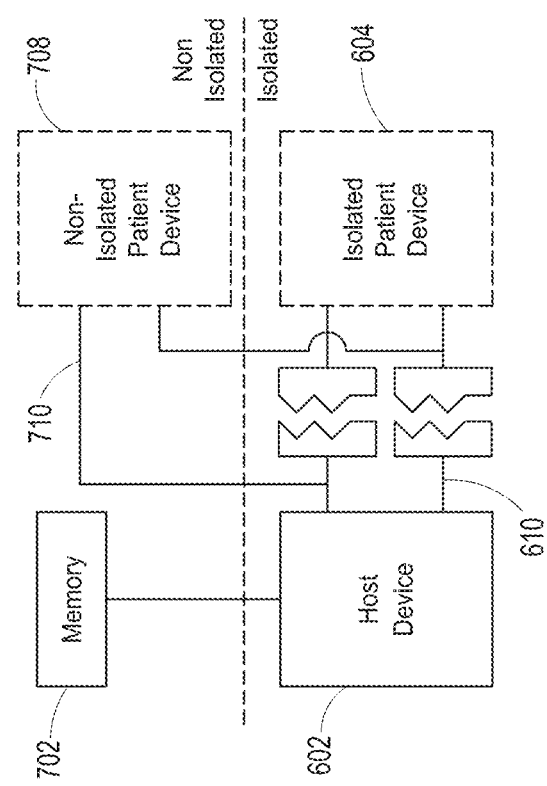

FIG. 7A illustrates a simplified block diagram of an example optional patient isolation system. As shown in FIG. 7A, the host device 602 can communicate with an isolated patient device 604 through the isolation devices 606. However, a memory 702 associated with a particular patient device can inform the host 602 whether that device needs isolated power. If a patient device 708 does not need isolated power, such as some types of cuffs, infusion pumps, ventilators, or the like, then the host 602 can provide non-isolated power through signal path 710. This power may be much higher that what can cost-effectively be provided through the isolated power conductor 608. The non-isolated patient devices 708 can receive isolated communication as such communication is typically at lower voltages and is not cost prohibitive. An artisan will recognize from the disclosure herein that communication could also be non-isolated. Thus, FIG. 7A shows a patient isolation system 700 that can provide optional patient isolation between a host 602 and a wide variety of potential patient devices 604, 708. The hub 100 can include the channel ports 212 that can also incorporate similar optional patient isolation principles.

FIG. 7B adds example optional non-isolation power levels for the system of FIG. 7A. As shown in FIG. 7B, once the host 602 understands that the patient device 604 includes a self-isolated patient device 708, and thus does not need isolated power, the host 602 can provide power through a separate conductor 710. Because the power is not isolated, the memory 702 may also provide power requirements to the host 602, which may select from two or more voltage or power levels. In FIG. 7B, the host 602 provides either high power, such as about 12 volts, which can also include a wide range of voltages or very high power such as about 24 volts or more, to the patient device 708. An artisan will recognize that supply voltages can advantageously be altered to meet the specific needs of virtually any device 708 and/or the memory could supply information to the host 602 which provided a wide range of non-isolated power to the patient device 708.

Moreover, using the memory 702, the host 602 may determine to simply not enable any unused power supplies, whether that be the isolated power or one or more of the higher voltage non-isolated power supplies, thereby increasing the efficiency of the host.

Figure 8:
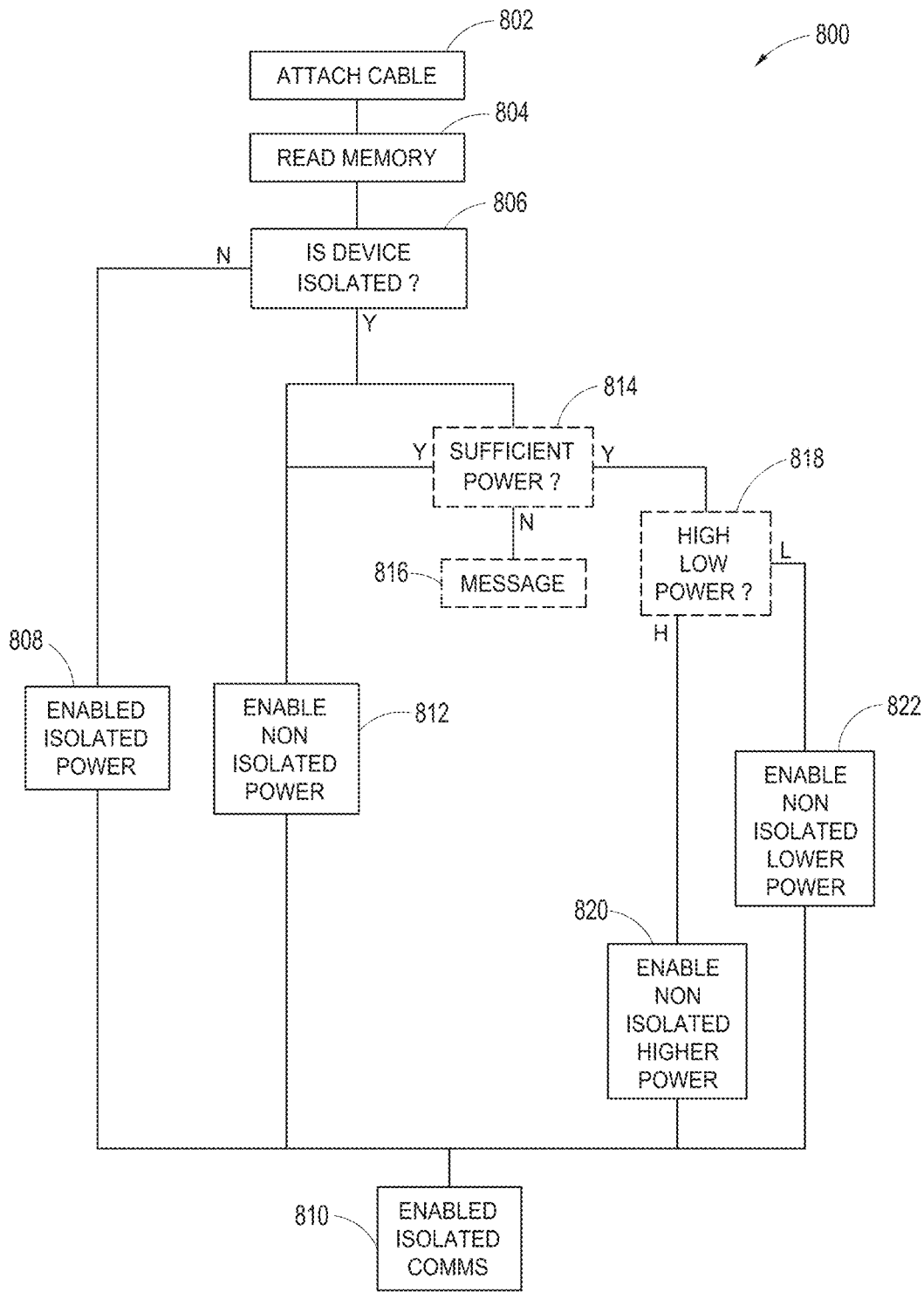
FIG. 8 illustrates a simplified example universal medical connector configuration process.

FIG. 8 illustrates a simplified example universal medical connector configuration process 800. As shown in FIG. 8, the process includes step 802, where a cable is attached to a universal medical connector incorporating optional patient isolation as disclosed in the foregoing. In step 804, the host device 602 or the hub 100, more specifically, the channel data board 316 or EPROM reader of the instrument board, reads the data stored in the memory 702 and in step 806, determines whether the connecting device requires isolated power. In step 808, when the isolated power is required, the hub 100 may advantageously enable isolated power and in step 810, enable isolated communications. In step 806, when isolated power is not needed, the hub 100 may simply in optional step 812 enable non-isolated power. Where communications remain isolated, step 810 can enable isolated communications. In step 806, when isolated power is not needed, the hub 100 in step 814 may use information from memory 702 to determine the amount of power needed for the patient device 708. When sufficient power is not available, because for example, other connected devices are also using connected power, in step 816 a message may be displayed indicating the same and power is not provided. When sufficient power is available, optional step 812 may enable non-isolated power. Alternatively, optional step 818 may determine whether memory 702 indicates higher or lower power is desired. When higher power is desired, the hub 100 may enable higher power in step 820 and when not, may enable lower power in step 822. The hub 100 in step 810 then enables isolated communication. The hub 100 in step 818 may simply determine how much power is needed and provide at least sufficient power to the self-isolated device 708.

An artisan will recognize from the disclosure herein that hub 100 may not check to see if sufficient power is available or may provide one, two or many levels of non-isolated voltages based on information from the memory 702.

Figure 9A:
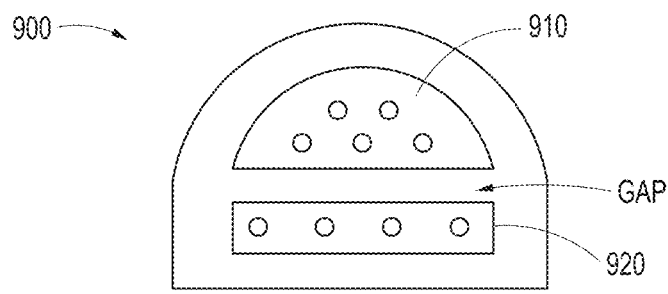
FIGS. 9A-9B illustrate simplified block diagrams of example universal medical connectors having a size and shape smaller in cross section than traditional isolation requirements.
Figure 9B:
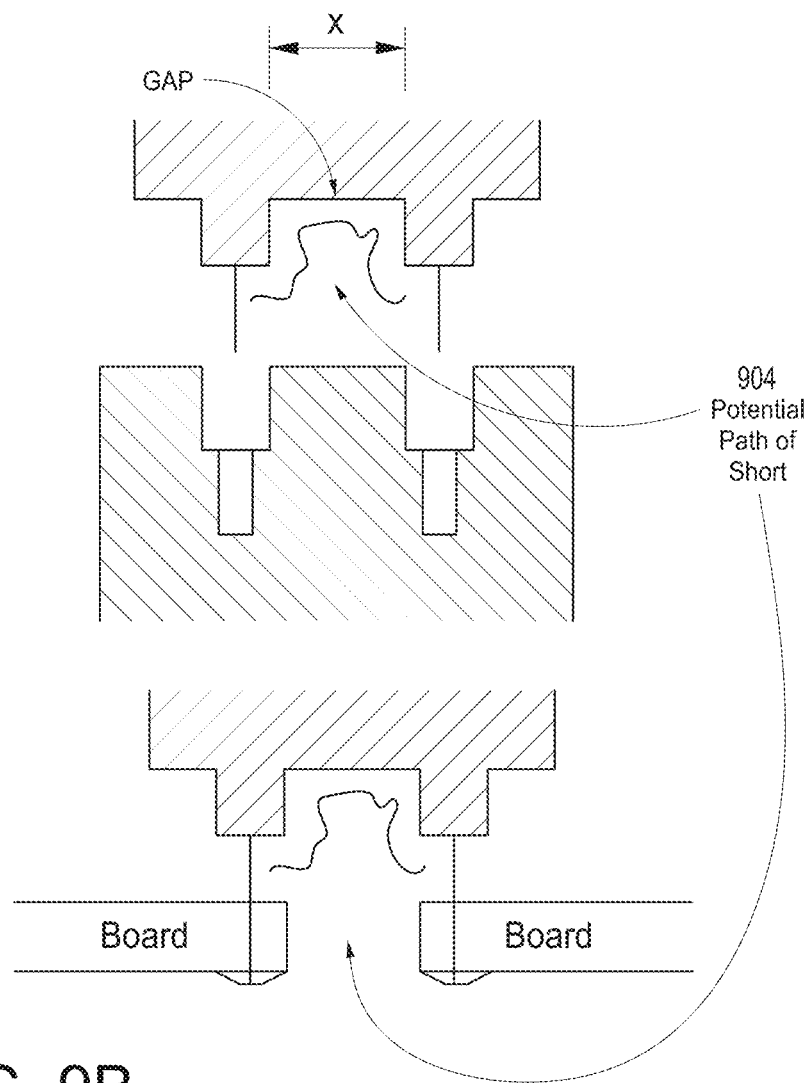

FIGS. 9A and 9B illustrate simplified block diagrams of example universal medical connectors 900 having a size and shape smaller in cross section than traditional isolation requirements. The connector 900 can physically separate non-isolated signals on one side 910 from isolated signals on another side 920, although the sides could be reversed. The gap between such separations may be dictated at least in part by safety regulations governing patient isolation. The distance between the sides 910 and 920 may appear to be too small.

As shown from a different perspective in FIG. 9B, the distance between connectors "x" appears small. However, the gap causes the distance to include a non-direct path between conductors. For example, any short would have to travel path 904, and the distance of such path is within or beyond such safety regulations, in that the distance is greater than "x." It is noteworthy that the non-straight line path 904 occurs throughout the connector, such as, for example, on the board connector side where solder connects various pins to a PCB board.

Figure 10:
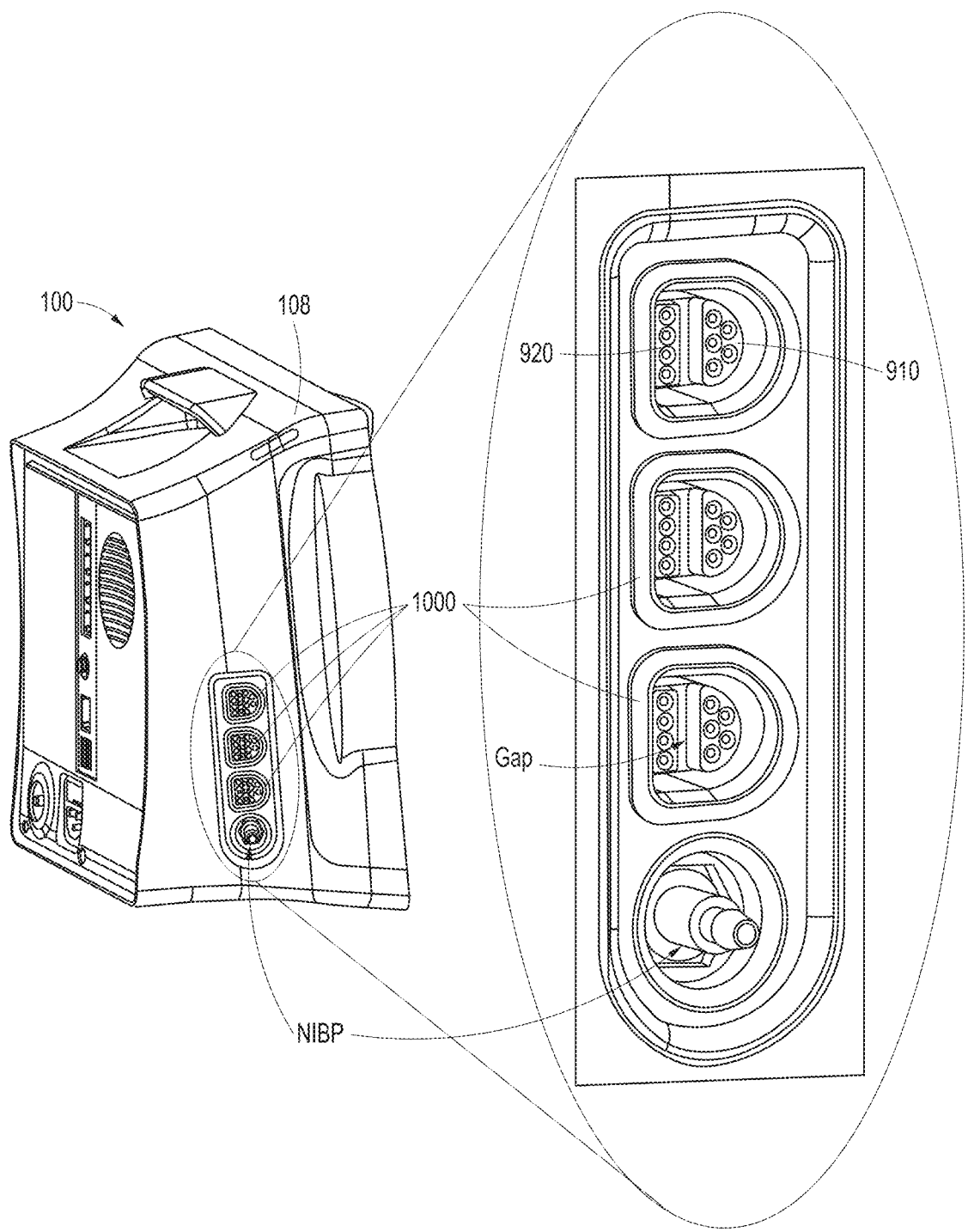
FIG. 10 illustrates a perspective view of a side of the hub of FIG. 1, showing example instrument-side channel inputs for example universal medical connectors.

FIG. 10 illustrates a perspective view of a side of the hub 100 of FIG. 1, showing example instrument-side channel inputs 1000 as example universal medical connectors. As shown in FIG. 10, the inputs can include the non-isolated side 910, the isolated side 920, and the gap. The memory 710 can communicate through pins on the non-isolated side.

Figure 11A:
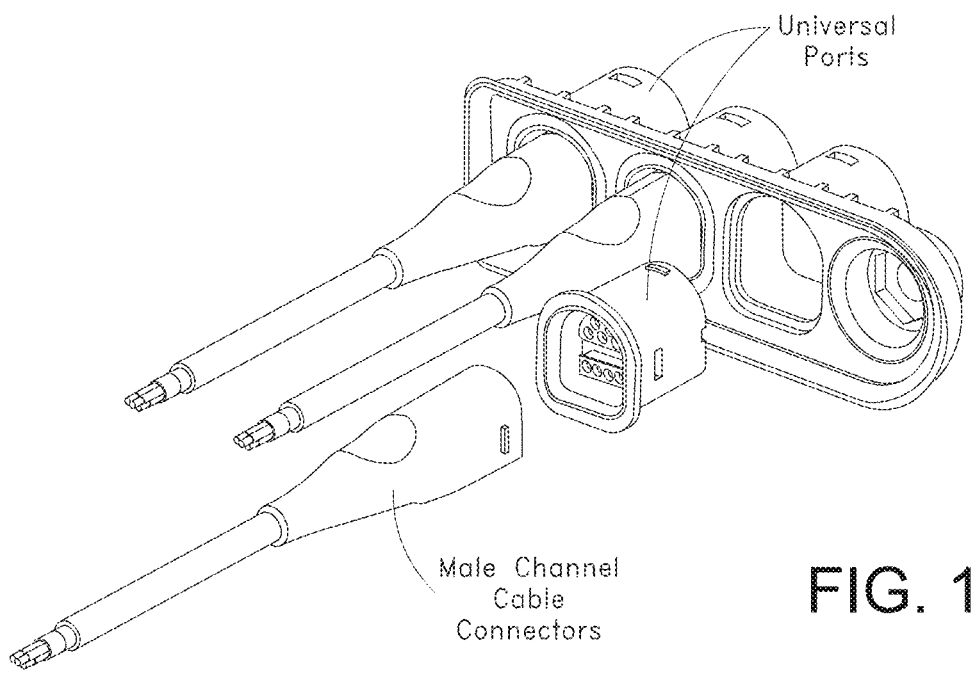
Figure 11B:
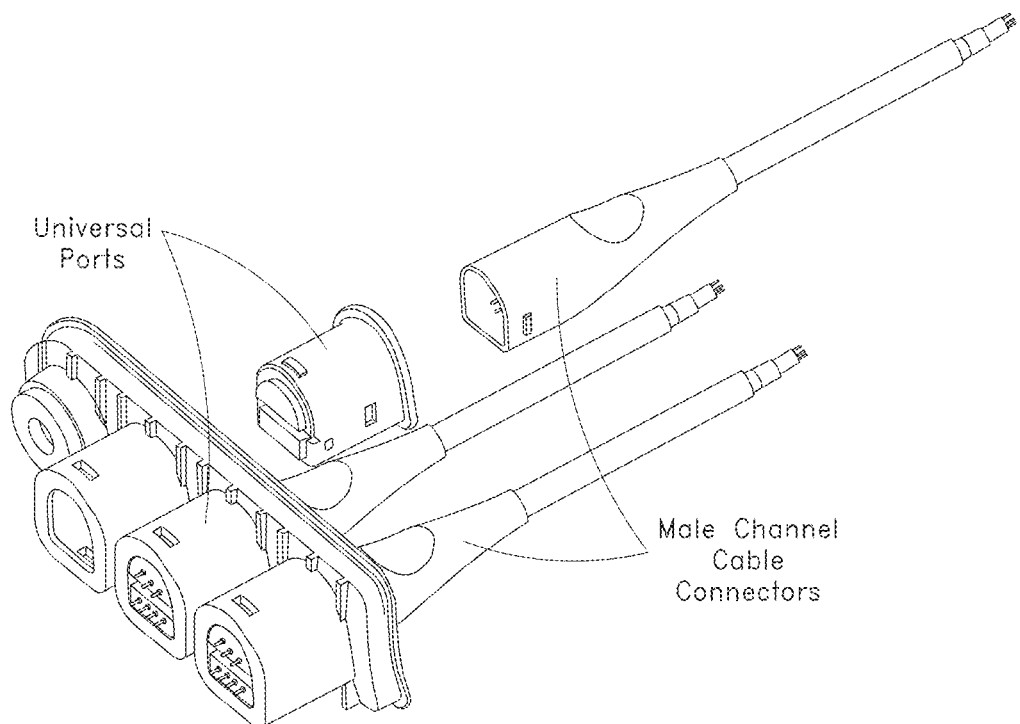
Figure 11C:
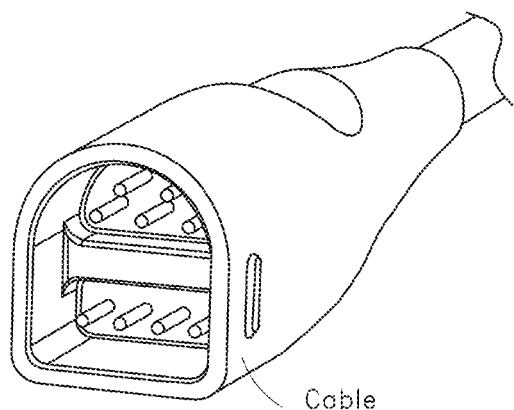
Figure 11D:
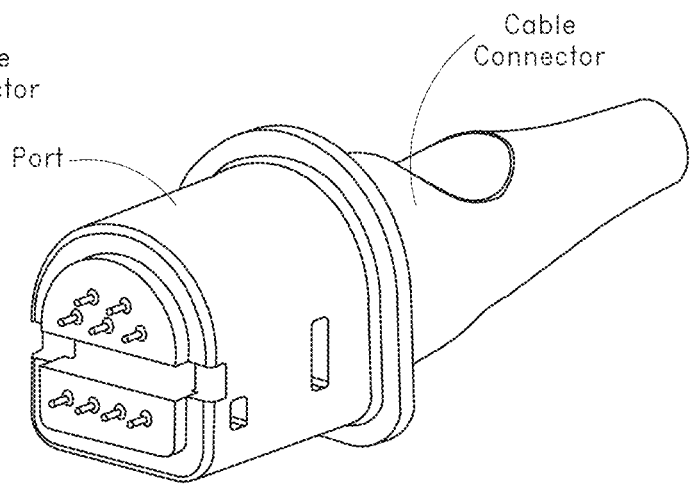
Figure 11E:
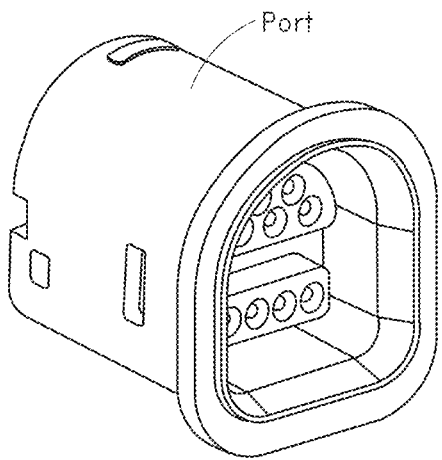
Figure 11F:
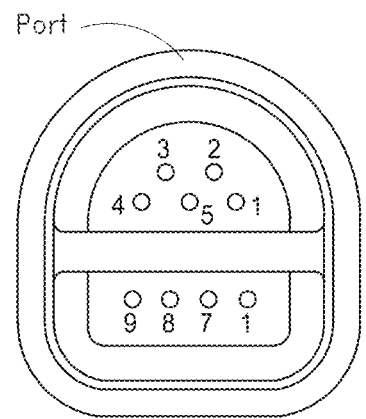
Figure 11J:
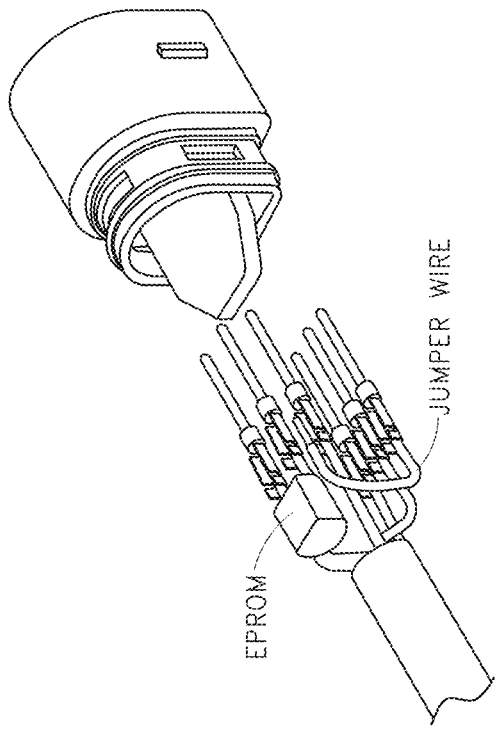
Figure 11I:
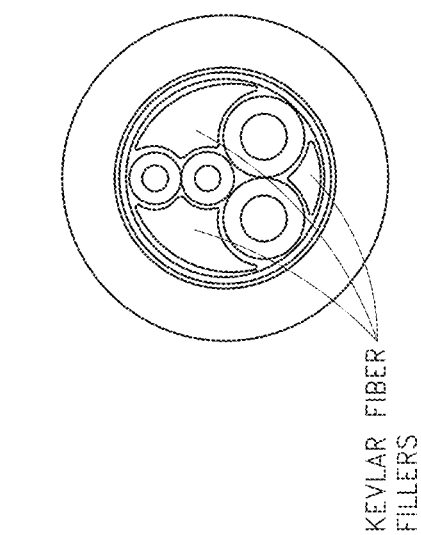
Figure 11K:
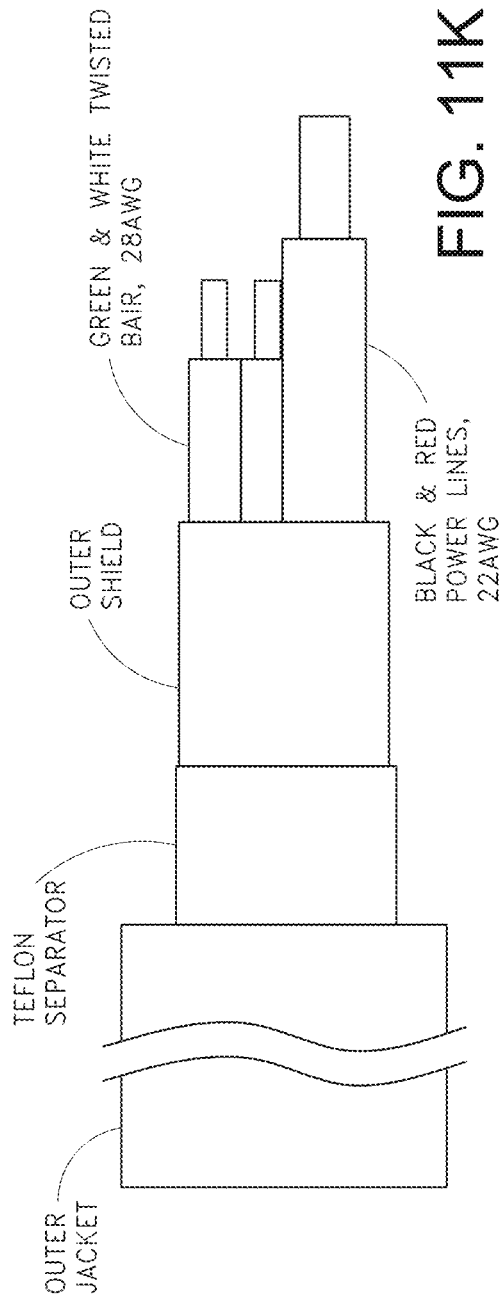

FIGS. 11A-11K illustrate various views of example male and mating female universal medical connectors. For example, FIGS. 11G1 and 11G2 shows various preferred but not required sizing, and FIG. 11H shows incorporation of electronic components, such as the memory 702 into the connectors. FIGS. 11I-11K illustrate wiring diagrams and cabling specifics of the cable itself as it connects to the universal medical connectors.

Figure 12:
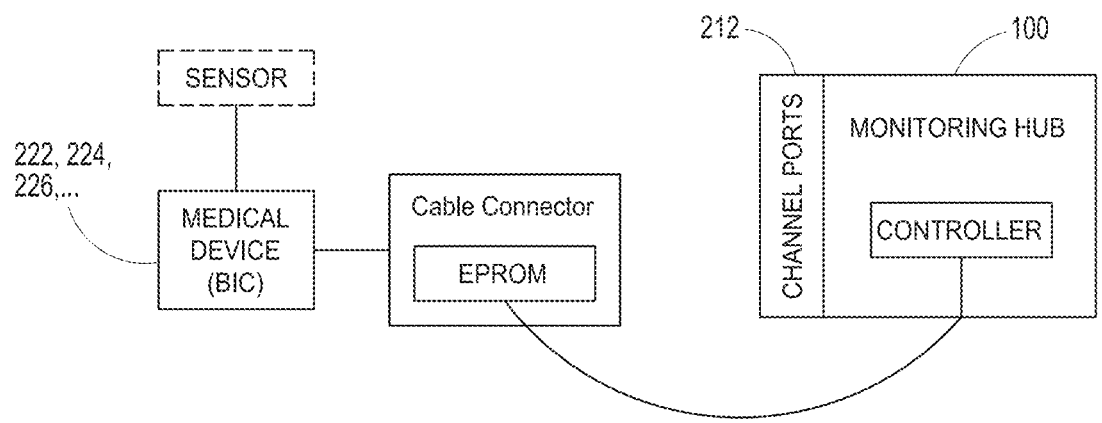
FIG. 12 illustrates a simplified block diagram of a channel system for the hub of FIG. 1.

FIG. 12 illustrates a simplified block diagram of a channel system for the hub of FIG. 1. As shown in FIG. 12, a male cable connector, such as those shown in FIG. 11 above, includes a memory such as an EPROM. The memory can advantageously store information describing the type of data the hub 100 can expect to receive, and how to receive the same. A controller of the hub 100 can communicate with the EPROM to negotiate how to receive the data, and if possible, how to display the data on display 104, alarm when needed, and the like. For example, a medical device supplier may contact the hub provider and receive a software developers' kit ("SDK") that guides the supplier through how to describe the type of data output from their device. After working with the SDK, a map, image, or other translation file may advantageously be loaded into the EPROM, as well as the power requirements and isolation requirements discussed above. When the channel cable is connected to the hub 100 through the channel port 212, the hub 100 can read the EPROM and the controller of the hub 100 can negotiate how to handle incoming data.

Figure 13:
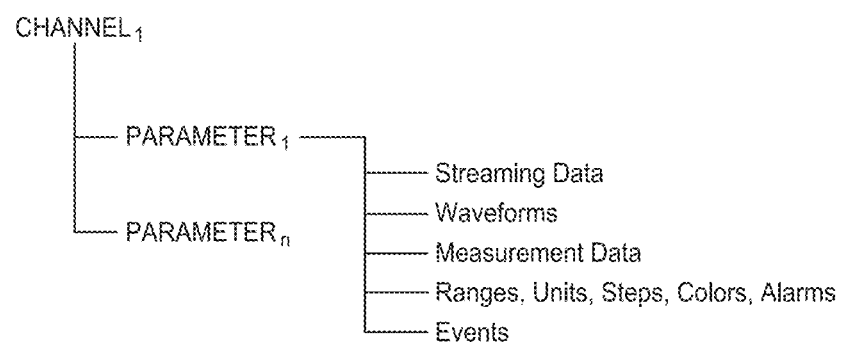
FIG. 13 illustrates an example logical channel configuration.

FIG. 13 illustrates an example logical channel configuration that may be stored in the EPROM of FIG. 12. As shown in FIG. 13, each incoming channel describes one or more parameters. Each parameter describes whatever the hub 100 should know about the incoming data. For example, the hub 100 may want to know whether the data is streaming data, waveform data, already determined parameter measurement data, ranges on the data, speed of data delivery, units of the data, steps of the units, colors for display, alarm parameters and thresholds, including complex algorithms for alarm computations, other events that are parameter value driven, combinations of the same or the like. Additionally, the parameter information may include device delay times to assist in data synchronization or approximations of data synchronization across parameters or other data received by the hub 100. The SDK can present a schema to the device supplier which self-describes the type and order of incoming data. The information can advantageously negotiate with the hub 100 to determine whether to apply compression and/or encryption to the incoming data stream.

Such open architecture can advantageously provide device manufacturers the ability to port the output of their device into the hub 100 for display, processing, and data management as disclosed in the foregoing. By implementation through the cable connector, the device manufacturer can avoid any reprogramming of their original device; rather, they simply let the hub 100 know through the cable connector how the already existing output is formatted. Moreover, by describing the data in a language already understood by the hub 100, the hub 100 also avoids software upgrades to accommodate data from "new-to-the-hub" medical devices.

Figure 14:
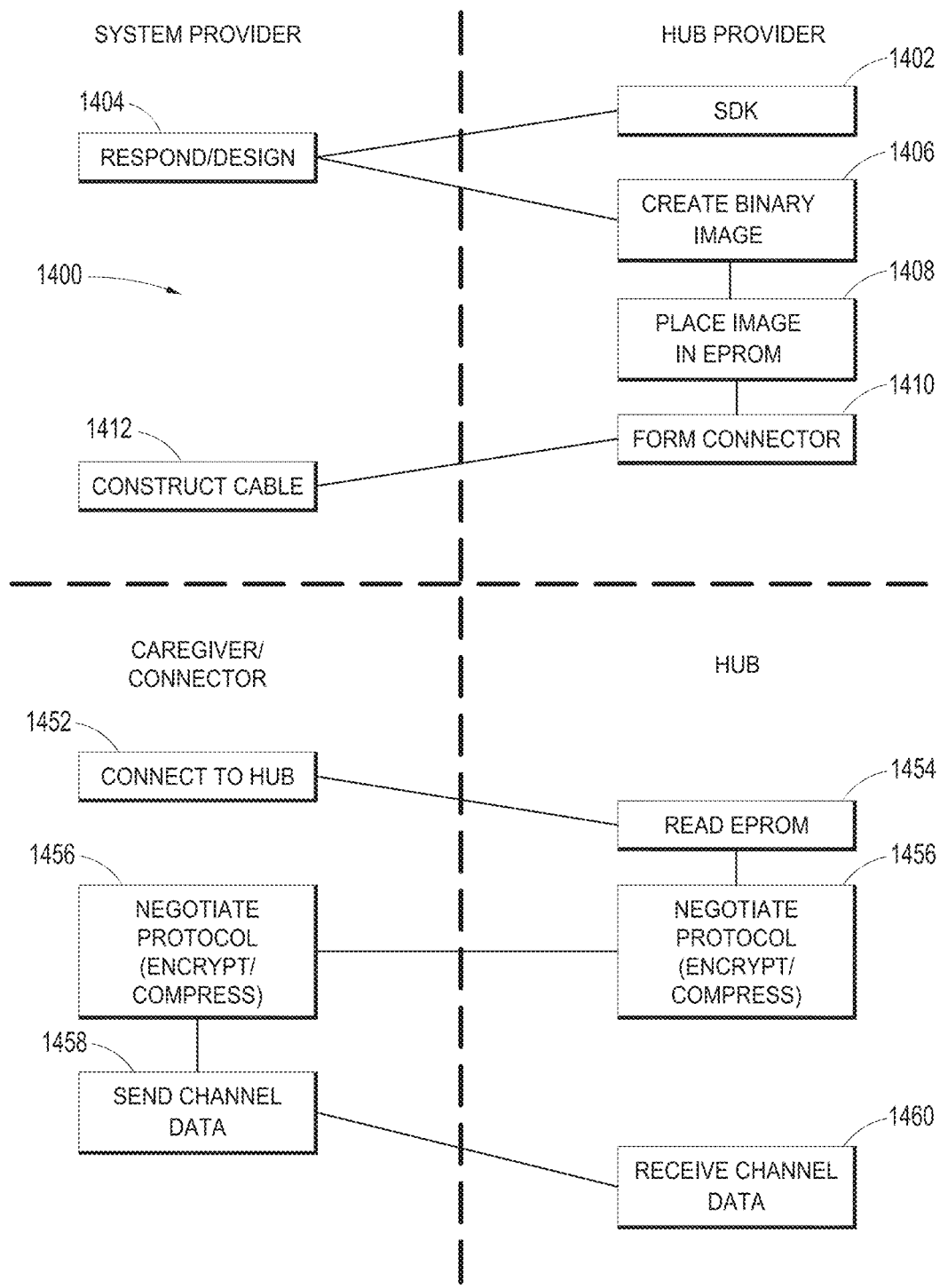
FIG. 14 illustrates a simplified example process for constructing a cable and configuring a channel.

FIG. 14 illustrates a simplified example process for configuring a channel. As shown in FIG. 14, the hub provider provides a device manufacturer with an SDK in step 1402, who in turn uses the SDK to self-describe the output data channel from their device in step 1404. The SDK can include a series of questions that guide the development. The SDK can also (or instead) provide a language and schema to describe the behavior of the data.

Once the device provider describes the data, the hub provider can create a binary image or other file to store in a memory within a cable connector in step 1405; however, the SDK may create the image and simply communicated it to the hub provider. The cable connector can be provided as an OEM part to the provider in step 1410, who constructs and manufactures the cable to mechanically and electrically mate with output ports on their devices in step 1412.

Once a caregiver has the appropriately manufactured cable, with one end matching the device provider's system and the other OEM'ed to match the hub 100 at its channel ports 212, in step 1452 the caregiver can connect the hub between the devices. In step 1454, the hub 100 reads the memory, provides isolated or non-isolated power, and the cable controller and the hub 100 negotiate a protocol or schema for data delivery. A controller on the cable can negotiate the protocol. The controller of the hub 100 can negotiate with other processors on the hub the particular protocol. Once the protocol is set, the hub 100 can use, display and otherwise process the incoming data stream in an intelligent manner.

Through the use of the universal medical connectors described herein, connection of a myriad of devices to the hub 100 can be accomplished through straightforward programming of a cable connector as opposed to necessitating software upgrades to each device.

Figure 15:
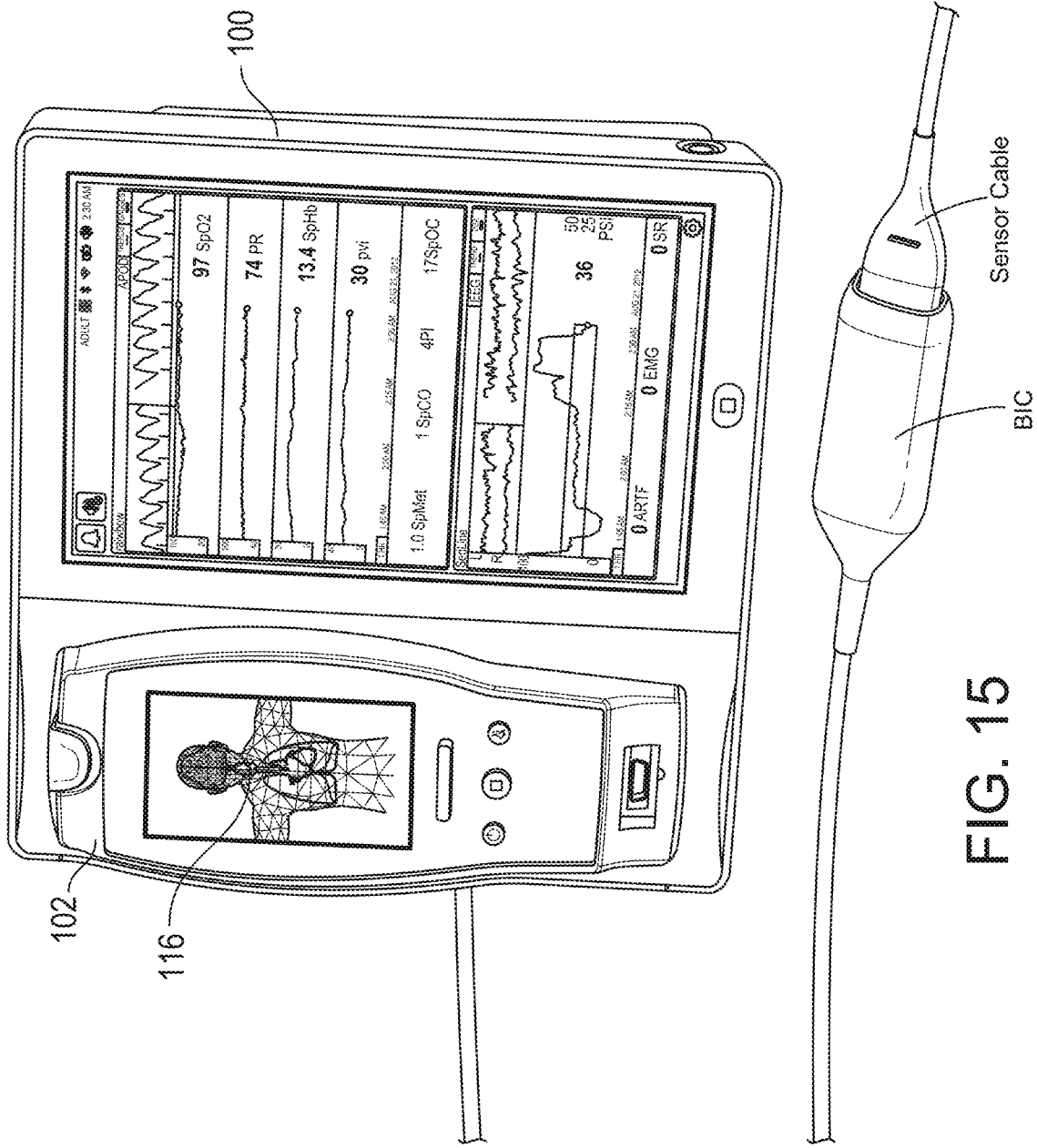
FIG. 15 illustrates a perspective view of the hub of FIG. 1, including an example attached board-in-cable to form an input channel.

FIG. 15 illustrates a perspective view of the hub of FIG. 1 including an example attached board-in-cable ("BIC") to form an input channel. As shown in FIG. 15, a SEDLine depth of consciousness board communicates data from an appropriate patient sensor to the hub 100 for display and caregiver review. As described, the provider of the board need only use the SDK to describe their data channel, and the hub 100 understands how to present the data to the caregiver.

Figure 16:
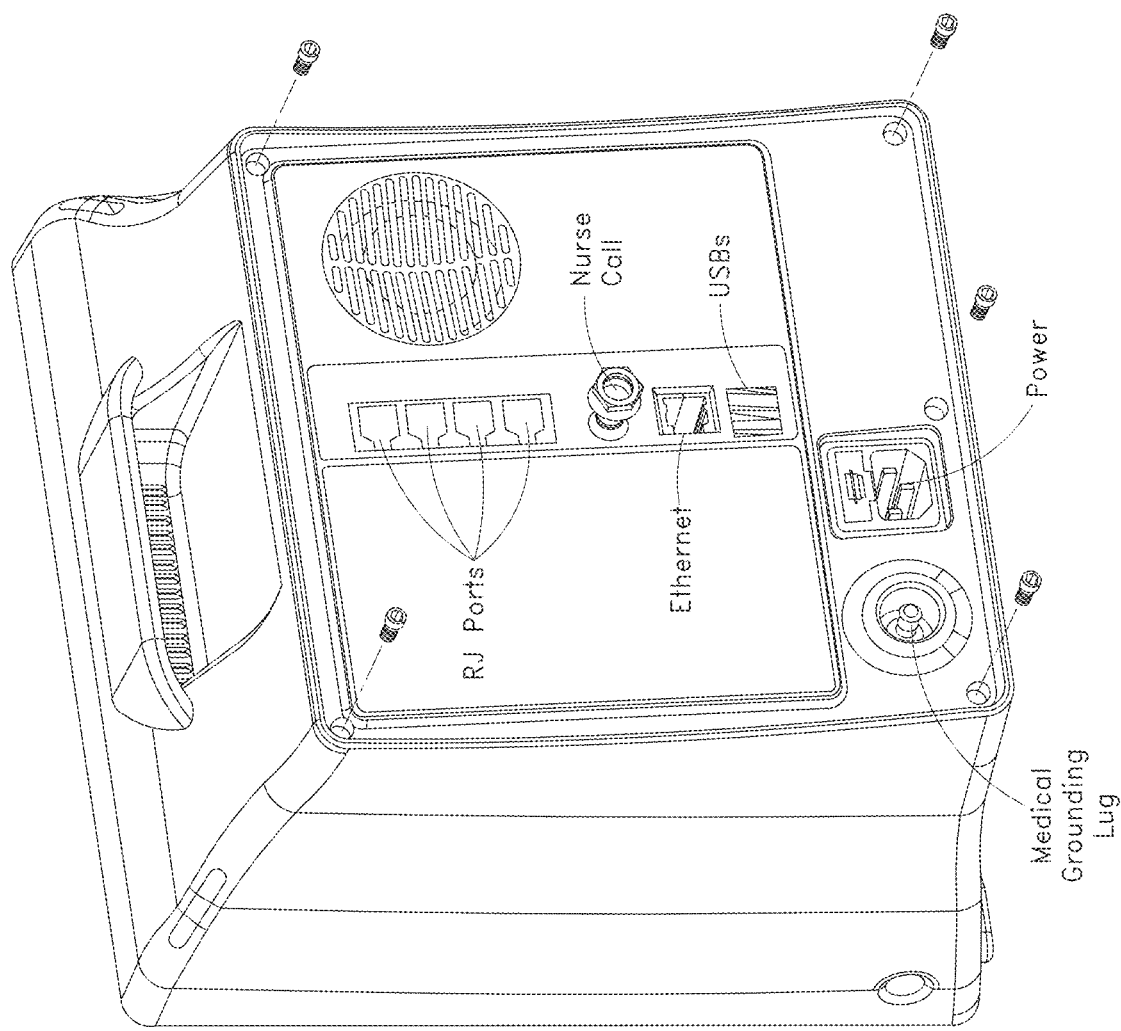
FIG. 16 illustrates a perspective view of a back side of the hub of FIG. 1, showing example instrument-side serial data inputs.

FIG. 16 illustrates a perspective view of a back side of the hub 100 of FIG. 1, showing example serial data inputs. The inputs can include such as RJ 45 ports. As is understood in the art, these ports can include data ports that may be similar to those found on computers, network routers, switches and hubs. A plurality of these ports can be used to associate data from various devices with the specific patient identified in the hub 100. FIG. 16 also shows a speaker, the nurse call connector, the Ethernet connector, the USBs, a power connector and a medical grounding lug.

Figure 17A:
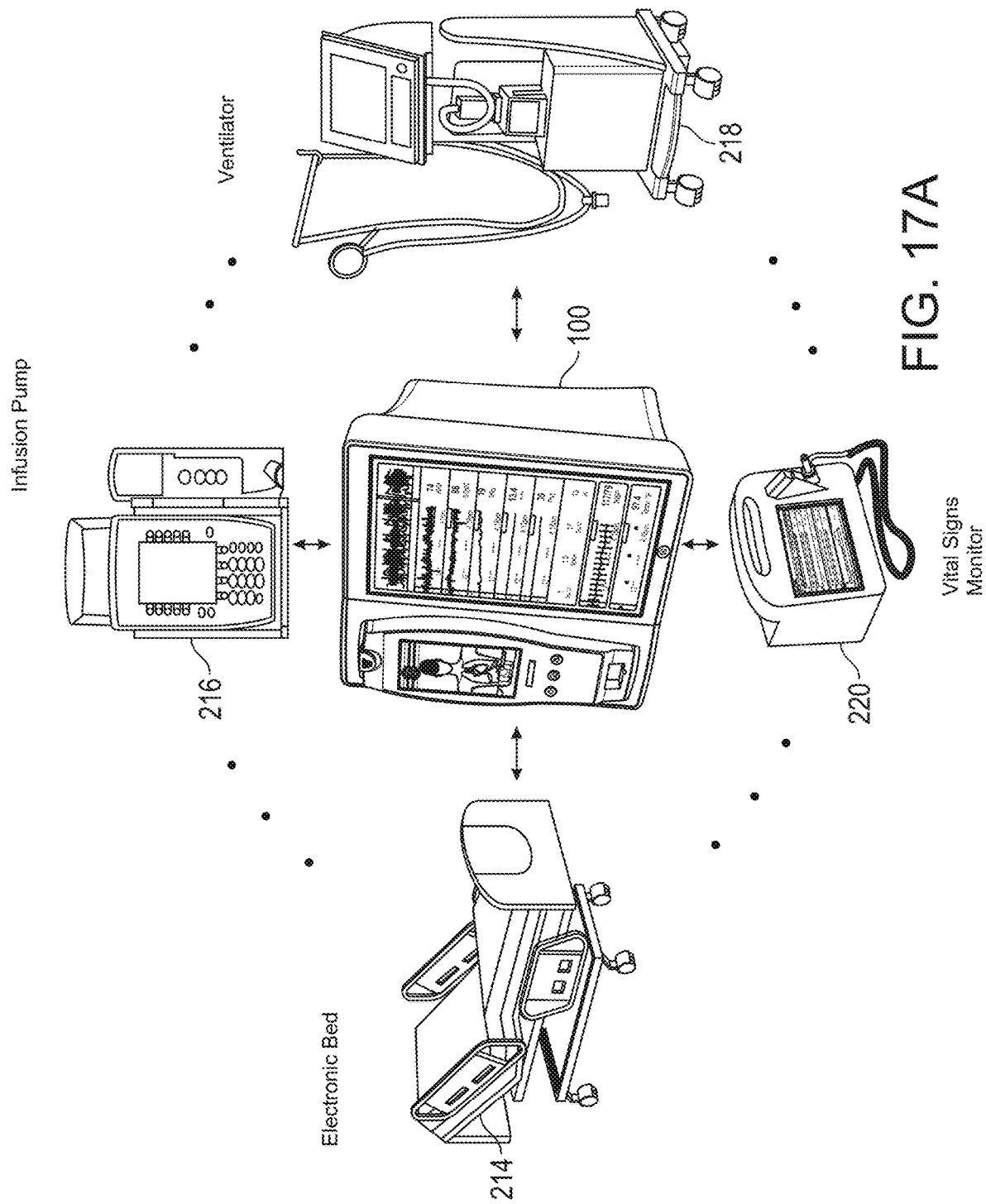
FIG. 17A illustrates an example monitoring environment with communication through the serial data connections of FIG. 16.

FIG. 17A illustrates an example monitoring environment with communication through the serial data connections of the hub 100 of FIG. 1. As shown and as discussed in the foregoing, the hub 100 may use the serial data ports 210 to gather data from various devices within the monitoring environment, including an electronic bed, infusion pumps, ventilators, vital sign monitors, and the like. The difference between the data received from these devices and that received through the channel ports 212 is that the hub 100 may not know the format or structure of this data. The hub 100 may not display information from this data or use this data in calculations or processing. However, porting the data through the hub 100 can conveniently associate the data with the specifically monitored patient in the entire chain of caregiver systems, including the foregoing server 214 and backend systems 206. The hub 100 may determine sufficient information about the incoming data to attempt to synchronize it with data from the hub 100.

Figure 17B:
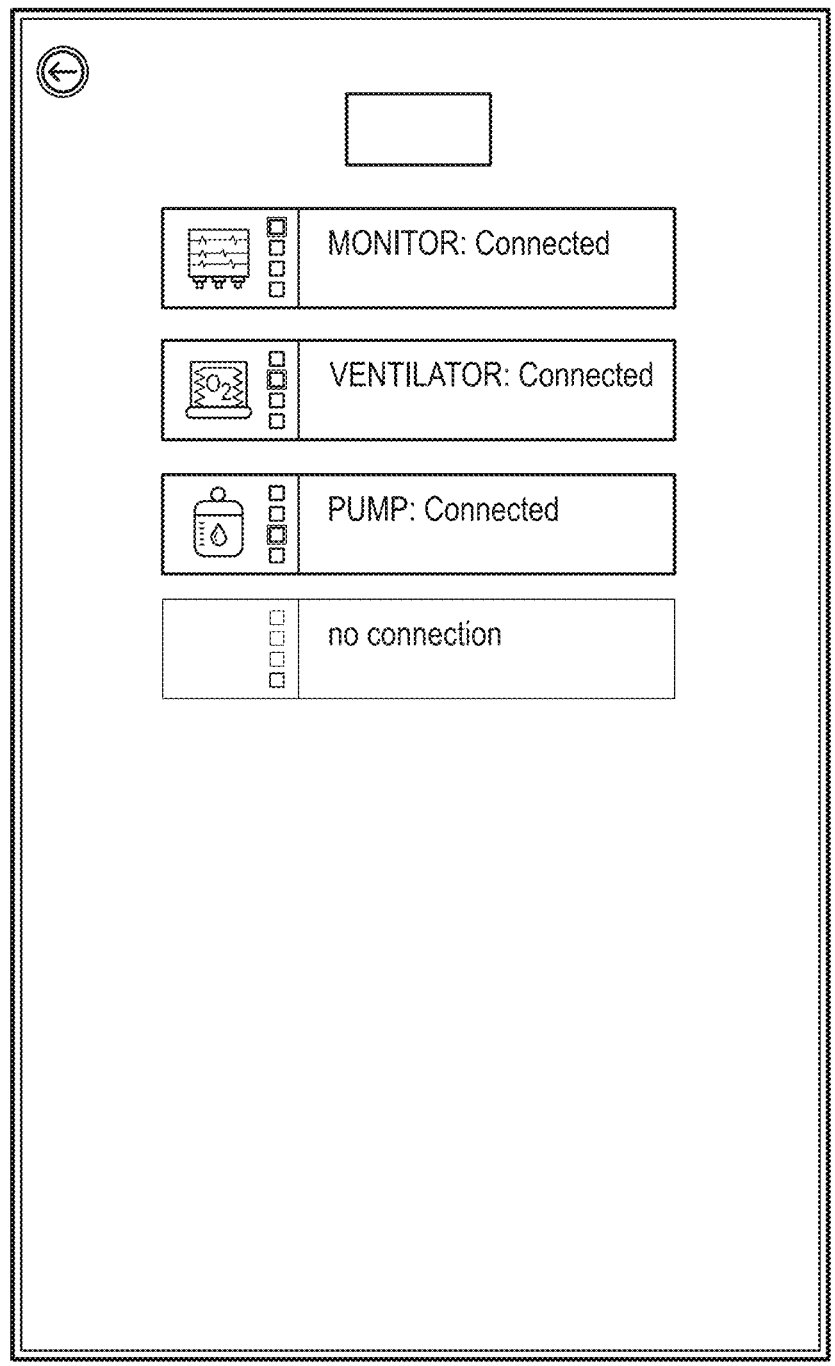
FIG. 17B illustrates an example connectivity display of the hub of FIG. 1.

In FIG. 17B, a control screen may provide information on the type of data being received. A green light next to the data can indicate a connection to a device and on which serial input the connection occurs.

Figure 18:
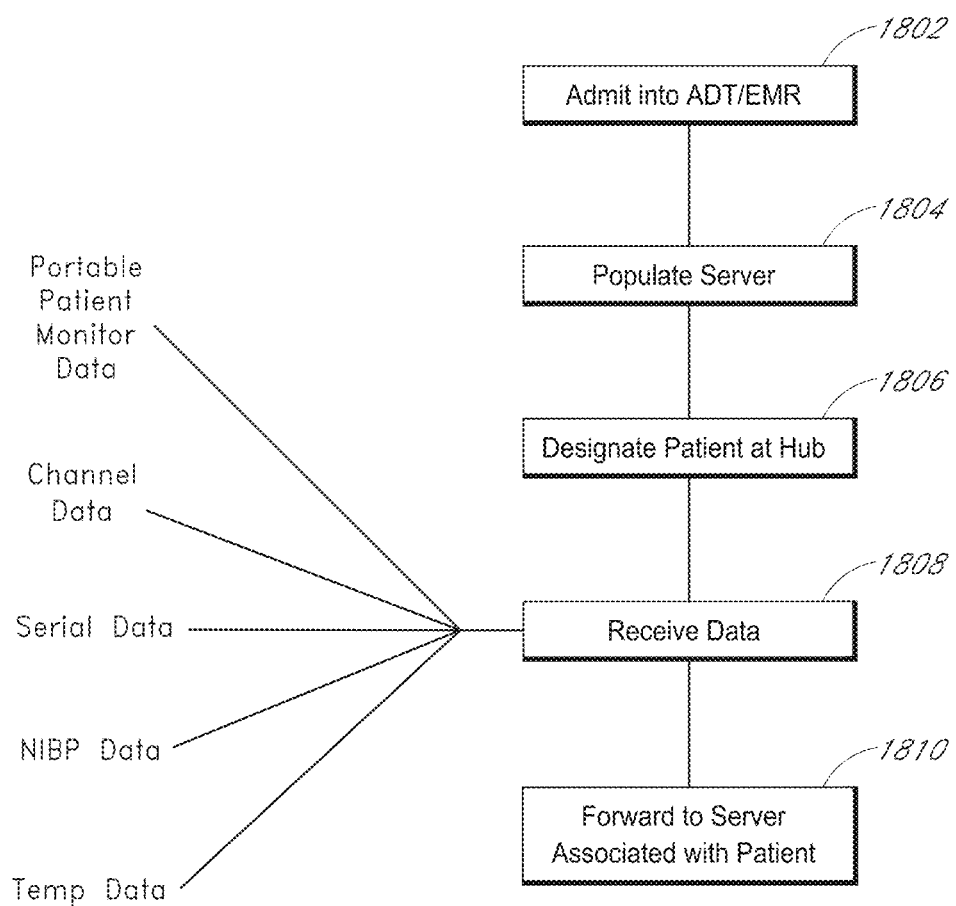
FIG. 18 illustrates a simplified example patient data flow process.

FIG. 18 illustrates a simplified example patient data flow process. As shown, once a patient is admitted into the caregiver environment at step 1802, data about the patient is populated on the caregiver backend systems 206. The server 214 may advantageously acquire or receive this information in step 1804, and then make it accessible to the hub 100. When the caregiver at step 1806 assigns the hub 100 to the patient, the caregiver simply looks at the presently available patient data and selects the particular patient being currently monitored. The hub 100 at step 1808 then associates the measurement, monitoring and treatment data it receives and determines with that patient. The caregiver need not again associate another device with the patient so long as that device is communicating through the hub 100 by way of (1) the docking station, (2) the universal medical connectors, (3) the serial data connectors, or (4) other communication mechanisms known to an artisan. At step 1810, some or the entirety of the received, processed and/or determined data is passed to the server systems discussed above.

Figure 19A:
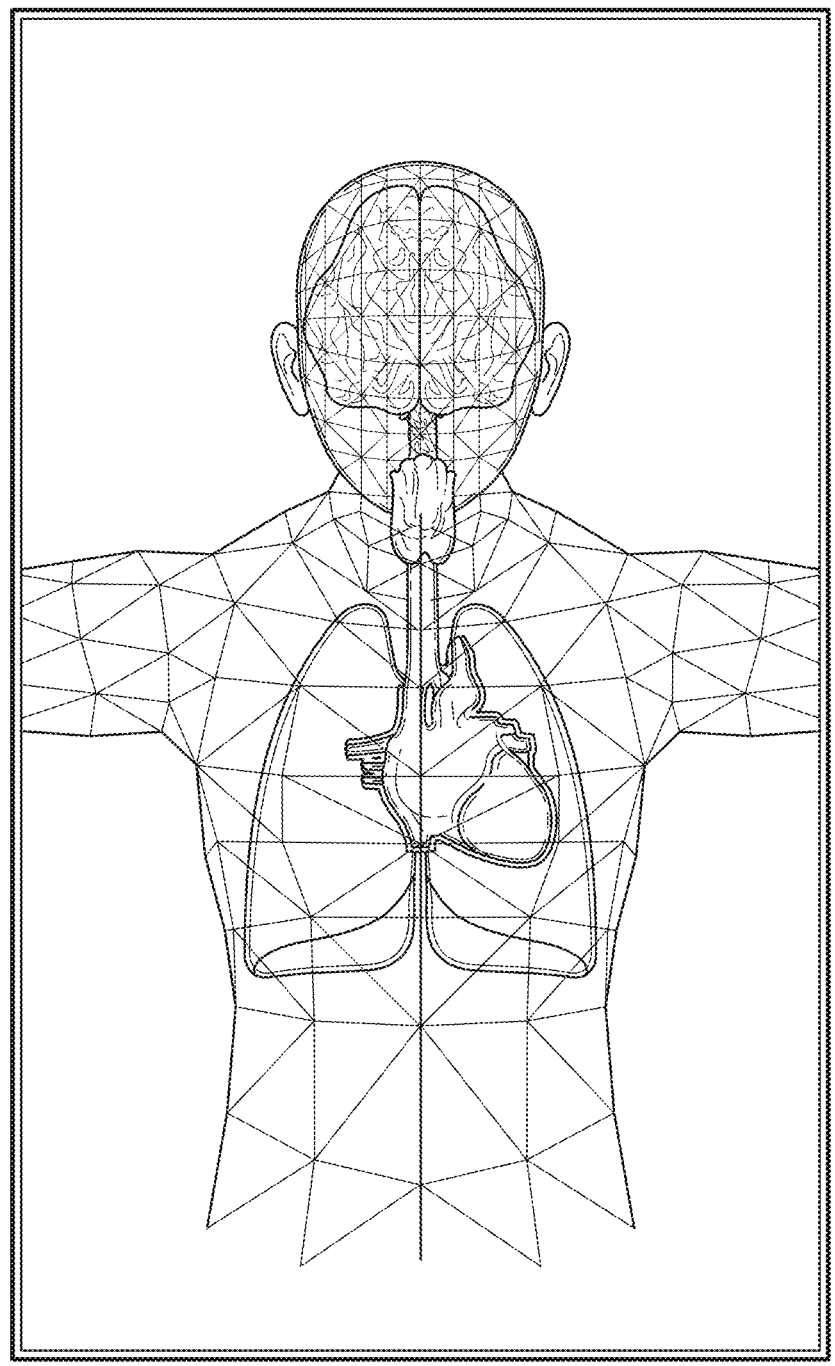
FIGS. 19A-19J illustrate example displays of anatomical graphics for the portable patient monitor of FIG. 1 docked with the hub of FIG. 1.

FIGS. 19A-19J illustrate example displays of anatomical graphics for the portable patient monitor docked with the hub 100 of FIG. 1. As shown in FIG. 19A, the heart, lungs and respiratory system are shown while the brain is not highlighted. Thus, a caregiver can readily determine that depth of consciousness monitoring or brain oximetry systems are not currently communicating with the hub 100 through the portable patient monitor connection or the channel data ports. However, it is likely that acoustic or other respiratory data and cardiac data is being communicated to or measured by the hub 100. Moreover, the caregiver can readily determine that the hub 100 is not receiving alarming data with respect to the emphasized body portions. The emphasized portion may animate to show currently measured behavior or, alternatively, animate in a predetermined fashion.

Figure 19B:
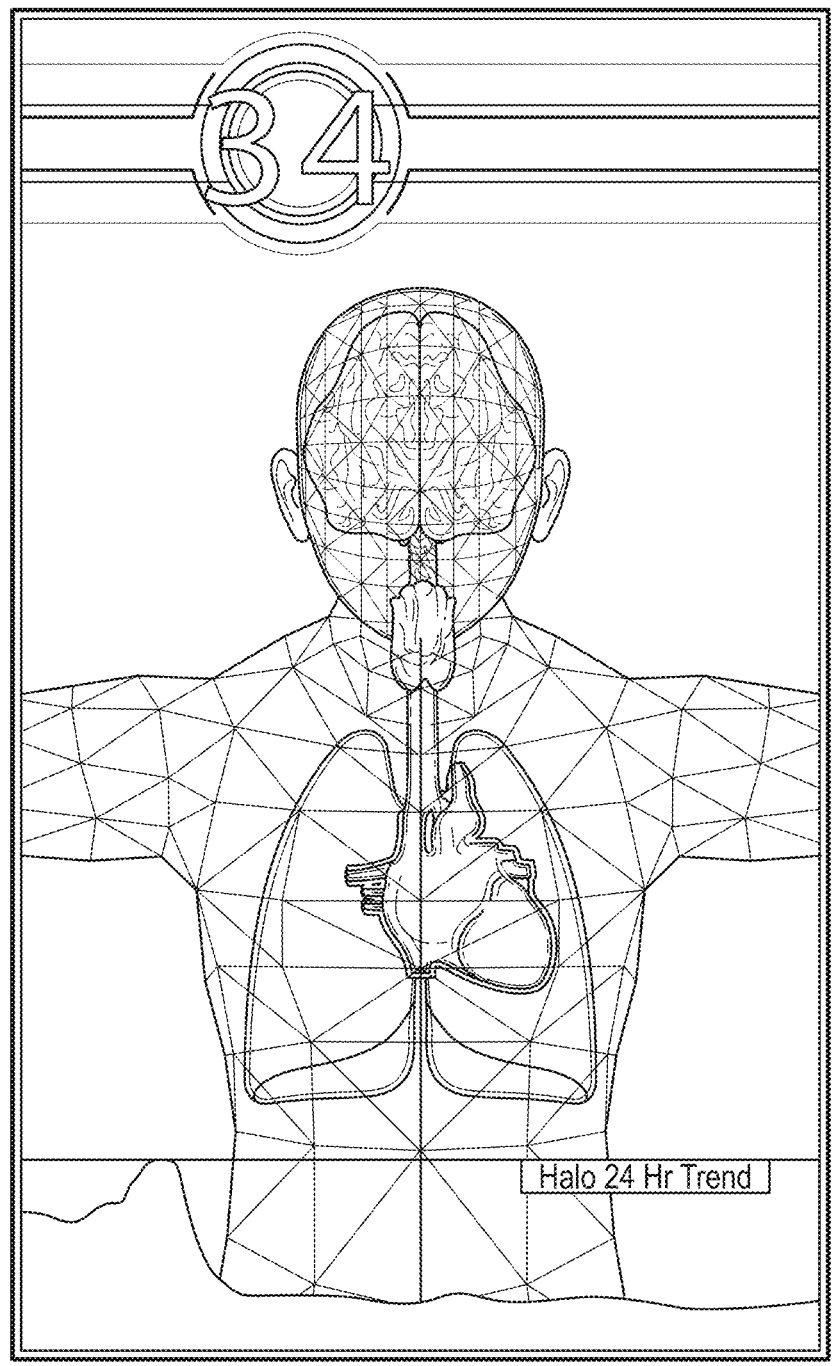
Figure 19C:
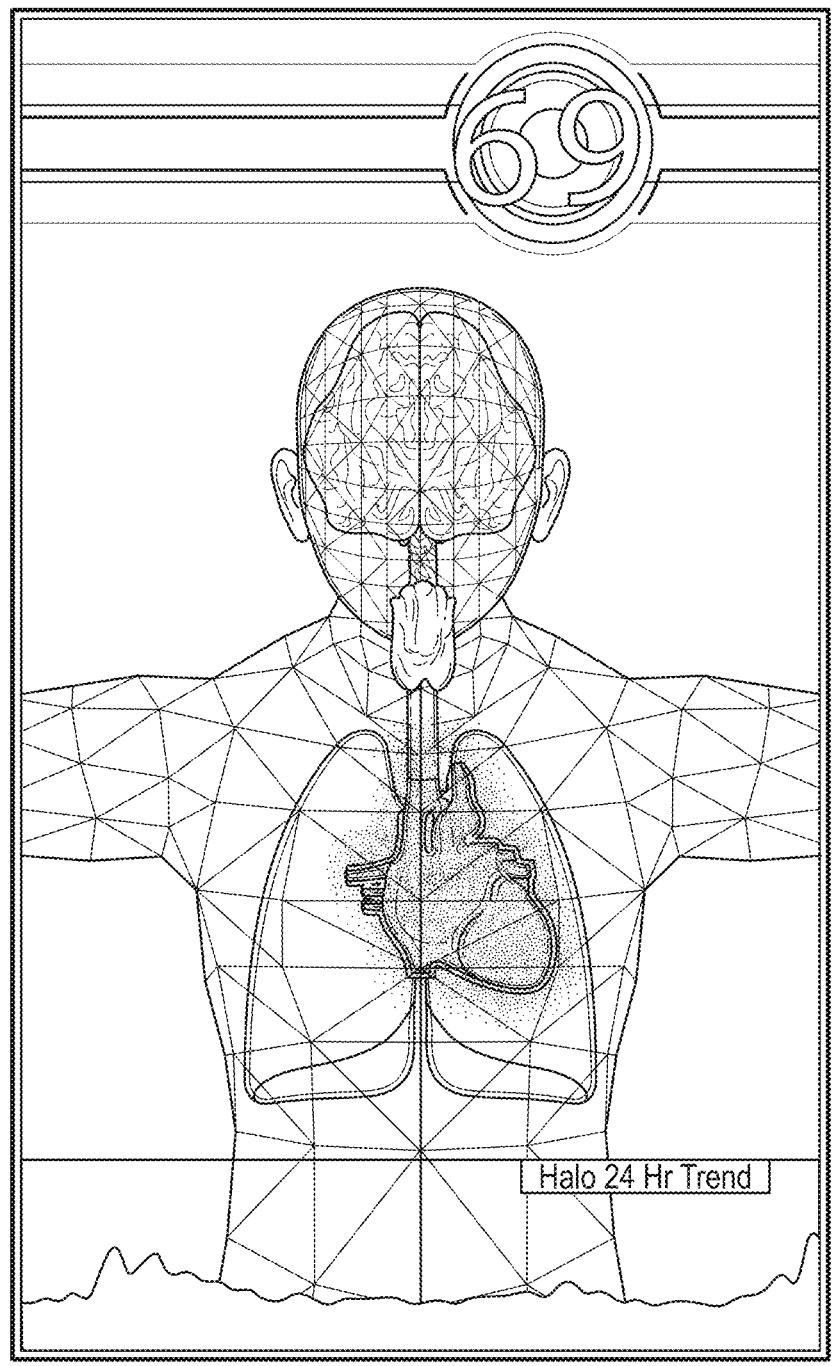

FIG. 19B shows the addition of a virtual channel showing an indication of wellness. As shown in FIG. 19B, the indication is positive as it is a "34" on an increasingly severity scale to "100." The wellness indication may also be shaded to show problems. In contrast to FIG. 19B, FIG. 19C shows a wellness number that is becoming or has become problematic and an alarming heart graphic. Thus, a caregiver responding to a patient alarm on the hub 100 or otherwise on another device or system monitoring or treating the patient can quickly determine that a review of vital signs and other parameters relating to heart function is needed to diagnose and/or treat the patient.

Figure 19D:
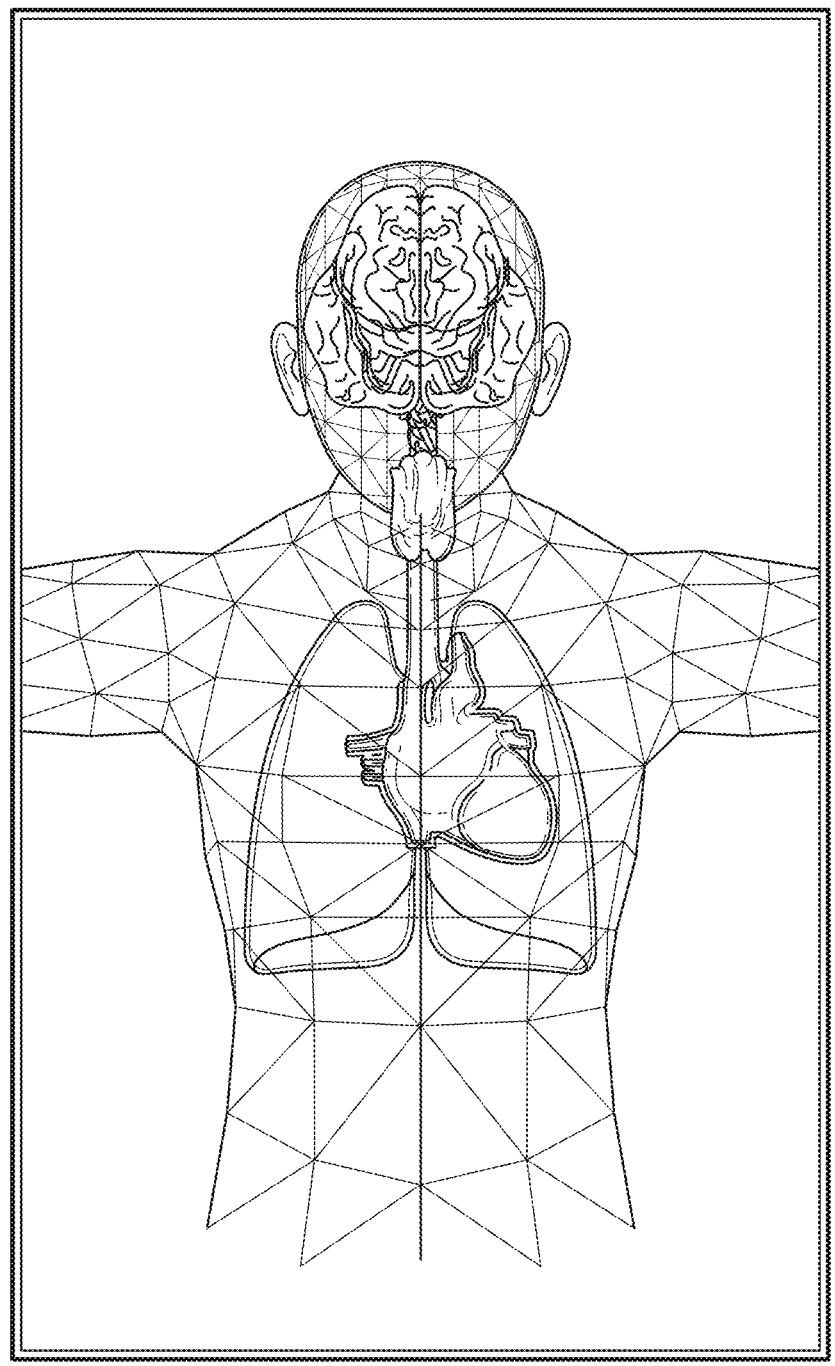
Figure 19E:
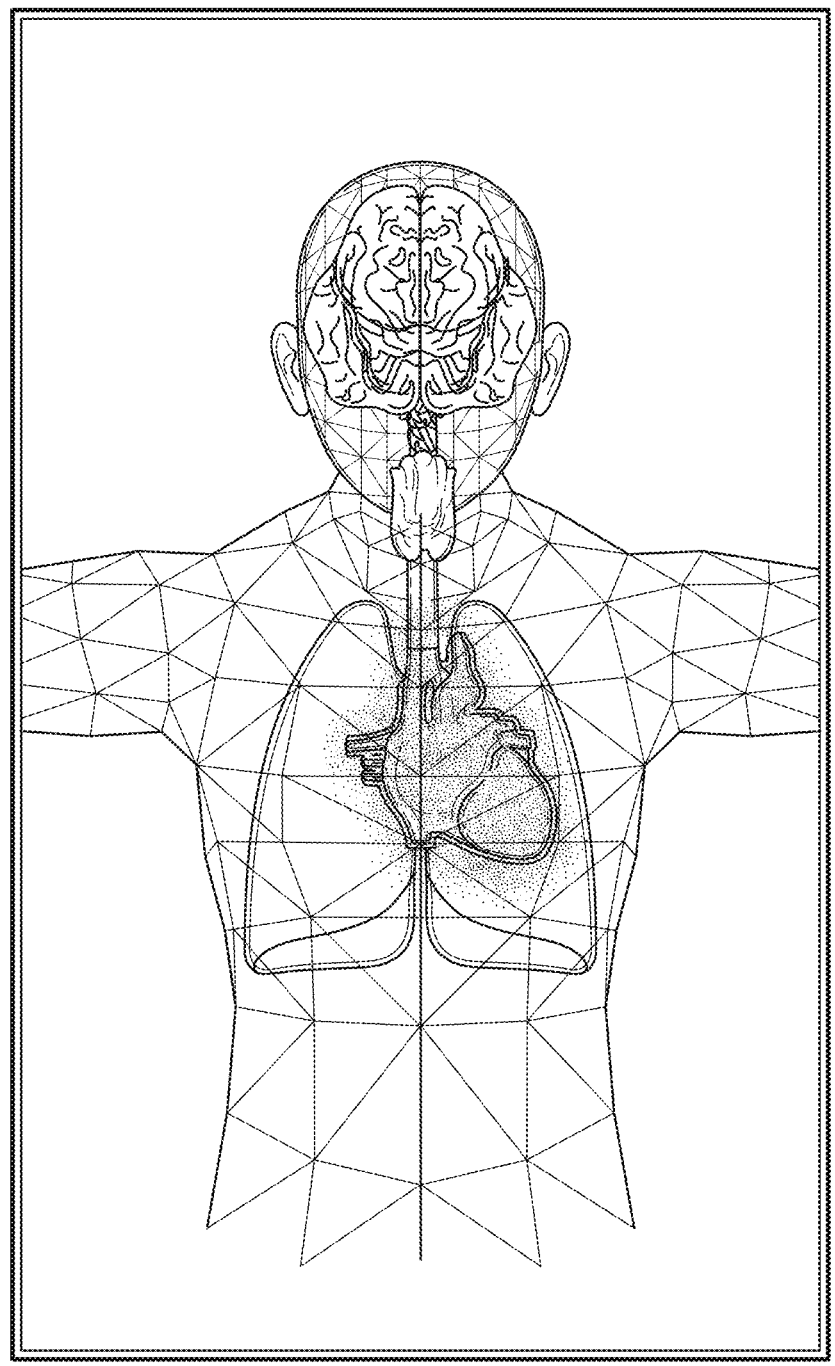

FIGS. 19D and 19E show the brain included in the emphasized body portions meaning that the hub 100 is receiving data relevant to brain functions, such as, for example, depth of sedation data or brain oximetry data. FIG. 19E additionally shows an alarming heart function similar to FIG. 19C.

Figure 19F:
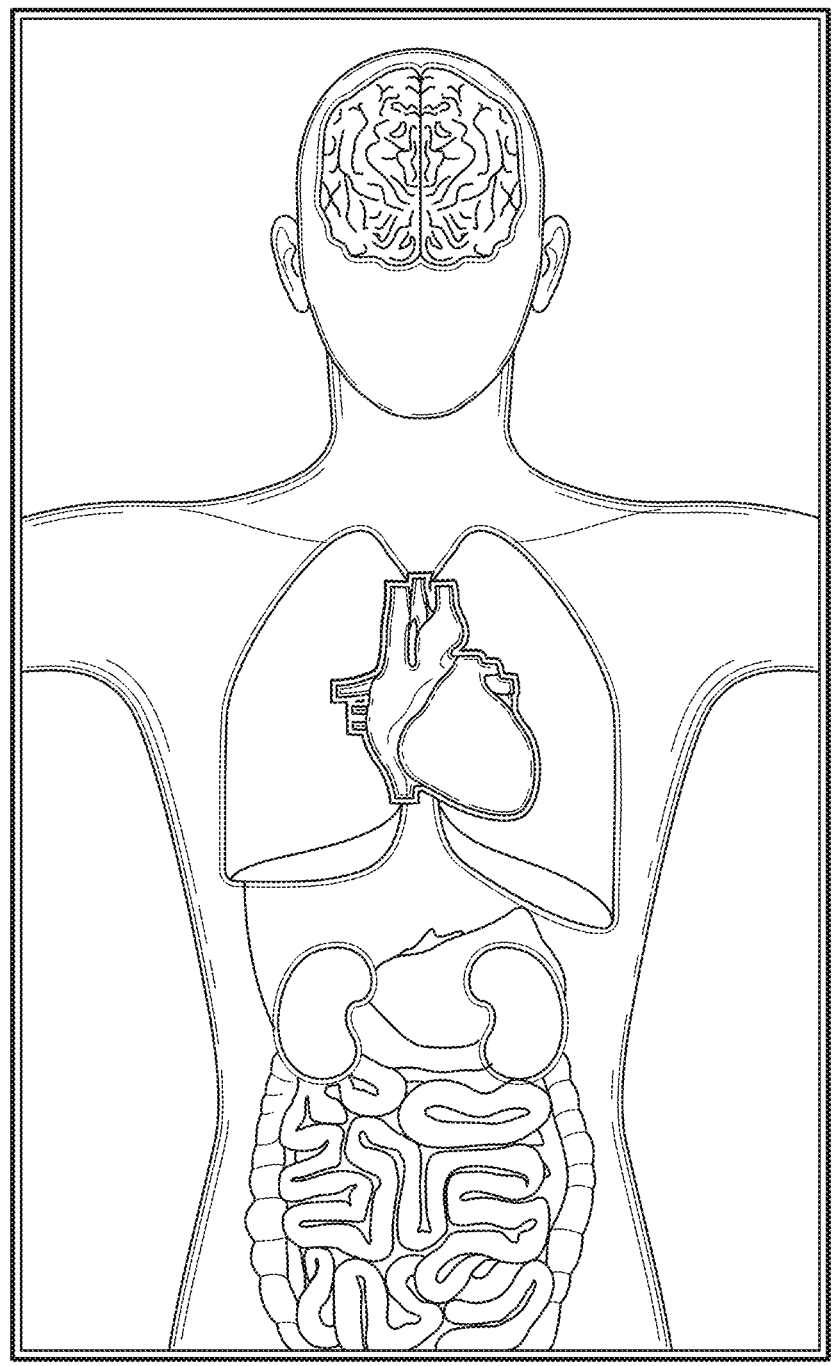
Figure 19G:
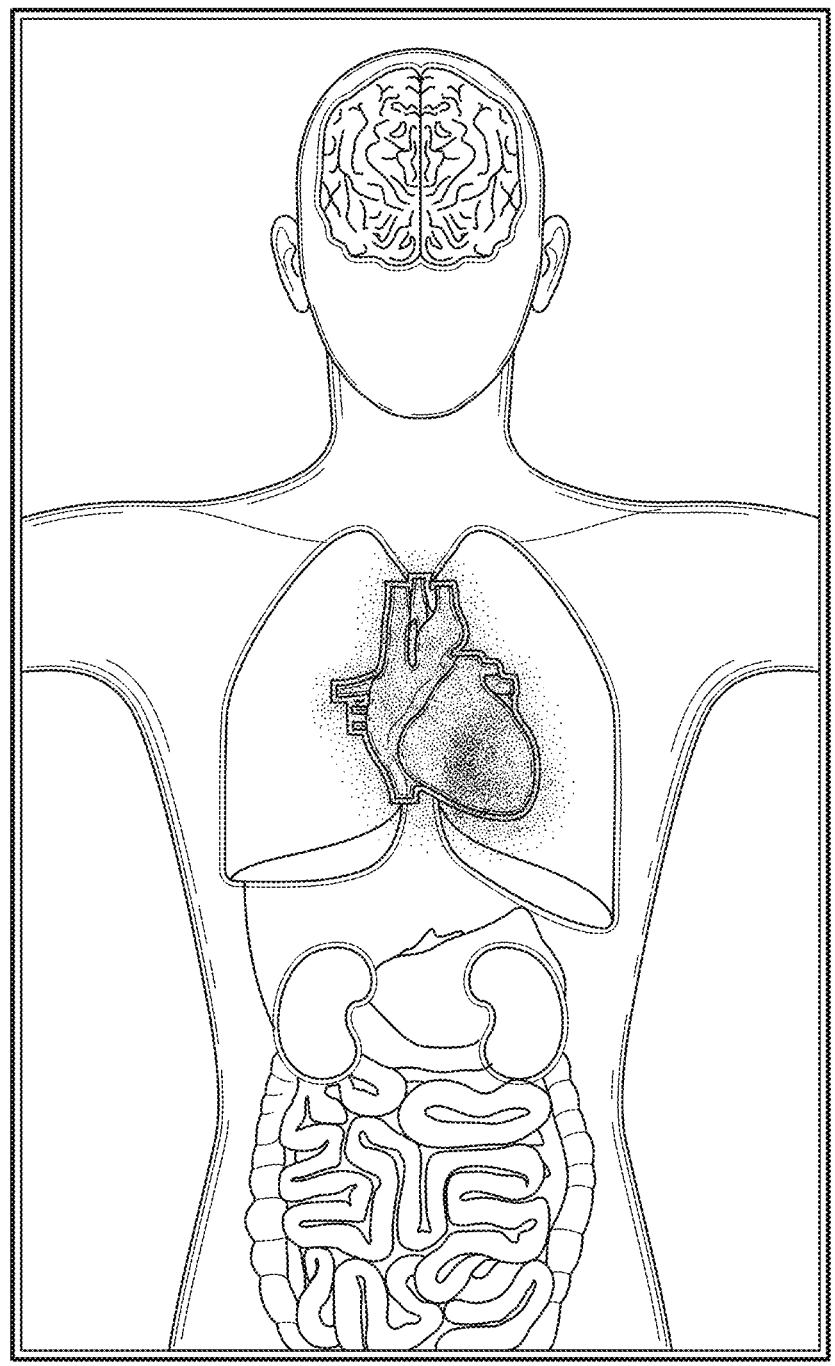
Figure 19H:
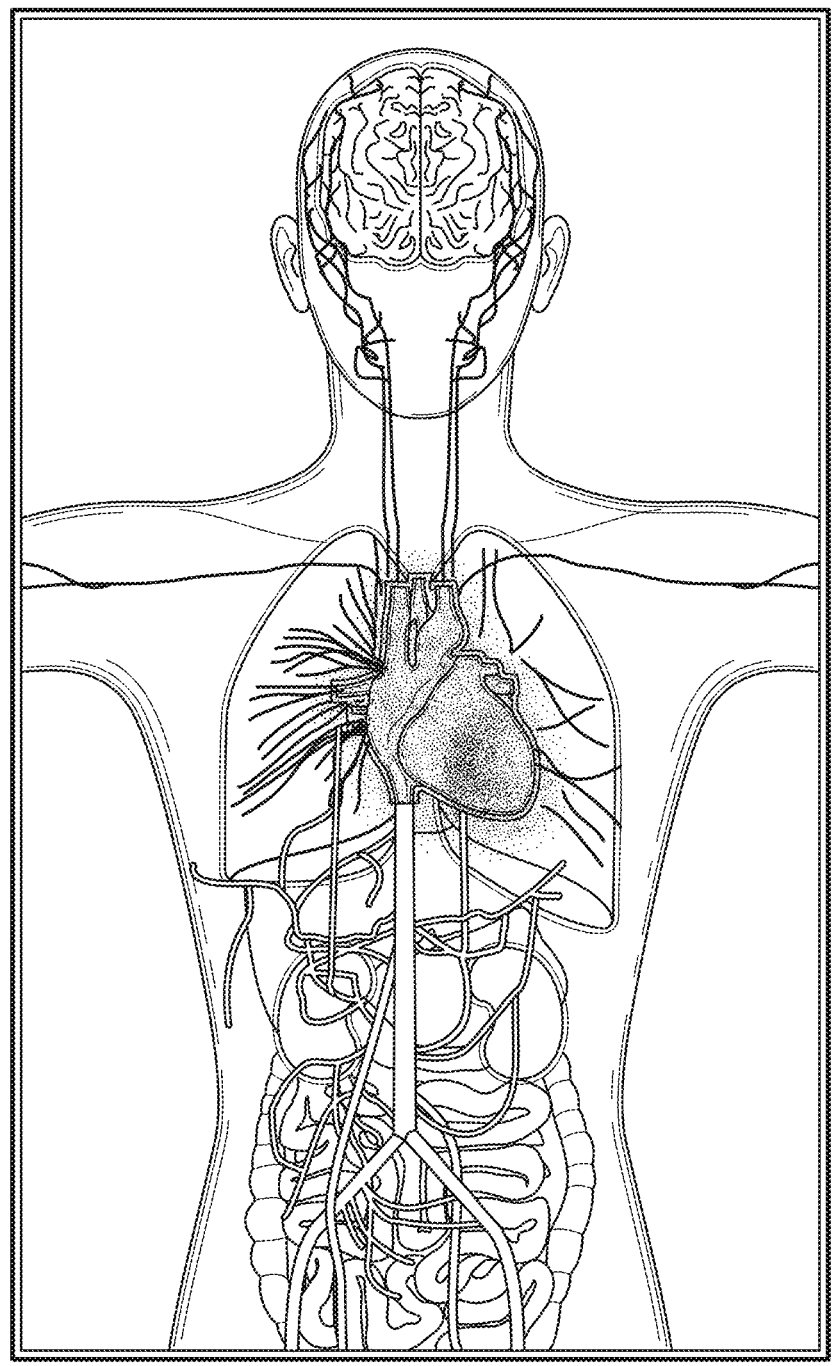
Figure 19I:
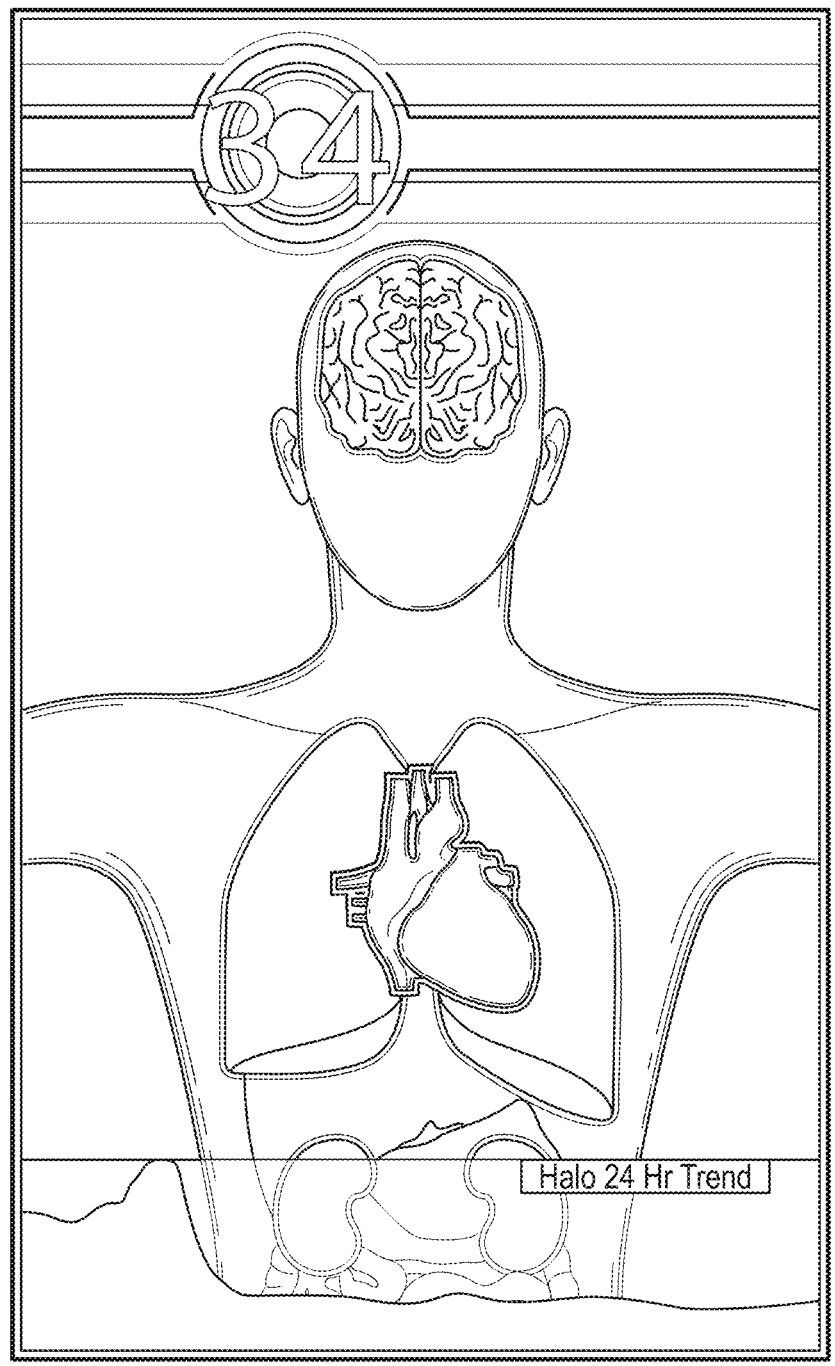
Figure 19J:
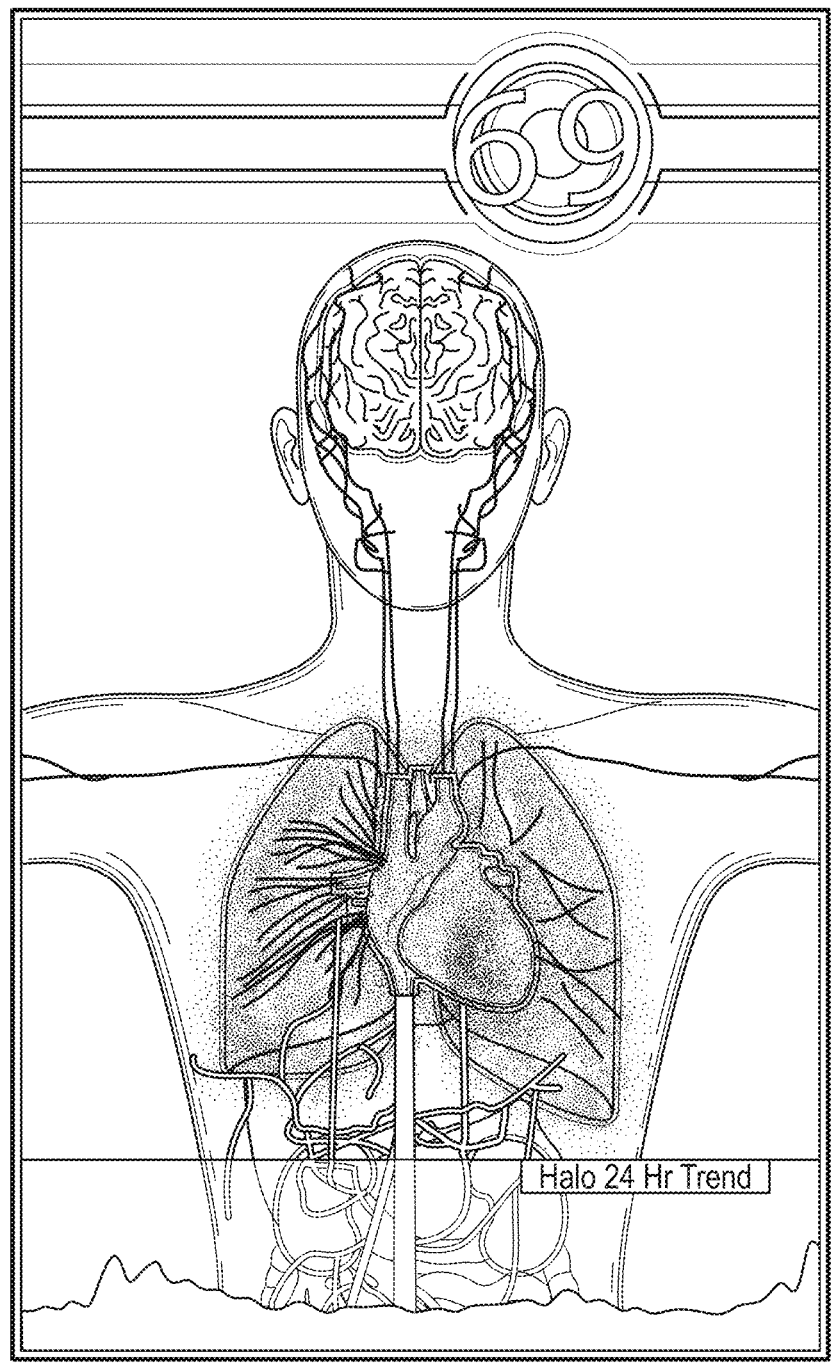

In FIG. 19F, additional organs, such as the kidneys are being monitored, but the respiratory system is not. In FIG. 19G, an alarming hear function is shown, and in FIG. 19H, an alarming circulatory system is being shown. FIG. 19I shows the wellness indication along with lungs, heart, brain and kidneys. FIG. 19J shows alarming lungs, heart, and circulatory system as well as the wellness indication. Moreover, FIG. 19J shows a severity contrast, such as, for example, the heart alarming red for urgent while the circulatory system alarms yellow for caution. An artisan will recognize other color schemes that are appropriate from the disclosure herein.

Figure 20A:
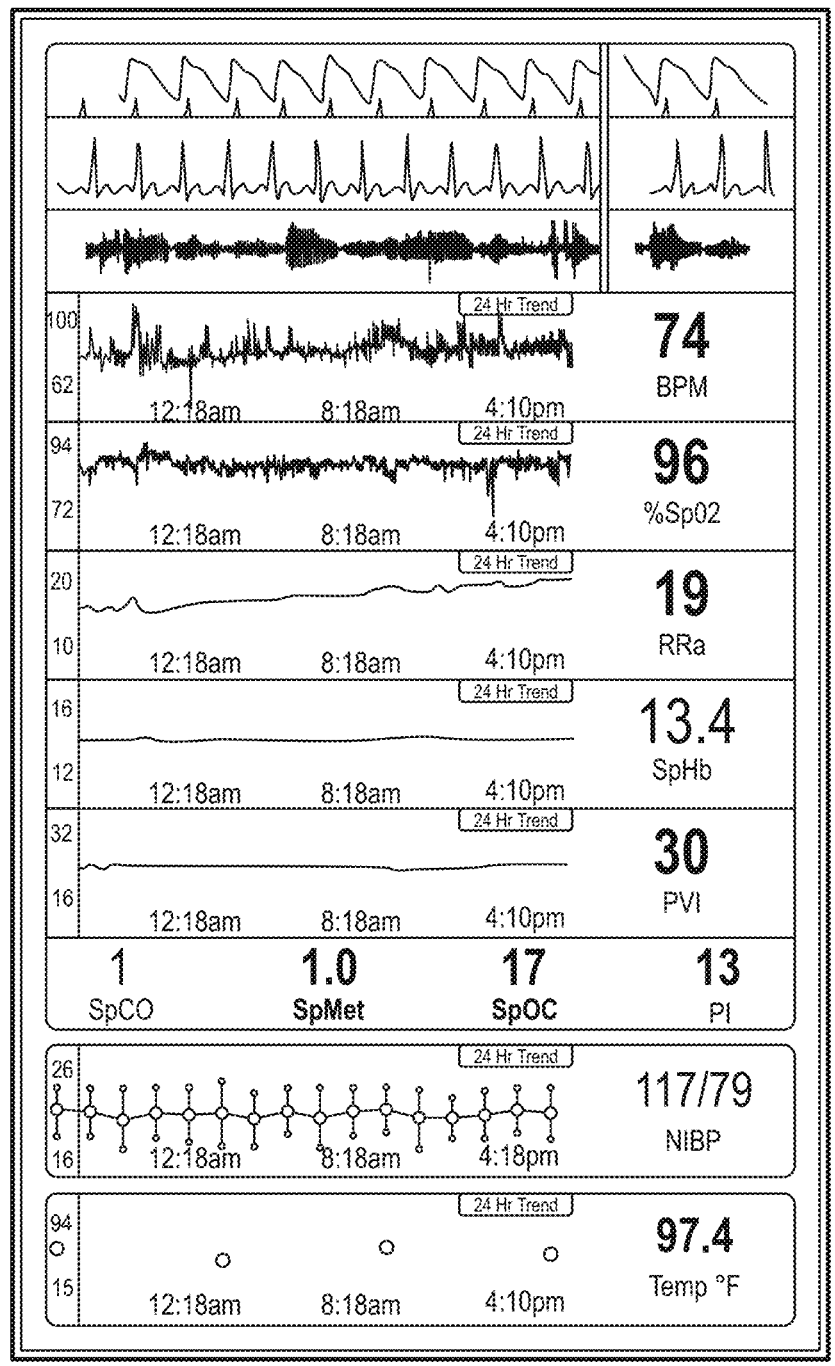
FIGS. 20A-20C illustrate example displays of measurement data showing data separation and data overlap on a display of the hub of FIG. 1, respectively.
Figure 20B:
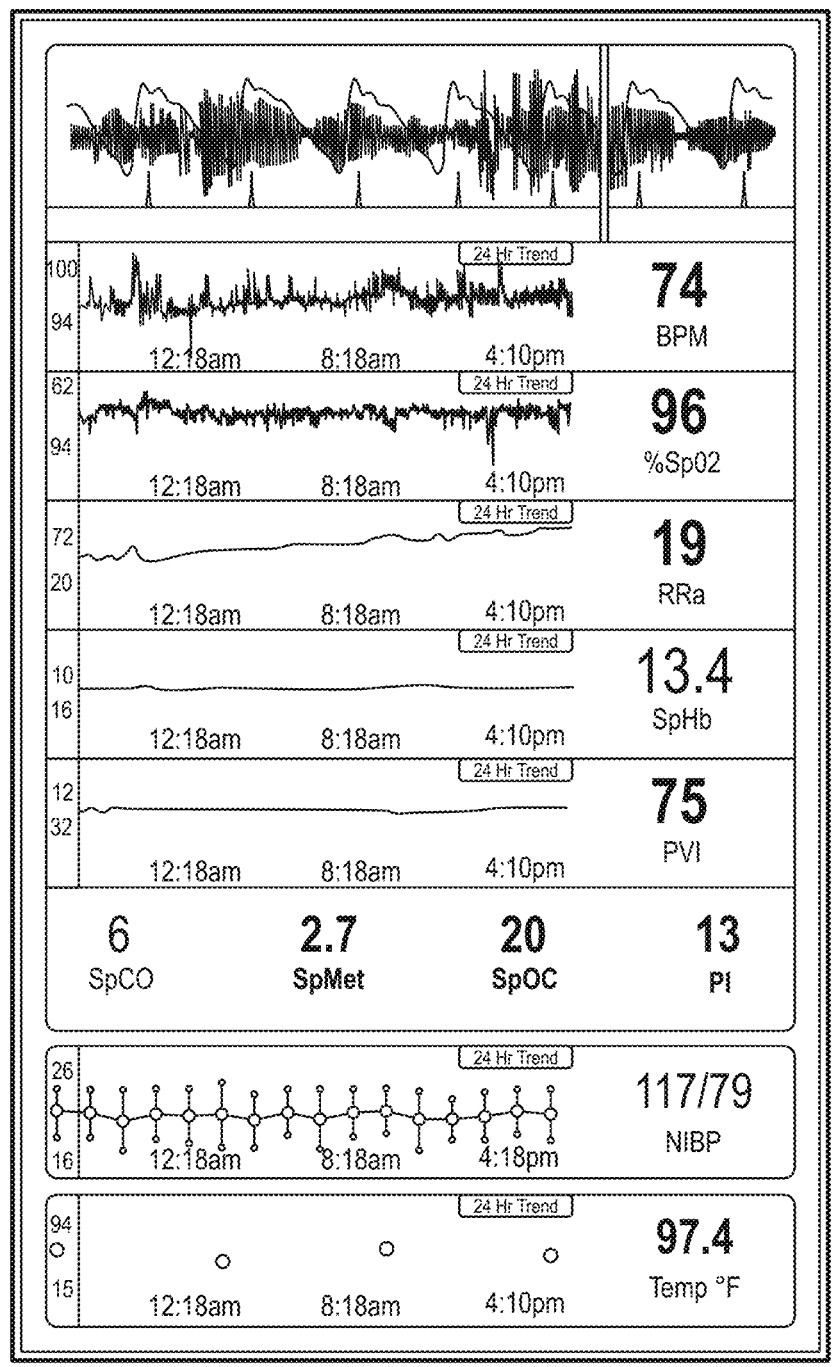
Figure 20C:
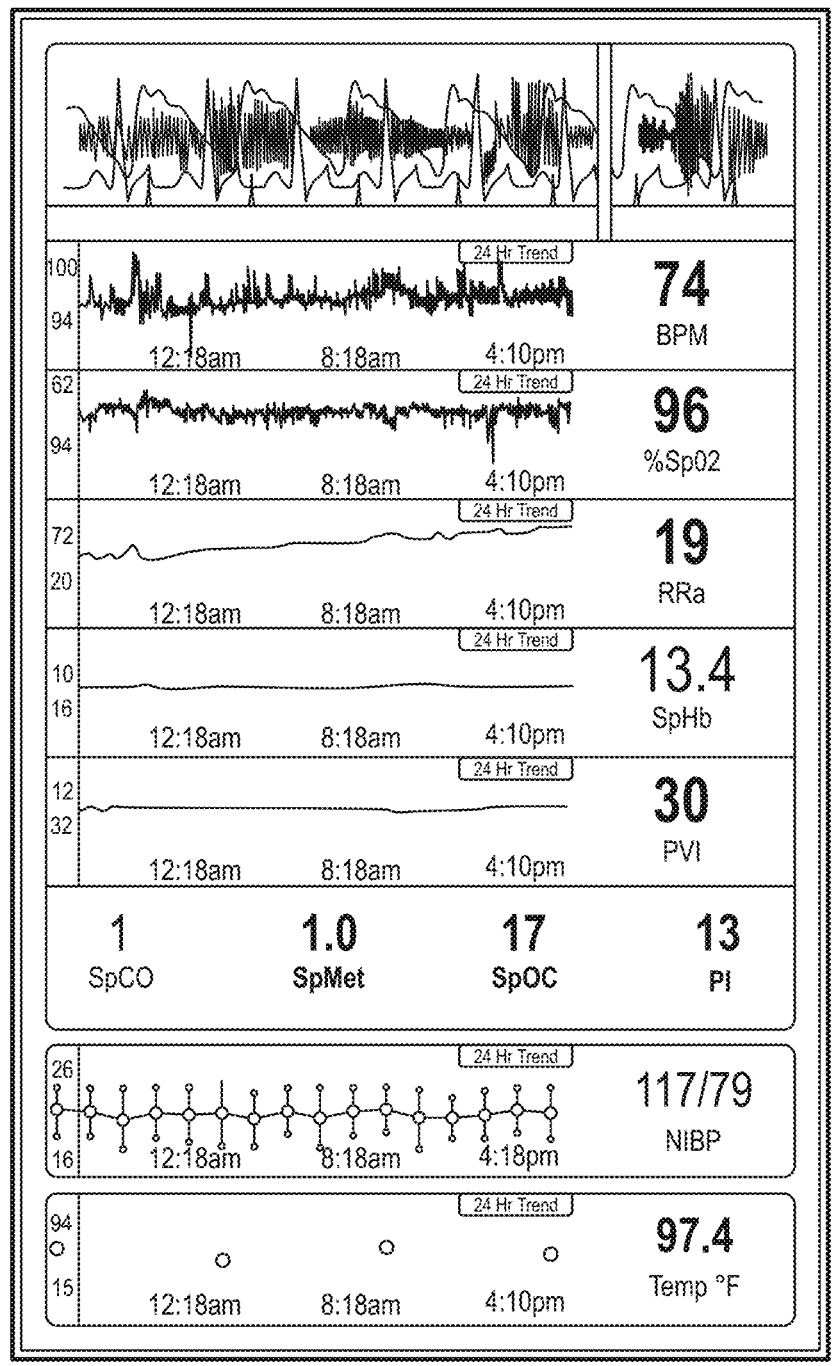
Figure 21A:
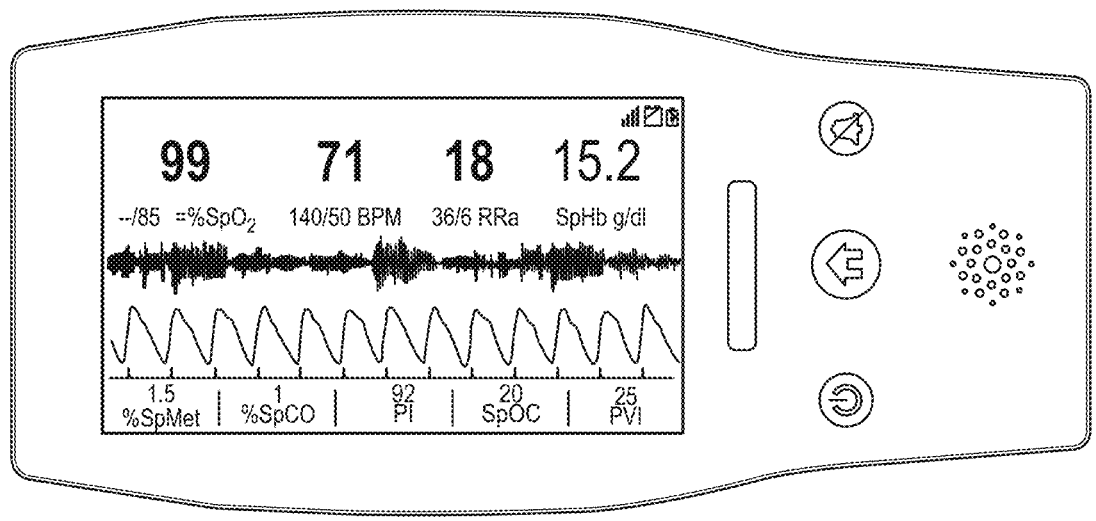
FIGS. 21A and 21B illustrate example displays of measurement data showing data separation and data overlap on a display of the portable patient monitor of FIG. 1, respectively.
Figure 21B:
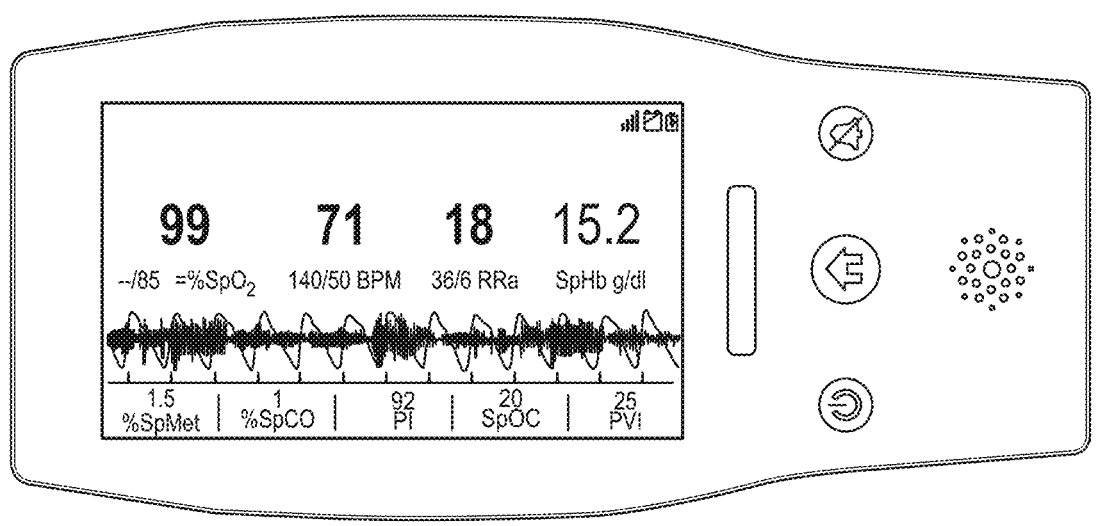

FIGS. 20A-20C illustrate example displays of measurement data showing data separation and data overlap, respectively. FIGS. 21A and 21B illustrate example displays of measurement data also showing data separation and data overlap, respectively.

For example, acoustic data from an acoustic sensor may advantageously provide breath sound data, while the plethysmograph and ECG or other signals can also be presented in separate waveforms (FIG. 20A, top of the screen capture). The monitor may determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases a system monitors other physiological sounds, such as heart rate to help with probe off detection, heart sounds (S1, S2, S3, S4, and murmurs), and change in heart sounds such as normal to murmur or split heart sounds indicating fluid overload.

Providing a visual correlation between multiple physiological signals can provide a number of valuable benefits where the signals have some observable physiological correlation. As one example of such a correlation, changes in morphology (e.g., envelope and/or baseline) of the plethysmographic signal can be indicative of patient blood or other fluid levels. And, these changes can be monitored to detect hypovolemia or other fluid-level related conditions. A pleth variability index may provide an indication of fluid levels, for example. And, changes in the morphology of the plethysmographic signal are correlated to respiration. For example, changes in the envelope and/or baseline of the plethysmographic signal are correlated to breathing. This is at least in part due to aspects of the human anatomical structure, such as the mechanical relationship and interaction between the heart and the lungs during respiration.

Thus, superimposing a plethysmographic signal and a respiratory signal (FIG. 20B) can give operators an indication of the validity of the plethysmographic signal or signals derived therefrom, such as a pleth variability index. For example, if bursts in the respiration signal indicative of inhalation and exhalation correlate with changes in peaks and valleys of the plethysmographic envelope, this gives monitoring personnel a visual indication that the plethysmographic changes are indeed due to respiration, and not some other extraneous factor. Similarly, if the bursts in the respiration signal line up with the peaks and valleys in the plethysmographic envelope, this provides monitoring personnel an indication that the bursts in the respiration signal are due to patient breathing sounds, and not some other non-targeted sounds (e.g., patient non-breathing sounds or non-patient sounds).

The monitor may also be configured to process the signals and determine whether there is a threshold level of correlation between the two signals, or otherwise assess the correlation. However, by additionally providing a visual indication of the correlation, such as by showing the signals superimposed with one another, the display provides operators a continuous, intuitive and readily observable gauge of the particular physiological correlation. For example, by viewing the superimposed signals, users can observe trends in the correlation over time, which may not be otherwise ascertainable.

The monitor can visually correlate a variety of other types of signals instead of, or in addition to plethysmographic and respiratory signals. For example, FIG. 20C depicts a screen shot of another example monitoring display. As shown in the upper right portion of FIG. 20C, the display superimposes a plethysmographic signal, an ECG signal, and a respiration signal. In other configurations, more than three different types of signals may be overlaid onto one another.

The hub 100 can provide a user interface through which the user can move the signals together to overlay on one another. For example, the user may be able to drag the respiration signal down onto the plethysmographic signal using a touch screen interface. Conversely, the user may be able to separate the signals, also using the touch screen interface. The monitor can include a button the user can press, or some other user interface allowing the user to overlay and separate the signals, as desired. FIGS. 21A and 21B show similar separation and joining of the signals.

In certain configurations, in addition to providing the visual correlation between the plethysmographic signal and the respiratory signal, the monitor can additionally be configured to process the respiratory signal and the plethysmographic signal to determine a correlation between the two signals. For example, the monitor may process the signals to determine whether the peaks and valleys in the changes in the envelope and/or baseline of the plethysmographic signal correspond to bursts in the respiratory signal. And, in response to the determining that there is or is not a threshold level of correlation, the monitor may provide some indication to the user. For example, the monitor may provide a graphical indication (e.g., a change in color of pleth variability index indicator), an audible alarm, or some other indication. The monitor may employ one or more envelope detectors or other appropriate signal processing componentry in making the determination.

The system may further provide an audible indication of the patient's breathing sounds instead of, or in addition to the graphical indication. For example, the monitor may include a speaker, or an earpiece (e.g., a wireless earpiece) that may be provided to the monitoring personnel that can provide an audible output of the patient sounds. Examples of sensors and monitors having such capability are described in U.S. Pat. Pub. No. 2011/0172561 and are incorporated by reference herein.

In addition to the above described benefits, providing both the acoustic and plethysmographic signals on the same display in the manner described can allow monitoring personnel to more readily detect respiratory pause events where there is an absence of breathing, high ambient noise that can degrade the acoustic signal, improper sensor placement, etc.

The user interface of the hub 100 can further be modified by user. A user can modify any of the user interfaces described herein, such as the user interfaces of FIGS. 20A-20C. For example, a user can modify any of the panels of FIG. 20A, such as the BPM, % Sp02, RRa, SpHb, PVI, PI, NIBP, or Temp panels. A user can remove one or more panels, add one or more panels, select a preset layout, rearrange, or expand one or more user interface elements. For example, using a finger or an input device, a user can drag a panel to a new location in the user interface, or select a panel to remove or modify it. The user may also access a display layout manager to choose from different automatically-generated display layouts, as described in U.S. application Ser. No. 15/902,193, titled "System for Displaying Medical Monitoring Data," filed concurrently herewith, (hereinafter "the Display Layout Manager application"), the disclosure of which is hereby incorporated by reference in its entirety. User interaction data can be received from the hub 100 and a user interface configuration can be determined from the user interaction data. Any of the user interfaces described herein, such as user interfaces for the portable patient monitor 102 or the auxiliary device 2040 (see FIG. 72A) can also (or instead) be modified in a similar manner to the described modifications for the user interface of the hub 100.

Figure 22A:
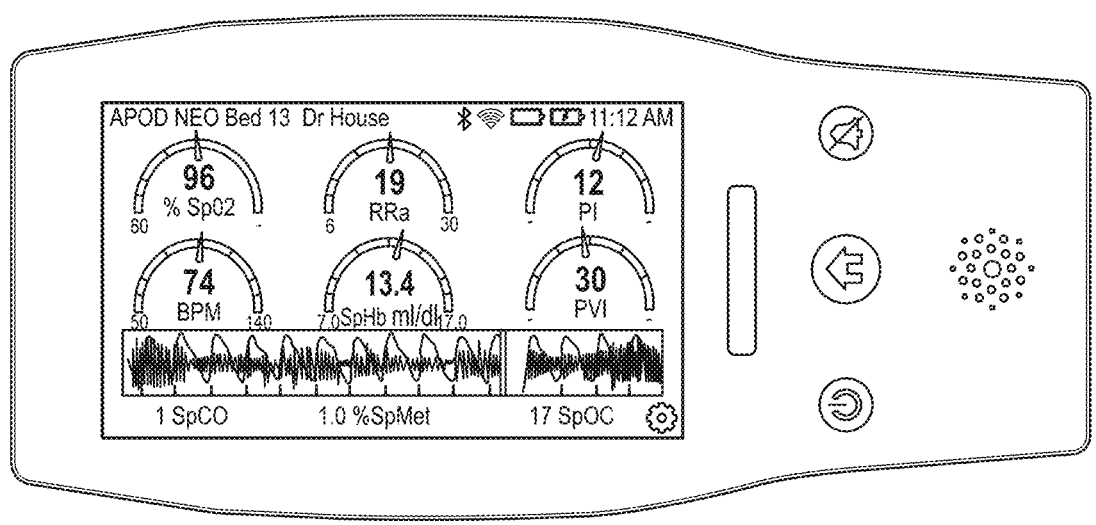
FIGS. 22A and 22B illustrate example analog display indicia.
Figure 22B:
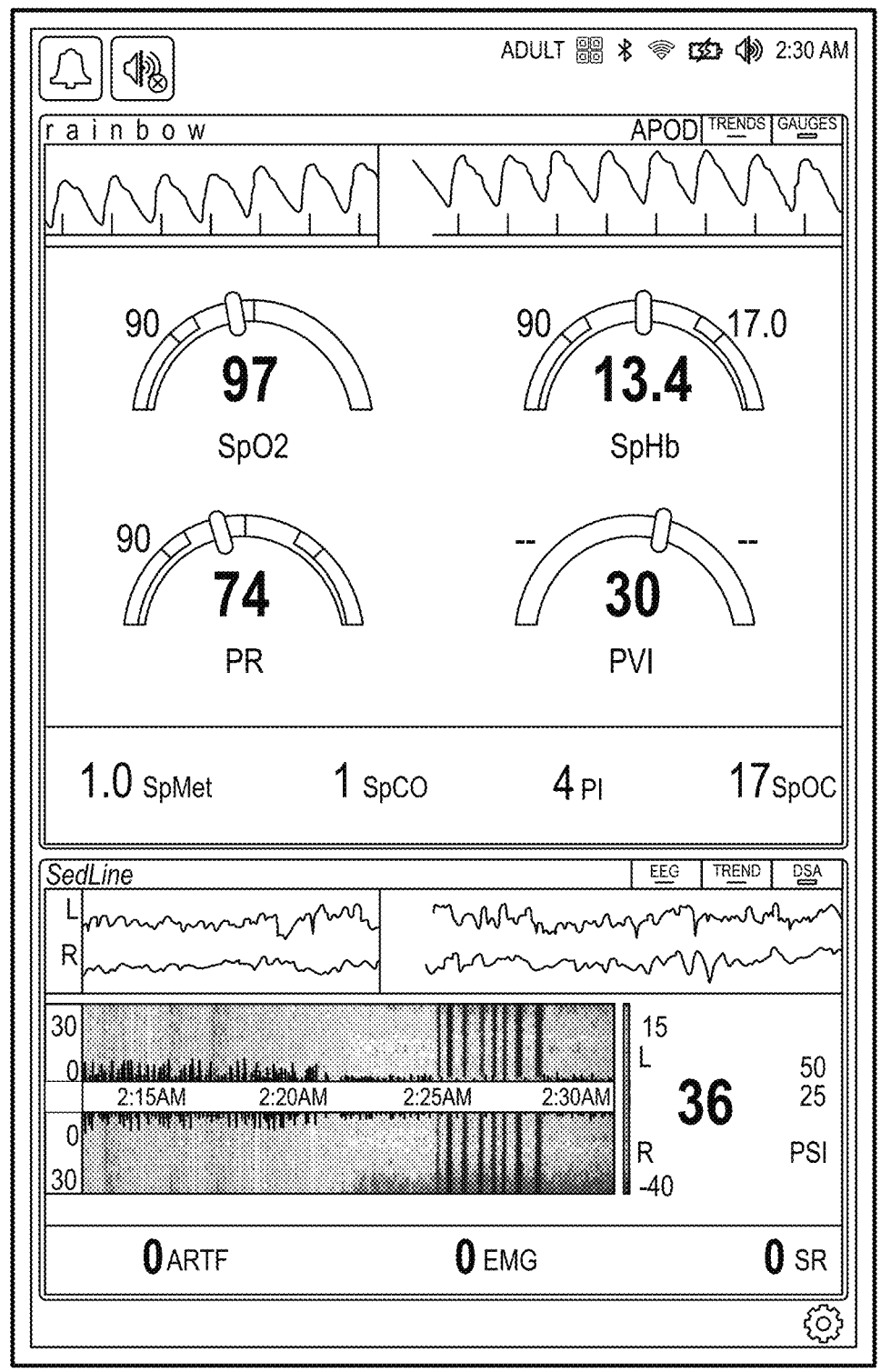

FIGS. 22A-22B illustrate example analog display indicia. As shown in FIGS. 22A and 22B, the user interfaces display health indicators of various physiological parameters, in addition to other data. Each health indicator can include an analog indicator and/or a digital indicator. Where the health indicator includes an analog and a digital indicator, the analog and digital indicators can be positioned in any number of formations, such as side-by-side, above, below, transposed, etc. As illustrated, the analog indicators are positioned above and to the sides of the digital indicators. In FIG. 22B, the analog displays may include colored warning sections, dashes indicating position on the graph, and digital information designating quantitate information form the graph. In FIG. 22B, for example, the pulse rate PR graph shows that from about 50 to about 140 beats per minute, the graph is either neutral or beginning to be cautionary, whereas outside those numbers the graph is colored to indicate a severe condition. Thus, as the dash moves along the arc, a caregiver can readily see where in the range of acceptable, cautionary, and extreme the current measurements fall.

Each analog indicator of the health indicator can include a dial that moves about an arc based on measured levels of monitored physiological parameters. As the measured physiological parameter levels increase the dial can move clockwise, and as the measured physiological parameter levels decrease, the dial can move counter-clockwise, or vice versa. In this way, a user can quickly determine the patient's status by looking at the analog indicator. For example, if the dial is in the center of the arc, the observer can be assured that the current physiological parameter measurements are normal, and if the dial is skewed too far to the left or right, the observer can quickly assess the severity of the physiological parameter levels and take appropriate action. Normal parameter measurements can also (or instead) be indicated when the dial is to the right or left, etc.

The dial can be implemented as a dot, dash, arrow, or the like, and the arc can be implemented as a circle, spiral, pyramid, or other shape, as desired. Furthermore, the entire arc can be lit up or only portions of the arc can be lit up based on the current physiological parameter measurement level. Furthermore, the arc can turn colors or be highlighted based on the current physiological parameter level. For example, as the dial approaches a threshold level, the arc and/or dial can turn from green, to yellow, to red, shine brighter, flash, be enlarged, move to the center of the display, or the like.

Different physiological parameters can have different thresholds indicating abnormal conditions. For example, some physiological parameters may have upper and lower threshold levels, while others only have an upper threshold or a lower threshold. Accordingly, each health indicator can be adjusted based on the physiological parameter being monitored. For example, the SpO2 health indicator can have a lower threshold that when met activates an alarm, while the respiration rate health indicator can have both a lower and upper threshold, and when either is met an alarm is activated. The thresholds for each physiological parameter can be based on typical, expected thresholds and/or user-specified thresholds.

The digital indicator can provide a numerical representation of the current levels of the physiological parameter the digital indicator may indicate an actual level or a normalized level and can also be used to quickly assess the severity of a patient condition. The display can include multiple health indicators for each monitored physiological parameter. The display can also include fewer health indicators than the number of monitored physiological parameters. The health indicators can cycle between different monitored physiological parameters.

Figure 23A:
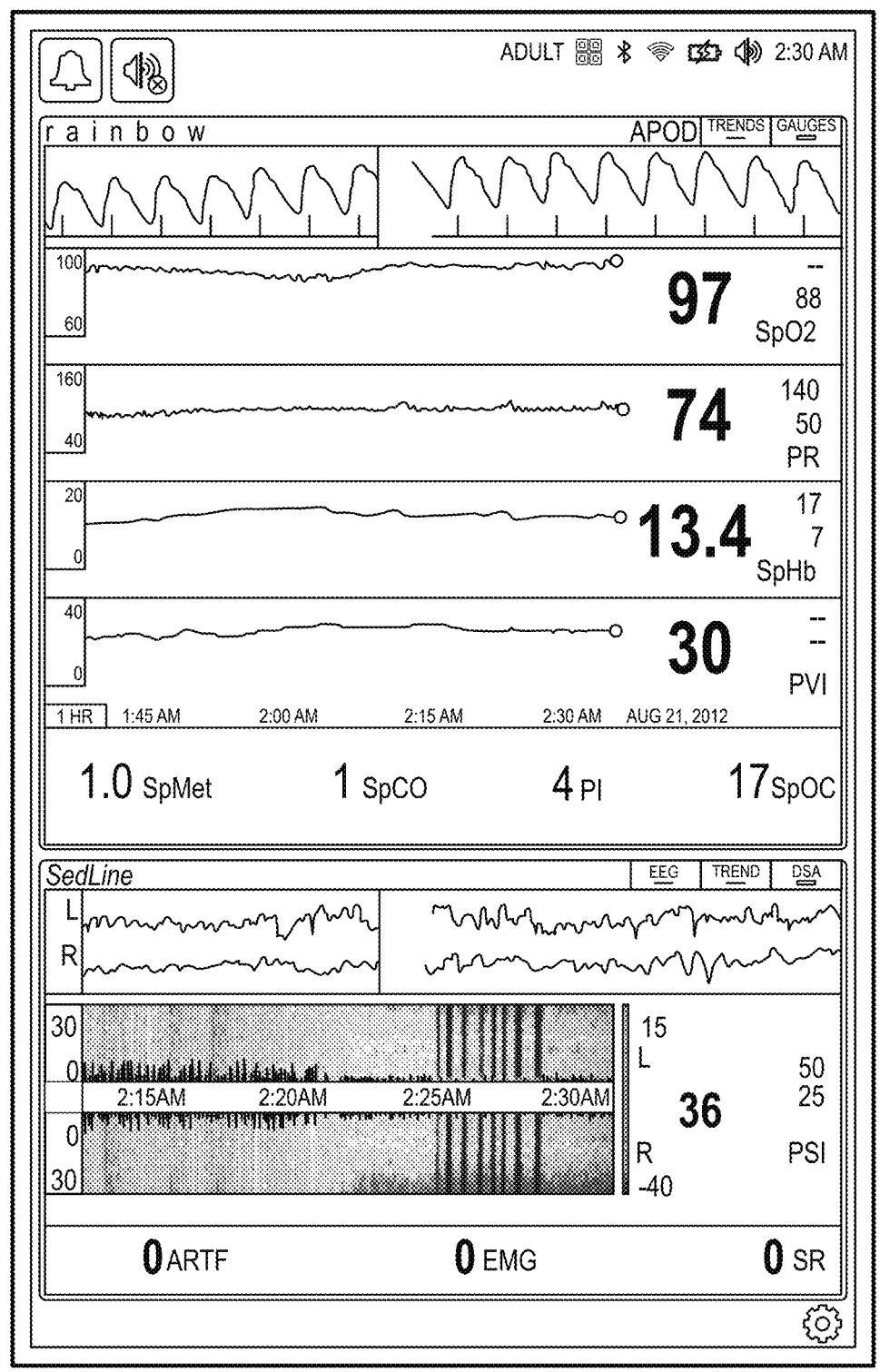
FIGS. 23A-23F illustrate example displays of measurement data showing, for example, data presentation in FIGS. 23A-23D when a depth of consciousness monitor is connected to a channel port of the hub of FIG. 1, data presentation in FIG. 23E when temperature and blood pressure sensors communicate with the hub of FIG. 1 and data presentation in FIG. 23F when an acoustic sensor is also communicating with the hub of FIG. 1.
Figure 23B:
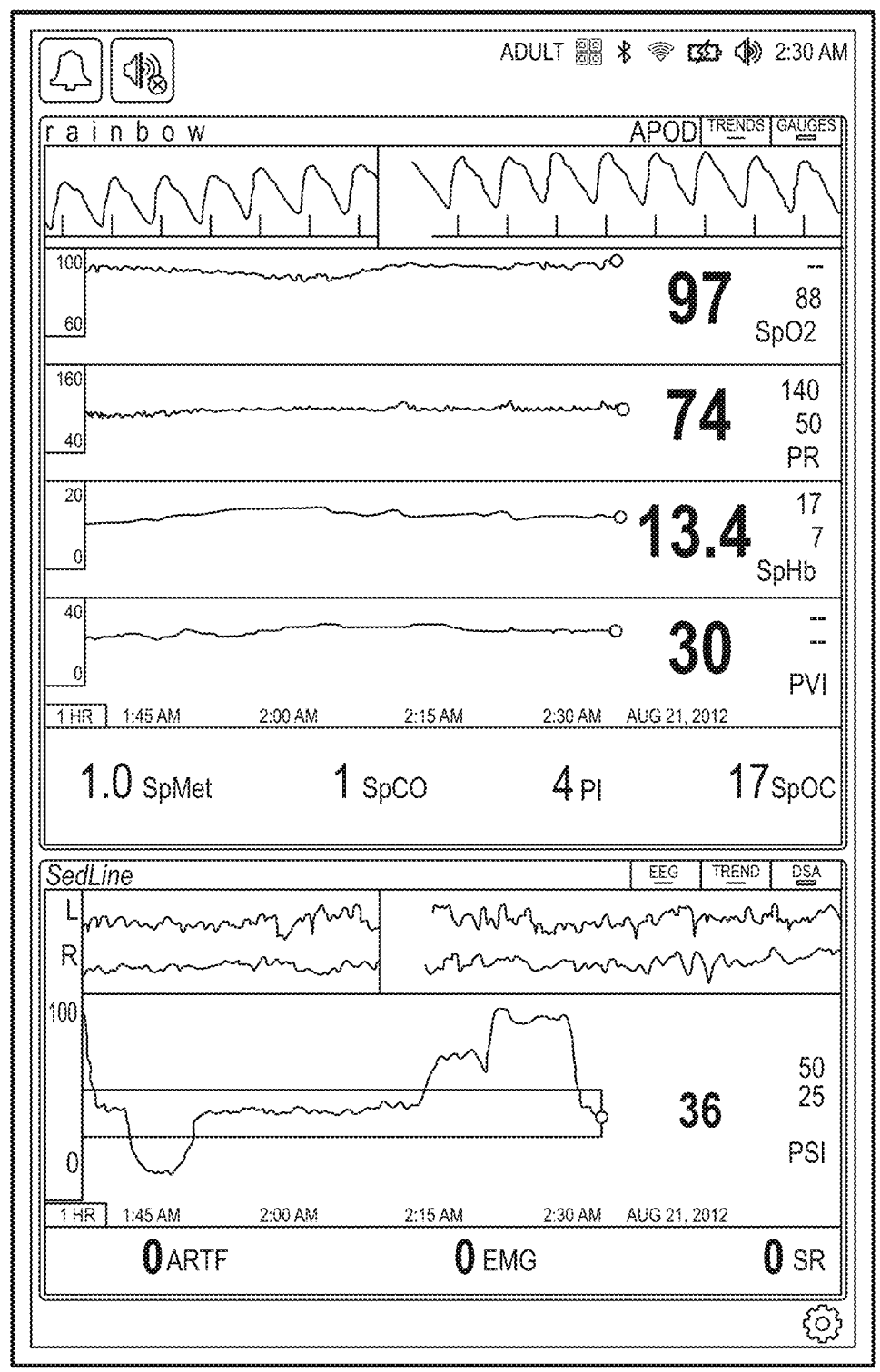
Figure 23C:
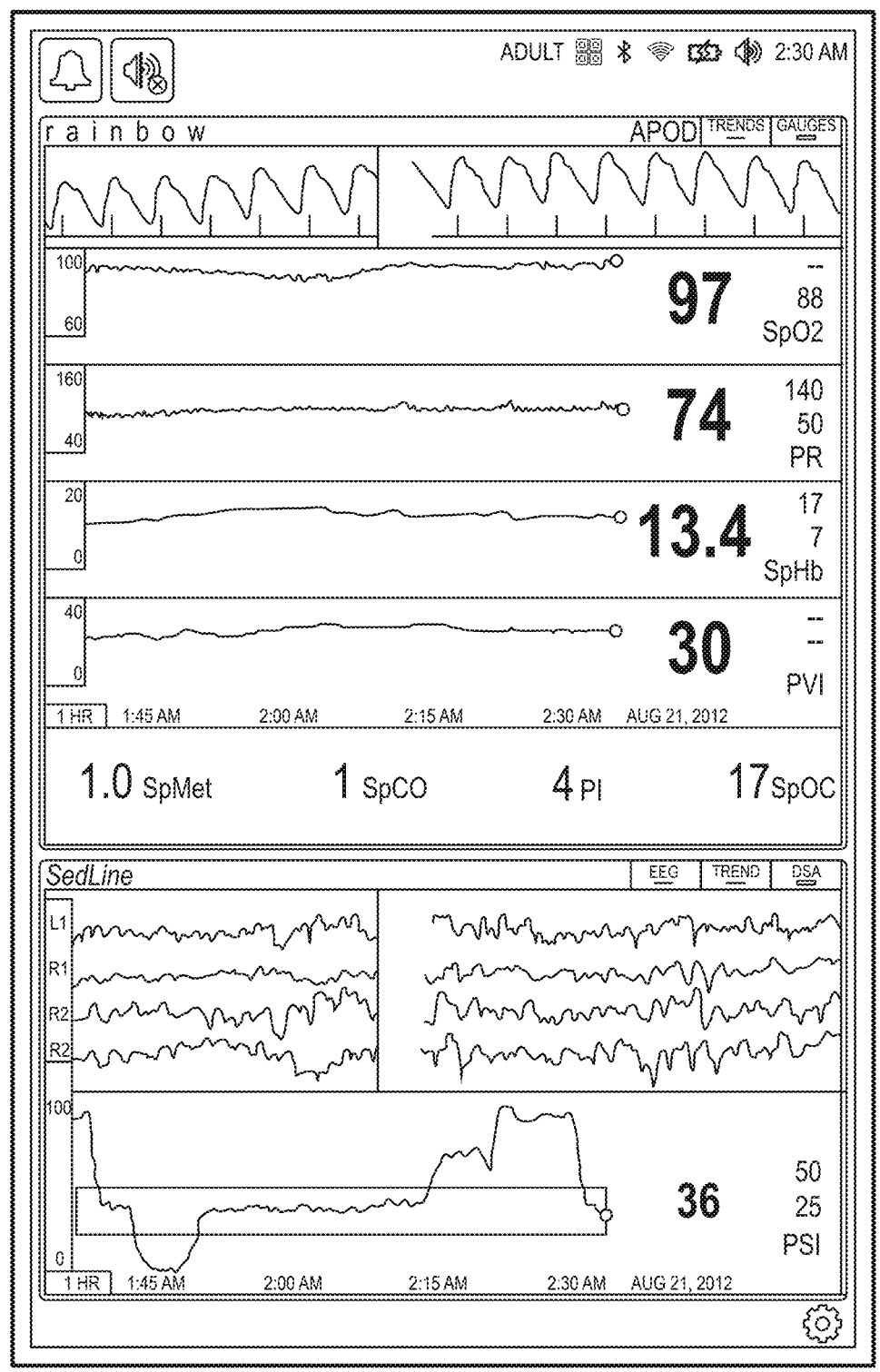
Figure 23D:
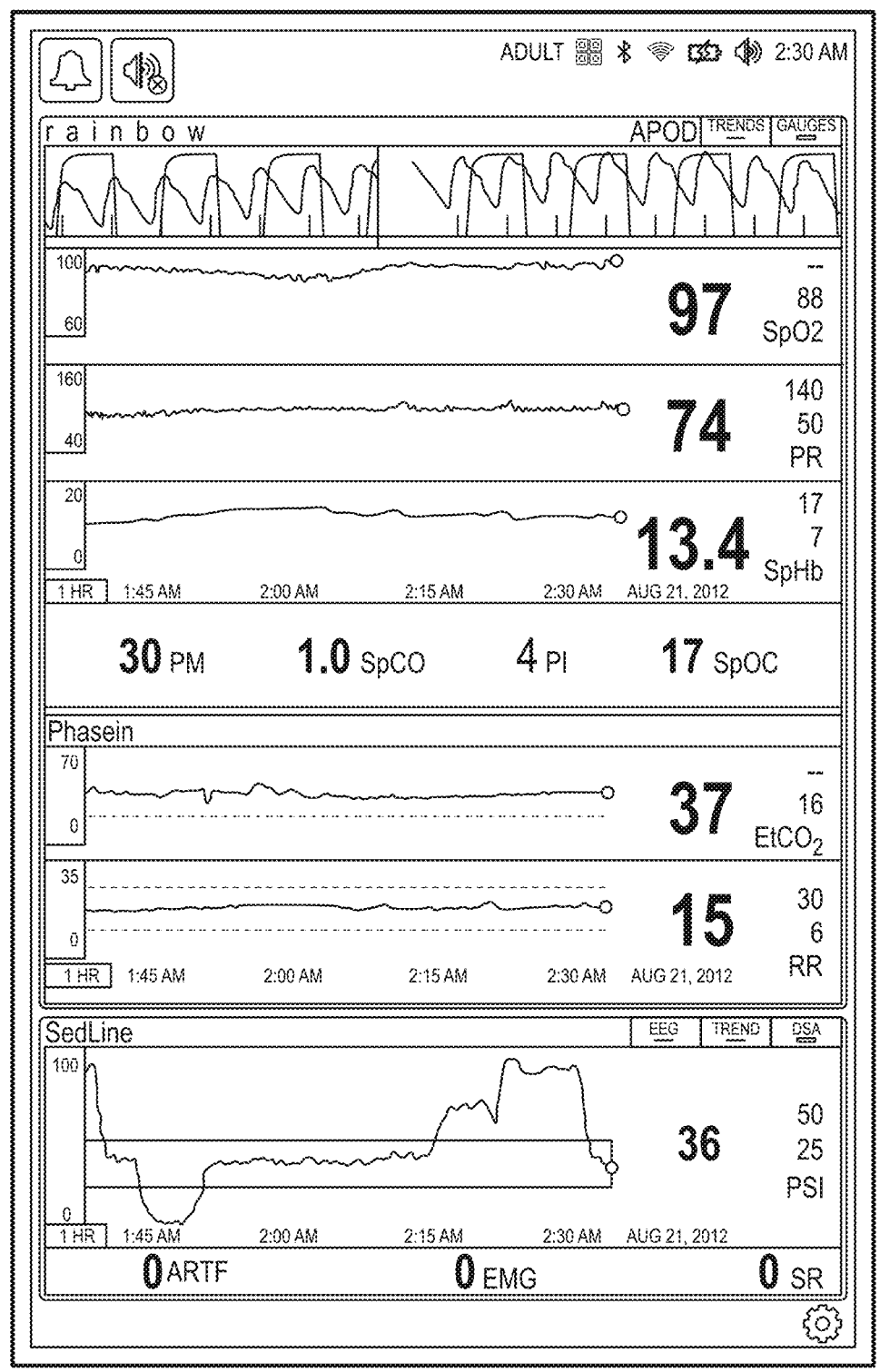
Figure 23E:
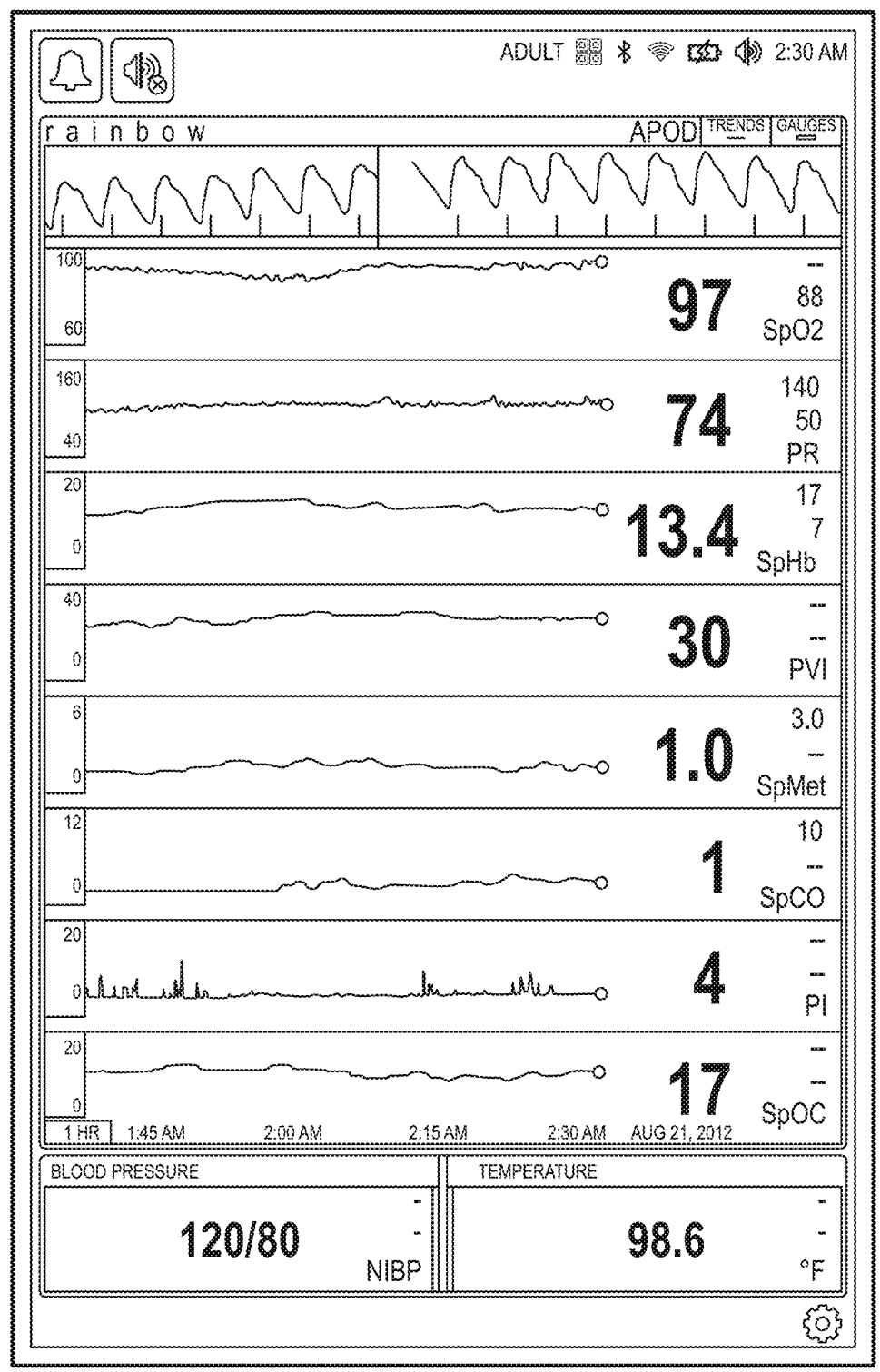
Figure 23F:
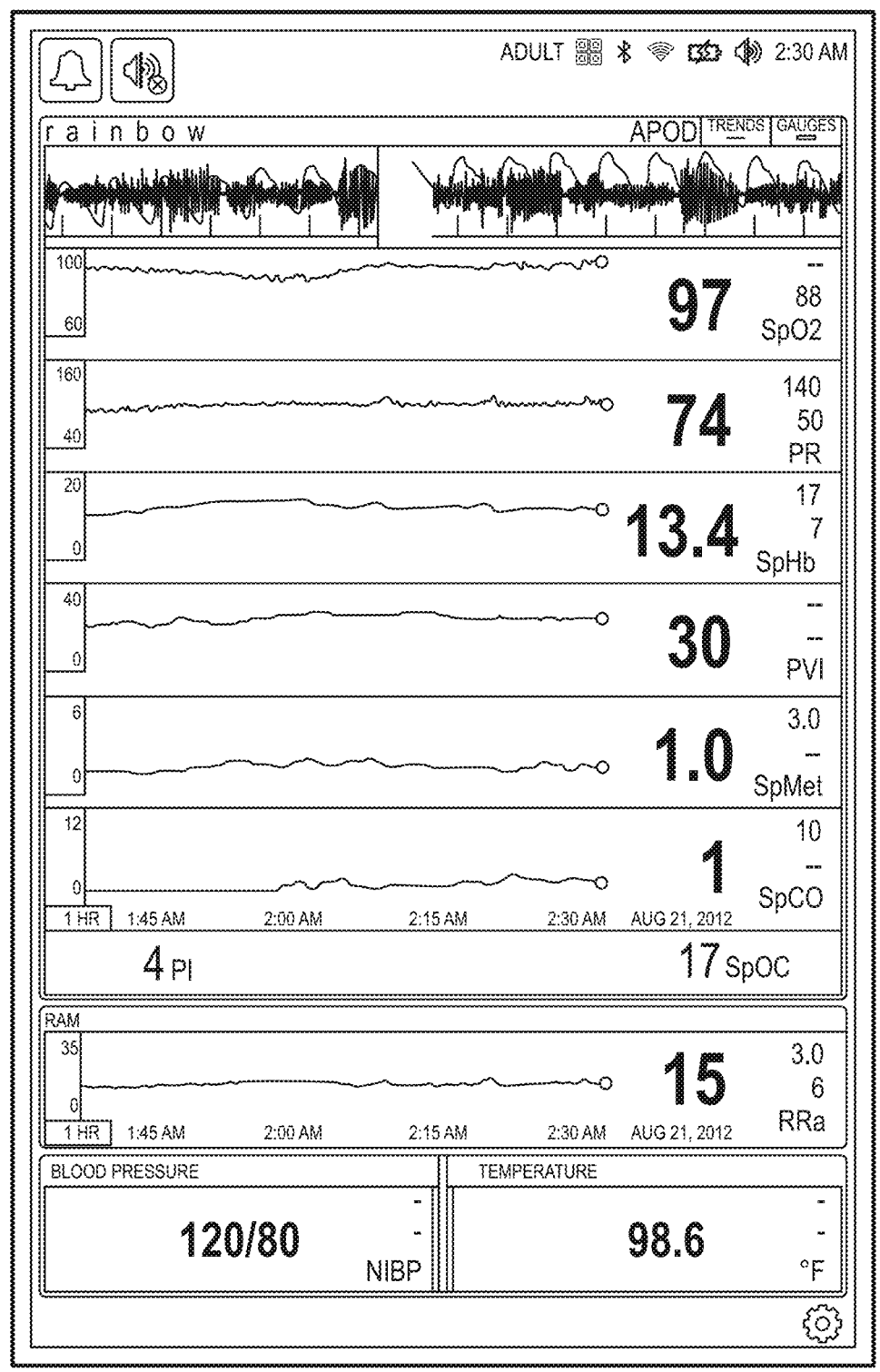

FIGS. 23A-23F illustrate example displays of measurement data showing, for example, data presentation in FIGS. 23A-23D when a depth of consciousness monitor is connected to a channel port of the hub of FIG. 1. As shown in FIGS. 23A-23C, the hub 100 can advantageously roughly bifurcates its display 104 to show various information from the, for example, SEDLine device, commercially available from Masimo Corp. of Irvine, Calif. In FIG. 23D, the hub 100 includes an attached PhaseIn device, commercially available by PHASEIN AB of Sweden, providing, for example, information about the patient's respiration. The hub 100 can also include the SEDLine information, so the hub 100 can divide the display 104 appropriately. In FIG. 23E, temperature and blood pressure sensors communicate with the hub of FIG. 1 and the hub 100 creates display real estate appropriate for the same. In FIG. 23F, an acoustic sensor is also communicating with the hub of FIG. 1, as well as the forgoing blood pressure and temperature sensor. Accordingly, the hub 100 adjust the display real estate to accommodate the data from each attached device.

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The term "plethysmograph" includes it ordinary broad meaning known in the art which includes data responsive to changes in volume within an organ or whole body (usually resulting from fluctuations in the amount of blood or air it contains).

III. Additional Monitoring Environment Examples

Figure 24:
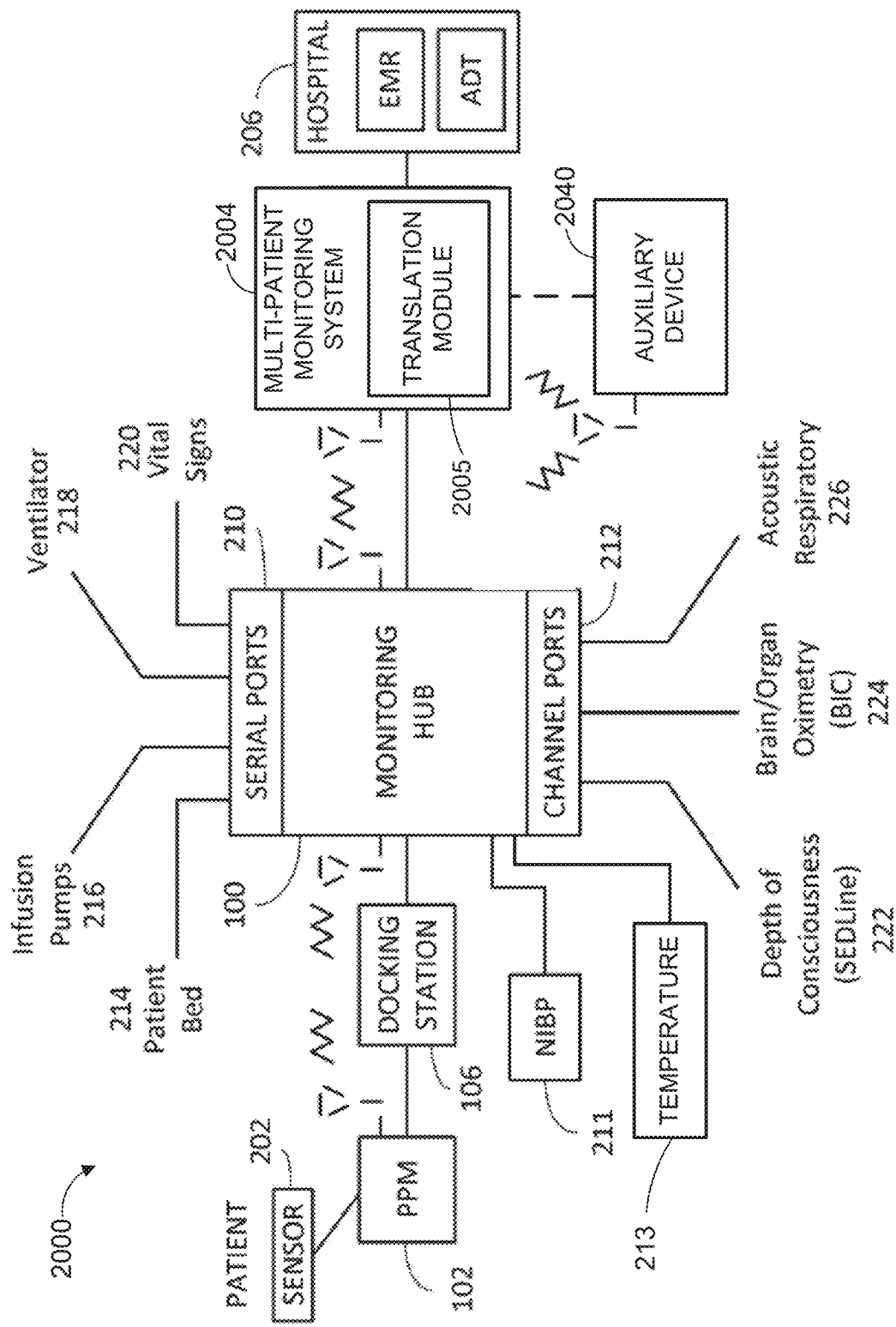
FIG. 24 illustrates another example of a monitoring environment including the hub of FIG. 1.

FIG. 24 illustrates another monitoring environment 2000 including the hub 100 of FIG. 1. The monitoring environment 2000 may include all the features of the monitoring environment 200 of FIG. 2, as well as any of the other features described above. In addition, the monitoring environment 2000 depicts another multi-patient monitoring system 204, namely, the multi-patient monitoring system (MMS) 2004. The MMS 2004 includes a translation module 2005 that can receive serial data, translate the serial data into a format recognizable by the monitoring hub 100, and provide the serial data to the monitoring hub 100 (among possibly other devices). Also shown is an auxiliary device 2040 that may communicate with the MMS 2004, the monitoring hub 100, or the PPM 102, wired or wirelessly.

As described above, the hub 100 may receive serial data from a variety of medical equipment, including the patient's bed 214, infusion pumps 216, a ventilator 218, and other vital signs monitors 220. The hub 100 can pass serial data from these sources on to the MMS 2004. As described above, the MMS 2004 may then store the serial data in a caregiver backend system 206 such as an EMR system or ADT system.

The medical equipment providing this serial data may use a variety of different proprietary protocols, messaging infrastructure, and the like that may not be natively recognizable by the hub 100. Accordingly, the hub 100 may not have native capability to read parameter values or other data from this medical equipment, and as a result, may not have the capability to display parameter values or other data from these devices. Advantageously, however, the translation module 2005 at the MMS 2004 can receive serial data from these devices, translate the serial data into a format recognizable by the monitoring hub 100, and provide the serial data to the monitoring hub 100. The monitoring hub 100 can then read parameter values and other data from the translated information and output these values or data to a display, such as any of the displays described above.

The translation module 2005 can apply one or more translation rules to the serial data to translate or transform the serial data from one format to another format. The serial data may be formatted according to a Health Level Seven ("HL7") protocol. The HL7 protocol has been developed to provide a messaging framework for the communication of clinical messages between medical computer systems and devices. However, the HL7 standard is quite flexible and merely provides a framework of guidelines. Consequently, medical devices or clinical computer systems that are all HL7-compliant may still be unable to communicate with each other. For example, the medical equipment 214-220 may each implement a version of the HL7 protocol, but these implementations may be different from an HL7 protocol implemented by the monitoring hub 100. Accordingly, the monitoring hub 100 may not be able to parse or read messages from the medical equipment 214-220, even though both use the HL7 standard. Further, the translation module 2005 may translate between different implementations of a common standard other than the HL7 protocol implemented by the hub 100 and medical equipment 214-220.

In addition to translating between different implementations of a common electronic medical communication protocol (e.g., different formatting of HL7 messages), the translation module 2005 can also translate between input and output messages adhering to different communication protocols. The translation module 2005 can be capable of responding to and translating messages from, for example, one medical communication protocol to a separate medical communication protocol. For example, the translation module 2005 can facilitate communication between messages sent according to the HL7 protocol, the ISO 11073 protocol, other open protocols, or proprietary protocols. Accordingly, the translation module 2005 can translate an input message sent according to the HL7 protocol to an output message according to a different protocol, or vice-versa. The translation module 2005 can implement any of the translation features described below in greater detail under the section entitled "Translation Module Embodiments," as well as further in U.S. application Ser. No. 14/032,132, filed Sep. 19, 2013, titled "Medical Monitoring System," the disclosure of which is hereby incorporated by reference in its entirety.

Advantageously, the translation module 2005 can pass translated serial data back to the hub 100 or PPM 102. Since the translated data is in a format readable by the hub 100 or PPM 102, the hub 100 or PPM 102 can output the data from the medical equipment 214-220 on the display of the hub 100 or PPM 102. In addition, the translation module 2005 can provide the translated data to devices other than the hub 100, including clinician devices (such as cell phones, tablets, or pagers) and an auxiliary device 2040 that will be described below. Moreover, since the serial data provided by the medical equipment 214-220 may include alarm notifications, the translation module 2005 can pass these alarm notifications to the hub 100 or PPM 102. The hub 100 or PPM 102 can therefore generate visual or audible alarms responsive to these alarm notifications. Further, the translation module 2005 can provide the alarm notifications to clinician devices, e.g., over a hospital network or wide area network (such as the Internet). In addition, the translation module 2005 can provide the alarm notifications to the auxiliary device 2040.

The translation module 2005 is shown as implemented in the MMS 2004 because it may be beneficial to maintain and update the translation rules of the translation module 2005 in a single location. However, the translation module 2005 may also be (or instead be) implemented in the hub 100 or PPM 102. Accordingly, the hub 100 or PPM 102 can access an internal translation module 2005 to translate serial data for output to the display of the hub 100 or PPM 102.

The auxiliary device 2040 can be a computing device having physical computer hardware, a display, and the like. For example, the auxiliary device 2040 may be a handheld computing device used by a clinician, such as a tablet, laptop, cellphone or smartphone, personal digital assistant (PDA), a wearable computer (such as a smart watch or glasses), or the like. The auxiliary device 2040 may also be simply a display device, such as a computer monitor or digital television. The auxiliary device 2040 can provide second screen functionality for the hub 100, PPM 102, or MMS 2004. As such, the auxiliary device 2040 can communicate wirelessly or through a wired connection with the hub 100, MMS 2004, or PPM 102.

As a second screen device, the auxiliary device 2040 can depict a copy of at least a portion of the display of the hub 100 (or the PPM 102) or a different version of the hub 100 (or the PPM 102) display. For instance, the auxiliary device 2040 can receive physiological parameter data, trend data, or waveforms from the hub 100, PPM 102, or MMS 2040 and display the parameter data, trend data, or waveforms. The auxiliary device 2040 can output any information available to the hub 100, PPM 102, or MMS 2004. One use of the auxiliary device 2040 is as a clinician device usable by a clinician to view data from the hub 100, PPM 102, or MMS 2004 while away from a patient's room (or even while in a patient's room). A clinician can use the auxiliary device 2040 to view more detailed information about physiological parameters than is displayed on the hub 100 or PPM 102 (see, e.g., FIG. 39). For instance, the auxiliary device 2040 may include zoom functionality or the like that enables a clinician to zoom into trends or waveforms to more closely inspect parameter activity.

One example reason for copying at least a portion of the display of the hub 100 or PPM 102 is to enable different clinicians to have the same view of the data during a surgical procedure. In some surgical procedures, for instance, two anesthesiologists monitor a patient, one anesthesiologist monitoring the brain function and brain oxygenation of the patient, while the other monitors peripheral oxygenation of the patient. A brain sensor, such as has been described above, may be attached to the patient and provide brain monitoring and oxygenation data that is output to the hub 100 or the PPM 102 for presentation to the first anesthesiologist. A finger or toe/foot optical sensor can also be attached to the patient and output data to the hub 100 or PPM 102. The hub 100 or PPM 102 can transmit this data to the auxiliary device 2040, which the second anesthesiologist can monitor to observe oxygenation in the patient's peripheral limbs. The second anesthesiologist may also need to know the oxygenation at the brain to help interpret the seriousness or lack thereof of poor peripheral oxygenation values. However, in many surgical procedures, a curtain or screen is placed over the patient as part of the procedure, blocking the second anesthesiologist's view of the hub 100 or PPM 102. Accordingly, the hub 100 or PPM 102 can output a copy of at least a portion of its display to the auxiliary device 2040 so that the second anesthesiologist can monitor brain function or oxygenation.

The auxiliary device can have a larger display area than the display of the hub 100. For instance, the hub 100 may have a relatively smaller display, such as about 10 inches, while the auxiliary device 2040 may be a television monitor or the like that has a 40 inch or larger display (although any size display may be used for the auxiliary device 2040). The auxiliary device 2040 can be a television that can include a hardware module that includes a processor, memory, and a wireless or wired networking interface or the like. The processor can execute programs from the memory, including programs for displaying physiological parameters, trends, and waveforms on the display of the television. Since a television monitor can be larger than the hub 100, the television monitor version of the auxiliary device 2040 can display more fine detail of patient waveforms and trends (see, e.g., FIG. 39).

The auxiliary device 2040 may display one portion of any of the displays described herein while the hub 100 displays another portion thereof. For instance, the auxiliary device 2040 may display any of the anatomical graphics described above with respect to FIGS. 19A-19J, while the hub 100 displays any of the parameter displays described above with respect to FIGS. 20A-23F (or vice versa). Likewise, the auxiliary device 2040 may display the translated data received from the translation module 2005 while the hub 100 displays channel data (or vice versa). The auxiliary device 2040 can display both translated data and channel data (see, e.g., FIG. 38).

The auxiliary device 2040 can also perform at least some processing of physiological parameters, including any of the functionality of the monitoring hub 100. For instance, the auxiliary device 2040 may include the translation module 2005 and perform the features thereof.

Figure 25:
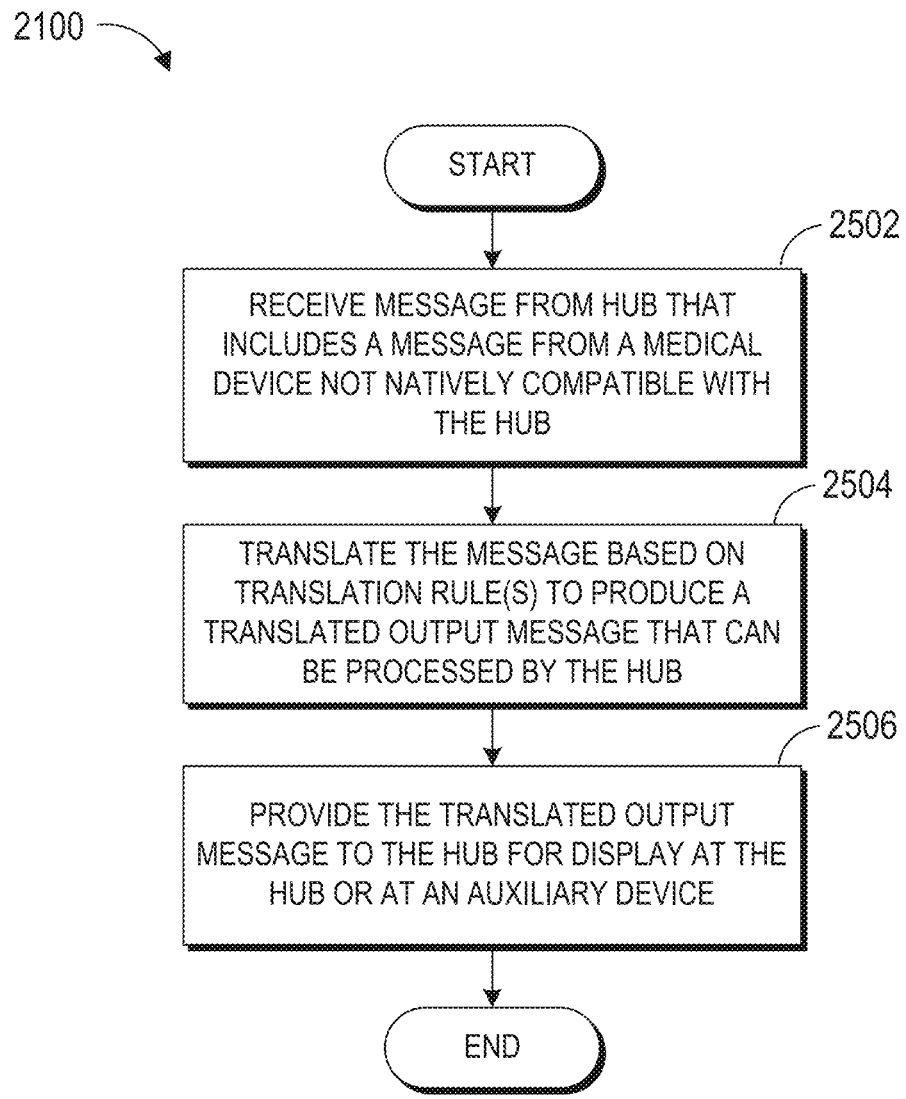
FIG. 25 illustrates an example of a translation message handling process.

FIG. 25 illustrates an example of a translation message handling process 2100. The process 2100 can be implemented by the translation module 2005 described above or by any other computing system. At block 2502, the translation module 2005 receives a message from the hub 100 (or PPM 102) that includes a message from a medical device not natively compatible with the hub 100 (or PPM 102). At block 2504, the translation module 2005 translate the message based on one or more translation rules to produce a translated output message that can be processed by the hub 100 (or PPM 102). At block 2506, the translation module provides the translated output message to the hub 100 for display at the hub 100 (or PPM 102) or at an auxiliary device 2040. The hub 100 (or PPM 102) may route the translated data to the auxiliary device 2040, or the auxiliary device 2040 may receive the translated data directly from the translation module 2005.

For example, a first medical device having digital logic circuitry receives a physiological signal associated with a patient from a physiological sensor, obtains a first physiological parameter value based on the physiological signal, and outputs the first physiological parameter value for display. The first medical device can also receive a second physiological parameter value from a second medical device other than the first medical device, where the second physiological parameter value is formatted according to a protocol not used by the first medical device, such that the first medical device is not able to process the second physiological parameter value to produce a displayable output value. The first medical device can pass the physiological parameter data from the first medical device to a separate translation module, receive translated parameter data from the translation module at the first medical device, where the translated parameter data is able to be processed for display by the first medical device, and output a second value from the translated parameter data for display. The first medical device may be, for example, the hub 100, PPM 102, or MMS 2004, and the second medical device may be the infusion pump 216 or ventilator 218 or the like.

FIGS. 26-38 and 46-71 illustrate additional example hub displays, including displays of measurement data. Each of these displays may be implemented by the auxiliary device 2040, although similar displays may also be output on the hub 100 (or PPM 102) directly. The example Figures shown are depicted as being implemented for a tablet computer that includes touchscreen functionality. Touchscreen functionality is optional and be replaced by other suitable input devices, such as keyboards, mice, track wheels, and the like.

Figure 26:
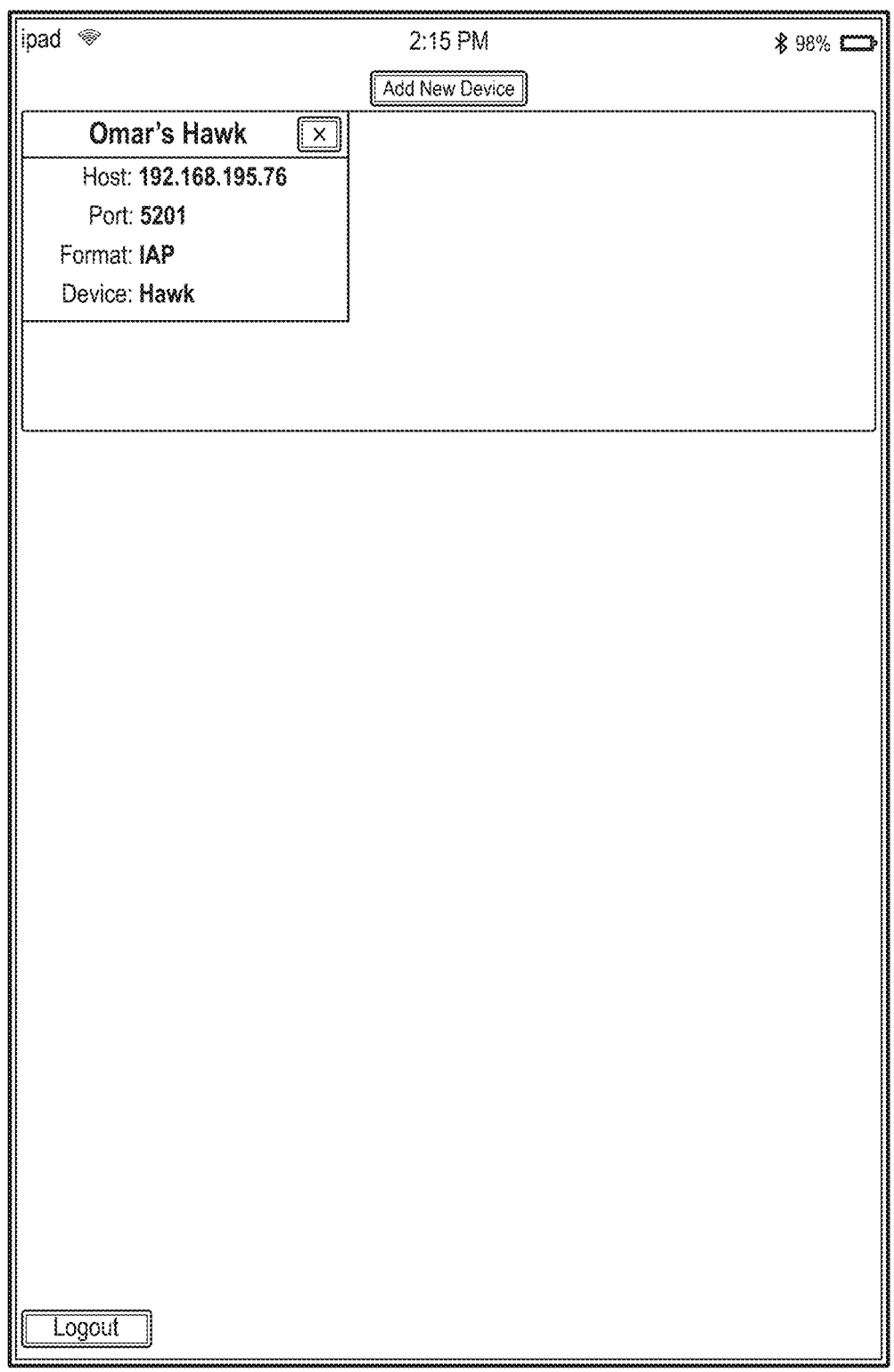
FIGS. 26-39 illustrate additional example hub displays, including displays of measurement data.

Turning to FIG. 26, the user interface shown depicts a device connected to the auxiliary device 2040. The device shown is "Omar's Hawk," which can be the monitoring hub 100. The auxiliary device 2040 is connected wirelessly to the hub 100 so as to receive data from the hub 100. The auxiliary device could also (or instead) connect wirelessly to the MMS 2004 or PPM 102.

Figure 27:
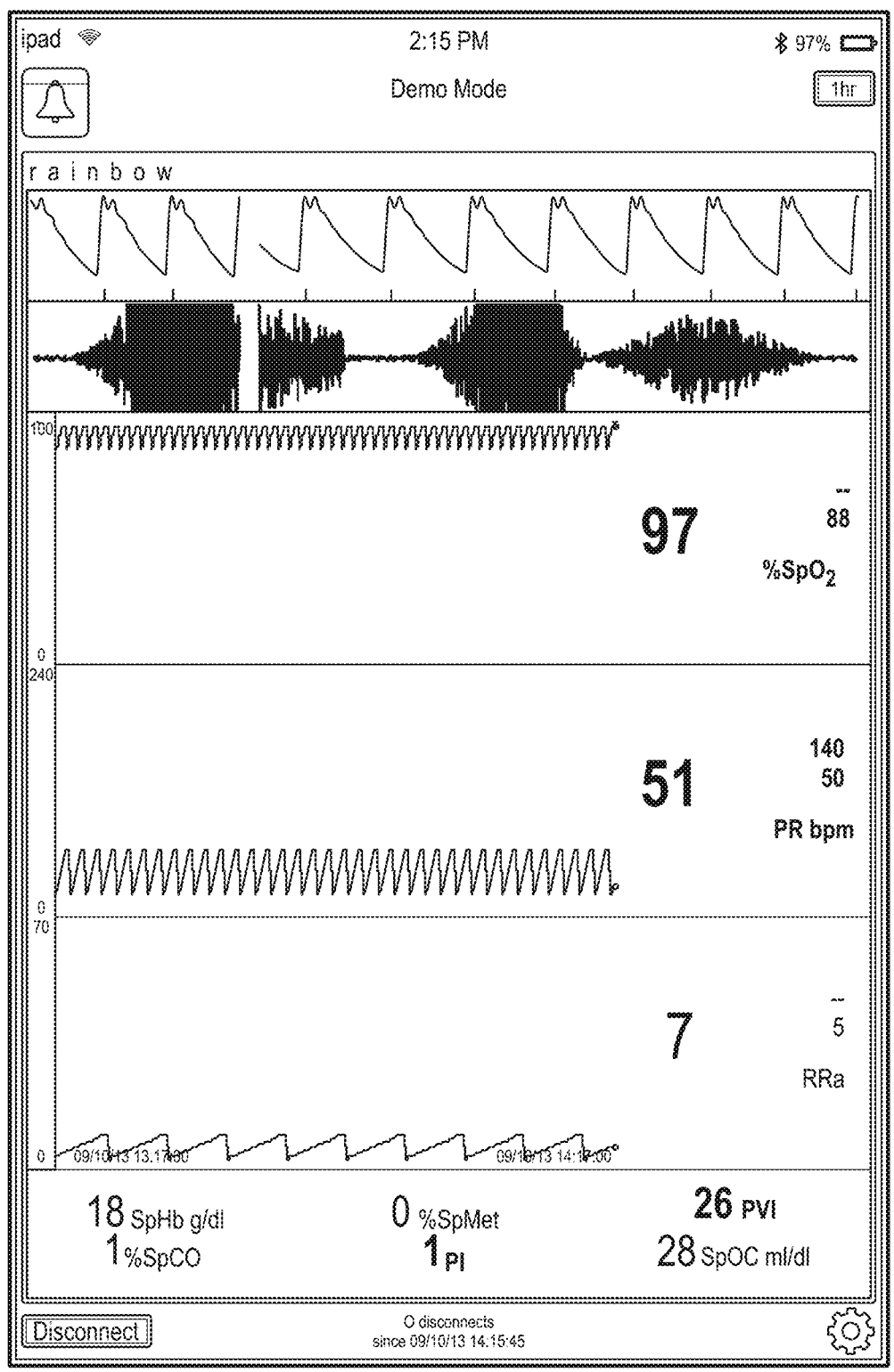
Figure 28:
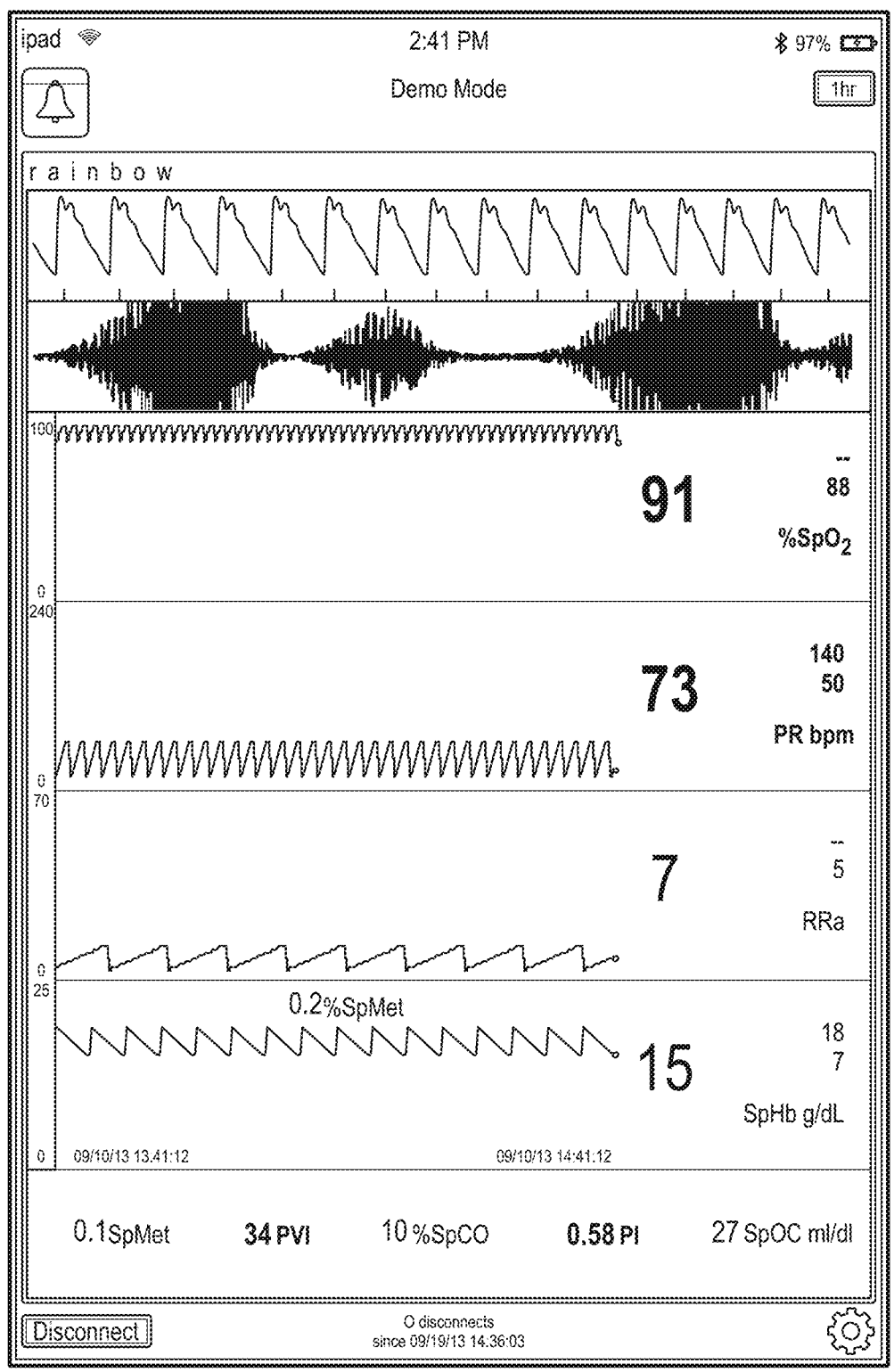

FIG. 27 depicts a default parameter view on the auxiliary device 2040. Parameter values are shown together with waveforms in an upper portion of the display, and other parameters (such as SpHb, SpMet, PVI, etc.) are shown at the bottom of the display without their corresponding waveforms. Any of these parameters at the bottom of the display may be dragged and dropped onto the upper portion of the display to cause their waveforms to be shown. For instance, FIG. 28 depicts a similar display as in FIG. 27 except that the SpHb parameter has been dragged and dropped onto the upper portion of the display, causing the SpHb waveform and additional details on alarm limits (18 and 7) to be shown. Similarly, FIG. 29 shows the same display as FIG. 28 except that the SpMet parameter has been dragged and dropped on the upper portion of the display, causing its waveform and alarm limit (3) to be shown.

Figure 29:
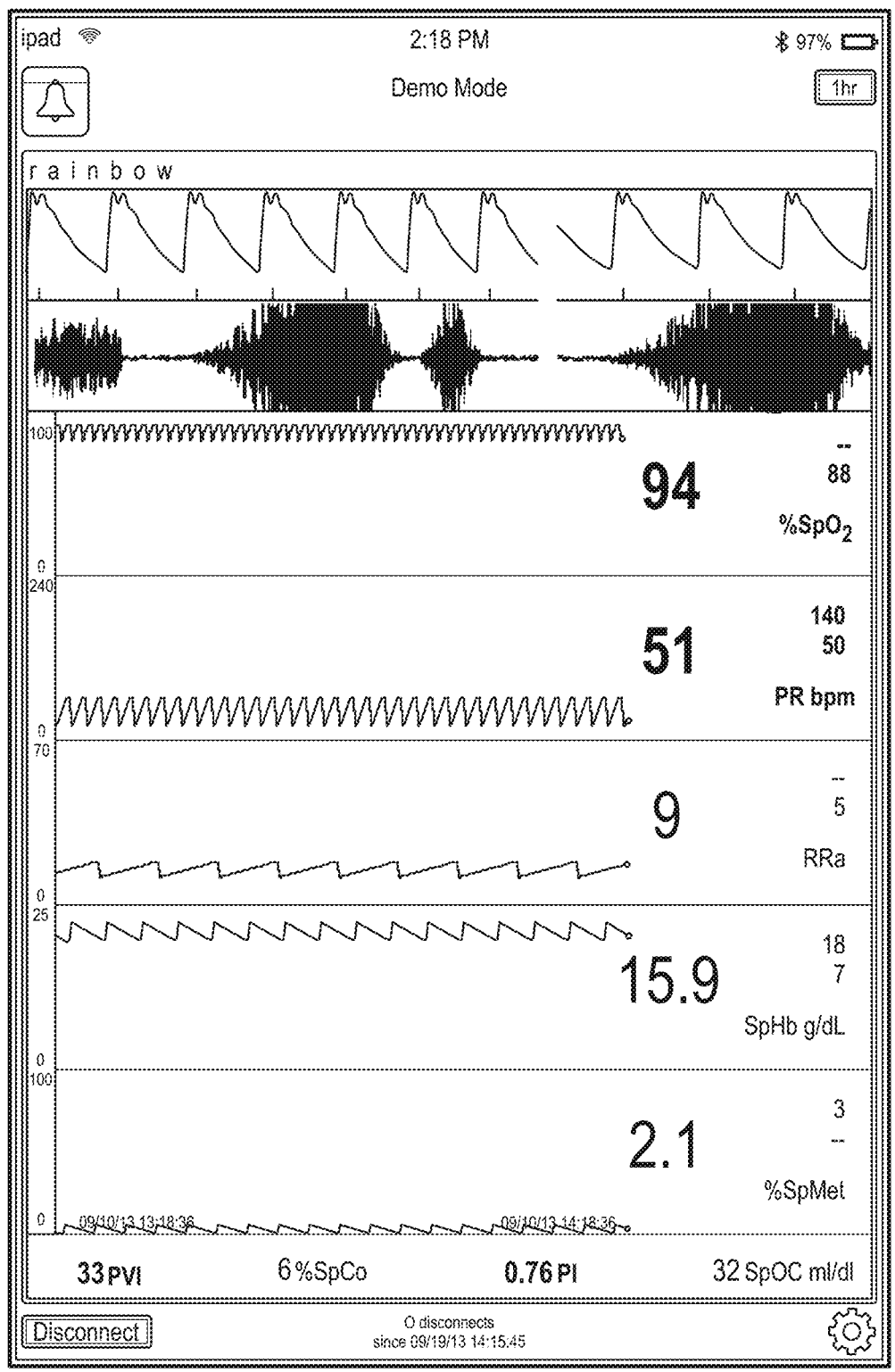
Figure 30:
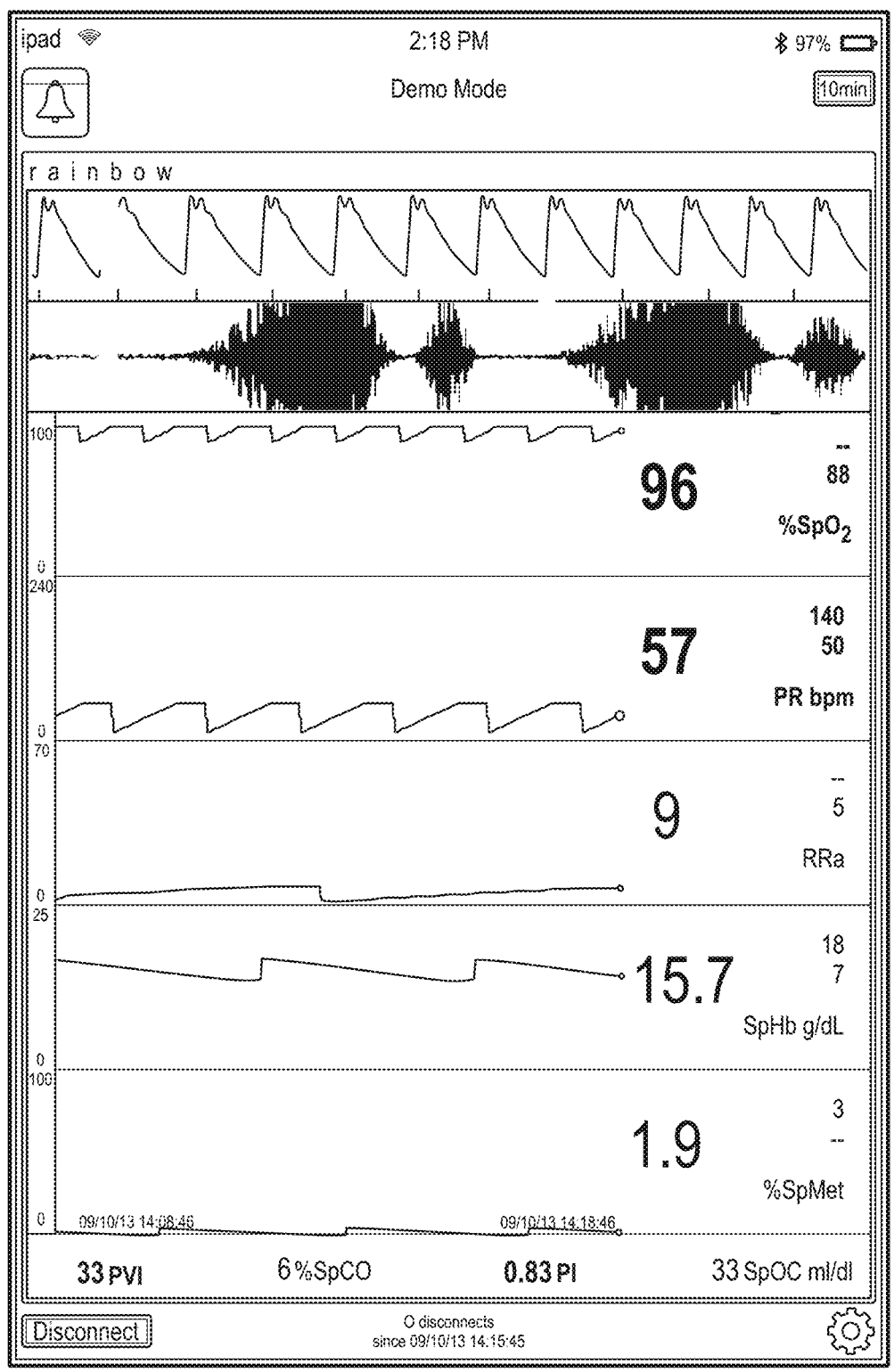

In each of the displays of FIGS. 27-29, a time window button is shown in the upper right corner. This time window button says "1 hr" in FIGS. 27-29 but may be selected by a user to change the time window, which can affect the window of trend or waveform data shown in the display. A user selection of this time window button and change to a 10 minute window is shown in FIG. 30. As can be seen, the waveforms in FIG. 30 are shown in a smaller window of time than in the previous Figures.

Figure 31:
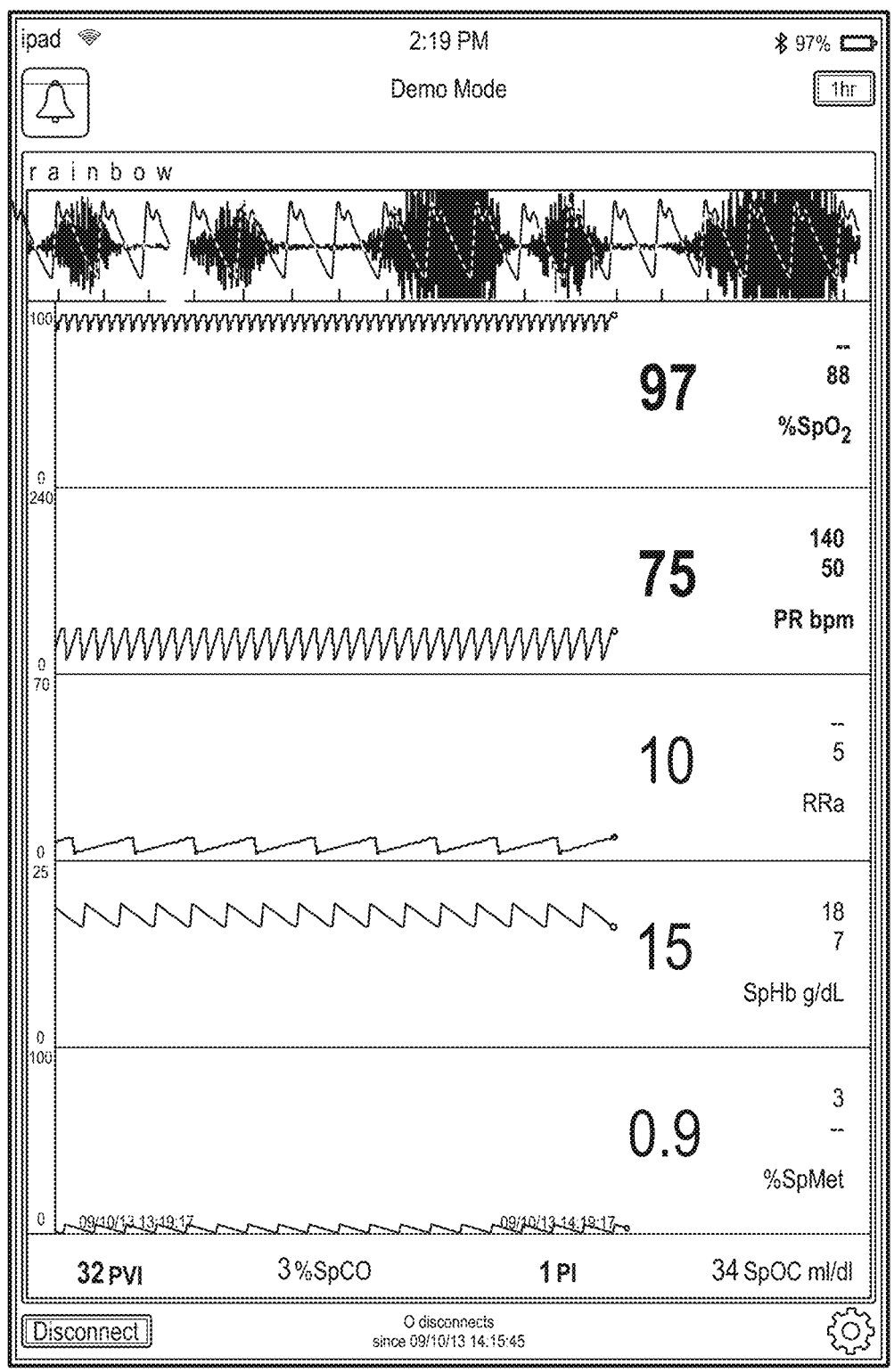
Figure 32:
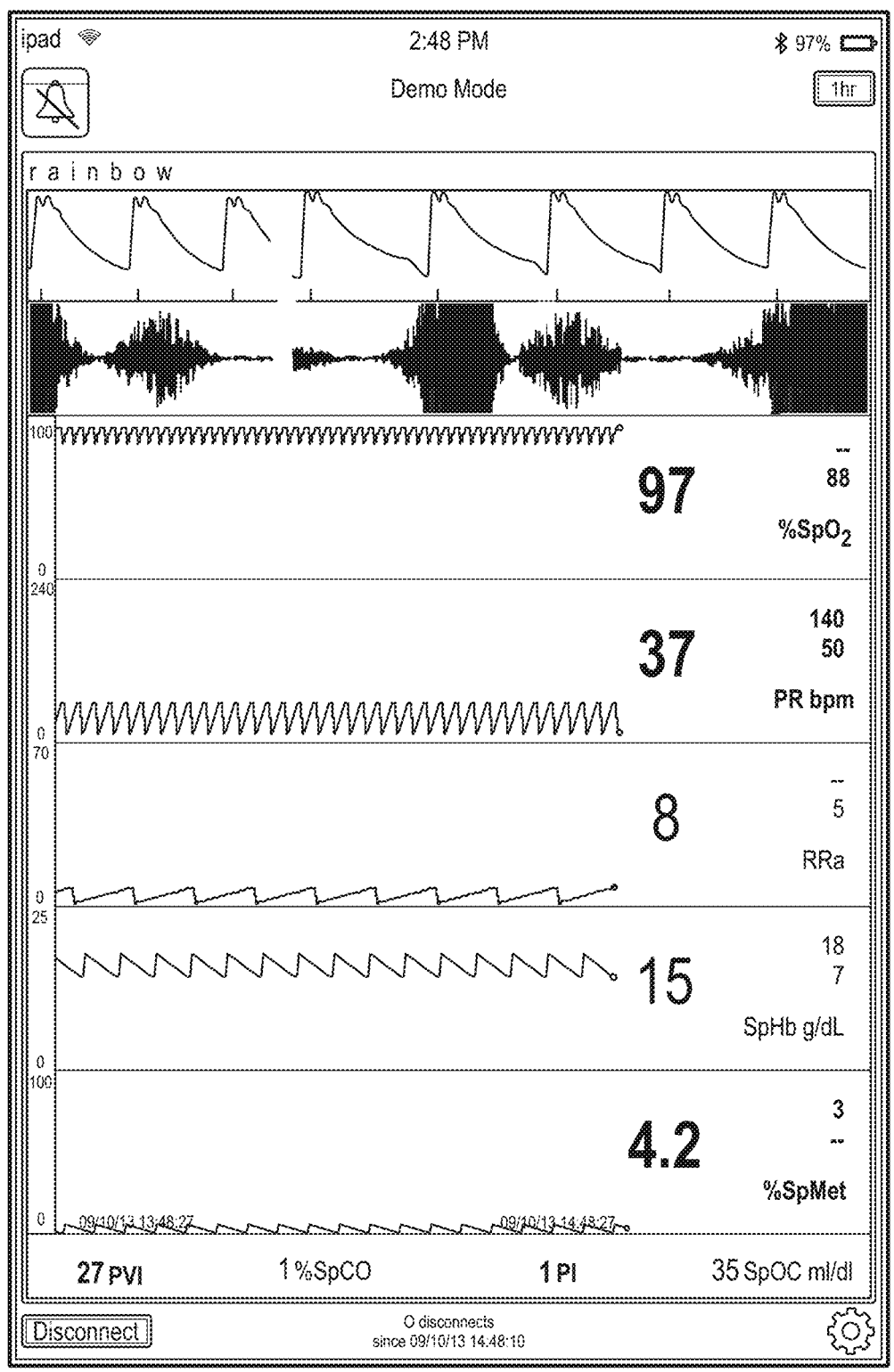

FIG. 31 shows another version of the display of FIG. 29 with stacked waveforms, including a stacked SpO2 and respiratory waveform, similar to other stacked waveforms described elsewhere herein. FIG. 32 shows a similar display to FIG. 29 with the pulse rate (PR) and SpMet (methemoglobin) parameters highlighted as being in alarm condition. The alarm condition can be represented as a red box around the parameter values and waveforms, or with red transparency coloring at least a portion of the box. The red box or transparency may also flash, and an audible alarm may sound. Other ways to represent an alarm condition can also be used.

Figure 33:
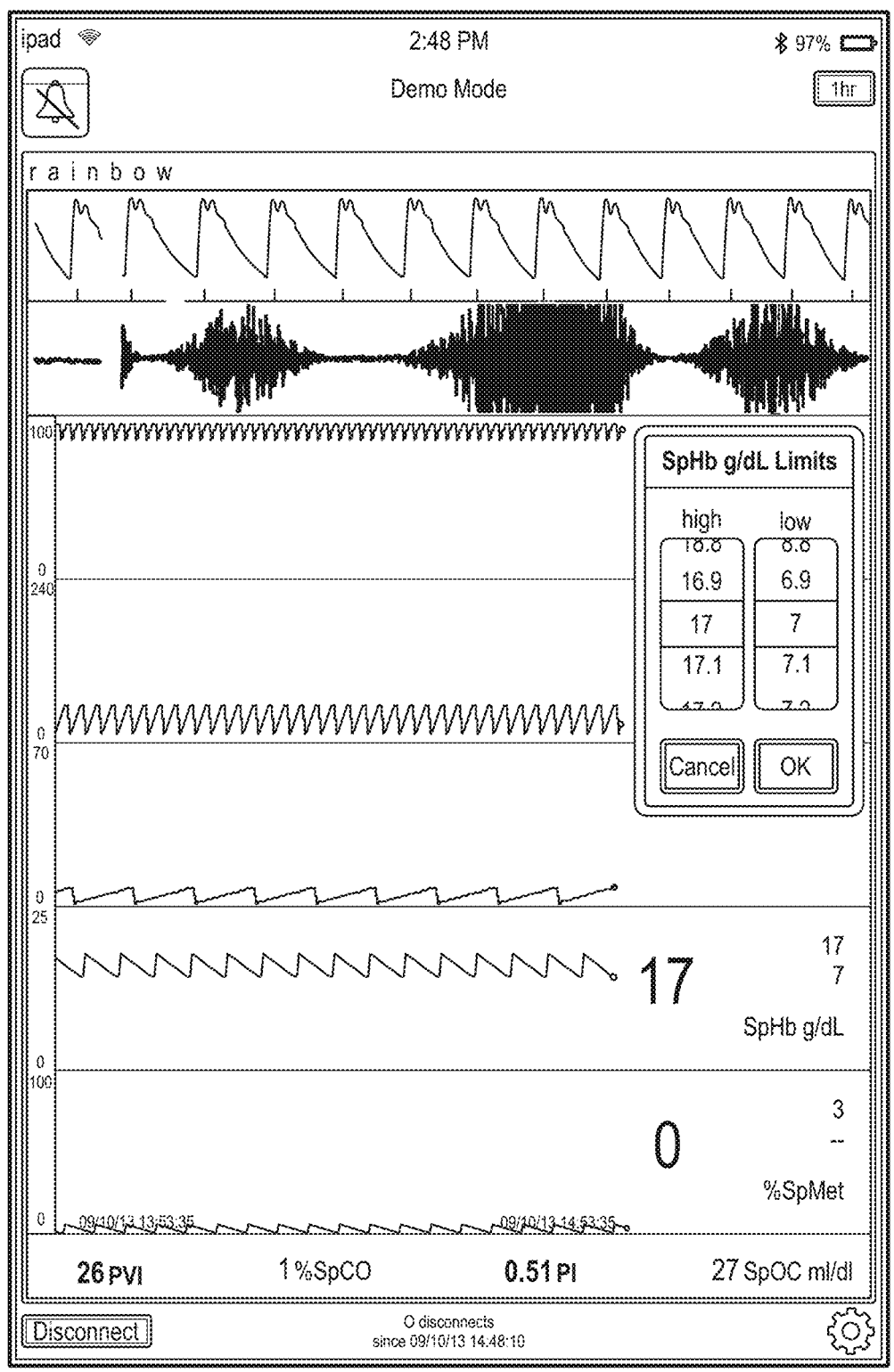

FIG. 33 shows a popup interface that enables a user to adjust alarm limits for a parameter (in this example, SpHb or total hemoglobin). The popup interface includes scroll wheels that allow a user to quickly scroll among and select possible parameter limit values.

Figure 34:
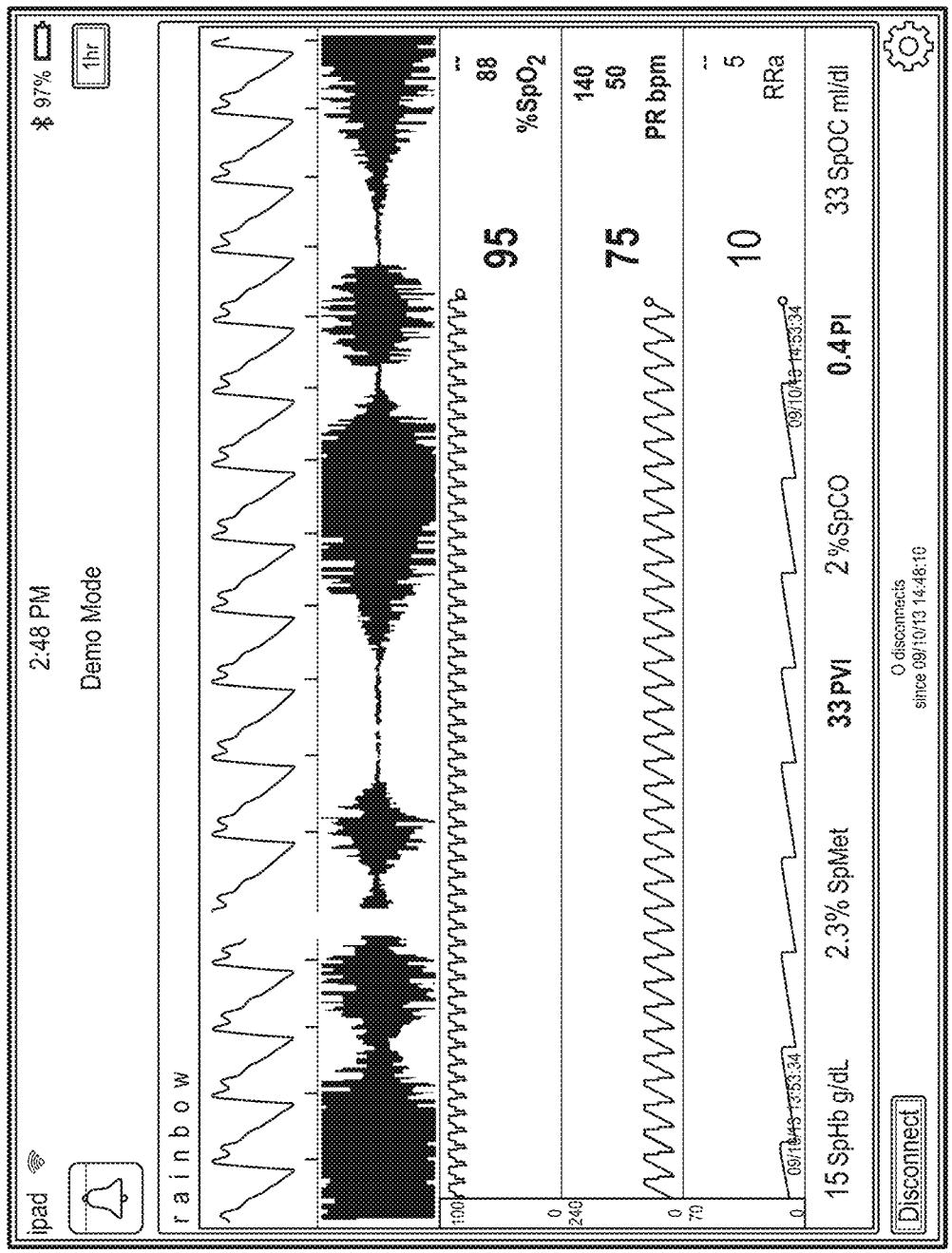
Figure 35:
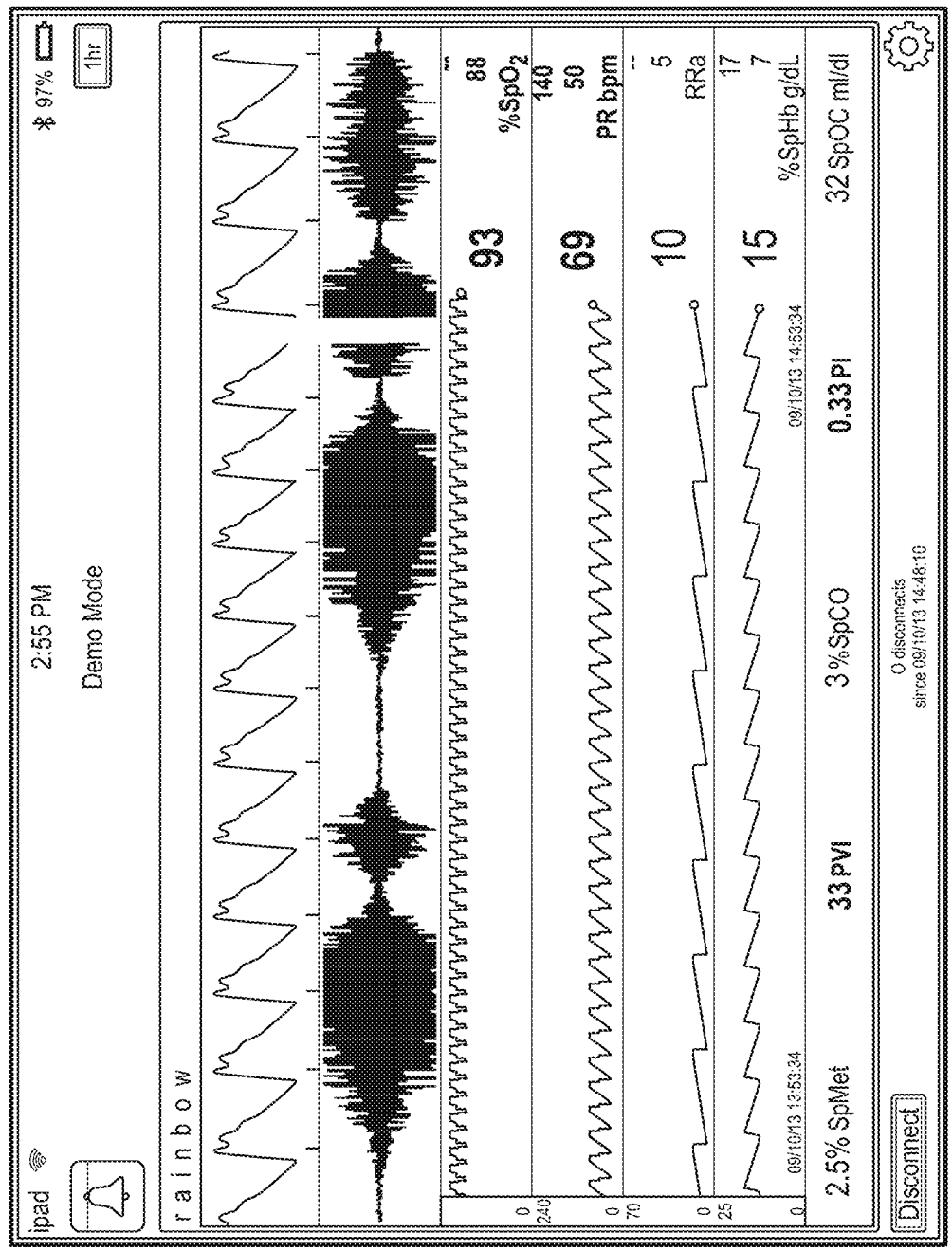
Figure 36:
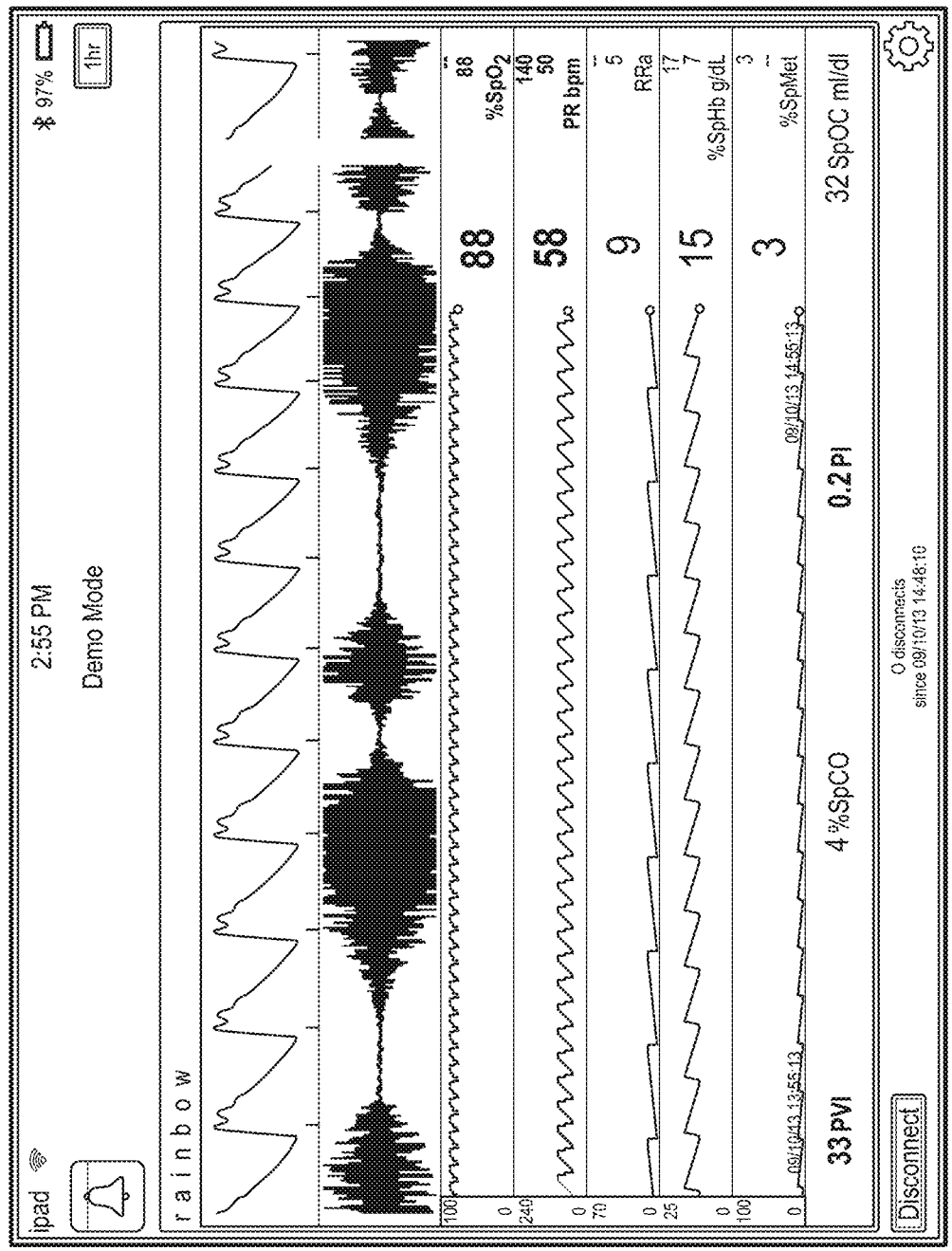
Figure 37:
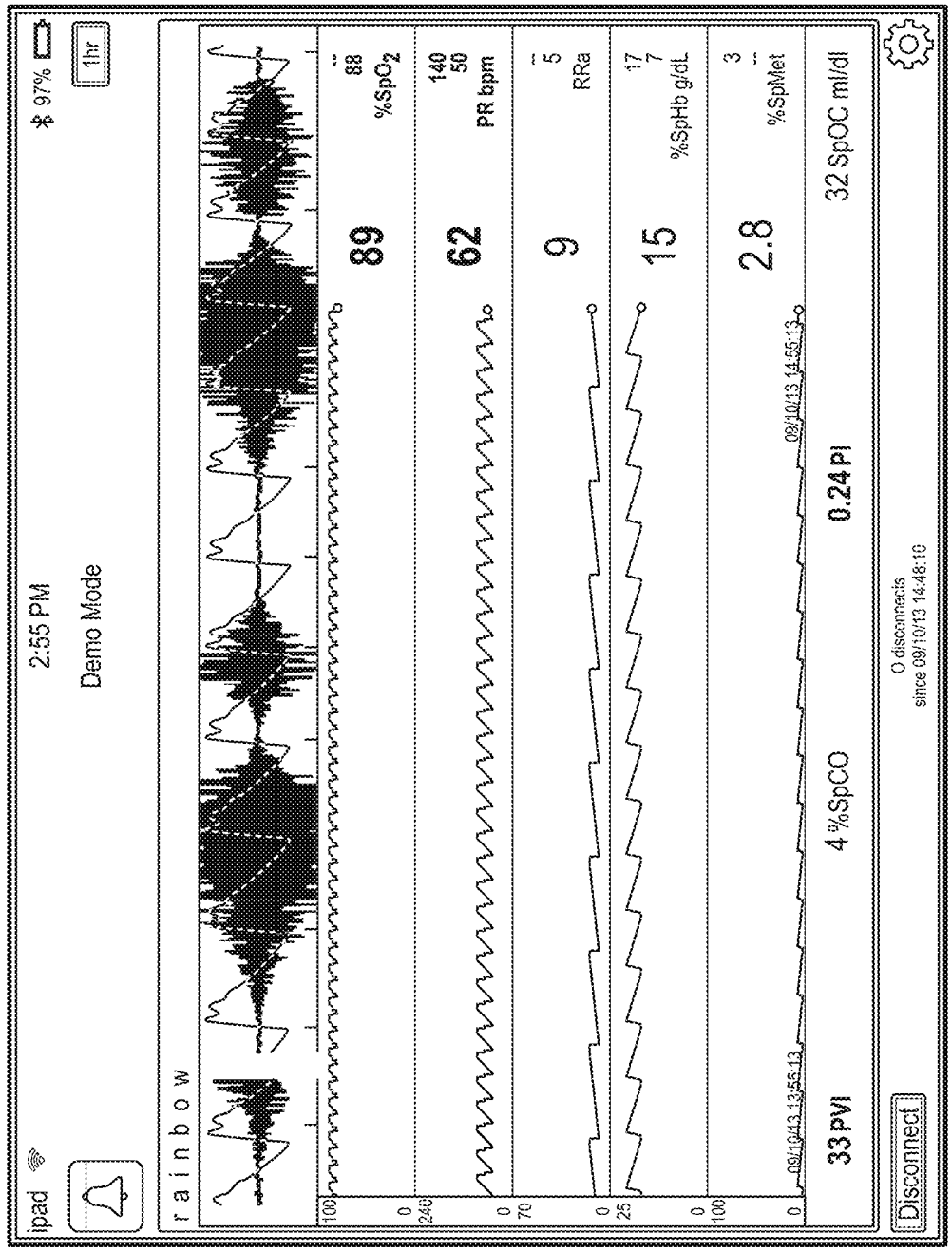
Figure 38:
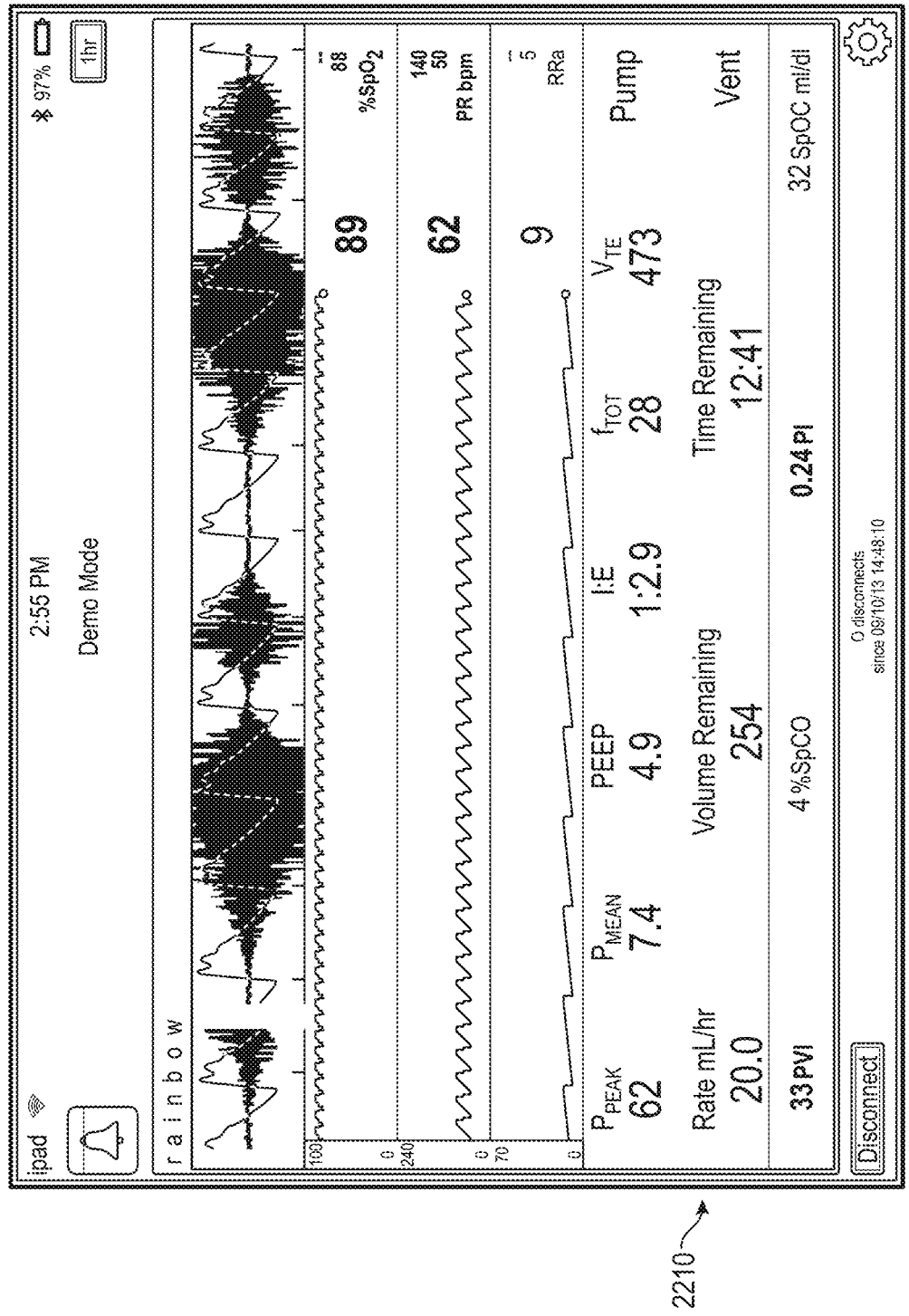

FIGS. 34-38 show landscape display views in contrast to the portrait-oriented displays of FIGS. 26-33. These landscape display views may be accessed by rotating the auxiliary device 2040 (such as tablet etc.) to a landscape orientation. FIG. 34 shows a first set of parameters, while FIGS. 35 and 36 add additional drag-and-dropped parameters with their waveforms and additional alarm limit details, similar to those described above with respect to FIGS. 27-29. FIG. 37 depicts stacked parameter waveforms, stacking SpO2 and respiratory waveforms. FIG. 38 depicts both channel parameters (such as SpO2, PR (pulse rate), and RRa (acoustically-measured respiratory rate)) while also showing translated serial data parameters 2210, including parameters from a pump and a vent. These translated serial data parameters 2210 may have been received from the translation module 2005, either through the hub 100 or directly from the MMS 2004.

Referring again to FIG. 24, as described above, the hub 100 or PPM 102 can output a copy of at least a portion of the display to the auxiliary device 2040. The hub 100 or PPM 102 can also (or instead) output data with respect to a subset of the full parameters shown on the hub 100 or PPM 102 to the auxiliary device 2040. For instance, the hub 100 or PPM 102 may provide functionality for a clinician to select one or more of the parameters displayed thereon to see just that one or more parameters displayed on the auxiliary device 2040. Doing so may allow the auxiliary device 2040 to show more detail about the selected one or more parameters because fewer parameters may be shown on the auxiliary device's 2040 display than on the hub 100 or PPM 102.

Figure 39:
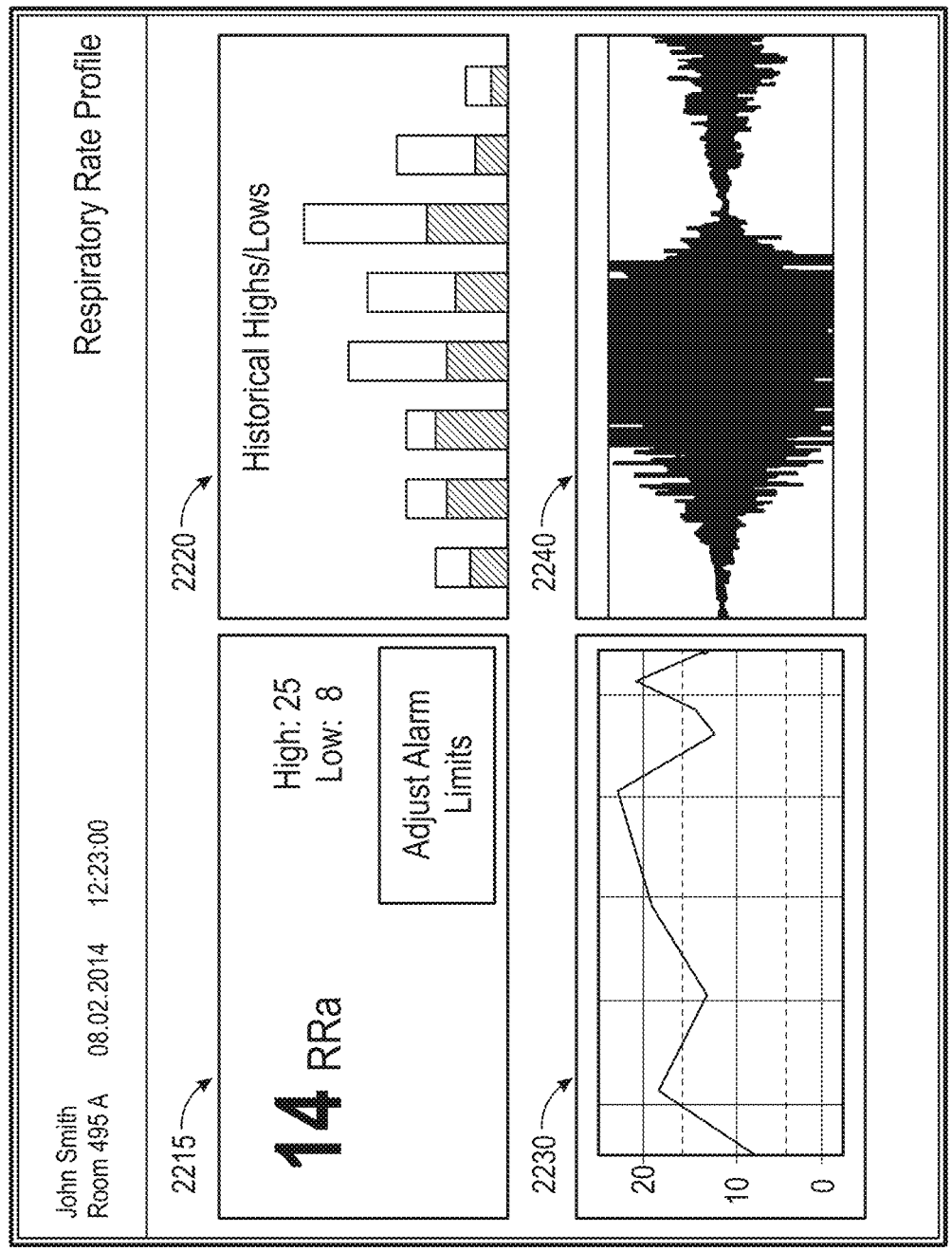

FIG. 39 depicts one example display of an auxiliary device 2040 that depicts data with respect to one parameter, respiratory rate. Unlike the main display of the hub 100 or PPM 102, the display shown in FIG. 39 includes more than just the current value 2215, a recent trend 2230, and small waveform of the respiratory rate. In addition, the display depicts a histogram 2220 of historical highs and lows (e.g., for the past several days) of the patient being monitored. In addition, a detailed waveform 2240 is shown, which may be larger than the waveforms shown on the main display of the hub 100 or PPM 102, which may give the user more detailed insight into the patient's respiratory condition. A user may choose to zoom into the waveform 2240 (or other aspects of the display), causing the waveform 2242 to be enlarged to fill the display in place of the other elements of the display, or the like. Other graphs, tables, waveforms, and data may be shown for the respiratory parameter on the auxiliary device display 2040. Of course, parameters other than respiratory rate may also be selected for detailed display on the auxiliary device 2040.

IV. Translation Module Examples

Any of the following features described with respect to FIGS. 40A through 45D can be implemented by the translation module 2005 of FIG. 24 or together with any of the devices described above with respect to FIG. 24.

Healthcare costs have been increasing and the demand for reasonably-priced, high-quality patient care is also on the rise. Health care costs can be reduced by increasing the effectiveness of hospital information systems. One factor which may affect the efficacy of a health institution is the extent to which the various clinical computer systems employed at the health institution can interact with one another to exchange information.

Hospitals, patient care facilities, and healthcare provider organizations typically include a wide variety of different clinical computer systems for the management of electronic healthcare information. Each of the clinical computer systems of the overall IT or management infrastructure can help fulfill a particular category or aspect of the patient care process. For example, a hospital can include patient monitoring systems, medical documentation and/or imaging systems, patient administration systems, electronic medical record systems, electronic practice management systems, business and financial systems (such as pharmacy and billing), and/or communications systems, etc.

The quality of care in a hospital or other patient care facility could be improved if each of the different clinical computer systems across the IT infrastructure (or even within the same hospital room; see, e.g., FIGS. 1 and 24) were able to effectively communicate with each other. This could allow for the exchange of patient data that is collected by one clinical computer system with another clinical computer system that could benefit from such patient data. For example, this may allow decisions relating to patient care to be made, and actions to be taken, based on a complete analysis of all the available information.

In current practice, individual clinical computer systems can be, and often are, provided by different vendors. As a result, individual clinical computer systems may be implemented using a proprietary network or communication infrastructure, proprietary communication protocols, etc.; the various clinical computer systems used in the hospital cannot always effectively communicate with each other.

Medical device and medical system vendors sometimes develop proprietary systems that cannot communicate effectively with medical devices and systems of other vendors in order to increase their market share and to upsell additional products, systems, and/or upgrades to the healthcare provider. Thus, healthcare providers are forced to make enterprise or system-wide purchase decisions, rather than selecting the best technology available for each type of individual clinical computer system in use.

One example where this occurs is in the area of life-saving technology available for patient monitoring. For example, many different bedside devices for monitoring various physiological parameters are available from different vendors or providers. One such provider may offer a best-in-class device for monitoring a particular physiological parameter, while another such provider may offer the best-in-class device for another physiological parameter. Accordingly, it may be desirable in some circumstances for a hospital to have the freedom to use monitoring devices from more than one manufacturer, but this may not be possible if devices from different manufacturers are incapable of interfacing and exchanging patient information. Accordingly, the ability to provide reasonably-priced, high-quality patient care can be compromised. In addition, since each hospital or patient care facility may also implement its own proprietary communication protocols for its clinical computer network environment, the exchange of information can be further hindered.

As described above, the Health Level Seven ("HL7") protocol has been developed to provide a messaging framework for the communication of clinical messages between medical computer systems and devices. The HL7 communication protocol specifies a number of standards, guidelines, and methodologies which various HL7-compliant clinical computer systems can use to communicate with each other.

The HL7 communication protocol has been adopted by many medical device manufacturers. However, the HL7 standard is quite flexible, and merely provides a framework of guidelines (e.g., the high-level logical structure of the messages); consequently, each medical device or medical system manufacturer or vendor may implement the HL7 protocol somewhat differently while still remaining HL7-compliant. For example, the format of the HL7 messages can be different from implementation to implementation, as described more fully herein. In some cases, the HL7 messages of one implementation can also include information content that is not included in messages according to another HL7 implementation. Accordingly, medical devices or clinical computer systems that are all HL7-compliant still may be unable to communicate with each other.

Consequently, a translation module can be provided that can improve the communication of medical messages between medical devices or systems that use different allowed implementations of an established communication protocol (e.g., HL7), thereby increasing the quality of patient care through the integration of multiple clinical computer systems.

Figure 40A:
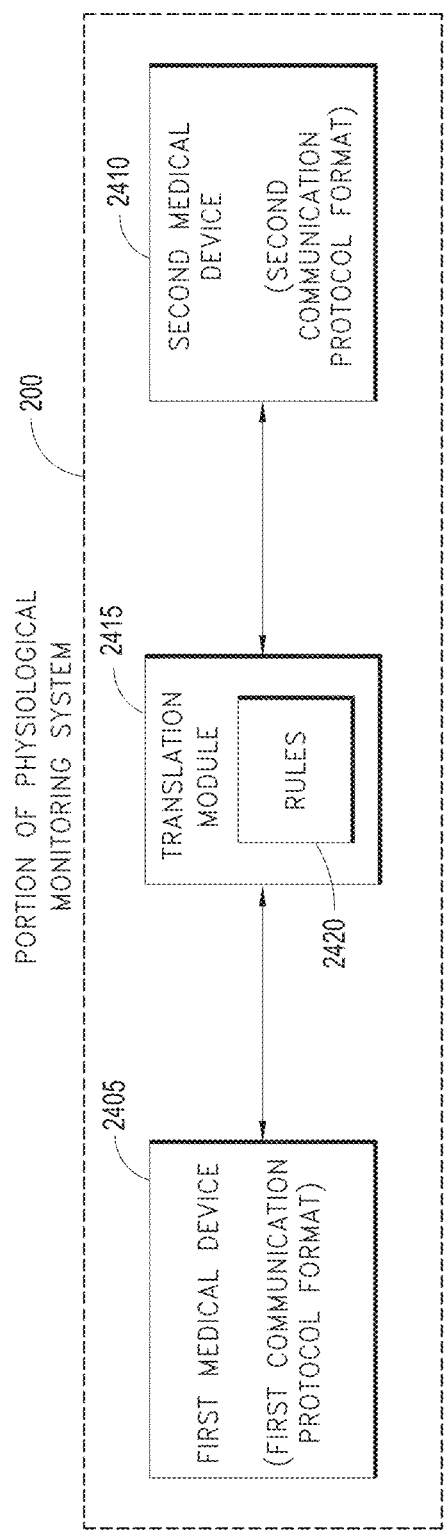
FIG. 40A illustrates an example first medical device and an example second medical device that communicate with one another via a translation module.

FIG. 40A illustrates a first medical device 2405 and a second medical device 2410 that communicate with one another via a translation module 2415. The first medical device 2405 is configured to transmit and receive messages according to a first allowed format or implementation of an accepted electronic medical communication protocol, while the second medical device 2410 is configured to transmit and receive messages according to a second allowed format or implementation of the electronic medical communication protocol. The first and second protocol formats can be different implementations of the HL7 communication protocol. Other electronic medical communication protocols besides HL7 can also be used.

The translation module 2415 receives input messages having the first protocol format from the first medical device 2405 and generates output messages to the second medical device 2410 having the second protocol format. The translation module 2415 also receives input messages having the second protocol format from the second medical device 2410 and generates output messages to the first medical device 2405 having the first protocol format. Thus, the translation module 2415 can enable the first and second medical devices 2405, 2410 to effectively and seamlessly communicate with one another without necessarily requiring modification to the communication equipment or protocol implemented by each device.

The translation module 2415 can determine the protocol format expected by an intended recipient of the input message based on, for example, the information in the input message or by referencing a database that stores the protocol format used by various devices, and then generates the output message based on the protocol format used by the intended recipient device or system. The output message can be generated based upon a comparison with, and application of, a set of translation rules 2420 that are accessible by the translation module 2415.

The translation rules 2420 can include rules that govern how to handle possible variations between formatting implementations within a common protocol. Examples of variations in formatting implementation of an electronic medical communication protocol include, for example, the delimiter or separator characters that are used to separate data fields, whether a particular field is required or optional, the repeatability of portions of the message (e.g., segments, fields, components, sub-components), the sequence of portions of the message (e.g., the order of fields or components), whether a particular portion of a message is included, the length of the message or portions of the message, and the data type used for the various portions of the message.

The translation rules 2420 can define additions, deletions, swappings, and/or modifications that should be performed in order to "translate" an input message that adheres to a first HL7 implementation into an output message that adheres to a second HL7 implementation. The output message can have, for example, different formatting than the input message, while maintaining all, or a portion of, the substance or content of the input message.

In addition to translating between different implementations of a common electronic medical communication protocol (e.g., different formatting of HL7 messages), the translation module 2415 can also translate between input and output messages adhering to different communication protocols. The translation module 2415 can be capable of responding to and translating messages from, for example, one medical communication protocol to a separate medical communication protocol. For example, the translation module 2415 can facilitate communication between messages sent according to the HL7 protocol, the ISO 11073 protocol, other open protocols, and/or proprietary protocols. Accordingly, an input message sent according to the HL7 protocol can be translated to an output message according to a different protocol, or vice-versa.

The operation of the translation module 2415 and the translation rules 2420 will be described in more detail below. Various examples of system architectures including the translation module 2415 will now be described.

The first medical device 2405, the second medical device 2410, and the translation module 2415 can be communicatively coupled via connection to a common communications network or directly (via cables or wirelessly), for example, through the hub 100, PPM 102, and/or MMS 2004. The translation module 2415 can be communicatively coupled between the first medical device 2405 and the second medical device 2410 (with or without a communications network) such that all messages between the first and second medical devices 2405, 2410 are routed through the translation module 2415. Other architectures are also possible.

The first and second medical devices 2405, 2410 and the translation module 2415 can be included in, for example, a portion of the monitoring environments of FIG. 1 or 24 described above. The first medical device 2405 may be, for example, the infusion pump(s) 216 or ventilator 218, while the second medical device 2410 may be, for example, the monitoring hub 100, PPM 102, MMS 2004, or auxiliary device 2040. The translation module 2415 is an example implementation of the translation module 2005.

The translation module 2415 can facilitate communication across multiple networks within a hospital environment. The translation module 2415 can also (or instead) facilitate communication of messages across one or more networks extending outside of the hospital or clinical network environment. For example, the translation module 2415 can provide a communications interface with banking institutions, insurance providers, government institutions, outside pharmacies, other hospitals, nursing homes, or patient care facilities, doctors' offices, and the like.

The translation module 2415 of FIG. 40A can be a component of, for example, the environment 2000 described above with respect to FIG. 24. For example, the translation module 2415 can be communicatively coupled with a hospital network or other networks or monitoring environments described above. The translation module 2415 can facilitate the exchange of patient monitoring information, including, for example, physiological parameter measurements, physiological parameter trend information, and physiological parameter alarm conditions between bedside medical monitor devices, nurses' monitoring stations, a Hospital or Clinical Information System (which may store Electronic Medical Records), and/or many other medical devices and systems. The translation module 2415 can enable seamless communication between different medical devices and systems, each of which may use a different implementation of an electronic medical communication protocol such as, for example, the HL7 communication protocol, within a clinical or hospital network environment.

The translation module 2415 can also facilitate communication between a first medical device that is part of the patient monitoring sub-system and a second medical device that is not part of, or is external to, the patient monitoring system 200. As such, the translation module 2415 can be capable of responding to externally-generated medical messages (such as patient information update messages, status query messages, and the like from an HIS or CIS) and generating external reporting messages (such as event reporting messages, alarm notification messages, and the like from patient monitors or nurses' monitoring stations).

The first and second medical devices 2405, 2410 can communicate with each other over a communication bus 2421. The communication bus 2421 can include any one or more of the communication networks, systems, and methods described above, including the Internet, a hospital WLAN, a LAN, a personal area network, etc. For example, any of the networks describe above can be used to facilitate communication between a plurality of medical devices, including first and second medical devices 2405, 2410, discussed above. One such example is illustrated in FIG. 40B.

Figure 40B:
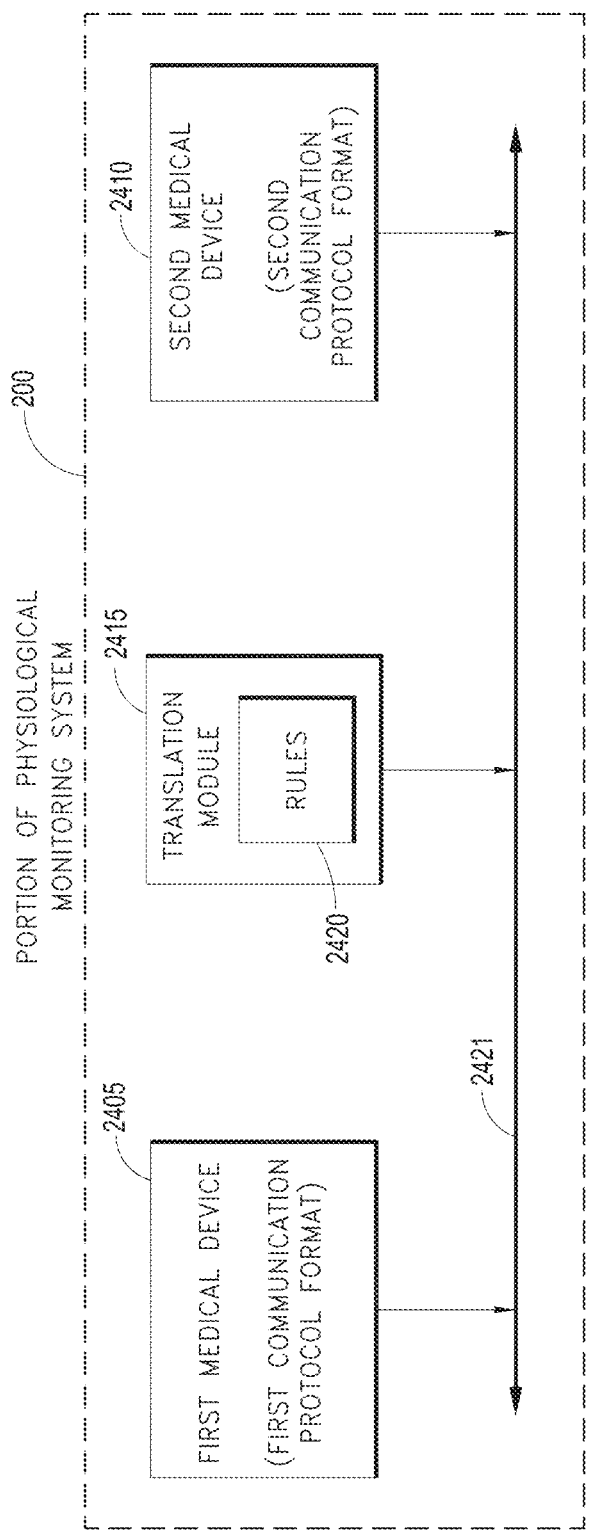
FIG. 40B illustrates an example first medical device and an example second medical device that communicate with one another via a translation module and a communication bus.

In FIG. 40B, the first medical device 2405 provides a message to the communication bus 2421. The message is intended for receipt by the second medical device 2410; however, because first and second medical devices 2405, 2410 communicate according to different communication protocol format, second medical device 2410 is unable to process the message.

The translation module 2415 monitors the communication bus 2421 for such messages. The translation module 2415 receives the message and determine that first medical device 2405 is attempting to communicate with second medical device 2410. The translation module 2415 determines that message translation would facilitate communication between first and second medical devices 2405, 2410. The translation module 2415 therefore utilizes an appropriate translation rule stored in a translation module 2420. The translation module 2420 can include a memory, EPROM, RAM, ROM, etc.

The translation module 2415 translates the message from the first medical device 2405 according to any of the methods described herein. Once translated, the translation module 2415 delivers the translated message to the communication bus 2421. The second medical device 2410 receives the translated message and responds appropriately. For example, the second medical device may perform a function and/or attempt to communication with the first medical device 2405. The translation module 2415 facilitates communication from the second medical device 2410 to the first medical device 2405 in a similar manner.

The first medical device 2405 and the second medical device 2410 can be, for example, any of the medical devices or systems communicatively coupled to a hospital network or hub 100, PPM 102, and/or MMS 2004. These medical devices or systems can include, for example, point-of-care devices (such as bedside patient monitors), data storage units or patient record databases, hospital or clinical information systems, central monitoring stations (such as a nurses' monitoring station), and/or clinician devices (such as pagers, cell phones, smart phones, personal digital assistants (PDAs), laptops, tablet PCs, personal computers, pods, and the like).

The first medical device 2405 can be a patient monitor that can be communicatively coupled to a patient for tracking a physiological parameter (e.g., oxygen saturation, pulse rate, blood pressure, etc.), and the second medical device 2410 can be a hospital information system ("HIS") or clinical information system ("CIS"). The patient monitor can communicate physiological parameter measurements, physiological parameter alarms, or other physiological parameter measurement information generated during the monitoring of a patient to the HIS or CIS for inclusion with the patient's electronic medical records maintained by the HIS or CIS.

The first medical device 2405 can be a HIS or CIS and the second medical device 2410 can be a nurses' monitoring station, as described herein. However, the translation module 2415 can facilitate communication between a wide variety of medical devices and systems that are used in hospitals or other patient care facilities. For example, the translation module 2415 can facilitate communication between patient physiological parameter monitoring devices, between a monitoring device and a nurses' monitoring station, etc.

Using the translation module 2415, a patient monitoring sub-system, such as those described herein (e.g., physiological monitoring system 200), can push data to the HIS or pull data from the HIS even if the HIS uses a different implementation of the HL7 protocol, or some other electronic medical communication protocol.

The patient monitoring sub-system can be configured to push/pull data at predetermined intervals. For example, a patient monitor or clinician monitoring station can download patient data automatically from the HIS at periodic intervals so that the patient data is already available when a patient is connected to a patient monitor. The patient data sent from the HIS can include admit/discharge/transfer ("ADT") information received upon registration of the patient. ADT messages can be initiated by a hospital information system to inform ancillary systems that, for example, a patient has been admitted, discharged, transferred or registered, that patient information has been updated or merged, or that a transfer or discharge has been canceled.

The patient monitoring sub-system can also (or instead) be configured to push/pull data to/from the HIS only when the HIS is solicited by a query. For example, a clinician may make a request for information stored in a patient's electronic medical records on the HIS.

The patient monitoring sub-system can also (or instead) be configured to push/pull data to/from the HIS in response to an unsolicited event. For example, a physiological parameter of a patient being monitored can enter an alarm condition, which can automatically be transmitted to the HIS for storing in the patient's electronic medical records. Moreover, any combination of the above methods or alternative methods for determining when to communicate messages to and from the HIS can be employed.

Example system architectures and example triggers for the communication of messages involving the translation module 2415 have been described. Turning now to the operation of the translation module, FIGS. 41A-41D illustrate an example medical message at different phases or steps of a translation process. The translation process will be described in more detail below in connection with FIGS. 42, 43A, and 43B.

FIG. 41A illustrates an example ADT input message 2505 received by the translation module 2415 from an HIS. The ADT input message 2505 is implemented according to the HL7 communication protocol and contains information related to the admission of a patient to a hospital. The ADT message 2505 includes multiple segments, including a message header segment 2506, an event segment, a patient identification segment, a patient visit segment, role segments, a diagnosis segment, and multiple custom segments.

The message header ("MSH") segment 2506 can define how the message is being sent, the field delimiters and encoding characters, the message type, the sender and receiver, etc. The first symbol or character after the MSH string can define the field delimiter or separator (in this message, a "caret" symbol). The next four symbols or characters can define the encoding characters. The first symbol defines the component delimiter ("~"), the second symbol defines the repeatable delimiter ("|"), the third symbol defines the escape delimiter ("\"), and the fourth symbol defines the sub-component delimiter ("&"). All of these delimiters can vary between HL7 implementations.

The example header segment 2506 can further include the sending application ("VAFC PIMS"), the receiving application ("NPTF-508"), the date/time of the message ("20091120104609-0600"), the message type ("ADT~A01"), the message control ID ("58103"), the processing ID ("P"), and the country code ("USA"). As represented by the consecutive caret symbols, the header segment can also contain multiple empty fields.

FIG. 41B illustrates the message header segment 2506 after it has been parsed into fields or elements based on an identified field delimiter (the caret symbol). The parsed input message can include an XML, message that is configured to be transformed according to extensible stylesheet language transformation (XSLT) rules.

The parsed input message can be encoded. FIG. 41C illustrates the parsed message header segment of the input message after being encoded (e.g., using a Unicode Transformation Format-8 ("UTF-8") encoding scheme).

The encoded message header segment shows some of the various data types that can be used in the message. For example, the sending application ("VAFC PIMS") of the third parsed field and the receiving application ("NPTF-508") of the fifth parsed field are represented using a hierarchic designator ("HD") name data type. The date/time field (the seventh parsed field) is represented using the time stamp ("TS") data type. The processing ID field (the eleventh parsed field) is represented using the processing type ("PT") data type. The fields that do not include a data type identifier are represented using the string ("ST") data type. Other possible data types include, for example, coded element, structured numeric, timing quantity, text data, date, entry identifier, coded value, numeric, and sequence identification. The data types used for the various fields or attributes of the segments can vary between formatting implementations.

FIG. 41D illustrates an example output message 2510 from the translation module 2415 based on the example input message 2505 of FIG. 41A. The output message 2510 includes a message acknowledgement segment 2512.

Turning to the operation of the translation module, the translation module 2415 can, for example, create, generate, or produce an output message that is reflective of the input message based on an application of the set of translation rules 2420. The translation module 2415 can, for example, translate, transform, convert, reformat, configure, change, rearrange, modify, adapt, alter, or adjust the input message based on a comparison with, and application of, the set of translation rules 2420 to form the output message. The translation module 2415 can, for example, replace or substitute the input message with an output message that retains the content of the input message but has a new formatting implementation based upon a comparison with, and application of, the set of translation rules 2420.

Figure 42:
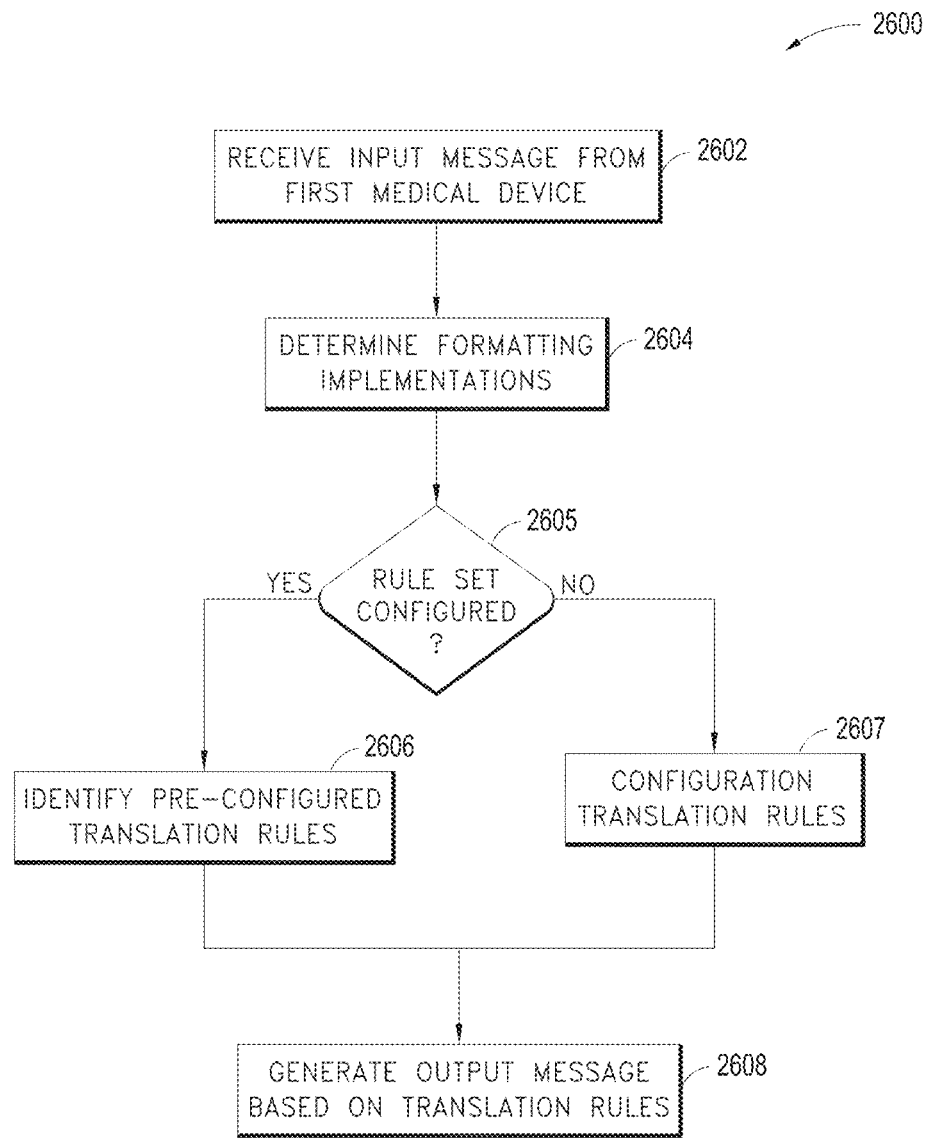
FIG. 42 illustrates an example translation process for generating an output message based on an input message and a comparison with translation rules associated with the translation module.

FIG. 42 illustrates a translation process 2600 for generating an output message based on an input message and a comparison with the set of translation rules 2420 associated with the translation module 2415. The translation process 2600 starts at block 2602 where the translation module 2415 receives an input message from a first medical device.

At block 2604, the translation module 2415 determines the formatting implementation of the input message and the formatting implementation to be used for the output message. The input message can include one or more identifiers indicative of the formatting implementation. The determination of the formatting implementation can be made, for example, by analyzing the message itself by identifying the delimiter or encoding characters used, the field order, the repeatability of segments, fields, or components, the data type of the fields, or other implementation variations. The translation module 2415 can separate or parse out the formatting from the content of the message (as shown in FIG. 41B) to aid in the determination of the formatting implementation. The translation module 2415 determines the formatting implementation of the input message by referencing a database that stores the implementation used by each device with which the translation module 2415 has been configured to interface.

The determination of the formatting implementation used by the output message can also be determined from the input message. For example, the input message can include a field that identifies the intended recipient application, facility, system, device, and/or destination. The input message can alternatively include a field that identifies the type of message being sent (e.g., ADT message) and the translation module 2415 can determine the appropriate recipient from the type of message being sent and/or the sending application, device, or system. The translation module 2415 can then determine the formatting implementation required by the intended recipient of the input message.

At decision block 2605, the translation module 2415 determines whether a rule set has been configured for the translation from the identified formatting implementation of the input message to the identified formatting implementation to be used for the output message. The rule set may have been manually configured prior to installation of the translation module software or may have been automatically configured prior to receipt of the input message. If a rule set has already been configured, then the translation process 2600 continues to block 2606. If a rule set has not been configured, then a rule set is configured at block 2607. The configuration of the rule set can be performed as described below in connection with FIGS. 44 and 45A-45D. The translation process 2600 then continues to block 2608.

At block 2606, the translation module 2415 identifies the pre-configured rules from the set of translation rules 2420 that govern translation between the determined formatting implementation of the input message and the formatting implementation of the output message. The identification of the pre-configured rules can be made manually.

At block 2608, the translation module 2415 generates an output message based on the configured rule set(s) of the translation rules 2420. The output message retains all, or at least a portion of, the content of the input message but has the format expected and supported by the intended recipient of the input message.

The translation rules 2420 can include, for example, unidirectional rules and/or bidirectional rules. A unidirectional rule can be one, for example, that may be applied in the case of a message from a first medical device (e.g., 2405) to a second medical device (e.g., 2410) but is not applied in the case of a message from the second medical device to the first medical device. For example, a unidirectional rule could handle a difference in the delimiters used between fields for two different formatting implementations of, for example, the HL7 communication protocol. The translation module 2415 can apply a field delimiter rule to determine if the field delimiter is supported by the intended recipient of the input message. If the field delimiter of the input message is not supported by the intended recipient, the field delimiter rule can replace the field delimiter of the input message with a field delimiter supported by the intended recipient.

For example, an input message from an input medical device can include a formatting implementation that uses a "caret" symbol ("^") as the field delimiter or separator. However, the formatting implementation recognized by the intended recipient medical device may use a "pipe" symbol ("|") as the field delimiter. The translation module 2415 can identify the field delimiter symbol used in the formatting implementation recognized by the intended recipient medical device from the set of translation rules 2420 and generate an output message based on the input message that uses the pipe field delimiter symbol instead of the caret field delimiter symbol used in the input message. The rule to substitute a pipe symbol for a caret symbol would, in this case, only apply to messages that are sent to a recipient device that recognizes the pipe symbol as a field delimiter. This rule could be accompanied by a complementary rule that indicates that a caret symbol should be substituted for a pipe symbol in the case of a message that is intended for a recipient device that is known to recognize the caret symbol as the field delimiter.

Another unidirectional rule can handle the presence or absence of certain fields between different formatting implementations. For example, an input message from an input medical device can include fields that would not be recognized by the intended recipient medical device. The translation module 2415 can generate an output message that does not include the unrecognized or unsupported fields. In situations where an input message does not include fields expected by the intended recipient medical device, the set of translation rules 2420 can include a rule to insert null entries or empty " " strings in the fields expected by the intended recipient medical device and/or to alert the recipient device of the absence of the expected field. The sender device may also be notified by the translation module 2415 that the recipient device does not support certain portions of the message.

Other unidirectional rules can facilitate, for example, the conversion of one data type to another (for example, string ("ST") to text data ("TX") or structured numeric ("SN") to numeric ("NM")), and the increase or decrease in the length of various portions of the message. Unidirectional rules can also be used to handle variations in repeatability of portions of the message. For example, the translation module 2415 can apply a field repeatability rule to repeated instances of a segment, field, component, or sub-component of the message to determine how many such repeated instances are supported by the recipient device, if any, and deleting or adding any repeated instances if necessary. For example, a phone number field of a patient identification segment can be a repeatable field to allow for entry of home, work, and cell phone numbers.

Bidirectional rules can also be used. Such rules may apply equally to messages between first and second medical devices (e.g., 2405, 2410) regardless of which device is the sender and which is the recipient. A bidirectional rule can be used to handle changes in sequence, for example. In certain implementations, an input message from an input medical device can include a patient name field, or fields, in which a first name component appears before a last name component. However, the intended recipient medical device may be expecting an implementation where the last name component appears before the first name component. Accordingly, the set of translation rules 2420 can include a bidirectional rule to swap the order of the first and last name components when communicating between the two medical devices, or between the two formatting implementations. In general, field order rules can be applied to determine whether the fields, components, or sub-components are in the correct order for the intended recipient and rearranging them if necessary. Other bidirectional rules can be included to handle, for example, other sequential variations between formatting implementations or other types of variations.

The translation rules 2420 can also include compound rules. For example, a compound rule can include an if-then sequence of rules, wherein a rule can depend on the outcome of another rule. Some translation rules 2420 may employ computations and logic (e.g., Boolean logic or fuzzy logic), etc.

Figure 43A:
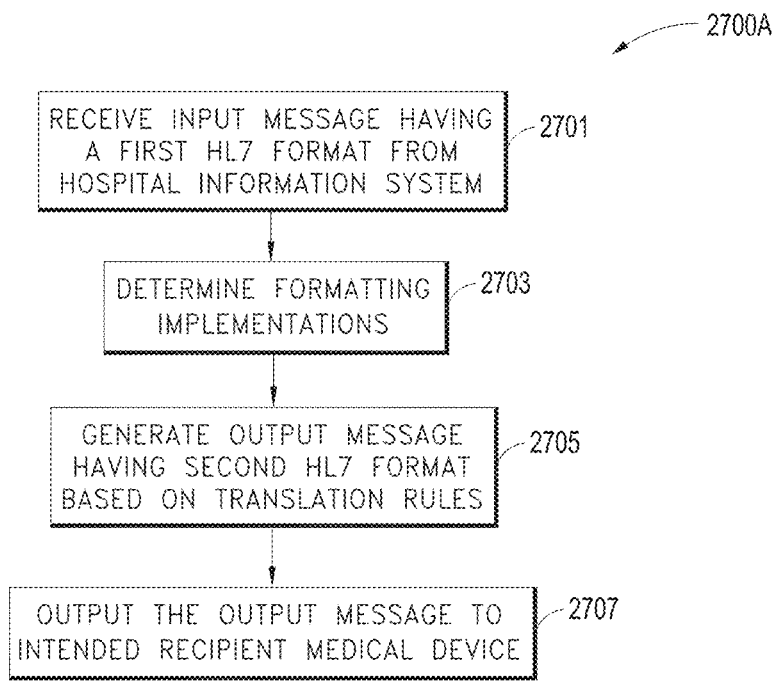
FIG. 43A illustrates an example translation process in which the translation module facilitates communication of an HL7 message from a Hospital Information System ("HIS") having a first HL7 format to an intended recipient medical device having a second HL7 format.
Figure 43B:
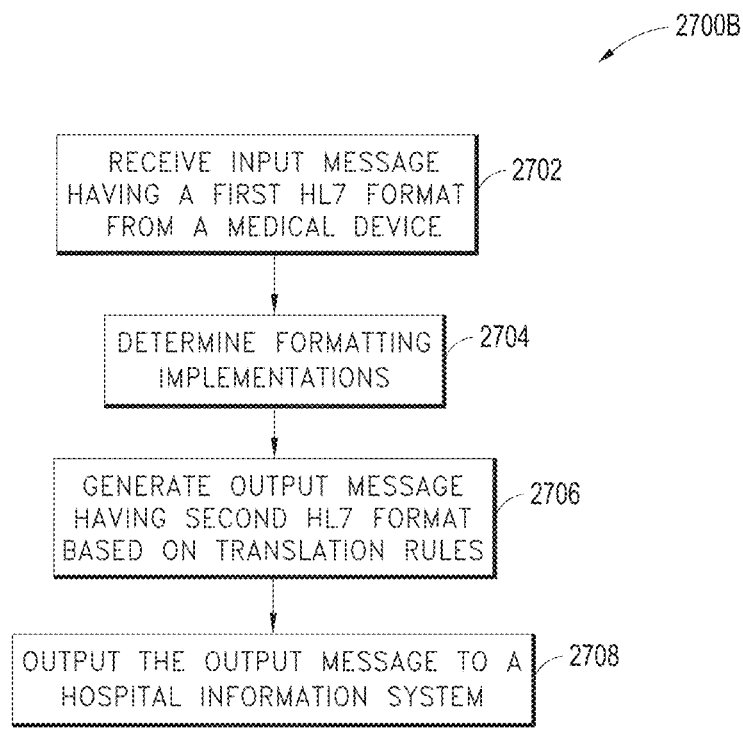
FIG. 43B illustrates an example translation process in which the translation module facilitates communication of an HL7 message from a medical device having a first HL7 format to a HIS having a second HL7 format.

As discussed above, the messages communicated over the hospital-based communication network can employ the HL7 protocol. FIGS. 43A and 43B illustrate translation processes 2700A, 2700B in which HL7 messages are communicated between a HIS and a medical device over a hospital-based communications network or a clinical network. The translation processes 2700A, 2700B will be described with the assumption that the rules governing "translation" between the first and second HL7 formats have already been configured.

FIG. 43A illustrates a translation process 2700A in which the translation module 2415 facilitates communication of an HL7 message, such as the ADT message of FIG. 41A, from an HIS having a first HL7 format to an intended recipient medical device, such as a patient monitor or a clinician monitoring station, having a second HL7 format.

The translation process 2700A starts at block 2701, where the translation module 2415 receives an input message having a first HL7 format from the HIS. The input message can include information regarding, for example, the admission of a patient and/or patient identification and patient medical history information from an electronic medical records database.

At block 2703, the translation module 2415 determines the formatting implementation of the input message and the formatting implementation to be used for the output message. These determinations can be made in a similar manner to the determinations discussed above in connection with block 2604 of FIG. 42.

At block 2705, the translation module 2415 identifies the rules that govern translation between the determined HL7 format of the input message and the HL7 format of the output message and generates an output message having the second HL7 format based on the identified rules. The output message can retain the content of the input message sent by the HIS but has the format expected and supported by the intended recipient of the input message.

At block 2707, the translation module 2415 can output the output message to the intended recipient over the hospital-based communications network. The intended recipient can transmit an acknowledgement message back to the hospital information system acknowledging successful receipt or reporting that an error occurred.

FIG. 43B illustrates a translation process 2700B in which the translation module 2415 facilitates communication of an HL7 message from a medical device, such as a patient monitor, having a first HL7 format to an HIS having a second HL7 format. For example, the patient monitor can transmit reporting event data m such as patient alarm data, to the HIS to store in the patient's electronic medical records.

The translation process 2700B starts at block 2702, where the translation module 2415 receives an input message having a first HL7 format from the medical device. The input message can include patient monitoring data or alarm data regarding one or more physiological parameters of the patient being monitored for storage in an electronic medical records database associated with the HIS.

At block 2704, the translation module 2415 determines the formatting implementation of the input message and the formatting implementation to be used for the output message. These determinations can be made in a similar manner to the determinations discussed above in connection with block 2604 of FIG. 42.

At block 2706, the translation module 2415 identifies the rules that govern translation between the determined HL7 format of the input message and the HL7 format of the output message and generates an output message having the second HL7 format based on the identified rules. The output message can retain the content of the input message sent by the medical device but has the format expected and supported by the HIS.

At block 2708, the translation module 2415 can output the output message to the hospital information system over the hospital-based communications network. The HIS can transmit an acknowledgement message back to the medical device acknowledging successful receipt or reporting that an error occurred.

FIGS. 42, 43A and 43B described the operation of the translator module 2415. FIGS. 44 and 45A-45D will be used to illustrate the description of the configuration of the translation rules 2420.

The translation rules 2420 can be implemented as one or more stylesheets, hierarchical relationship data structures, tables, lists, other data structures, combinations of the same, and/or the like. The translation rules 2420 can be stored in local memory within the translation module 2415. The translation rules 2420 can also (or instead) be stored in external memory or on a data storage device communicatively coupled to the translation module 2415.

The translation module 2415 can include a single rule set or multiple rule sets. For example, the translation module 2415 can include a separate rule set for each medical device/system and/or for each possible communication pair of medical devices/systems coupled to the network or capable of being coupled to the network. The translation module 2415 can include a separate rule set for each possible pair of formatting implementations that are allowed under a medical communication protocol such as, for example, the HL7 protocol.

Figure 44:
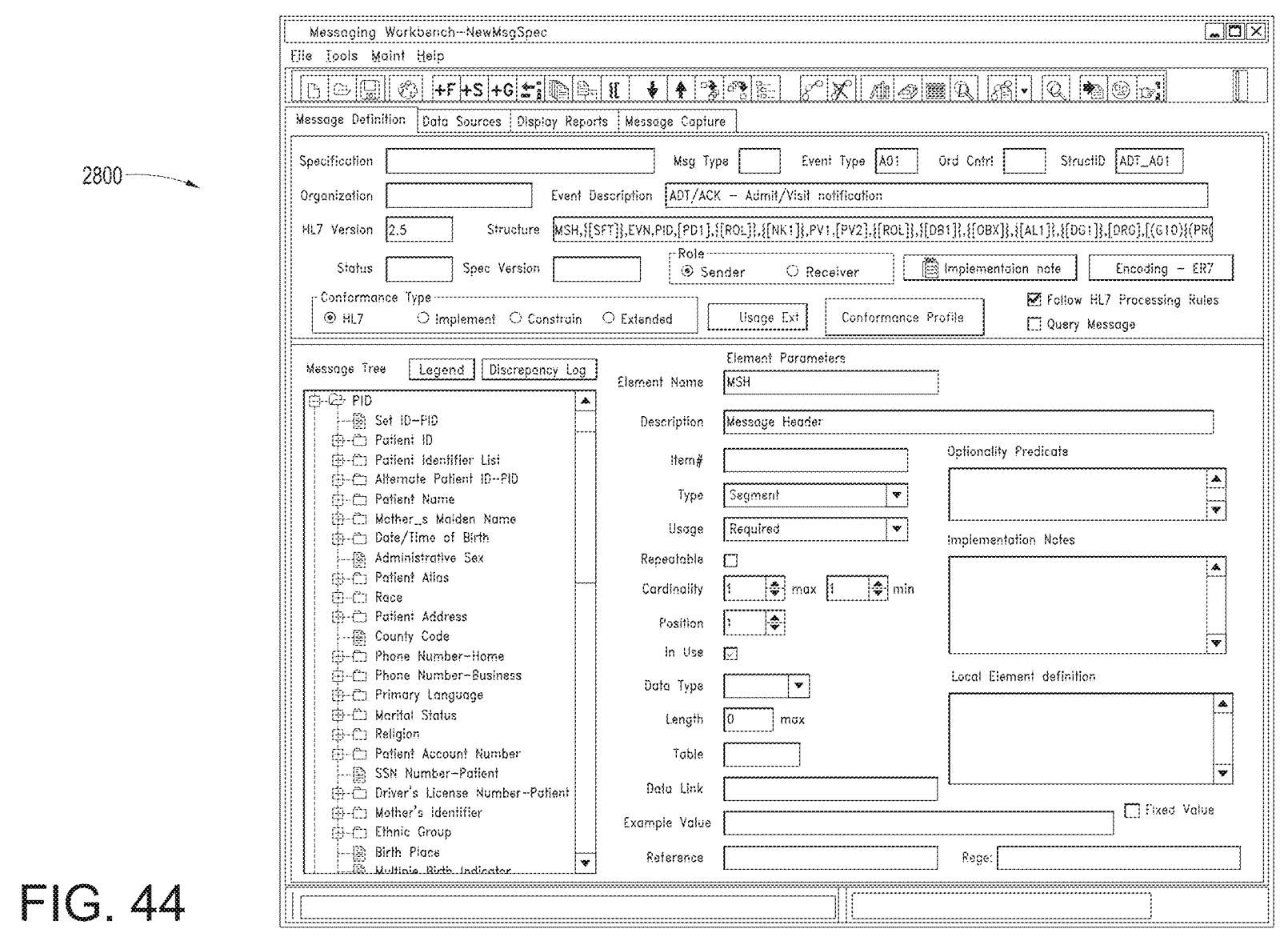

The translation rules 2420 can be manually inputted using, for example, the messaging implementation software tool 2800 illustrated in FIG. 44. For example, the software developer for a particular hospital network can determine the protocol message formats used by the devices and/or systems that are or can be coupled to the hospital network and then manually input rules to facilitate "translation" between the various protocol message formats supported or recognized by the devices and/or systems.

FIG. 44 illustrates an example screenshot from a messaging implementation software tool 2800 for manually configuring translation rules 2420 to be used by the translation module 2415. The screenshot from the messaging implementation software tool 2800 illustrates various parameters that may differ between formatting implementations of an electronic medical communication protocol, such as HL7. The screenshot also includes areas where a user can input information that defines, or is used to define, translation rules for converting between different HL7 implementations. The messaging implementation software tool 2800 can store a variety of pre-configured rule sets based, for example, on known communication protocol implementations of various medical devices. A user may configure one or more translation rules 2420 to be used in communications involving such devices by entering identification information, such as the device manufacturer, model number, etc. Based on this identification information, the messaging implementation tool 2800 can identify a pre-configured set of translation rules for communication with that device.

The translation rules 2420 can also (or instead) be automatically generated. For example, the automatic generation of a new set, or multiple sets, of rules can be triggered by the detection of a newly recognized "communicating" medical device or system on a network. The automatic generation of a new set or multiple sets of rules can occur at the time a first message is received from or sent to a new "communicating" medical device or system coupled to the network. The automatic generation of rule sets can include updating or dynamically modifying a pre-existing set of rules.

The automatic generation of translation rule sets can be carried out in a variety of ways. For example, the translation module 2415 can automatically initiate usage of a pre-configured set of translation rules 2420 based upon, for example, the make and model of a new device that is recognized on the network. The translation module 2415 can request one or more messages from the new device or system and then analyze the messages to determine the type of formatting being implemented, as illustrated by the automatic rule configuration process 2900A of FIG. 45A. The automatic rule configuration process 2900A starts at block 2901, where the translation module 2415 receives one or more messages from a detected medical device or system on the network. The messages can be received upon transmission to an intended recipient medical device or system or in response to a query sent by the translation module 2415 or another medical device or system coupled to the network.

At block 2903, the translation module 2415 determines the protocol of the one or more received messages by, for example, analyzing the message or by consulting a database that indicates what communication protocol/format is implemented by each medical device or system on the network. The translation module 2415 can be configured to handle medical messages implemented using a single common protocol, such as HL7. Accordingly, if a determination is made that the received messages are implemented using a non-supported or non-recognized protocol, the translation module can ignore the messages received from the detected medical device or system, output an alert or warning, or allow the messages to be sent without being translated.

At block 2905, the translation module 2415 determines the formatting implementation of the received message(s). The received messages can include one or more identifiers indicative of the formatting implementation. The determination of the formatting implementation can also (or instead) be made, for example, by analyzing the message itself by checking field order, the delimiter or encoding characters used, or other implementation variations. The translation module 2415 can separate or parse out the formatting from the content of the message to aid in the determination of the formatting implementation.

At block 2907, the translation module 2415 configures one or more rules or rule sets to handle messages received from and/or sent to the detected medical device or system. The configuration of the rules can involve the creation or generation of new rules. The configuration of the rules can also (or instead) involve the alteration or updating of existing rules. The configured rules or rule sets can be included with the translation rules 2420. If a set of rules already exists for the formatting implementation used by the new device or system, then the configuration of new translation rules may not be required. Instead, existing translation rules can be associated with the new device or system for use in communication involving that device or system. The translation module 2415 can also (or instead) create a new set of rules geared specifically for the new device or system or can modify an existing set of rules based on subtle formatting variations identified.

The translation module 2415 can also (or instead) generate test message(s) that may be useful in identifying the communication protocol and implementation used by a device or system. For example, the translation module can generate test messages to cause the newly detected device or system to take a particular action (e.g., store information) and then query information regarding the action taken by the newly detected device to determine whether or how the test message was understood. This is illustrated by the automatic rule configuration process 2900B of FIG. 45B.

The automatic rule configuration process 2900B starts at block 2902, where the translation module 2415 transmits one or more test, or initialization, messages to a remote device or system detected on a network. The test messages can be configured, for example, to instruct the remote device or system to take a particular action (e.g., store patient information). The test messages can be configured to generate a response indicative of the type of formatting recognized or supported by the remote device or system. The test messages can also (or instead) be configured such that only devices or systems supporting a particular formatting implementation will understand and properly act on the test messages.

At block 2904, the translation module 2415 queries the remote device or system to receive information regarding the action taken based on the test message sent to the remote device or system to determine whether the test message was understood. For example, if the test message instructed the remote device or system to store patient information in a particular location, the translation module 2415 can query the information from the location to determine whether the test message was understood. If the test message was not understood, the translation module 2415 can, for example, continue sending test messages of known formatting implementations until a determination is made that the test message has been understood.

At block 2906, the translation module 2415 determines the protocol and formatting implementation based on the information received. As an example, the test message can include an instruction to store patient name information. The test message can include a patient name field having a first name component followed by a surname component. The translation module 2415 can then query the remote device or system to return the patient surname. Depending on whether the patient surname or the first name is returned, this query can be useful in determining information about the order of fields in the formatting implementation being used by the remote device or system. As another example, the test messages can instruct the detected device or system to store repeated instances of a component. The translation module 2415 can then query the device or system to return the repeated instances to see which, if any, were stored. This repeatability information can also be useful in determining whether certain fields are allowed to be repeated in the formatting implementation being used by the remote device for system, and, if so, how many repeated instances are permitted.

At block 2908, the translation module 2415 configures one or more rules to handle messages received from and/or sent to the detected medical device or system. For example, the rules can convert messages from the message format used by a first medical device to that used by a second medical device, as described herein. The configuration of the rules can involve the creation or generation of new rules. The configuration of the rules can also (or instead) involve the alteration or updating of existing rules. If a set of rules already exists for the formatting implementation used by the new device or system, then the configuration of new translation rules may not be required. Instead, existing translation rules can be associated with the new device or system for use in communication involving that device or system.

Figure 45A:
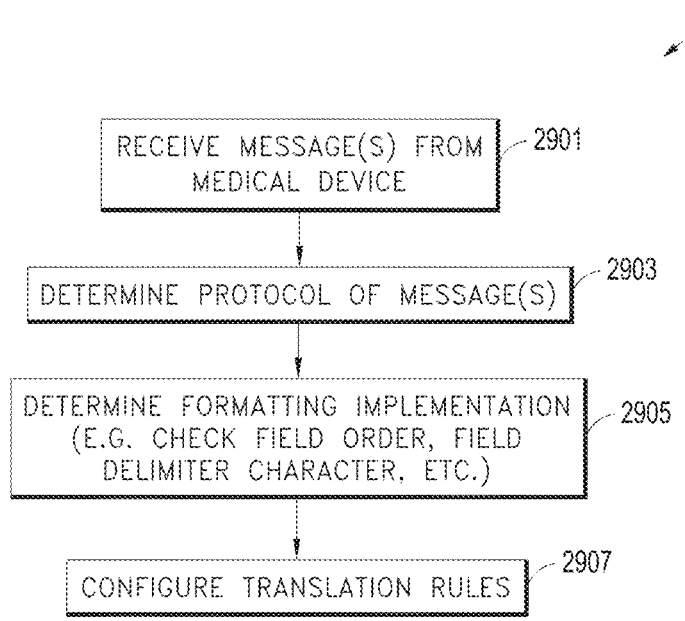
FIGS. 45A and 45B illustrate example automatic rule configuration processes that can be performed by the translation module.
Figure 45B:
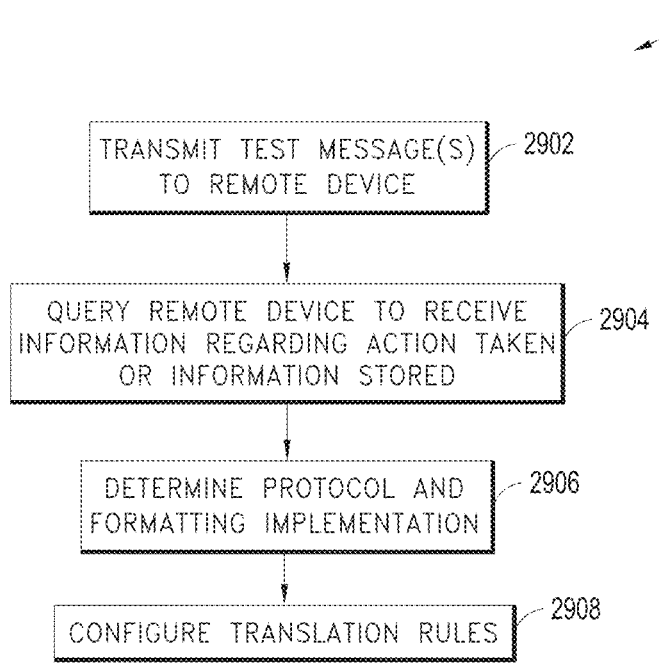
Figure 45C:
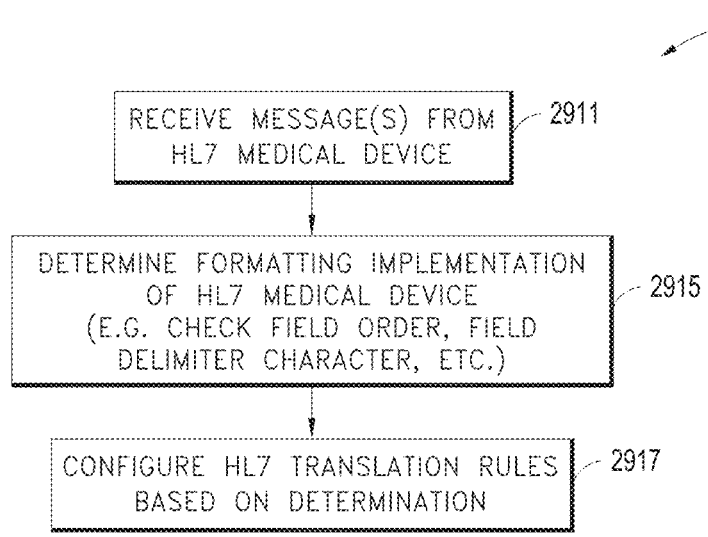
FIGS. 45C and 45D illustrate example automatic rule configuration processes that can be performed by the translation module for messages utilizing the HL7 protocol.
Figure 45D:
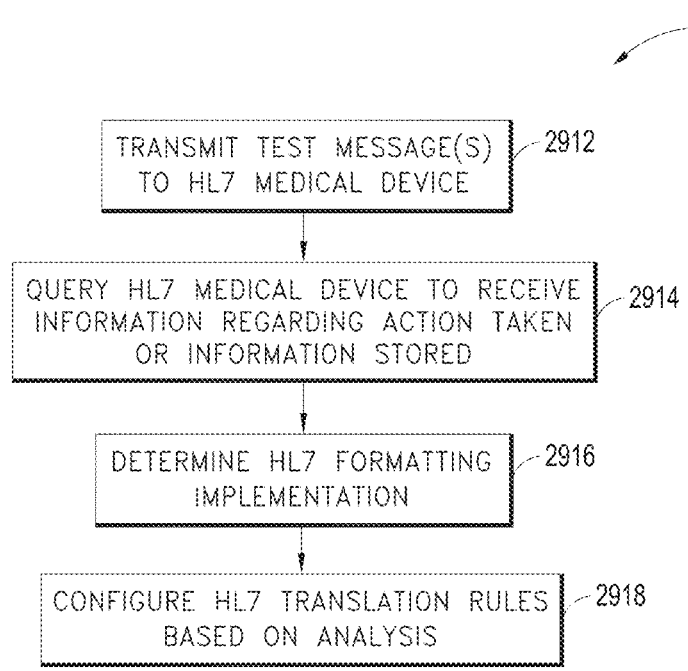
Figure 46:
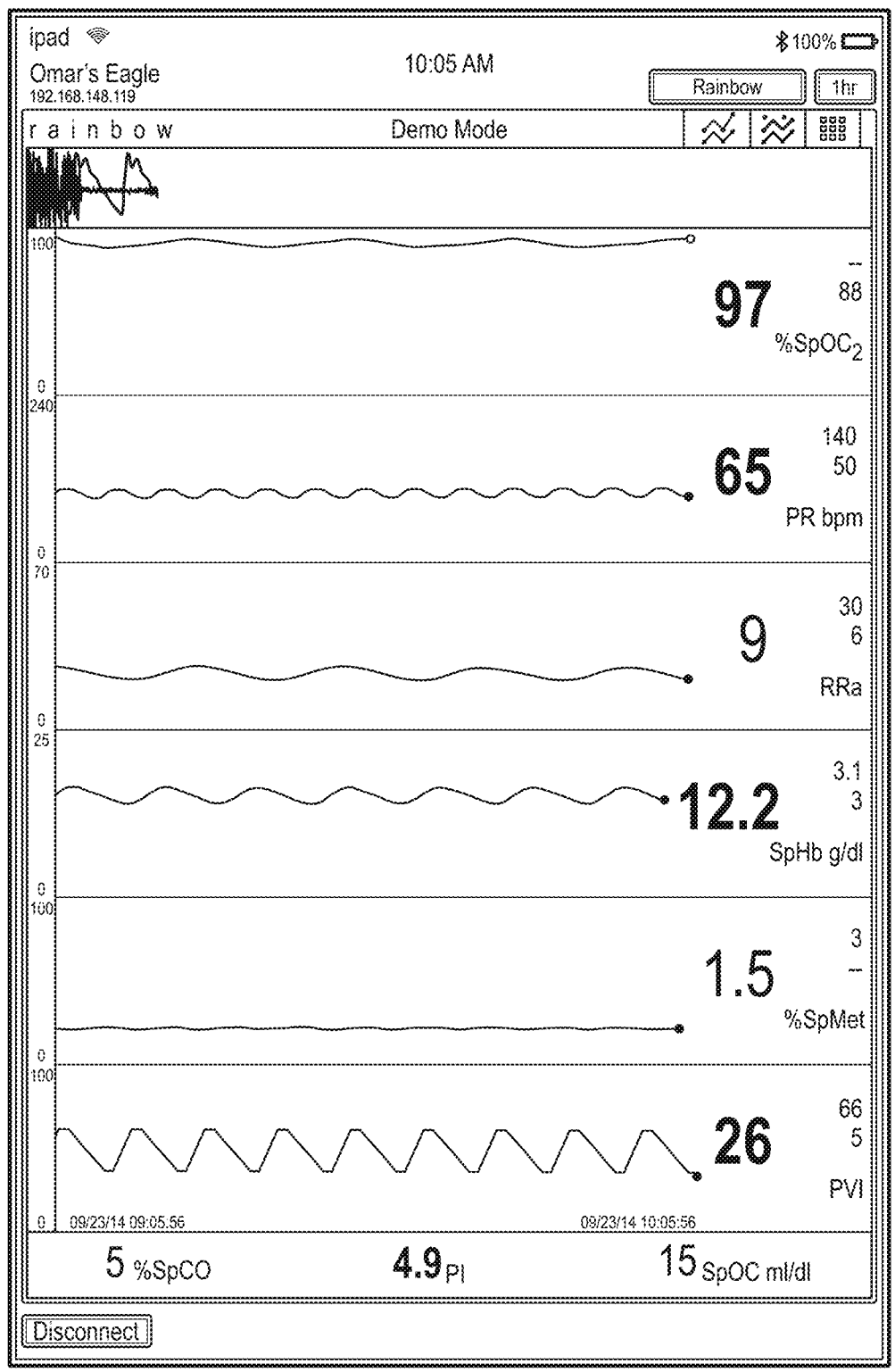
FIGS. 46-71 illustrate additional example hub displays, including displays of measurement data.
Figure 47:
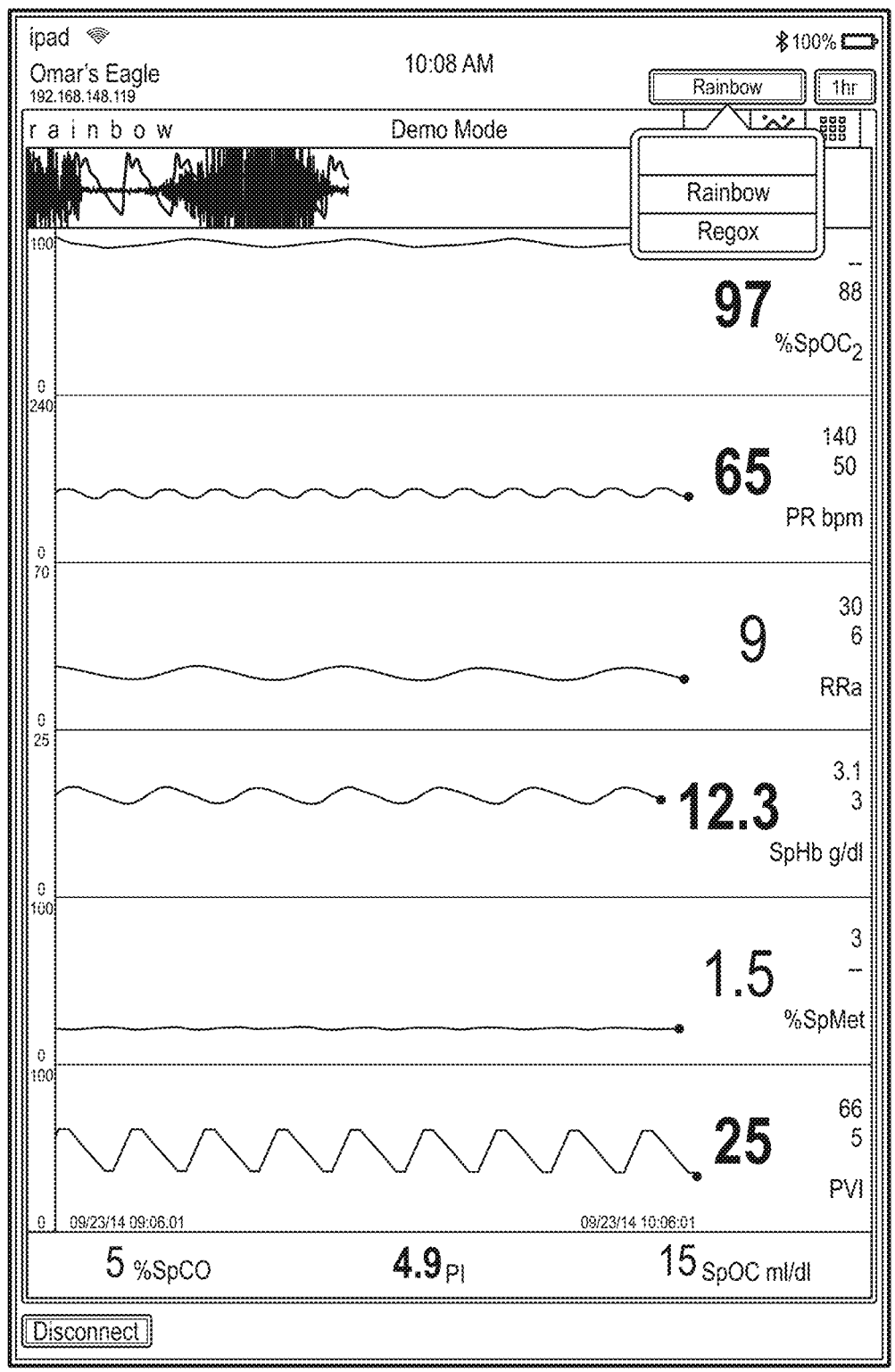
Figure 48:
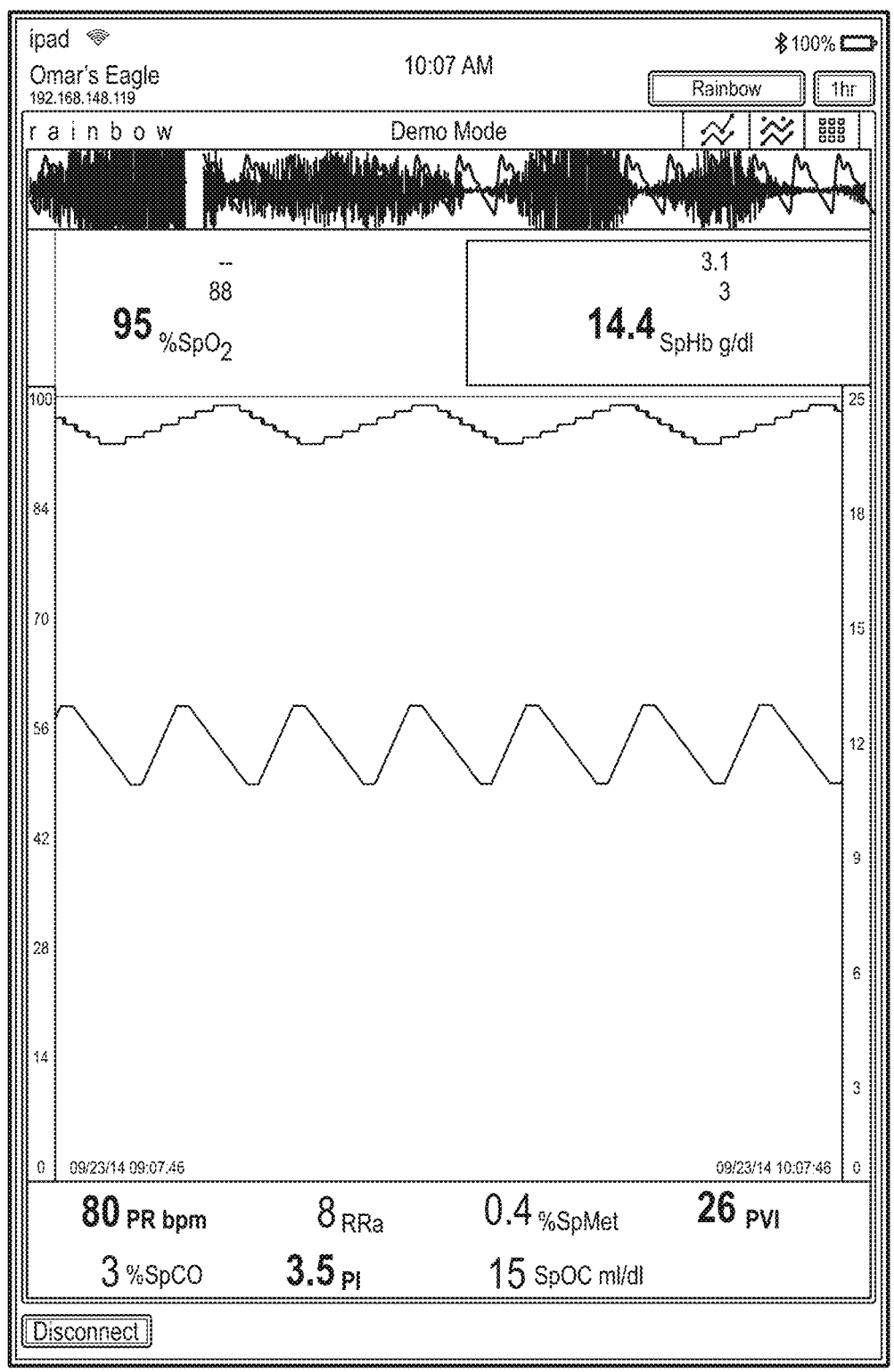
Figure 49:
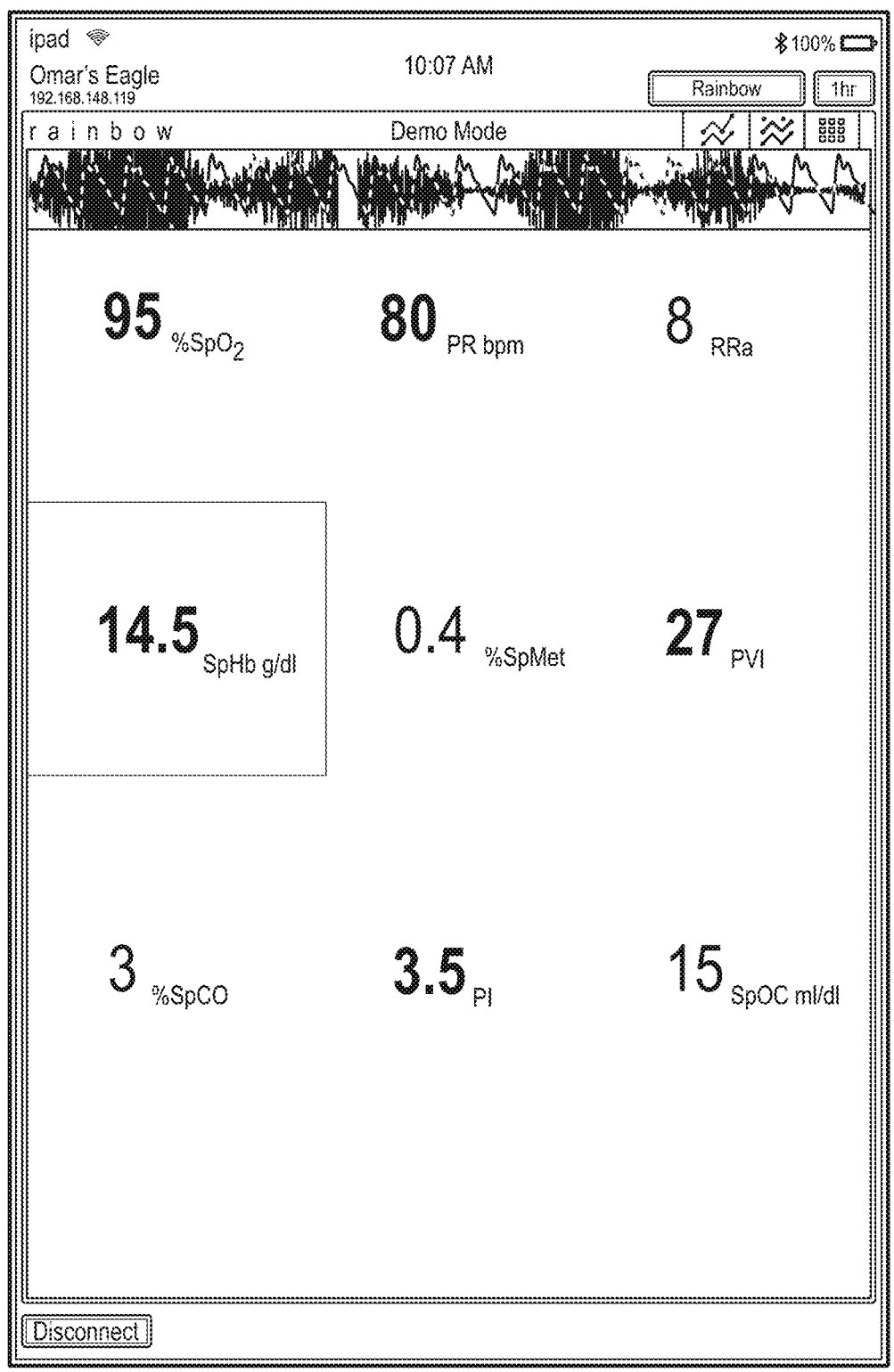
Figure 50:
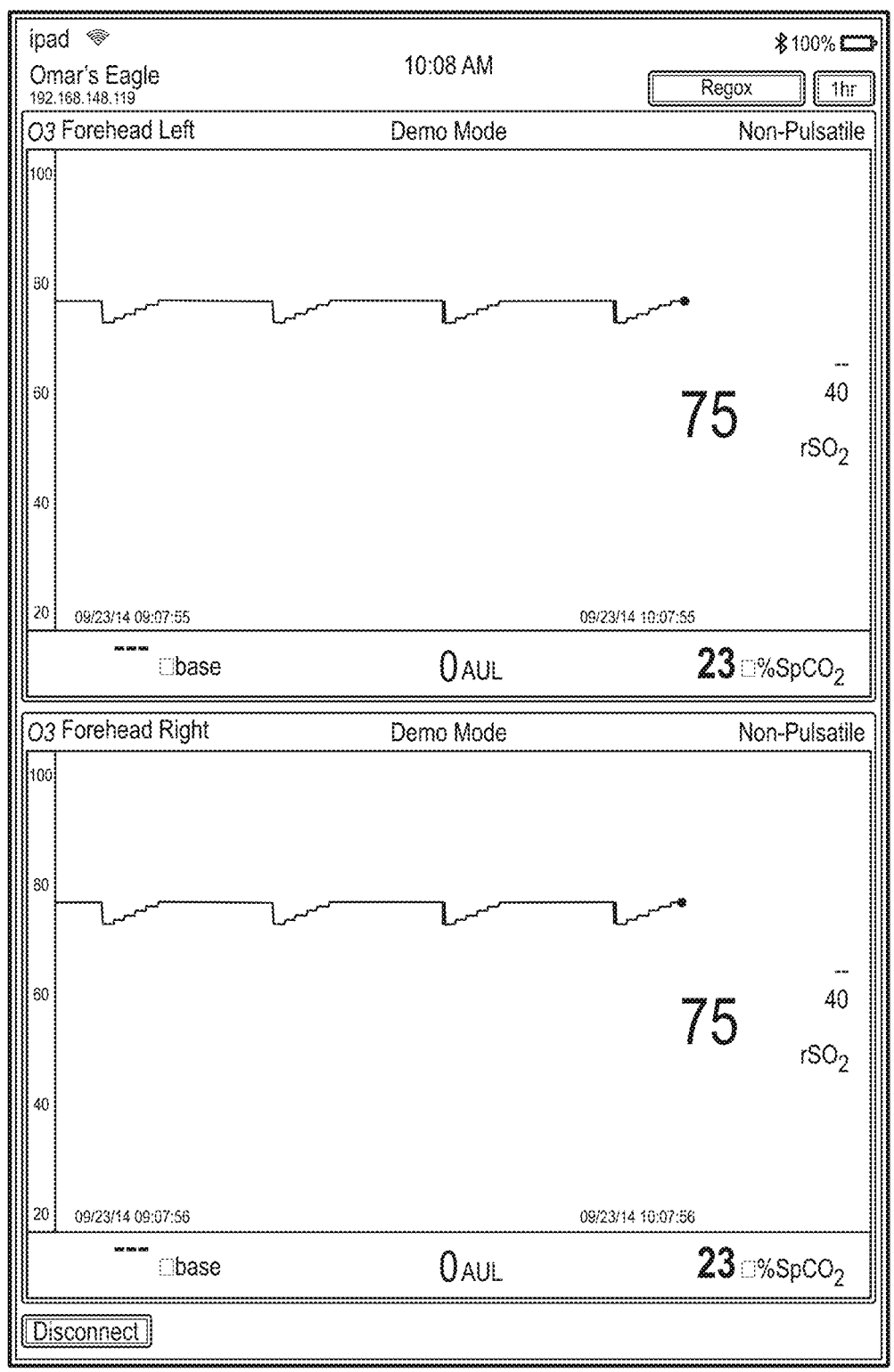
Figure 51:
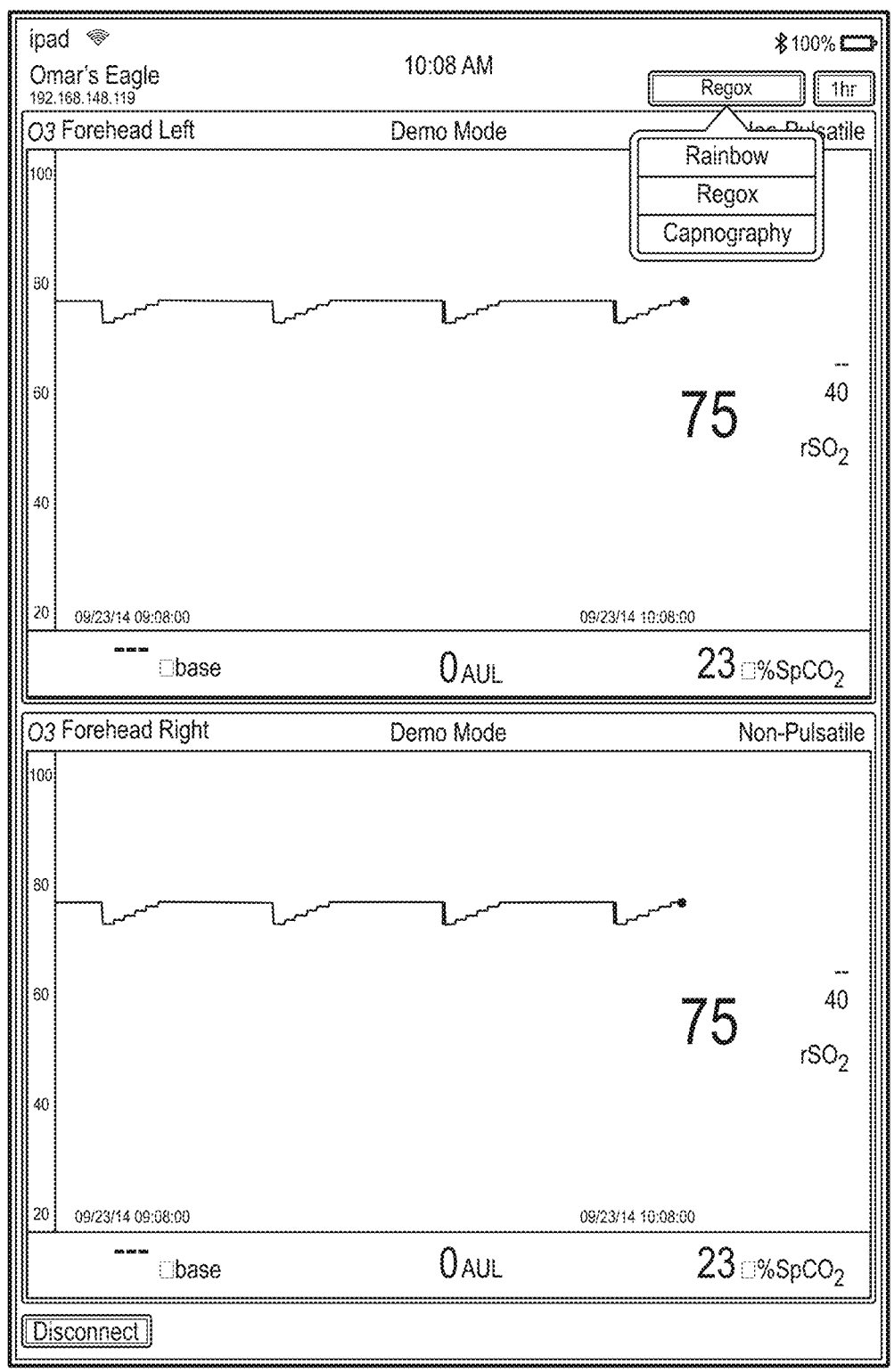
Figure 52:
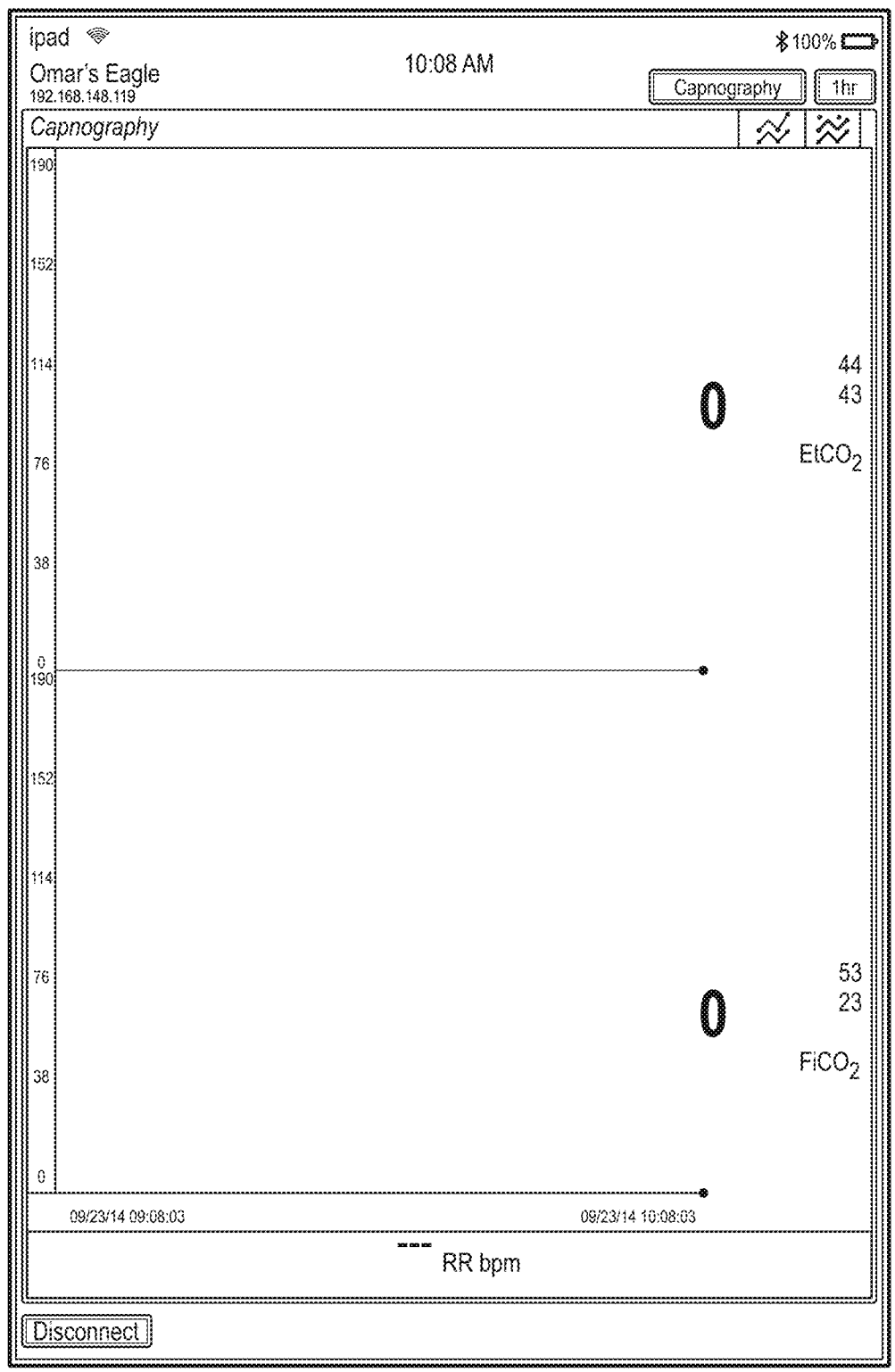
Figure 53:
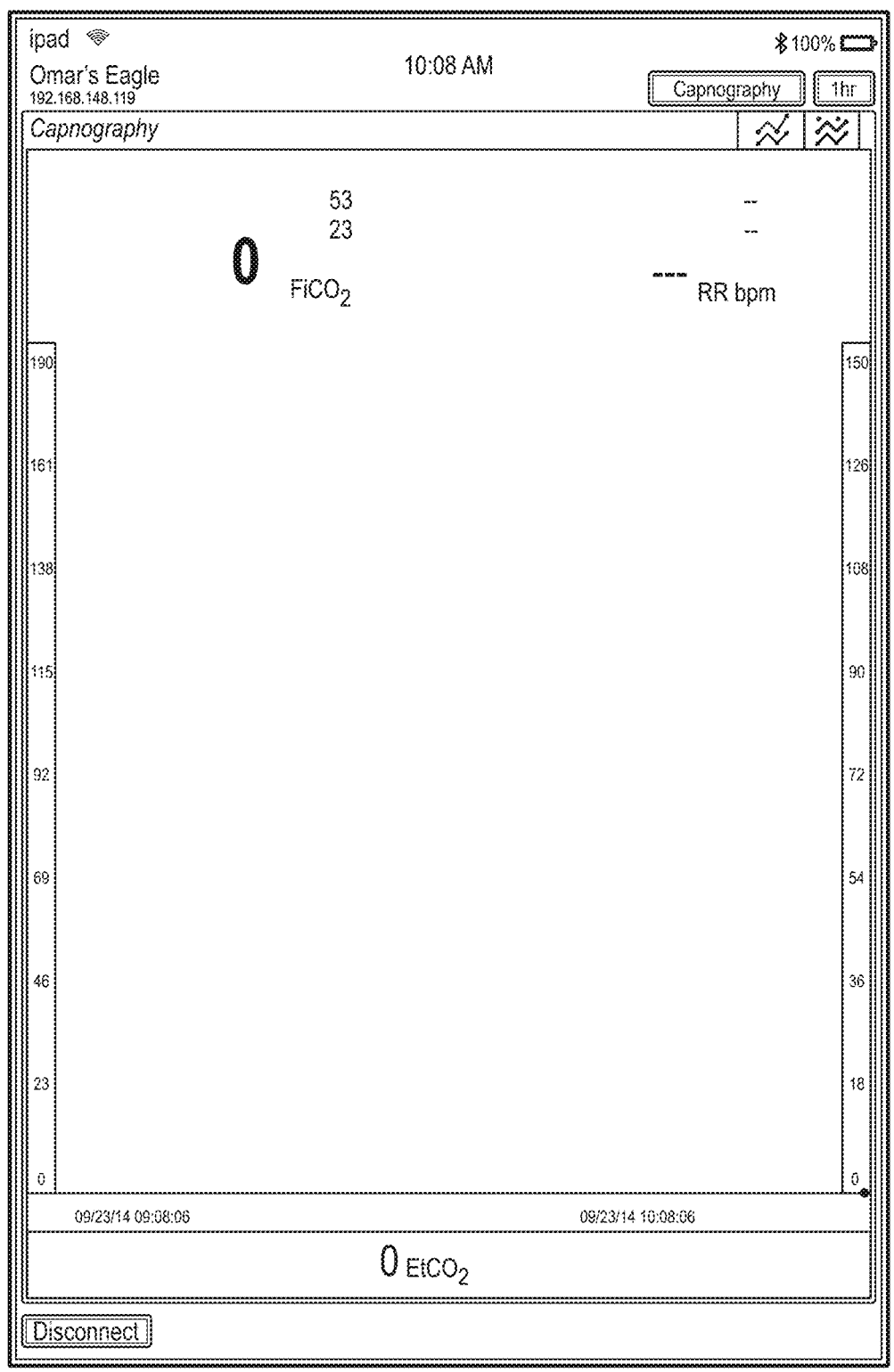
Figure 54:
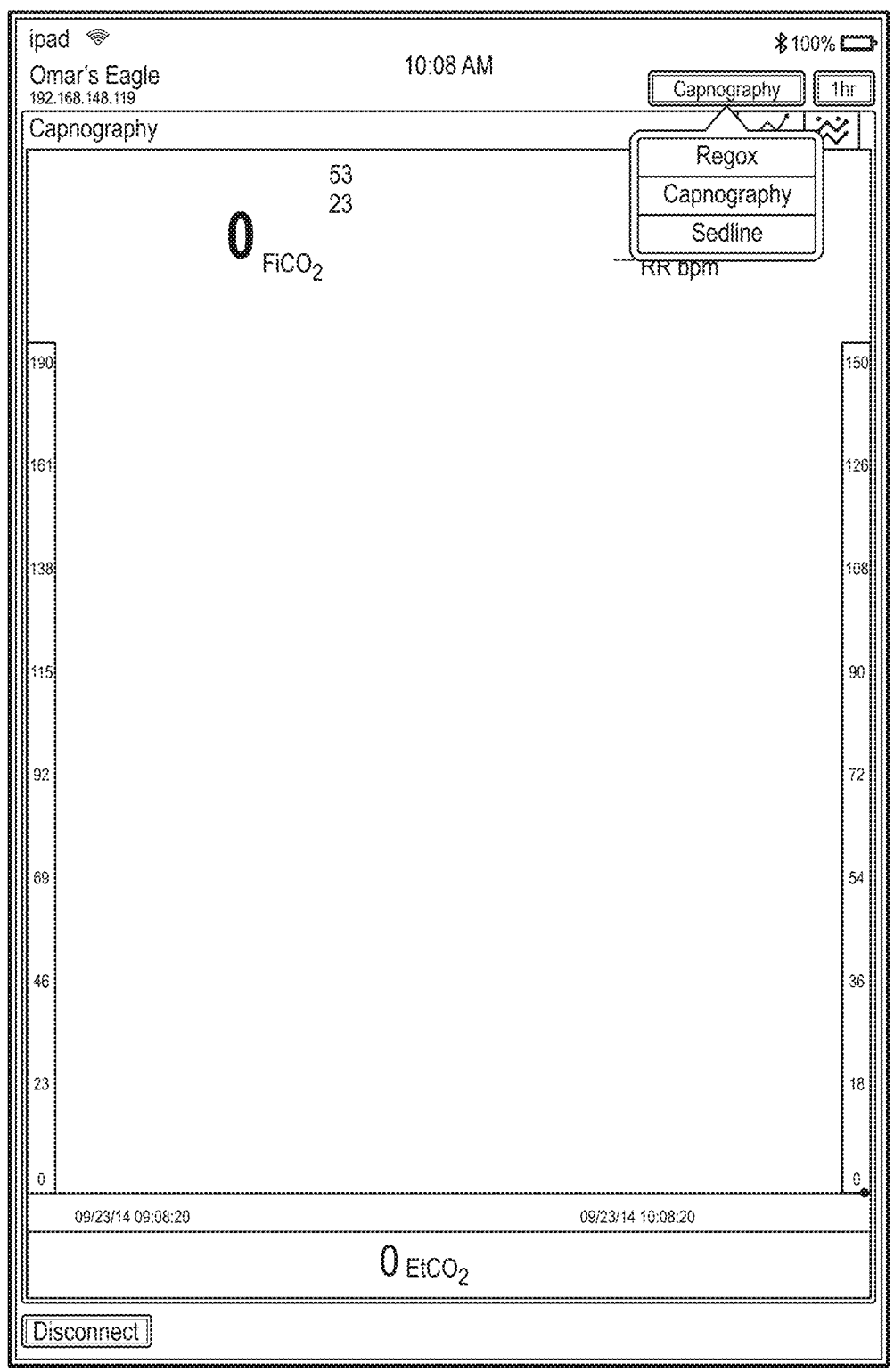
Figure 55:
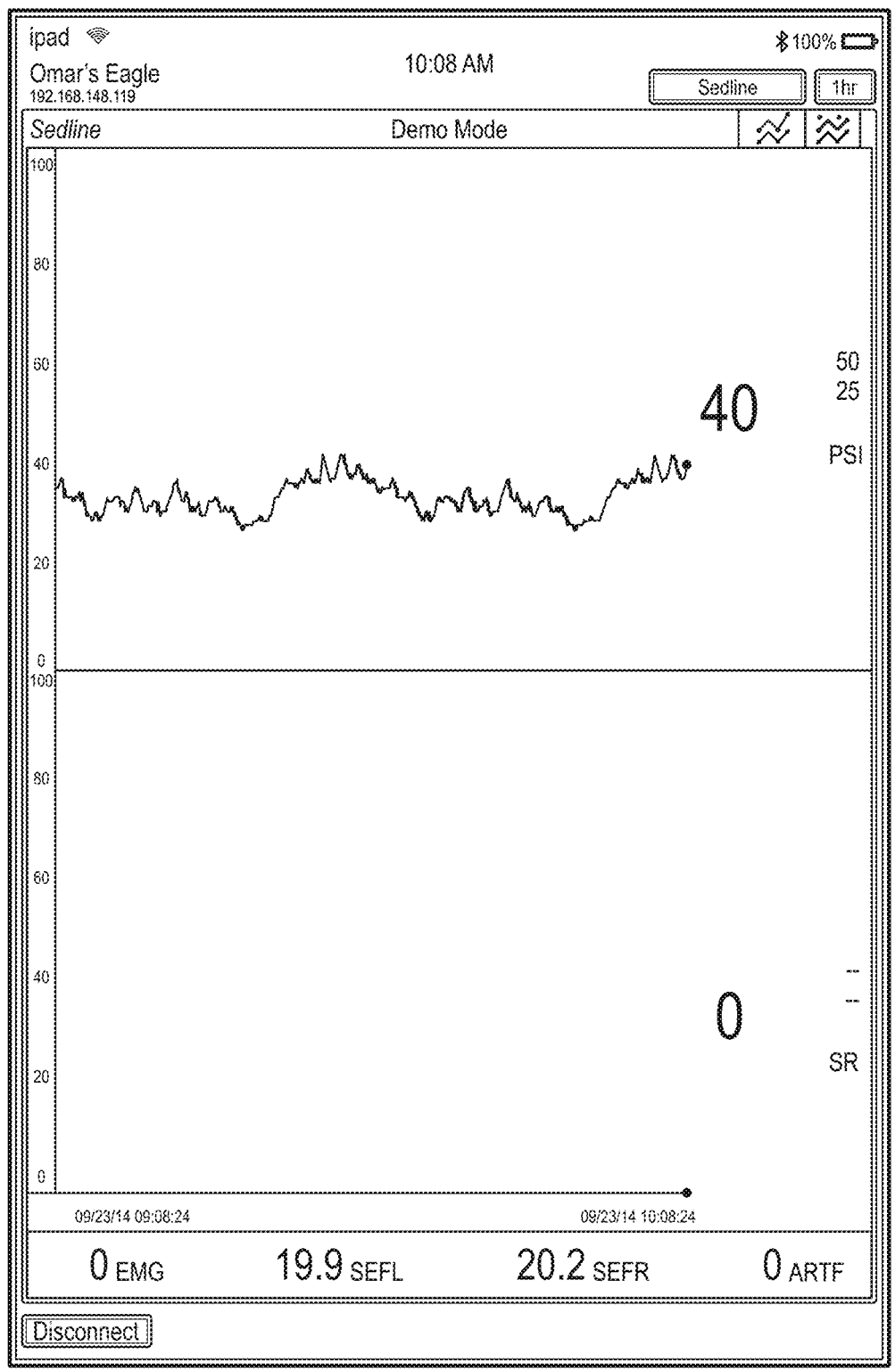
Figure 56:
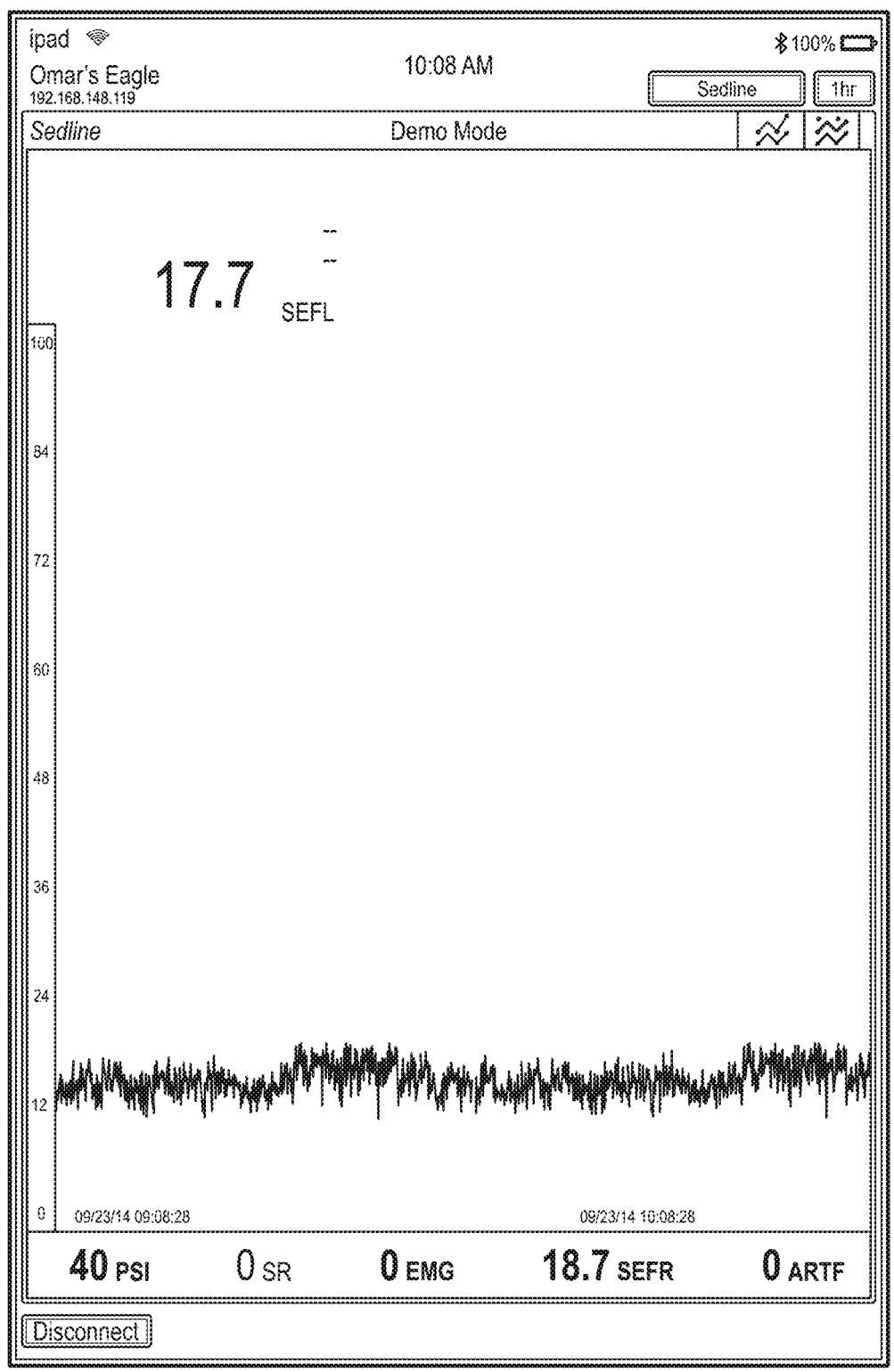
Figure 57:
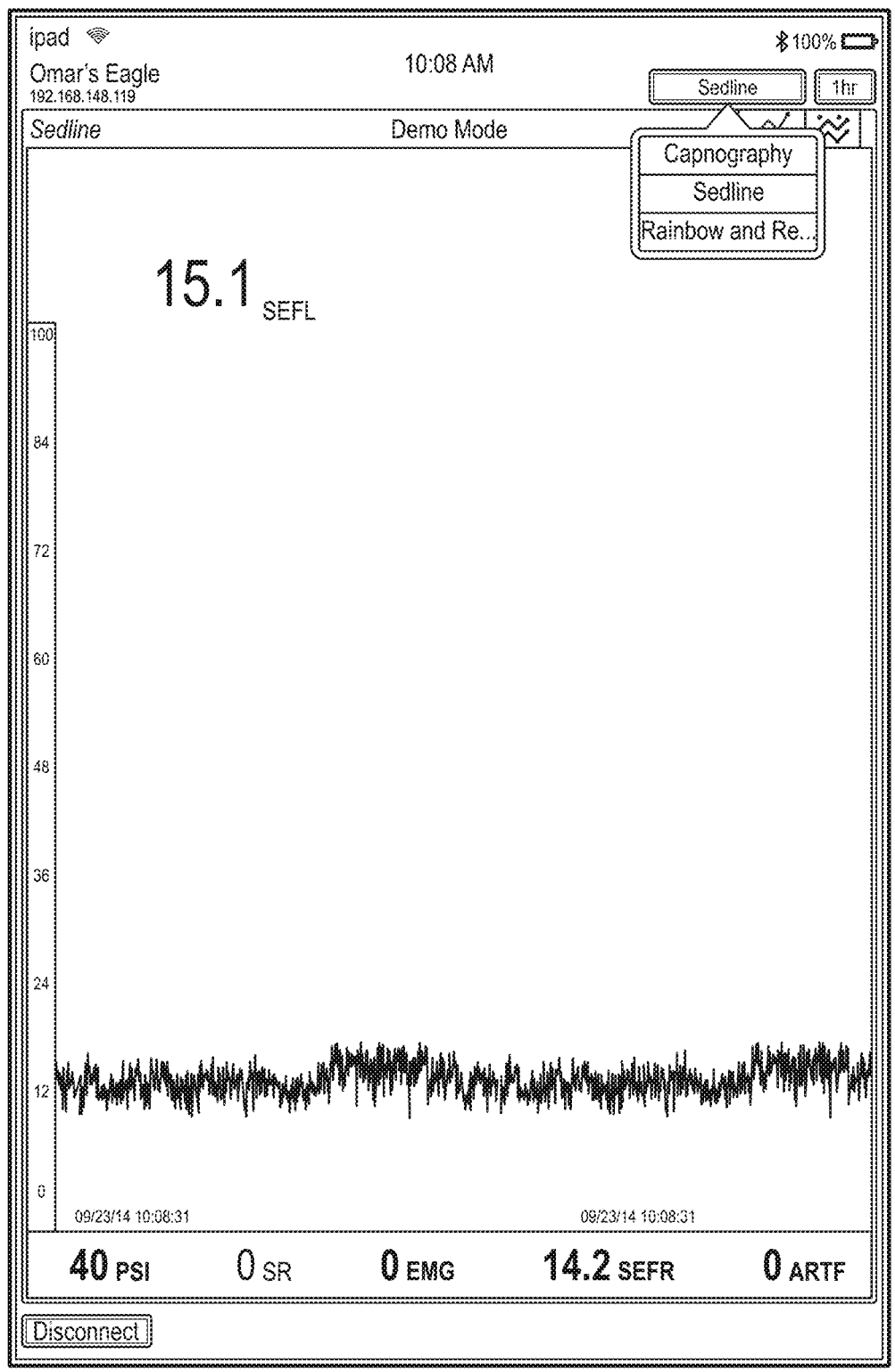
Figure 58:
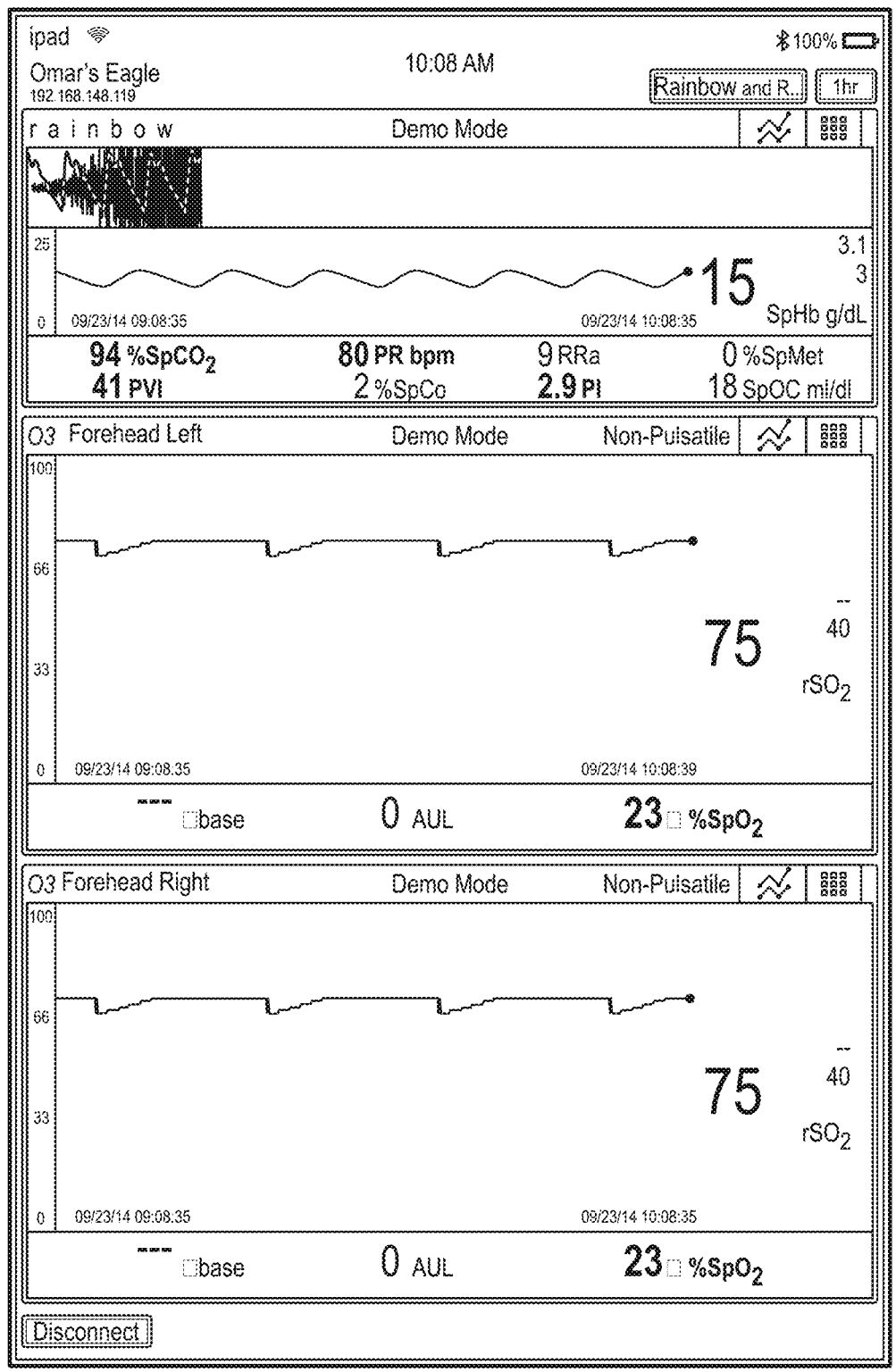
Figure 59:
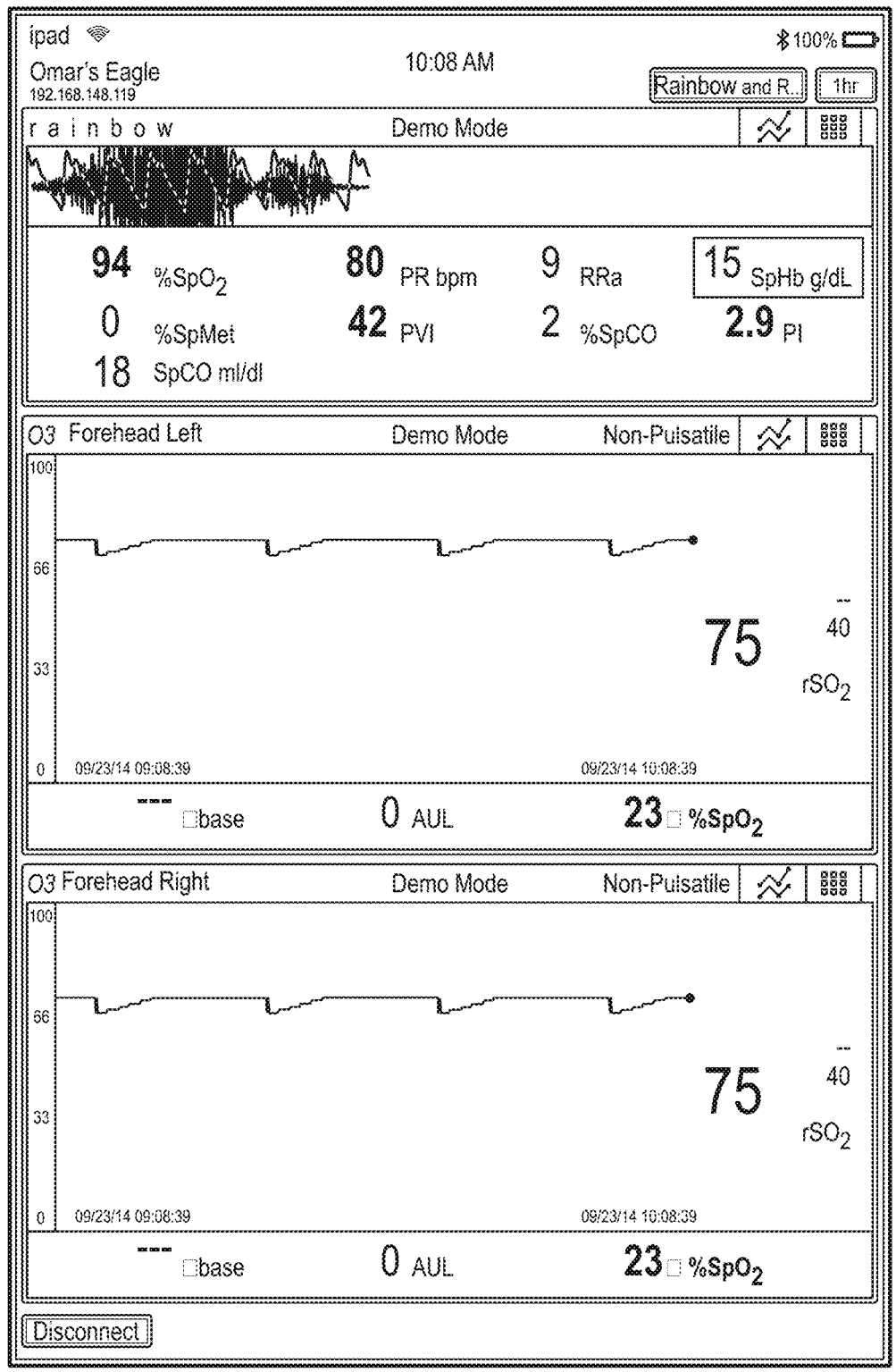
Figure 60:
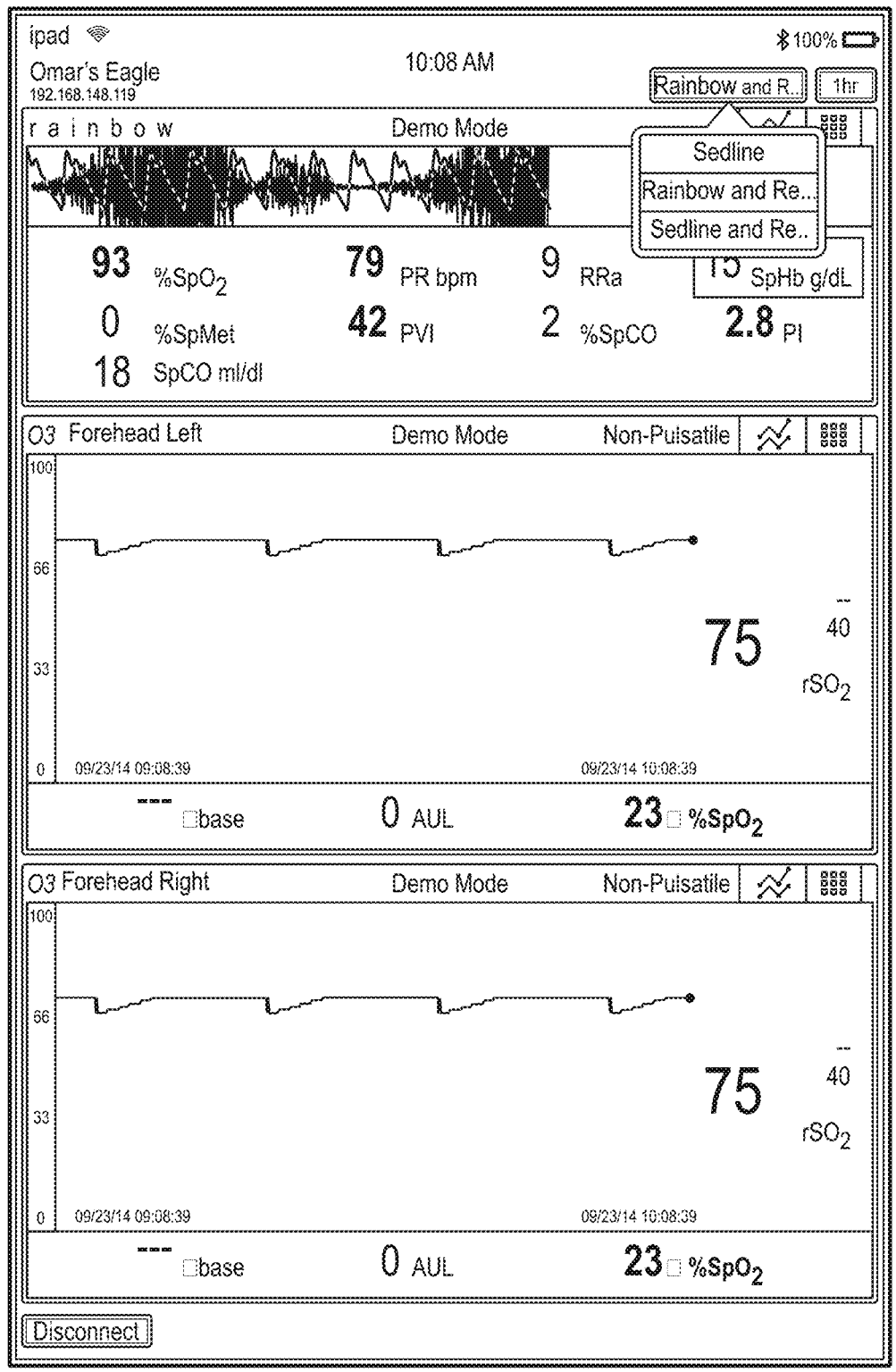
Figure 61:
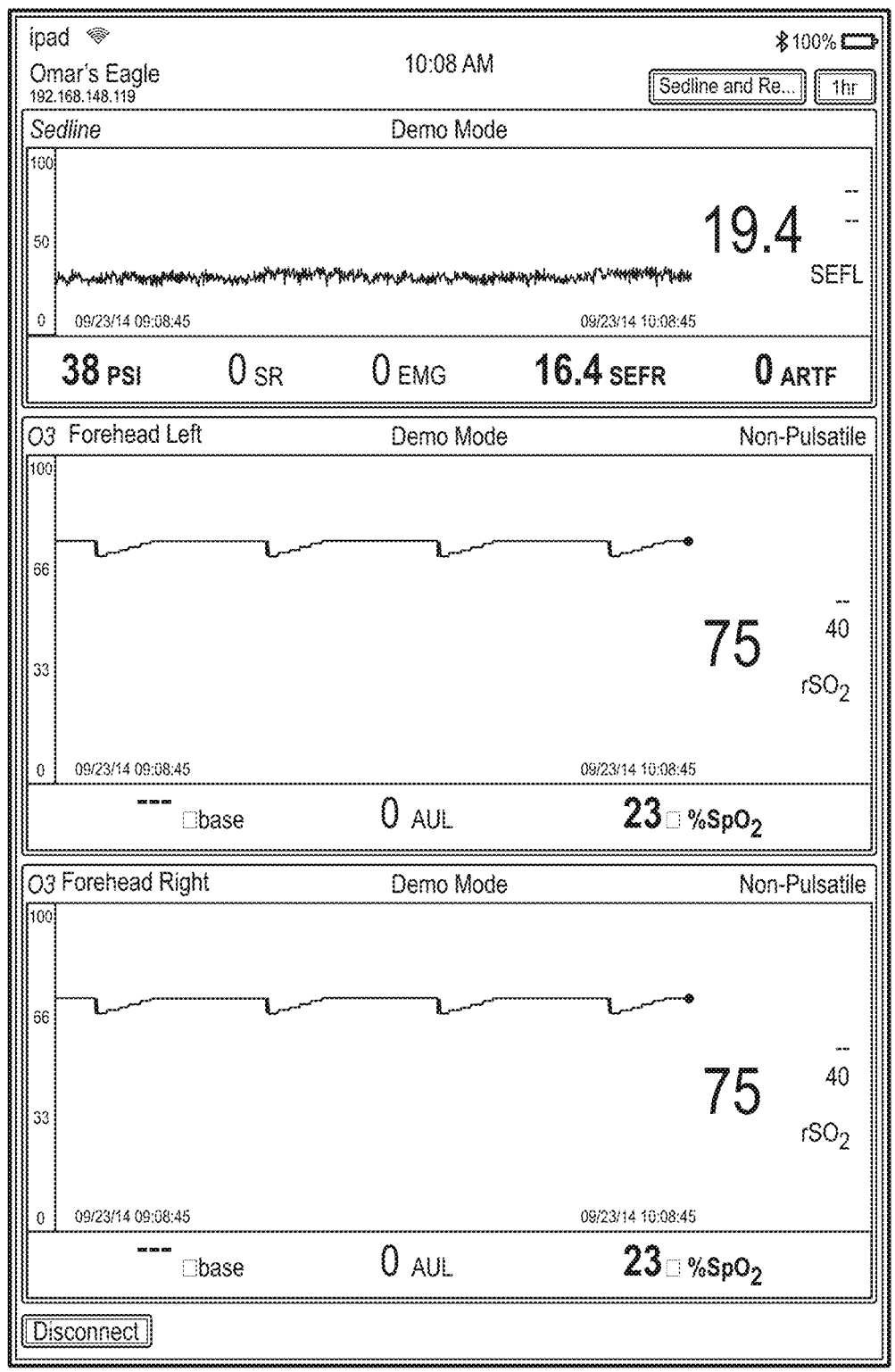
Figure 62:
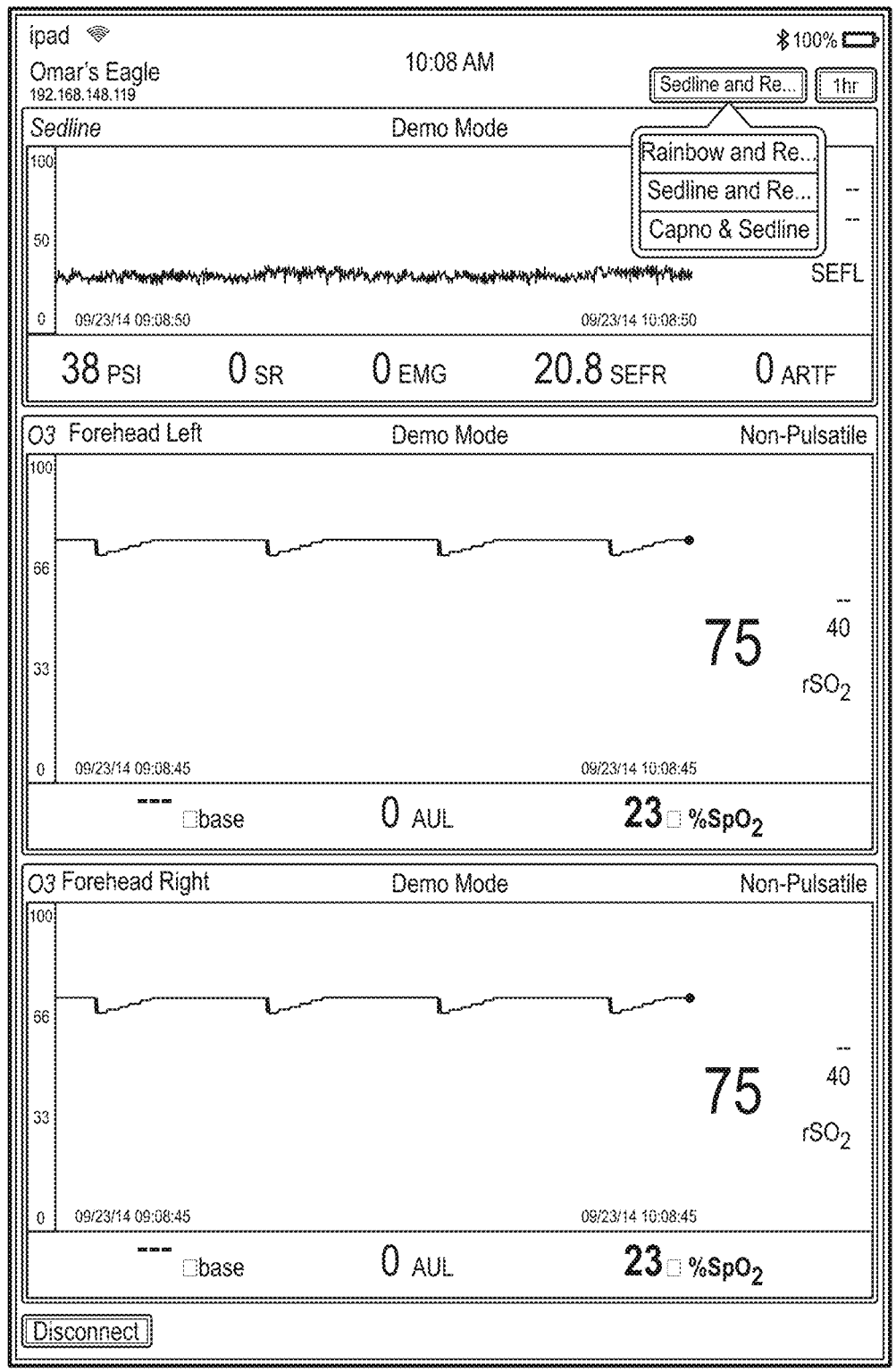
Figure 63:
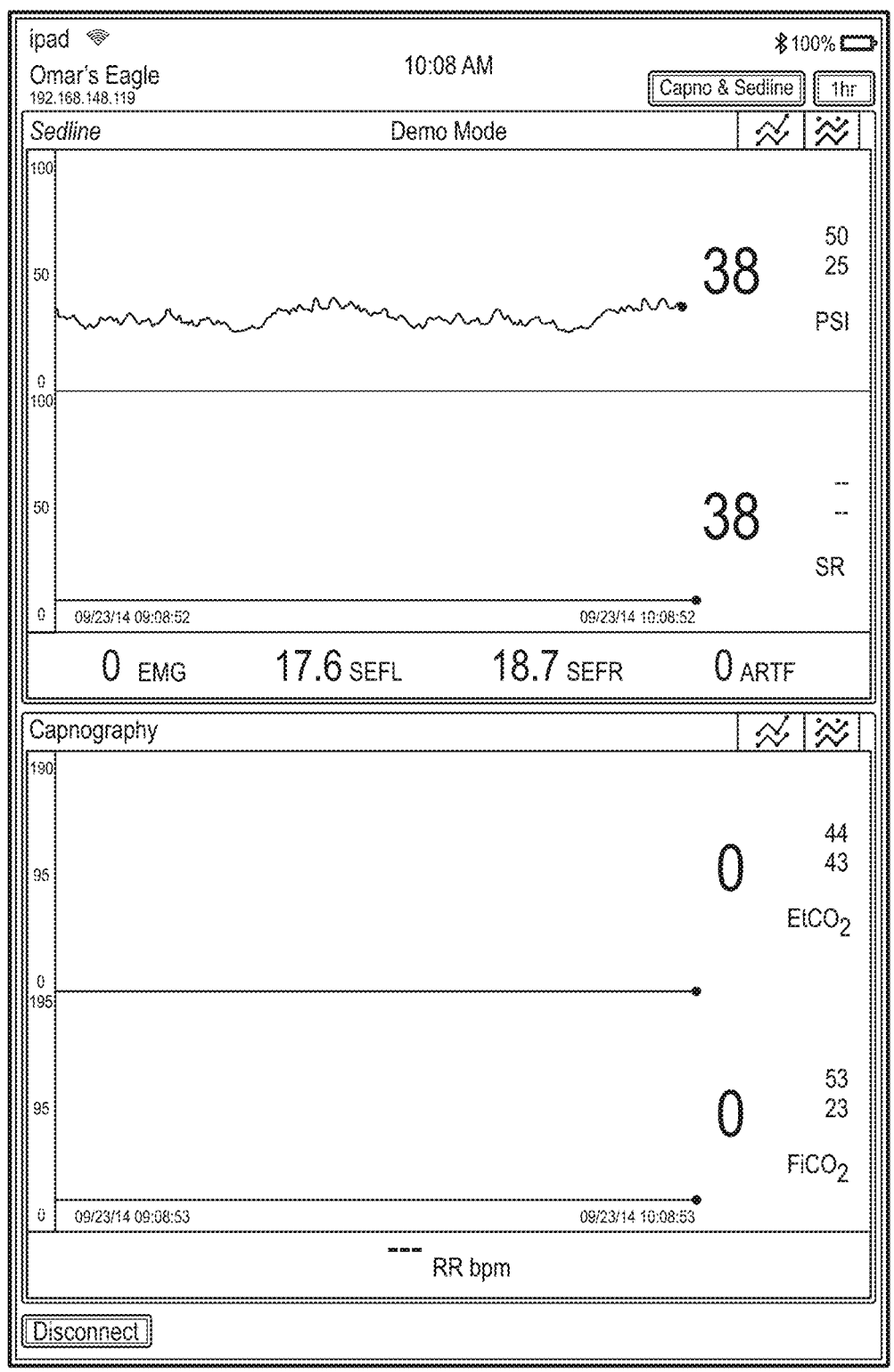
Figure 64:
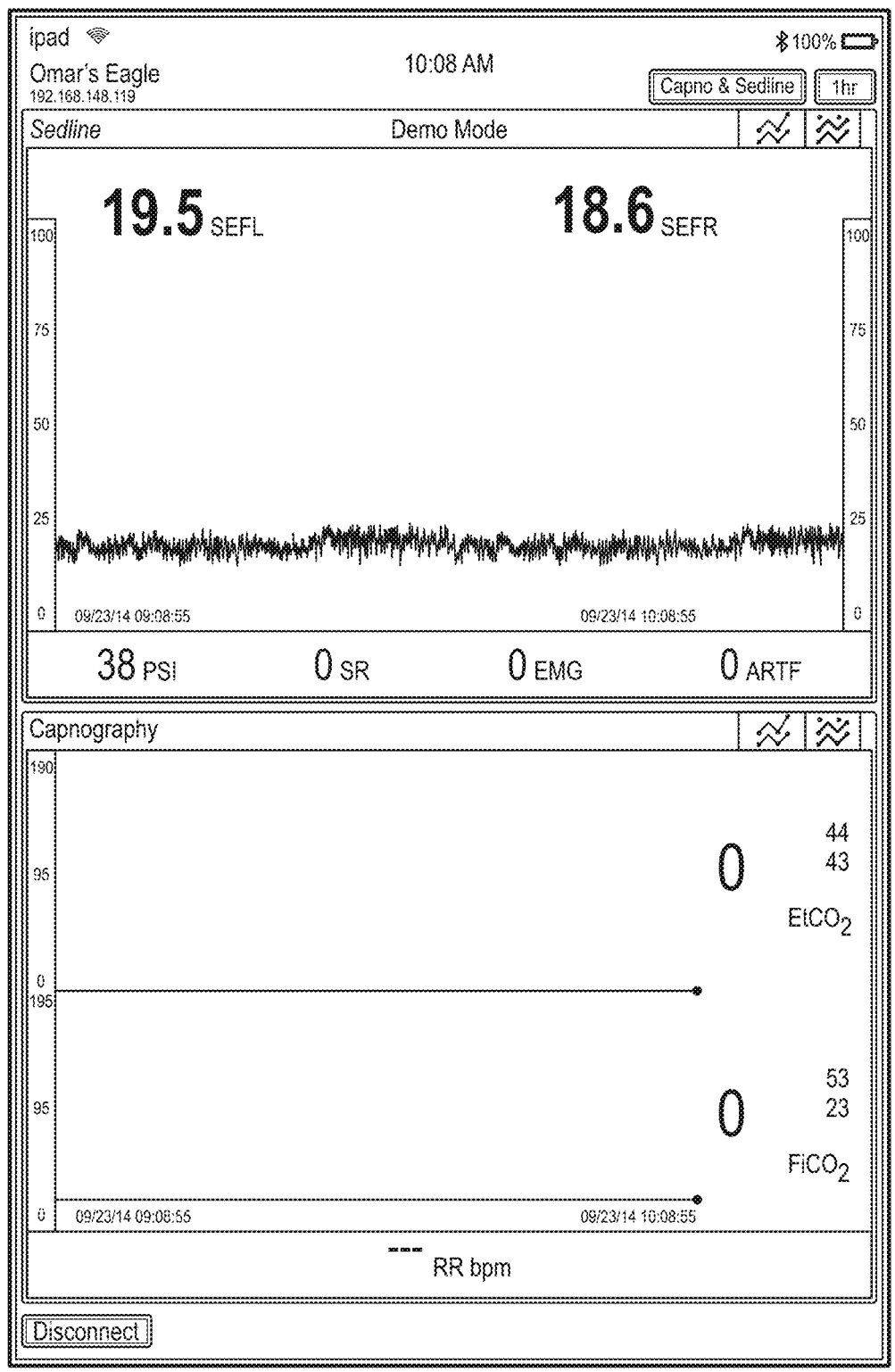
Figure 65:
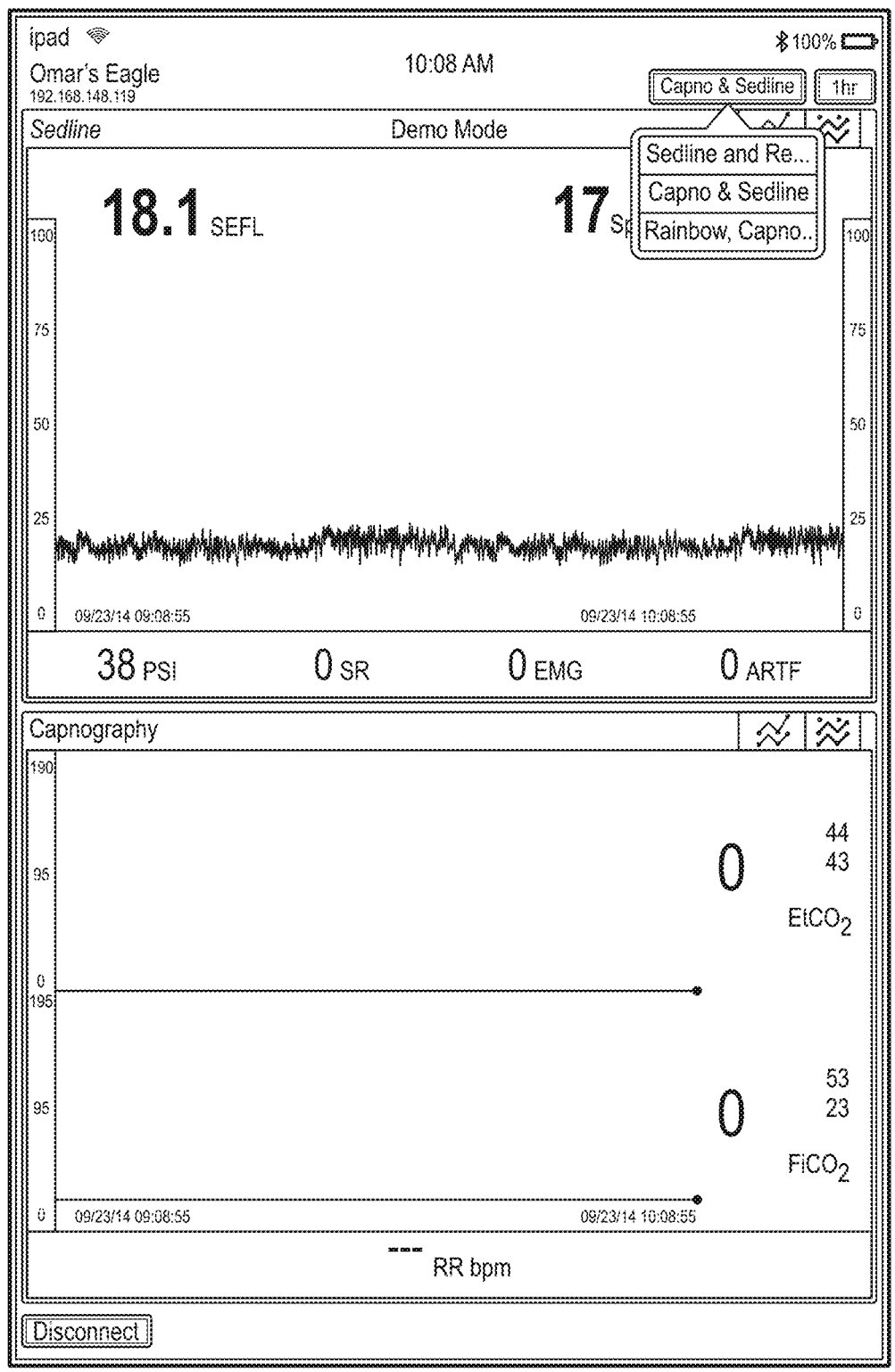
Figure 66:
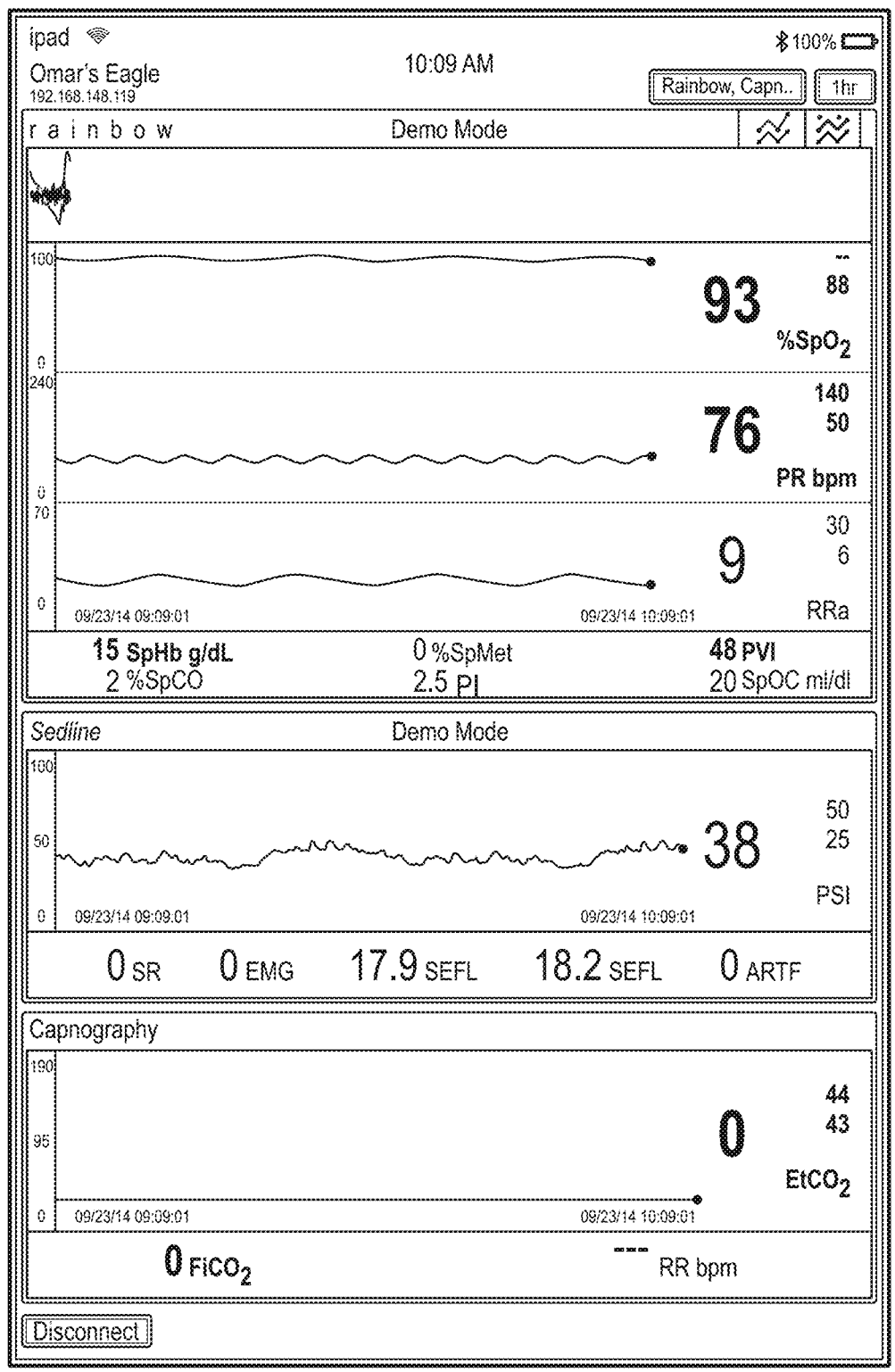
Figure 67:
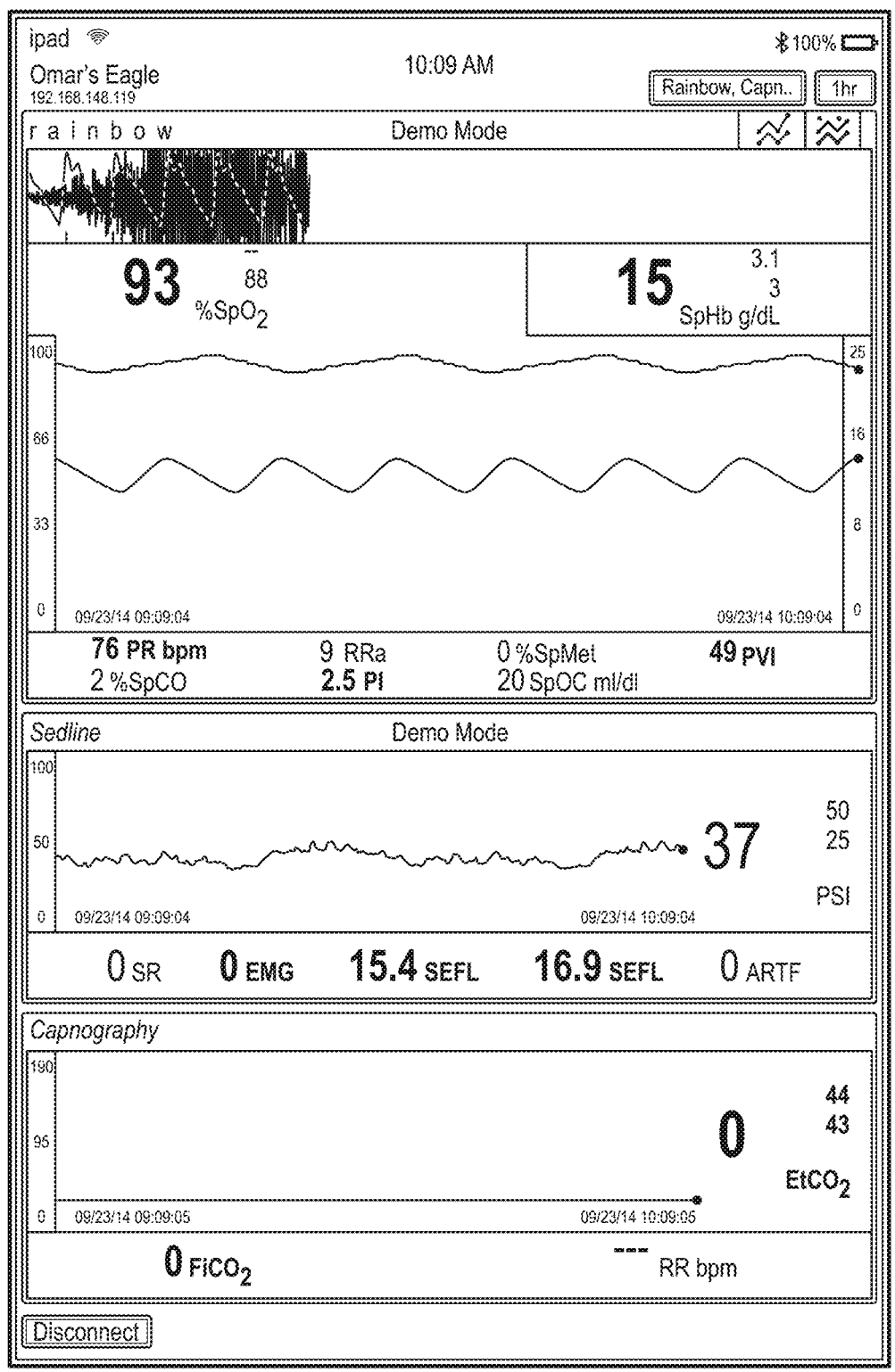
Figure 68:
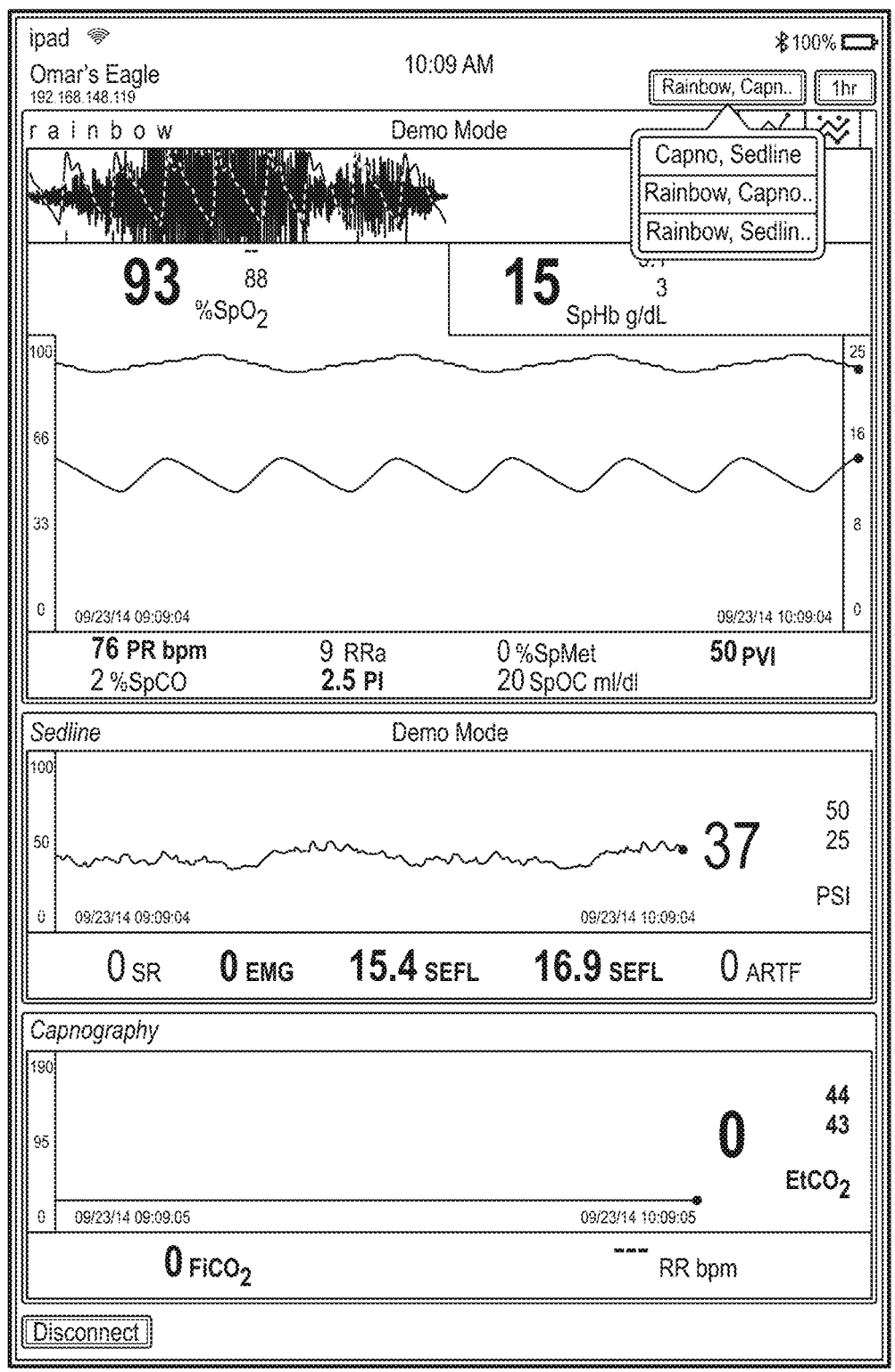
Figure 69:
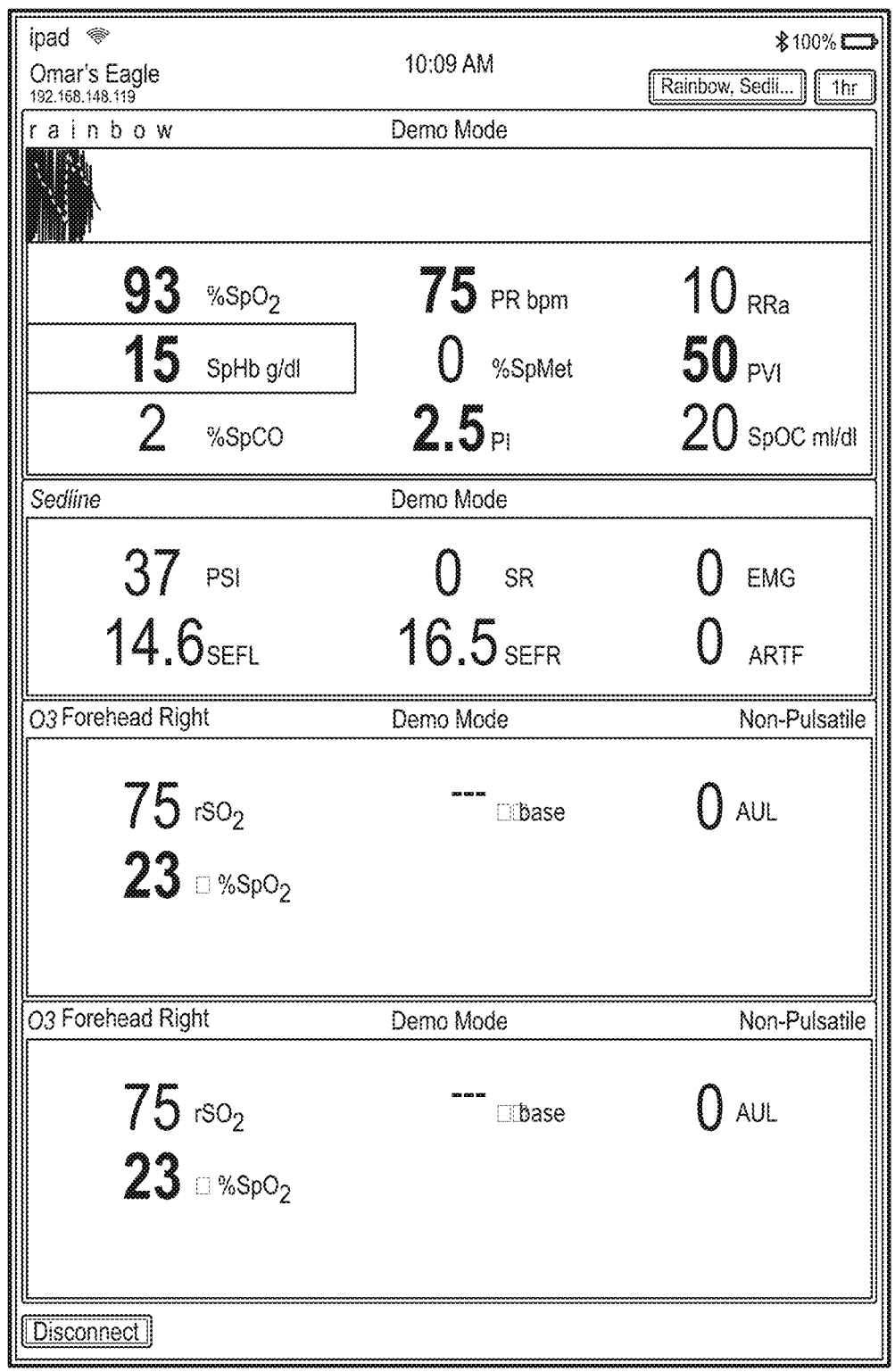
Figure 70:
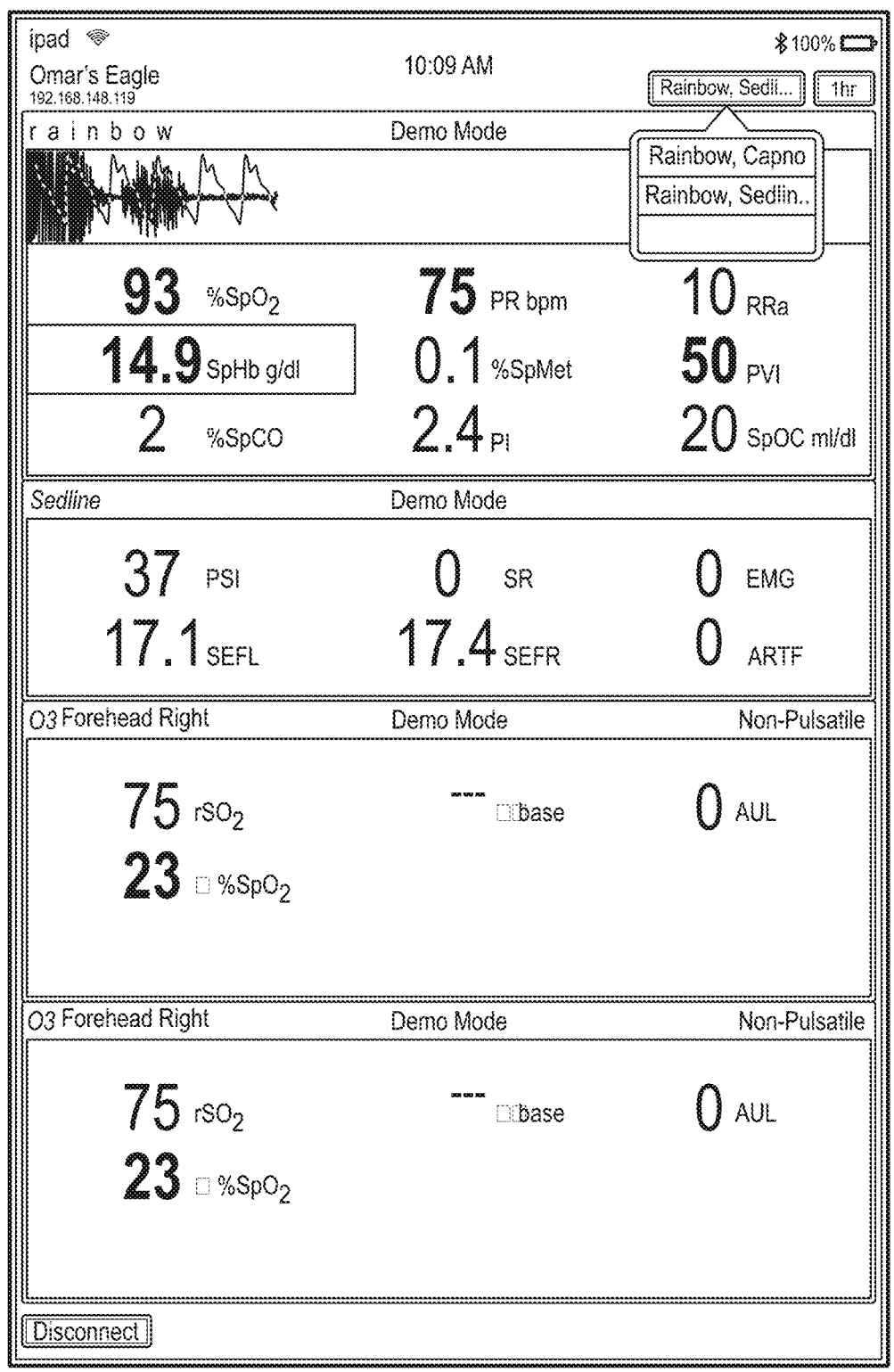
Figure 71:
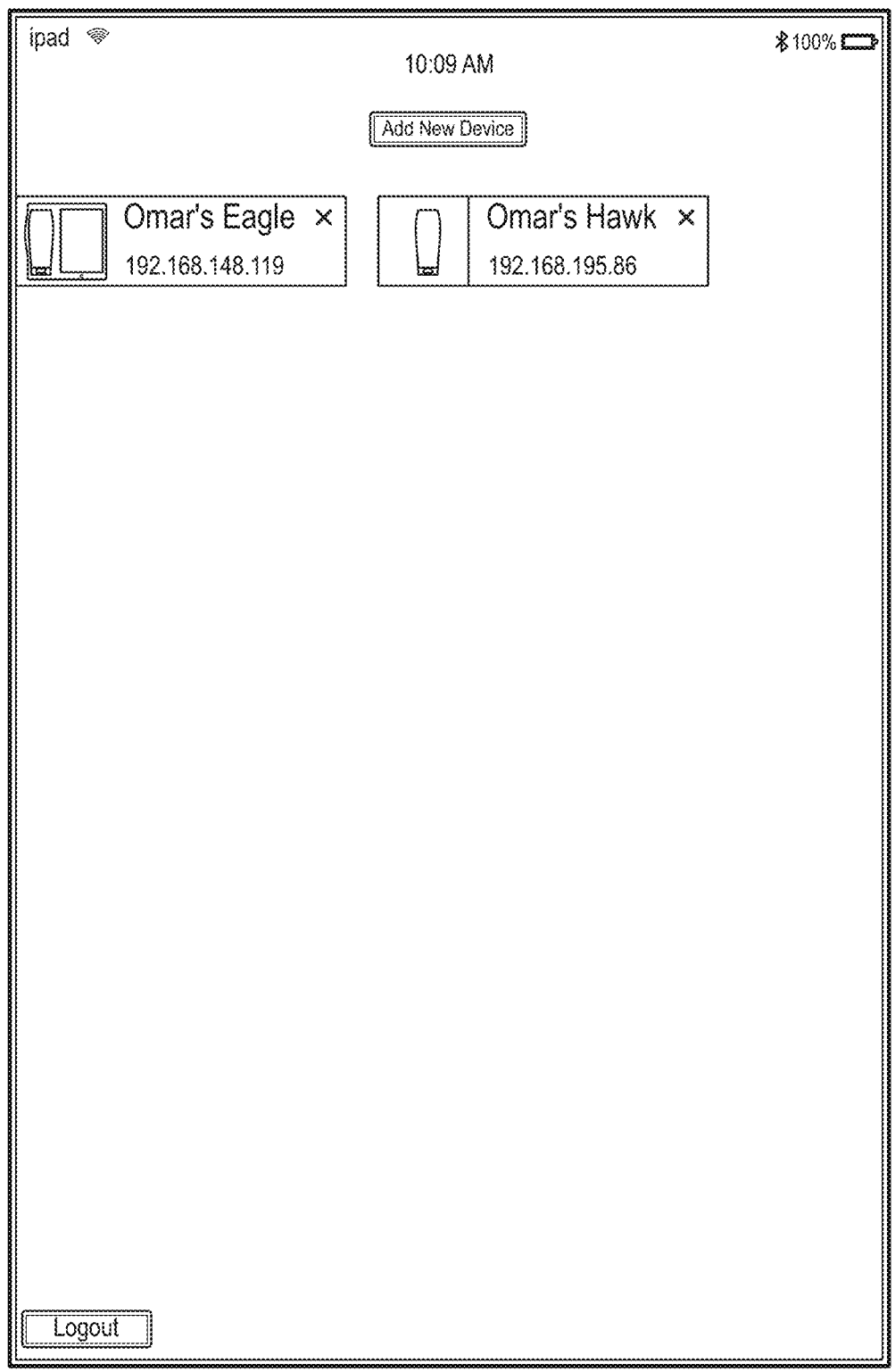

FIGS. 45C and 45D illustrate automatic rule configuration processes performed by the translation module 2415 for messages utilizing the HL7 protocol. The HL7 protocol can be used, for example, to communicate electronic messages to support administrative, logistical, financial, and clinical processes. For example, HL7 messages can include patient administration messages, such as ADT messages, used to exchange patient demographic and visit information across various healthcare systems.

The automatic rule configuration process 2900C illustrated in FIG. 45C is similar to the process 2900A illustrated in FIG. 45A. At block 2911, the translation module 2415 receives one or more messages from an HL7 medical device. At block 2915, the translation module 2415 determines the formatting implementation of the HL7 medical device from the one or more messages received. As discussed above, the determination of the formatting implementation can be made, for example, by checking field order or sequence, field delimiter characters, repeatability, cardinality, and other HL7 implementation variations.

At block 2917, the translation module 2415 configures one or more rules to handle messages received from and/or sent to the HL7 medical device. The configuration of the rules can involve the creation or generation of new rules for the detected formatting implementation. The configuration of the rules can also (or instead) involve the dynamic alteration or updating of existing rules. If a set of rules already exists for the formatting implementation used by the new HL7 medical device, then the configuration of new translation rules may not be required. Instead, existing translation rules can be associated with the new HL7 medical device for use in communication involving that device.

The automatic rule configuration process 2900D illustrated in FIG. 45D is similar to the process 2900B illustrated in FIG. 45B. At block 2912, the translation module 2415 transmits one or more test, dummy, or initialization messages to an HL7 medical device. The translation module 2415 can also (or instead) cause one or more test messages to be transmitted to the new HL7 medical device from another HL7 medical device. As described above, the test messages can include messages having known HL7 formats configured to determine whether the HL7 device understands the test messages. The test messages can include test ADT messages, for example.

At block 2914, the translation module 2415 queries the HL7 medical device to receive information regarding an action taken or information stored in response to the test message. At block 2916, the translation module 2415 determines the formatting implementation of the HL7 device based on the information received. The translation module 2415 can analyze the information received to determine whether the test message or messages were properly understood. If none of the test messages were properly understood, the translation module 2415 can send additional test messages having other known HL7 formats and repeat blocks 2914 and 2916.

At block 2918, the translation module 2415 configures one or more translation rules to handle messages received from and/or sent to the detected HL7 medical device. The configuration of the translation rules can involve the creation or generation of new translation rules. The configuration of the rules can also (or instead) involve the alteration or updating of existing rules. If a set of translation rules already exists for the formatting implementation used by the new HL7 medical device, then the configuration of new translation rules may not be required. Instead, existing translation rules can be associated with the new HL7 medical device for use in communication involving that HL7 medical device.

The automatic rule configuration processes described above can be triggered by the detection of a network device or system by the translation module 2415. The medical devices referred to in FIGS. 45A-45D can include any of the devices or systems illustrated in FIG. 1 or 24.

The automatic generation of translation rules can advantageously occur post-installation and post-compilation of the messaging sub-system software, which includes the translation module 2415. The automatic generation or dynamic modification of the translation rules 2420 can occur without having to recompile or rebuild the translation module software. This feature can be advantageous in terms of efficiently complying with U.S. Food and Drug Administration ("FDA") requirements regarding validation of software used in healthcare environments.

Take, for example, a situation where a medical device manufacturer plans to use the translation module 2415 to facilitate communication between a particular medical device or system that is to be installed in a hospital (e.g., a patient monitoring system, as described herein), or other patient care facility, and other devices or systems that are already installed at the hospital (e.g., the HIS or CIS). Any software required for the operation of the new medical device to be installed may be at least partially validated for FDA compliance prior to installation at the hospital despite the fact that, for example, the HL7 implementations of other existing devices or systems at the hospital may still be unknown. For example, any aspects of the software for the new medical device that are dependent upon receiving messages from other hospital devices can be validated pre-installation as being capable of fully and correctly operating when the expected message format is received. Then, once the medical device is installed at the hospital, the validation of the software can be completed by showing that the translation module 2415 is able to provide messages of the expected format to the newly installed device. In this way, FDA validation tasks can be apportioned to a greater extent to the pre-installation timeframe where they can be more easily carried out in a controlled manner rather than in the field.

In addition, the translation module 2415 can further help streamline FDA validation, for example, when a medical device or system is expected to be installed at different hospitals whose existing devices use, for example, different implementations of the HL7 protocol. Normally, this type of situation could impose the requirement that the entire functionality of the software for the new medical device be completely validated at each hospital. However, if the translation module 2415 is used to interface between the new medical device and the hospital's existing devices, then much of the software functionality could possibly be validated a single time prior to installation, as just described. Then, once installed at each hospital, the software validation for the medical device can be completed by validating that correct message formats are received from the translation module (the translation rules for which are field-customizable). This may result in making on-site validation procedures significantly more efficient, which will advantageously enable more efficient FDA compliance in order to bring life-saving medical technology to patients more quickly by the use of field-customizable translation rules.

V. Additional Examples

A system for providing medical data translation for output on a medical monitoring hub can include a portable physiological monitor comprising a processor that can: receive a physiological signal associated with a patient from a physiological sensor, calculate a physiological parameter based on the physiological signal, and provide a first value of the physiological parameter to a monitoring hub for display. The monitoring hub can include a docking station that can receive the portable physiological monitor. The monitoring hub can: receive the first value of the physiological parameter from the portable physiological monitor; output the first value of the physiological parameter for display; receive physiological parameter data from a medical device other than the portable physiological monitor, the physiological parameter data formatted according to a protocol other than a protocol natively readable or displayable by the monitoring hub; pass the physiological parameter data to a translation module; receive translated parameter data from the translation module, where the translated parameter data can be readable and displayable by the monitoring hub; and output a second value from the translated parameter data for display.

The system of the preceding paragraph can be combined with any subcombination of the following features: the monitoring hub is further configured to output the first value of the physiological parameter and the second value from the translated parameter data on separate displays; the monitoring hub is further configured to output the second value from the translated parameter data to an auxiliary device having a separate display from a display of the monitoring hub; the auxiliary device is selected from the group consisting of a television, a tablet, a phone, a wearable computer, and a laptop; the physiological parameter data comprises data from an infusion pump; the physiological parameter data comprises data from a ventilator; and the translation module is configured to translate the physiological parameter data from a first Health Level 7 (HL7) format to a second HL7 format.

A method of providing medical data translation for output on a medical monitoring hub can include: under the control of a first medical device comprising digital logic circuitry, receiving a physiological signal associated with a patient from a physiological sensor; obtaining a first physiological parameter value based on the physiological signal; outputting the first physiological parameter value for display; receiving a second physiological parameter value from a second medical device other than the first medical device, where the second physiological parameter value is formatted according to a protocol not used by the first medical device, such that the first medical device is not able to process the second physiological parameter value to produce a displayable output value; passing the physiological parameter data from the first medical device to a separate translation module; receiving translated parameter data from the translation module at the first medical device, the translated parameter data able to be processed for display by the first medical device; and outputting a second value from the translated parameter data for display.

The method of the preceding paragraph can be combined with any subcombination of the following features: further including translating the message by at least translating the message from a first Health Level 7 (HL7) format to a second HL7 format; the message can include data from a physiological monitor; the message can include data from an infusion pump or a ventilator; and the message can include data from a hospital bed.

A system for providing medical data translation for output on a medical monitoring hub can include a first medical device including electronic hardware that can: obtain a first physiological parameter value associated with a patient; output the first physiological parameter value for display; receive a second physiological parameter value from a second medical device other than the first medical device, the second physiological parameter value formatted according to a protocol not used by the first medical device, such that the first medical device is not able to process the second physiological parameter value to produce a displayable output value; pass the physiological parameter data from the first medical device to a translation module; receive translated parameter data from the translation module at the first medical device, the translated parameter data able to be processed for display by the first medical device; and output a second value from the translated parameter data for display.

The system of the preceding paragraph can be combined with any subcombination of the following features: the first medical device can also output the first value of the physiological parameter and the second value from the translated parameter data on the same display; the first medical device can also output the first value of the physiological parameter and the second value from the translated parameter data on separate displays; the first medical device can also output the second value from the translated parameter data to an auxiliary device; the auxiliary device can be a television monitor; the auxiliary device can be selected from the group consisting of a tablet, a phone, a wearable computer, and a laptop; the first medical device can include the translation module; the first medical device can also pass the physiological parameter data to the translation module over a network; and the physiological parameter data can include data from an infusion pump or a ventilator.

VI. Augmented Reality Examples

Today's patient monitoring environments provide one more traditional displays or screens for clinicians that present data from one or more electronic medical devices associated with a wide variety of monitoring, treatments, or procedures for a patient. Thus, during such patient monitoring, treatments, or procedures a clinician typically reviews one or more traditional displays to gather information about a patient. However, while a clinician looks at the one or more traditional displays their attention may be diverted away from the patient, such as a clinician looking away from the patient to a traditional display during a surgical procedure. For example, during some surgical procedures, such as an endoscopy or an epidural, it is common for the operating clinician to look at the patient to see where a probe is going but the clinician has to look away from the patient to view a traditional display, which is inefficient and potential dangerous to the patient.

The systems and methods described herein advantageously may improve the presentation of data or provide improved interactive user interfaces using augmented reality. For example, a clinician using an augmented reality device, such as wearing augmented reality glasses, is presented with medical monitoring data that may be received from the medical monitoring hub, as described herein. An advantage of augmented reality is that the augmented reality display can overlay real world visual information. Accordingly, a clinician can remain visually focused on a patient while simultaneously receiving augmented reality information. An advantage of augmented reality is that the display area for an augmented reality user interface may be larger than traditional displays, such as device screens. For example, an augmented reality display area may be ten times larger than a traditional display area. The following are examples of improved augmented reality user interfaces.

An example augmented reality device presents one or more user interfaces. Example user interfaces that may be presented on the augmented reality device include any of the user interfaces described herein. Further, augmented reality user interfaces can improve the efficiency of surgical procedures. For example, during certain procedures, such as an endoscopy or an epidural, the clinician can efficiently maintain his or her view of the patient to see where a probe is going and simultaneously view an overlay user interface that includes data that would have previously only been available on a traditional display. An augmented reality user interface may be pinned to a particular area within a three-dimensional space or the patient room. For example, a clinician can interact with the augmented reality device to pin an augmented reality user interface to a physical device, a location, or to the patient. Continuing with the example, the clinician using the augmented reality device can view the pinned augmented reality user interface when looking near the physical device or the location that was pinned; however, if the clinician looks away from the physical device or the location then the augmented reality user interface is not presented (in this example). The auxiliary device 2040 may be optional or any information displayed on the auxiliary device 2040 may be presented through the augmented reality device.

Another example of improved user interfaces using augmented reality is the presentation of analog display indicia as superimposed on a patient. Example analog display indicia that may be presented on the augmented reality device include any of the analog display indicia described herein. The example analog display indicia, such as a two-dimensional or three-dimensional lungs, heart, brain, or circulatory system, can be superimposed on a patient. Accordingly, a clinician looking at the patient can see the superimposed analog display indicia. The analog display indicia can be pinned to the patient such that if the clinician looks away from the patient then the analog display indicia is no longer presented. As described herein, the analog display indicia can present health indicators of various physiological parameters. Example health indicators include color-coded analog display indicia, such as green, yellow, or red indicia, which may indicate nominal, cautionary, or severe situations, respectively, which are described in further detail herein.

Improved augmented reality user interfaces described herein can enable a user to configure or interact with the user interface. For example, the augmented reality user interface may be a dashboard where a user can add or remove one or more virtual display panels or change the arrangement or the location of the augmented reality panels or objects. The augmented reality device may receive user input corresponding to user interactions. Example user interactions include voice input or commands, visual or eye commands, touch input, or movement, such as head movement or hand gestures. Example head gestures include head tilt, bobbing, or nodding. As another example, a clinician may receive augmented reality patient data when outside of the patient's room or area. In the example, a clinician walking past a patient's room interacts with the augmented reality device to receive data regarding the patient or from the electronic medical devices within the patient's room. Continuing with the example, the clinician executes a hand gesture that virtually grabs the patient's data and causes presentation of the data in their augmented reality device without entering the patient room. As another example, patient data may be virtually posted outside of rooms. A clinician can pass by a room, look at the room and see a virtual user interface for the patient monitor inside the room, and pin the virtual user interface outside of the room using a gesture or verbal command. Additionally or alternatively, the patient data may be available anywhere within a healthcare facility or even remotely, such as a clinician being tens or hundreds of miles away from the physical location of the patient.

Additional example user interfaces and systems for patient monitoring and notifications are disclosed in U.S. patent application Ser. No. 14/511,972 by the assignee of the present disclosure and is incorporated by reference herein.

Figure 72A:
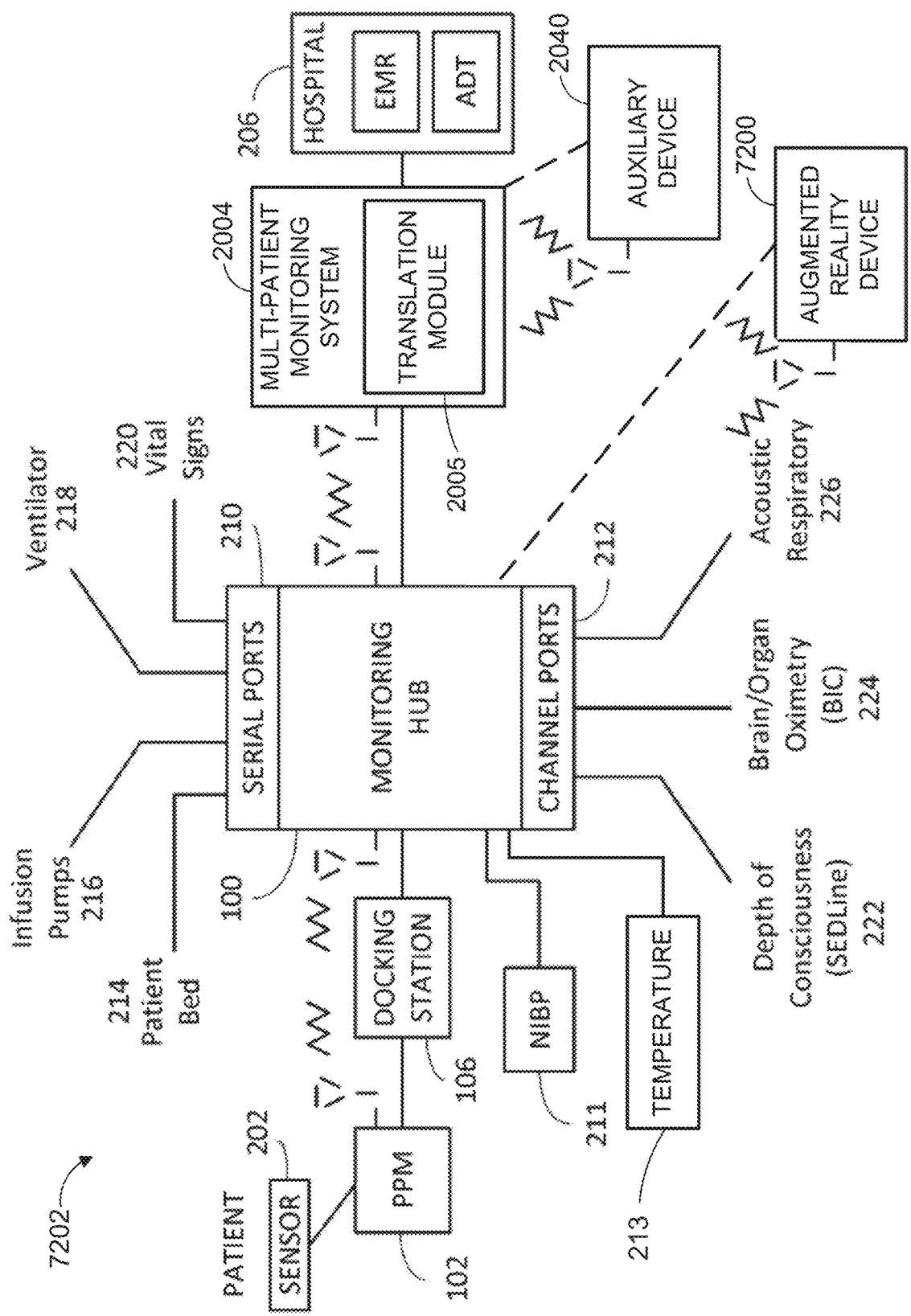
FIG. 72A illustrates another example monitoring environment including an augmented reality device.

FIG. 72A illustrates another example of a monitoring environment 7202 including the hub 100 of FIG. 1 and the devices of FIG. 24. The monitoring environment 7202 may include all or some of the features of the monitoring environment 200 of FIG. 2 or the monitoring environment 2000 of FIG. 24, as well as any of the other features described above. In addition, the monitoring environment 7202 depicts the multi-patient monitoring system (MMS) 2004. The MMS 2004 includes a translation module 2005 that can receive serial data, translate the serial data into a format recognizable by the monitoring hub 100, and provide the serial data to the monitoring hub 100 (among possibly other devices). Also shown is an auxiliary device 2040 that may communicate with the MMS 2004, the monitoring hub 100, or the PPM 102, wired or wirelessly. Similarly, the augmented reality device 7200 may communicate with the MMS 2004, the monitoring hub 100, or the PPM 102, wired or wirelessly. The hub 100, the PPM 102, and the auxiliary device 2040 are each an example of a patient monitor.

The example augmented reality device 7200 includes augmented reality glasses, head-mounted displays, head-up displays, contact lenses, a smartphone, or a tablet. The augmented reality device 7200 may include some combination of one or more hardware processors, displays, sensors, or input devices. For example, the augmented reality device 7200 can include a camera, an accelerometer, gyroscope, a GPS device, or a solid-state compass. The augmented reality device 7200 may include one or more wired or wireless devices that enable communication over Bluetooth, USB, wired networks, or one or more wireless networks, such as a Global System for Mobile Communications (GSM) network, a Code Division Multiple Access (CDMA) network, a Long Term Evolution (LTE) network, Wi-Fi, or some other type of wireless network. The augmented reality device 7200 may also communicate with an augmented reality server (not illustrated), which may handle some augmented reality processing. Accordingly, the example augmented reality device can offload some or all of the augmented reality processing to be performed by the augmented reality server (which may be in a cloud computing center) in a distributed manner.

Figure 72B:
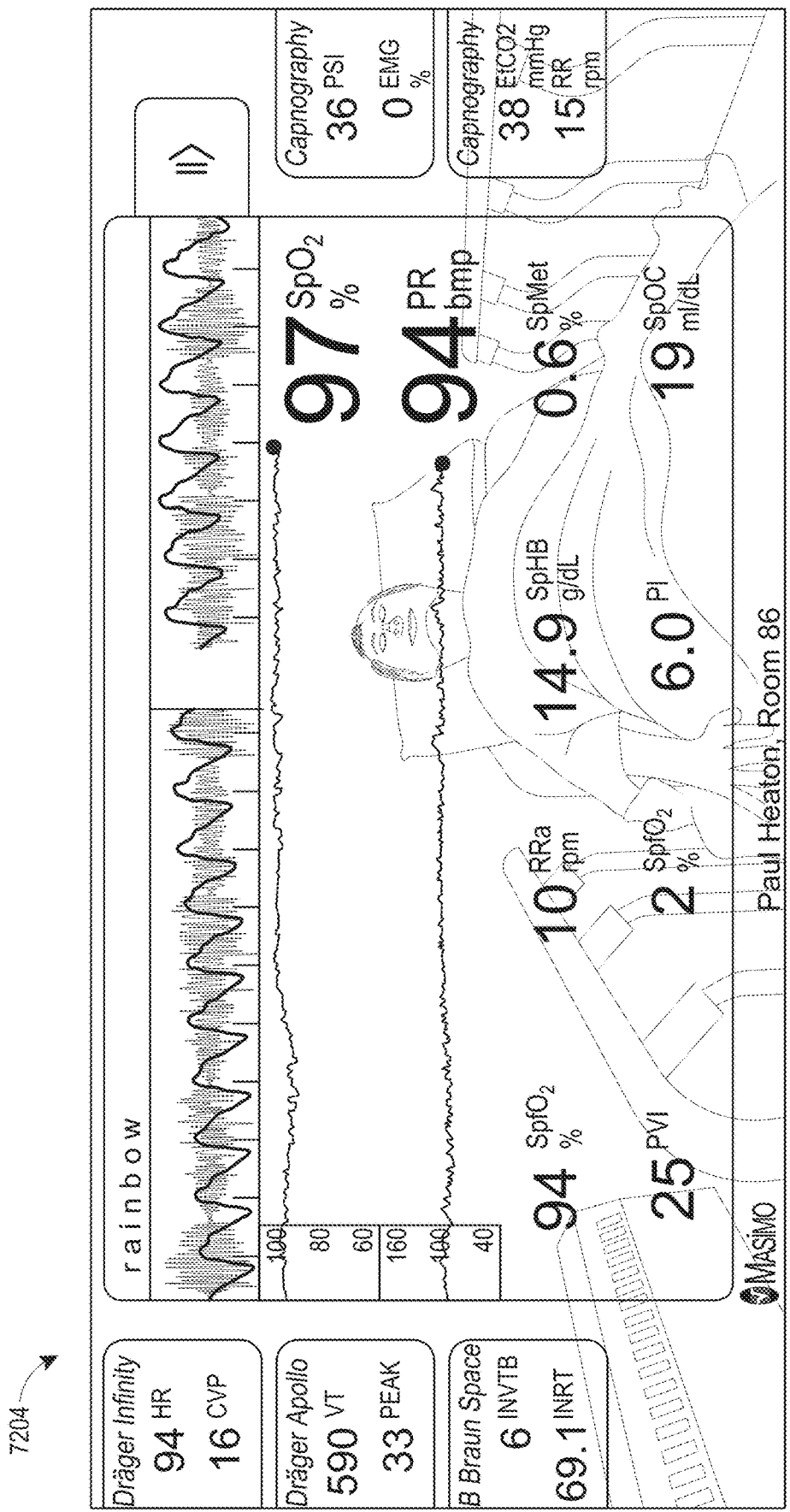
FIGS. 72B-72F illustrates example augmented reality user interfaces.

FIG. 72B depicts an example augmented reality user interface 7204. The example augmented reality user interface 7204 includes one or more augmented reality user interface objects. As described herein, the medical monitoring system may receive one or more physiological signals associated with a patient that is being monitored via one or more physiological sensors. The medical monitoring system may calculate physiological parameters based on the physiological signals. The augmented reality device 7200 or another device of the medical monitoring environment may generate the one or more augmented reality user interface objects from the physiological monitoring data that includes the physiological parameters. As described herein, the physiological monitoring data may update in a real-time or near-time manner; accordingly, the augmented reality user interface objects displaying the physiological monitoring data may update in a real-time or near-time manner. The clinician using the augmented reality device may configure the augmented reality user interface. For example, the augmented reality device may receive user input corresponding to user interactions that configure the augmented reality user interface. Example user configuration of the augmented reality user interface includes additions or removals of augmented reality objects, a change in the position of augmented reality objects, selections to cycle through different augmented reality user interfaces, or a selection of a particular augmented reality user interface. For example, a first augmented reality user interface can correspond to a first collection of augmented reality objects for monitoring patient physiological data, a second augmented reality user interface can correspond to a second collection of augmented reality objects for presenting patient medical history, and a third augmented reality user interface can correspond to a third collection of augmented reality objects for presenting patient demographics data.

Figure 72C:
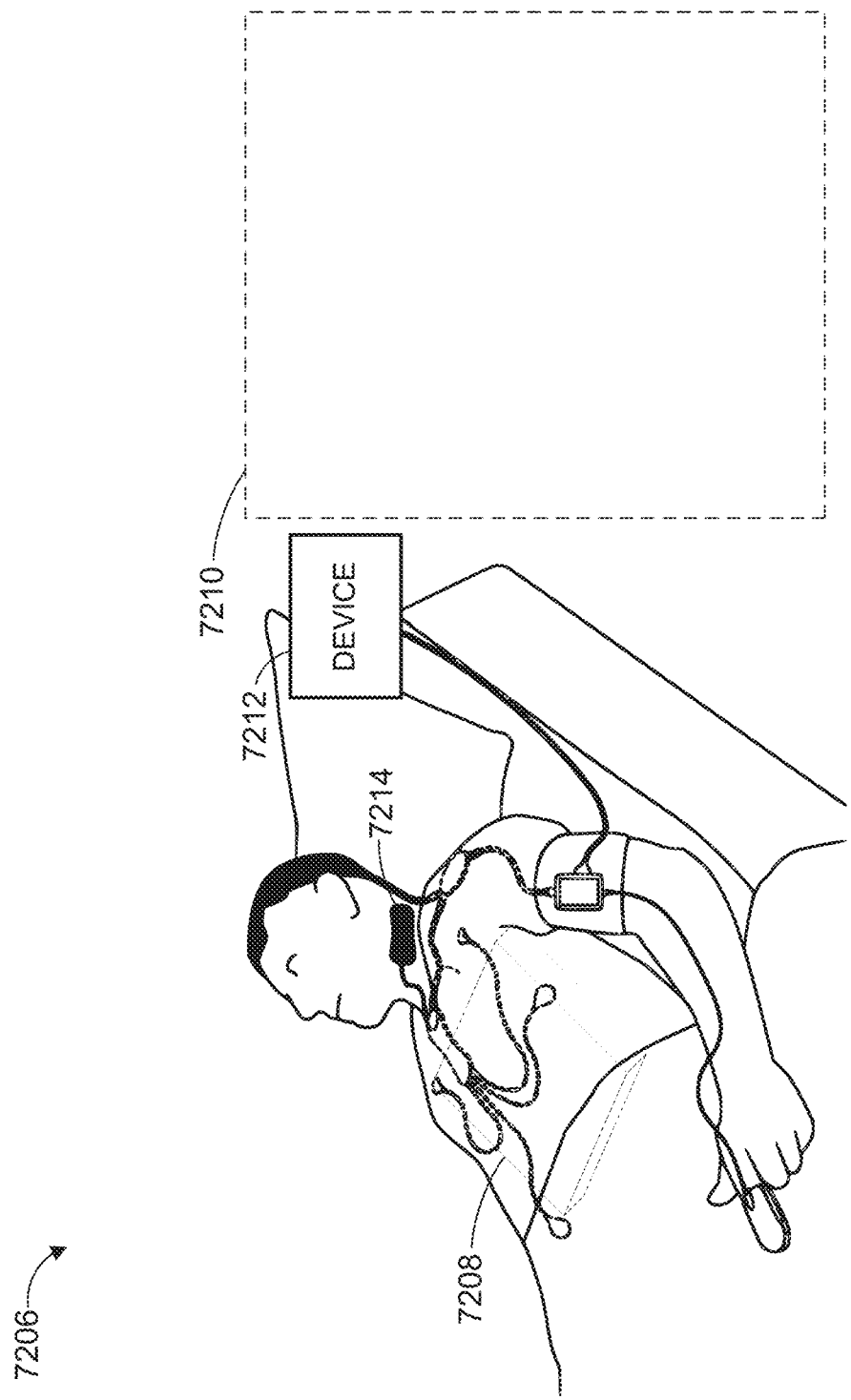

FIG. 72C depicts another example augmented reality user interface 7206. The example augmented reality user interface 7206 includes one or more augmented reality objects 7208 and an augmented reality display area 7210. As described herein, the example augmented reality object 7208 includes analog display indicia that are superimposed on the patient. For example, the augmented reality object 7208 can correspond to a color-coded visual representation of lungs that indicates the status of the patient's lungs. The patient may be connected to or may be wearing one or more devices 7214, which is further connected to another device 7212 that may correspond to the hub, the monitoring system, or a traditional display, for example. An augmented reality system, such as the augmented reality device 7200 or an augmented reality server, can determine the position of the augmented reality object 7208 based on positional information derived from the one or more devices 7214. For example, the one or more devices 7214 may include tracking sensors, such as cameras, optical sensors, accelerometers, GPS, gyroscopes, solid state compasses, RFID, or wireless sensors. Additionally or alternatively, the one or more devices 7214 may include visual markers that can be detected by the augmented reality device 7200 for image registration, or the patient may be wearing one or more visual markers for image registration. The clinician using the augmented reality device 7200 may pin the augmented reality display area 7210 to the device 7212. The augmented reality display area 7210 may include any of the example user interfaces described herein.

Similar to the visual markers or tracking sensors associated with the patient or the one or more devices 7214, the augmented reality system may determine the position of the augmented reality display area 7210 based on visual markers or tracking sensors associated with the device 7210. As described herein, the example augmented reality system can determine the position of the augmented reality display area 7210 by identifying a reference object, here the device 7212, determining a reference position for the reference object, and calculating a positional offset from the reference position. The positional offset may be calculated as a predetermined or configurable distance and direction from the reference object. Continuing with the example, the clinician using the augmented reality device may change or update the positional offset of the augmented reality display area 7210.

Figure 72D:
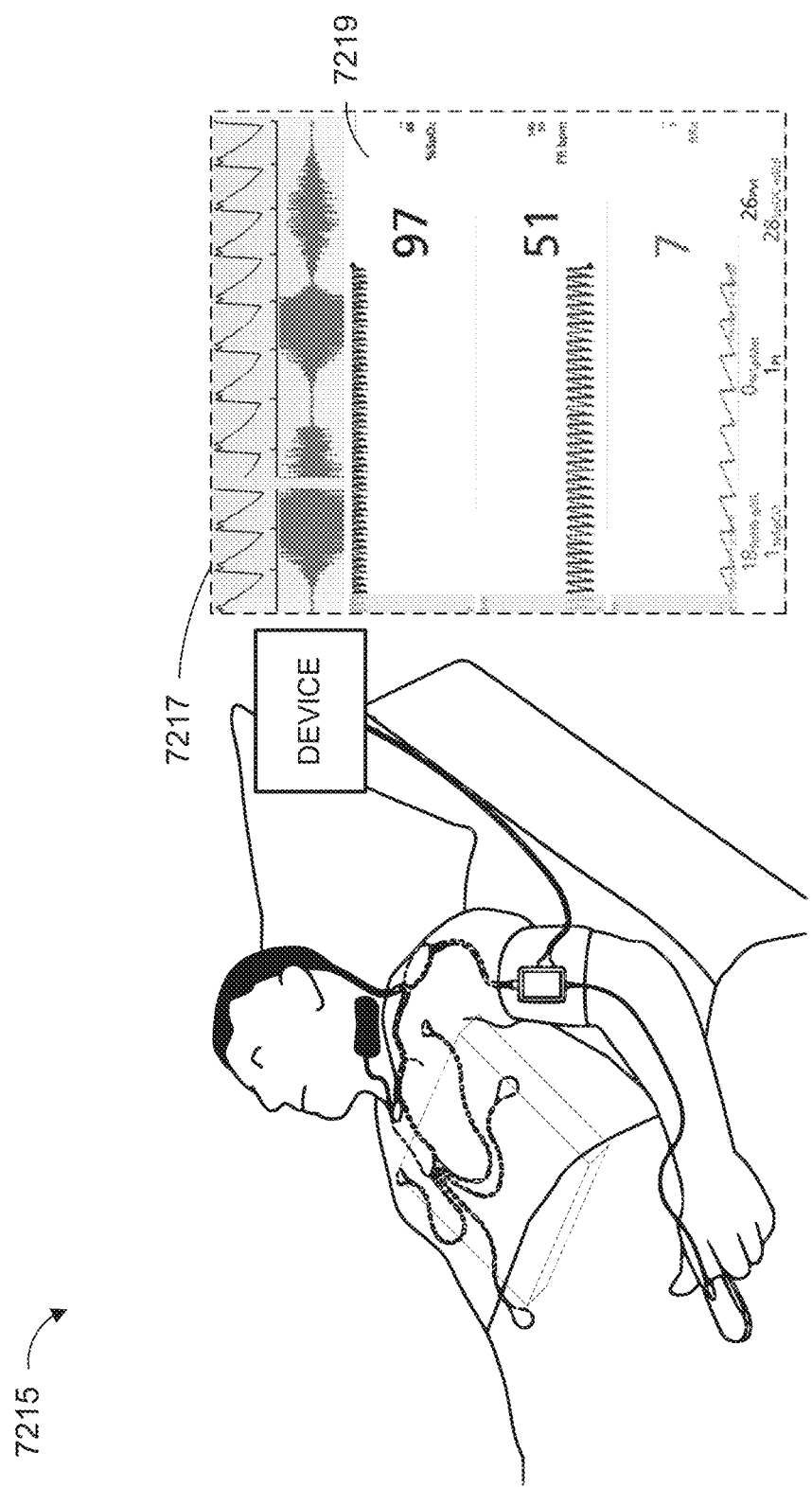
Figure 72E:
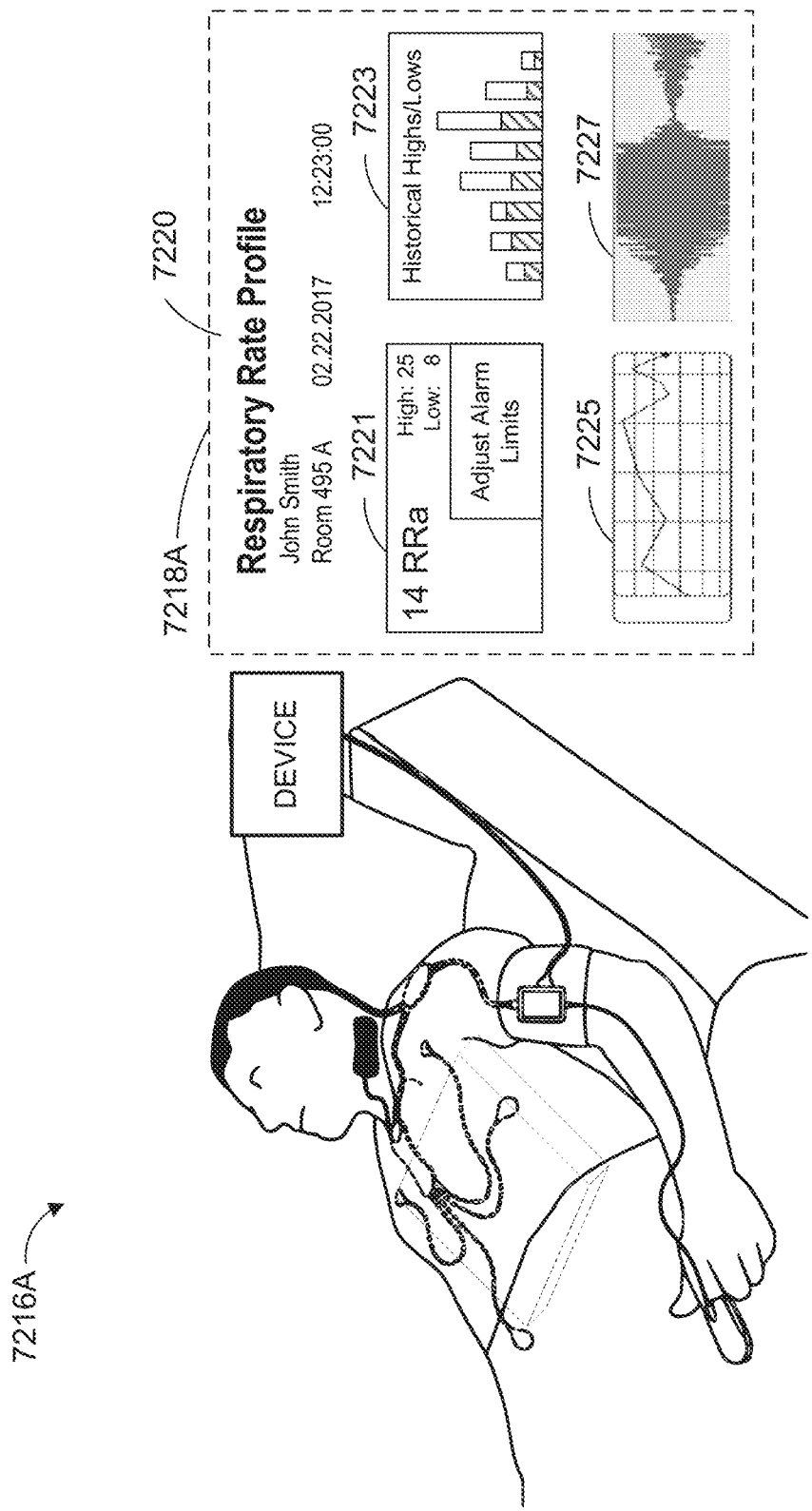
Figure 72F:
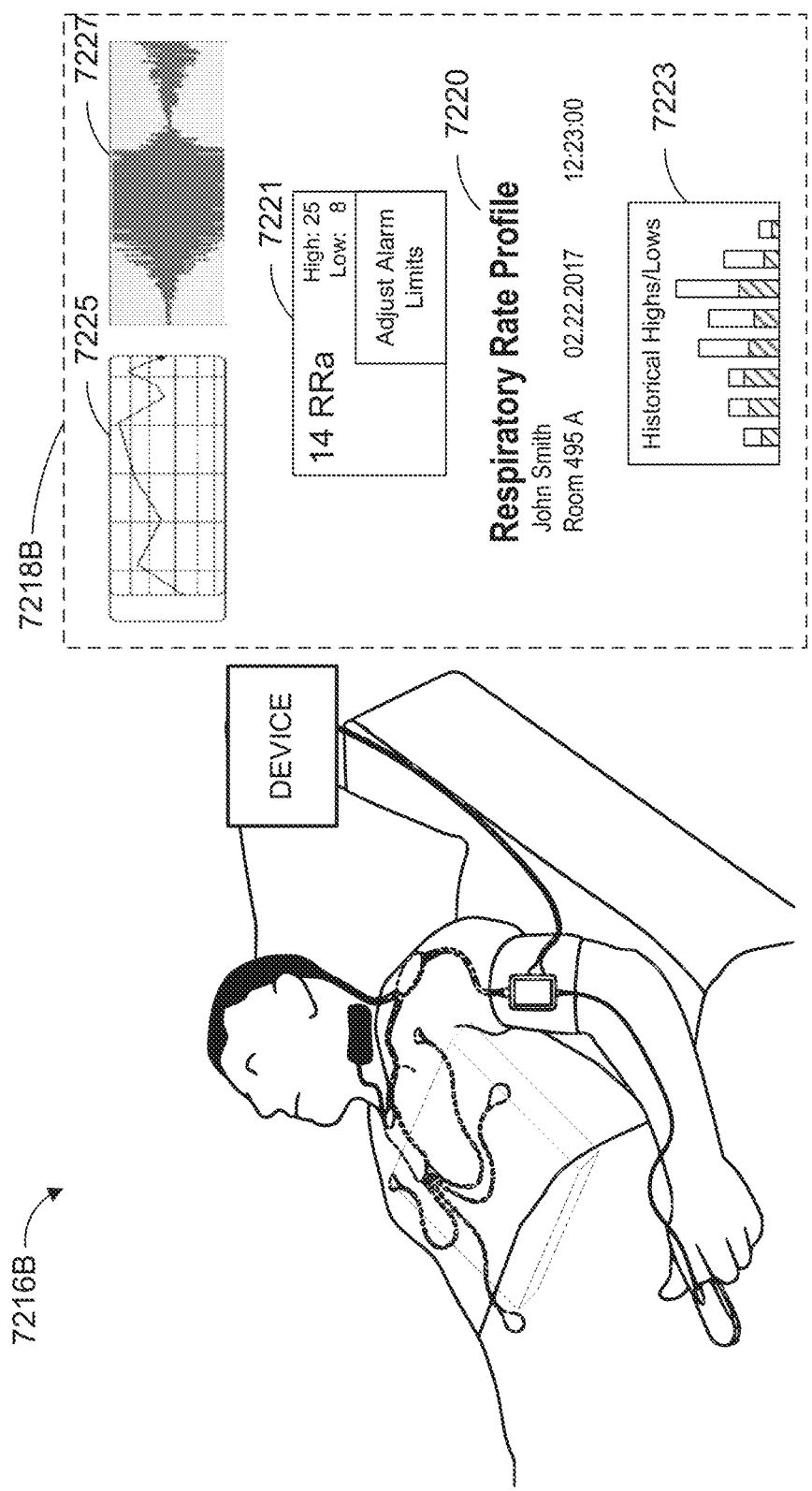

FIGS. 72D, 72E, and 72F depict additional example augmented reality user interfaces 7215, 7216A, and 7216B respectively. The augmented reality user interfaces 7215, 7216A, and 7216B may be similar to the augmented reality user interface 7206 of FIG. 72C. As illustrated, the augmented reality user interface 7215 includes the user interface display area 7217, which includes user interface objects 7219. The augmented reality user interfaces 7216A and 7216B include the user interface display areas 7218A and 7218B, respectively, which includes user interface objects 7220, 7221, 7223, 7225, and 7227. The user interface objects 7219, 7220, 7221, 7223, 7225, and 7227 may correspond to the example user interfaces described herein.

FIGS. 72E and 72F depict example rearrangements of objects in an augmented reality user interface. In FIG. 72E, the user interface objects 7220, 7221, 7223, 7225, and 7227 can be in a first arrangement. Following a user interaction, the user interface objects 7220, 7221, 7223, 7225, and 7227 can be presented in a second arrangement in the augmented reality user interface 7216B of FIG. 72F.

Figure 72G:
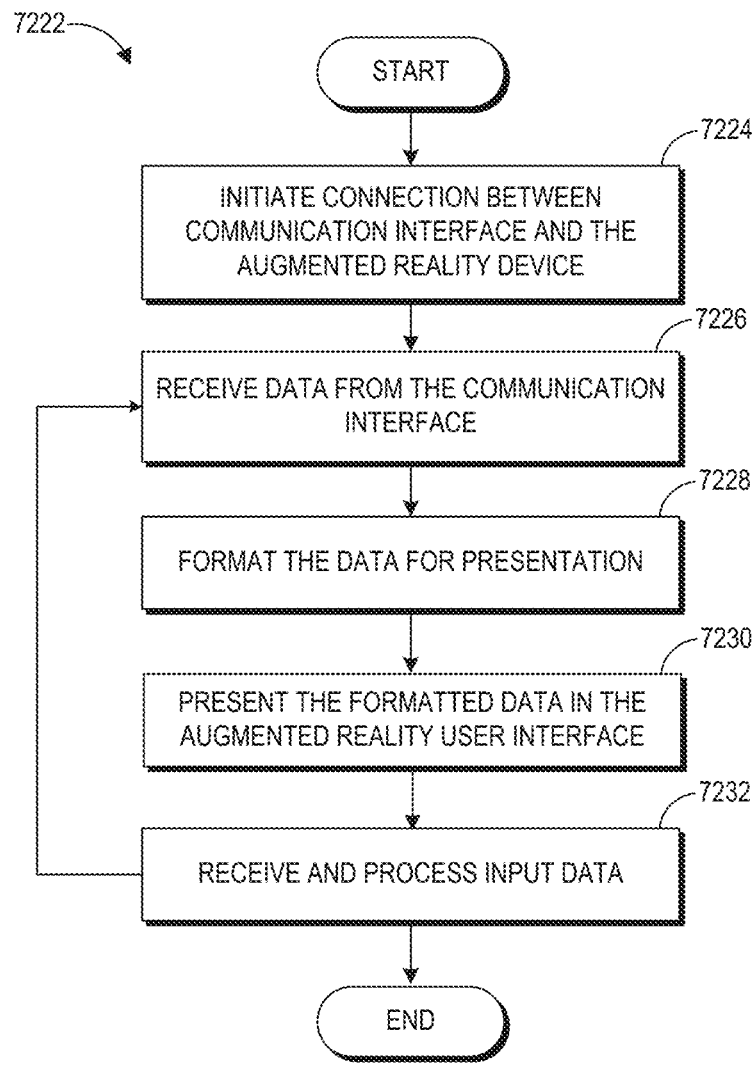
FIG. 72G illustrates an example of an augmented reality display generation process.

FIG. 72G depicts an augmented reality display generation process 7222. The process 7222 illustrates an example mode of operation of the environment 7202 of FIG. 72A and may be implemented by the various components shown in the environment 7202, such as the augmented reality device 7200 or by an augmented reality server separate from the augmented reality device 7200. For convenience, the process 7222 is described in the context of the environment 7202 (such as being implemented by the augmented reality device 7200 or by an augmented reality server, which will be referred to herein as an augmented reality system) but may instead be implemented by other systems described herein or other computing systems not shown. Further, the process 7222 provides an example approach by which the augmented reality device 7200 or an augmented reality server can generate an augmented reality display. The process of FIG. 72G may include fewer or additional blocks or the blocks may be performed in order different than is illustrated.

At block 7224, the augmented reality system server initiates a connection with a communication interface. For example, the augmented reality device 7200 may connect to a communication interface of the MMS 2004, the monitoring hub 100, or the PPM 102, wired or wirelessly. The augmented reality device 7200 can be authenticated via one or more security protocols before a connection with the communication interface can be established.

At block 7226, the augmented reality system receives data from the communication interface. As described herein, example data includes physiological monitoring data, which may include physiological parameter data from a patient that is calculated from physiological signals that are captured by physiological sensors monitoring the patient.

At block 7228, the augmented reality system formats the received data for presentation. For example, the augmented reality system may access user interface configuration data that indicates which augmented reality objects should be displayed or the arrangement of the augmented reality objects. A clinician using the augmented reality device 7200 may update or modify the user interface configuration data via one or more user interactions with the augmented reality device 7200, as described herein. Accordingly, the augmented reality system can format the received data, such as the physiological monitoring data, into user interface display data according to the user interface configuration data. For example, the augmented reality system can generate one or more augmented reality objects from the physiological monitoring data according to the user interface configuration data that specifies which objects are to be generated or where the objects should be presented on the augmented reality device display.

At block 7230, the augmented reality system presents the formatted data in a display of the augmented reality device. Example augmented reality user interfaces are shown and described in further detail with reference to FIGS. 72B-72F.

At block 7232, the augmented reality system receives and processes input data. Example input data includes user interaction data that is received from the augmented reality system. For example, a clinician may interact with the augmented reality user interface to modify the user interface. Example user interactions include voice input or commands by the user (e.g., detectable by a microphone and interpretable by voice recognition software installed in the augmented reality system), visual or eye commands by the user (e.g., detectable by a camera and interpretable by image processing software installed in the augmented reality system), touch input, and/or movement by the user, such as head movement or hand gestures (e.g., detectable by a movement sensor such an accelerometer or gyroscope and interpretable by movement processing software installed in the augmented reality system). Accordingly, the augmented reality system may return to block 7226 to receive additional data to continue processing user interaction data, display data, or monitoring data to present updated augmented reality user interfaces at blocks 7228 and 7230. For example, the augmented reality user interfaces may update in near-real time or real-time based on the physiological sensors capturing updated data from the patient or from new data received from the MMS 2004, the monitoring hub 100, or the PPM 102.

The augmented reality system can perform gesture recognition using the input data. A clinician can virtually pin a user interface display area in space (such as next to or superimposing a monitor display) or to an object in reality (such as a hospital room door) using a gesture such as a hand or finger gesture. The user interface display area can be pinned to or near to a physical device, a location, or to the patient. A gesture with respect to an augmented reality user interface and a physical device, a location, or the patient can cause the user interface to be pinned to that object. The user interface display area can be pinned to any device, such as the hub 100, the PPM 102, or the auxiliary device 2040. A gesture can be recorded by a camera of the augmented reality system, such as a camera of the augmented reality device 7200 or a camera or screen of hub 100, the PPM 102, or of the auxiliary device 2040. The augmented reality system can process the video or image data to perform gesture recognition. The augmented reality system can use currently-available gesture recognition algorithms. Example gesture recognition algorithms can be based on three-dimensional models or based on appearance, such as by using images or videos for direct interpretation, and/or some combination thereof. The example gesture recognition algorithms can include mean shift algorithms, continuous adaptive mean shift (CAMSHIFT) algorithms, pose estimation algorithms, volumetric algorithms, skeletal algorithms, motion algorithms, and/or some combination thereof. An example gesture recognition process is described in more detail below with respect to FIG. 72I. Additional details regarding the CAMSHIFT algorithm and object tracking, any teachings of which may be used herein, are described in John G. Allen, Richard Y. D. Xu, & Jesse S. Jin, "Object Tracking Using Camshift Algorithm and Multiple Quantized Feature Spaces," in 5th Pan-Sydney Area Workshop on Visual Information Processing 3-7 (2004), which is hereby incorporated by reference in its entirety.

The user input data can include image data. Detecting the gesture from the user input data can include determining color histogram data from the image data. A search window can be located within the image data according to the color histogram data, such as by identifying a range of flesh colors within the image. Multiple images can be processed in a similar manner. Multiple positions of the search window in the image data can be identified that corresponds to a gesture, such as a hand or finger swipe in a direction. The augmented reality system can identify a predefined gesture based on definitions of gesture that can correspond to, for example, swiping left, swiping right, swiping up, or swiping down. Additional details regarding example gesture detection techniques are described in further detail with respect to FIG. 72I. The augmented reality system can also enable a user to use a gesture such as a flick to create an augmented reality (AR) display. For instance, when a user points at the patient monitor, the user can flick away from the patient monitor to cause the current display of the patient monitor to move to the side of the patient monitor as a new AR display. A camera in the patient monitor, the AR glasses, or a movement sensor or any other detector described herein can perform this detection. Thus, any screen (or multiple screens) on the patient monitor can be pinned somewhere in AR.

The augmented reality user interface can update in response to user input. Where an augmented reality user interface is pinned to a physical device, such as the hub 100, the PPM 102, or the auxiliary device 2040, a clinician looking at the device and/or augmented reality user interface can cause the user interface to update a characteristic of the augmented reality user interface. For instance, in response to a clinician looking at the hub 100, the PPM 102, or the auxiliary device 2040, the augmented reality user interface can increase in size (e.g., enlarging from 12 inches in width or height to 50 inches in width or height). The physical user interface shown on the physical patient monitor can increase in size, for instance, as an augmented reality display (i.e., the AR display can be a copy of the physical display only larger). If the clinician looks away, the augmented reality user interface can reduce in size. The augmented reality system can detect a clinician looking at a device, user interface, or at a location via tracking technologies and devices that can include computer vision recognition techniques, image registration, optical sensors, accelerometers, GPS, gyroscopes, solid state compasses, RFID, or wireless sensors.

The augmented reality user interface can also (or instead) update in different ways. If the clinician looks away from the monitor such as by looking at the patient, then the augmented reality user interface can present no data or a reduced amount of data, to become uncluttered, unless the clinician looks back at the monitor (then the clinician may see the pinned user interfaces wherever they were pinned). Accordingly, the clinician can see the patient without having some or all augmented reality data in the way. Movement of the clinician's head or a clinician hand gesture can enable data to be viewed or not viewed. If the clinician moves her head toward the patient, the data view might change (or disappear, or move to the side of the patient, e.g., to the edge of the clinician's field of view, etc.). The clinician can also (or instead) see more augmented reality interface when looking at the patient unless the clinician makes a head or hand gesture (e.g., captured by a camera or movement sensor) to move the augmented reality interface to the side of the patient or dismiss it from view entirely.

The arrangement of objects in an augmented reality user interface can update in response to user input. Augmented reality objects can be presented in a first arrangement. For example, as described with respect to FIG. 72E, the augmented reality objects 7220, 7221, 7223, 7225, and 7227 are presented in a first arrangement. User interaction data can be received from a user input device. The received user interaction data can indicate a second arrangement of the augmented reality objects. The user interaction data can indicate that a user virtually manipulated, such as by making a moving gesture with a hand, one or more augmented reality objects. The augmented reality system can generate user interface configuration data from the user interaction data. The augmented reality objects can be associated with a position in the user interface display area in a first arrangement. Based on the user interaction data, new positions for the augmented reality objects can be determined in the second arrangement. For example, each of the objects can be associated with a coordinate in a 2D or 3D coordinate system, and new coordinates for the objects can be generated. The coordinates may be relative to a pinned location or object or relative to the physical patient monitor. The augmented reality system can then present augmented reality objects in the second arrangement according to the user interface configuration data. For example, as described with respect to FIG. 72F, the augmented reality objects 7220, 7221, 7223, 7225, and 7227 are presented in an example second arrangement.

The augmented reality user interface can be configurable via a device different from the augmented reality device. The arrangement and/or selection of objects in an augmented reality user interface can be based on user input. As described above with respect to FIGS. 20A-20C, a user can interact with a user interface of the hub 100, the portable patient monitor 102, and/or the auxiliary device 2040. Any of the devices can include a touchscreen or other user input devices, such as buttons or controls. Accordingly, a user can remove, add, rearrange, and/or or expand one or more user interface elements, including selecting a preset layout from a display layout manager (as discussed in the Display Layout Manager application). For example, hub user interaction data can be received from the hub 100, and a hub user interface configuration can be determined from the hub user interaction data. In FIG. 20A, a user may have selected and/or arranged the user interface elements, including the BPM, % Sp02, RRa, SpHb, PVI, PI, NIBP, or Temp elements. Accordingly, the hub (or monitor or auxiliary device) user interface configuration can include indications of the user interface elements and/or the arrangement of those elements. The presentation of an augmented reality user interface can be in accordance with the hub user interface configuration (or another device's user interface configuration, such as for the portable patient monitor 102, and/or the auxiliary device 2040). The user interface configuration data for the augmented reality user interface can correspond to or be indicative of the hub user interface configuration (or another device's user interface configuration). For example, the objects of the augmented reality user interface may be similar to the user interface elements of the hub 100, the portable patient monitor 102, and/or the auxiliary device 2040. Thus, when a user initiates the augmented reality user interface, such as with a swipe or a flick, the augmented reality user interface may be similar to the user interface of another device such as the hub 100, the portable patient monitor 102, and/or the auxiliary device 2040.

More generally, the user interface of a patient monitor can be reflected in an augmented reality user interface. A user can modify a view of a patient monitor, initiate an augmented reality user interface (with a flick or other gesture), and the initiated augmented reality user interface can present the modified view of the patient monitor. At least some of the plurality of augmented reality objects in the in the augmented reality user interface can correspond to the hub, monitor, or auxiliary device user interface configuration. Specifically, the hub (or monitor or auxiliary device) user interface configuration can include user interface elements. Each element of the user interface elements can include a physiological parameter value. Each element of the user interface elements can correspond to an object from the plurality of augmented reality objects presented in the augmented reality user interface.

Figure 72H:
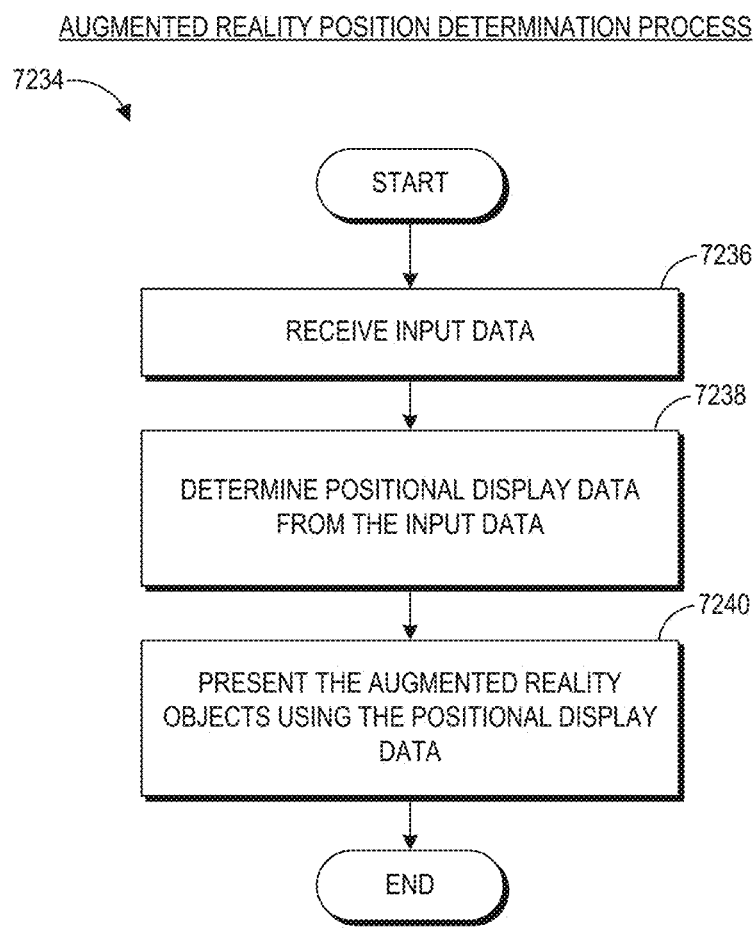
FIG. 72H illustrates an example of an augmented reality position determination process.

FIG. 72H depicts an augmented reality position determination process 7234. The process 7234 illustrates an example mode of operation of the environment 7202 of FIG. 72A and may be implemented by the various components shown in the environment 7202, such as the augmented reality device 7200 or by an augmented reality server separate from the augmented reality device 7200. For convenience, process 7234 is described in the context of the environment 7202 (such as being implemented by the augmented reality system) but may instead be implemented by other systems described herein or other computing systems not shown. Further, the process 7234 provides an example approach by which the augmented reality system determines positions for one or more augmented reality objects. The process of FIG. 72H may include fewer or additional blocks or the blocks may be performed in order different than is illustrated. Further, the blocks of the process 7234 may correspond to one or more blocks of the process 7222 of FIG. 72H, such as blocks 7226, 7228, 7230, or 7232.

At block 7236, the augmented reality system receives input data. Example input data includes a tagged or pinned reference object or location. An example tagged pinned reference object may correspond to one or more physical objects, such as an auxiliary display, a device of the monitoring system, or a patient. Additionally or alternatively, the example input data includes positional or positional-related data, such as image data, video data, accelerometer data, GPS data, gyroscopic data, solid state compass, RFID data, or wireless data. Example positional or positional-related data may correspond to data captured by the augmented reality device or one or more devices of the monitoring system, such as the auxiliary display or one or more devices attached to the patient. As another example, the image or video data may capture a known visual marker (also known as or referred to as a fiducial marker as used herein) that is attached to a patient or device of the monitoring system.

At block 7238, the augmented reality system determines positional display data from the input data. For example, the augmented reality system determines or calculates a reference position for the reference object from the image data, video data, accelerometer data, GPS data, gyroscopic data, solid state compass data, RFID data, or wireless data. Typically GPS data is accurate within several meters. Accordingly, the augmented reality system may use other positional-related data, such as image or video data, accelerometer data, gyroscopic data, solid state compass data, RFID data, or wireless data to determine a more accurate position for a reference object. In a computer vision example, the augmented reality system can execute an image registration process to identify known visual markers through one or more feature detection techniques such as corner detection, blob detection, edge detection, thresholding, or other image processing techniques. Additionally or alternatively, the augmented reality system can determine a three-dimensional position for the reference object using a pose estimation technique. The augmented reality system can generate a real-world coordinate system from the obtained or generated positional data. An example real world coordinate system at least includes three-dimensional coordinates.

The example augmented reality system generates positional display data from the obtained or generated positional data. In the pinning example, the augmented reality system can determine a positional offset from a reference object, such as a patient or a display or device of the monitoring system. The augmented reality system may calculate a position offset from a predefined or configurable distance and direction from the reference object. An example predefined distance includes five or ten centimeters to the right or left of the reference object. User interaction input received from a clinician may update the position offset. For example, a clinician can interact with the augmented reality objects by moving them (virtually), such as with push, pull, or hand wave gestures. In the direct overlay or superimposed example, the augmented reality system may display one or more augmented reality objects at the reference position for the reference object. For example, the reference position of the patient may correspond to a particular coordinate within the coordinate system and the augmented reality system presents the object at the coordinate. As described herein, the augmented reality system can present analog display indicia at the reference position that corresponds to the patient, such as the coordinate position of the lung, heart, or brain areas of the patient. Accordingly, if the reference object moves, the one or more pinned augmented reality objects may move with the reference object.

Figure 72I:
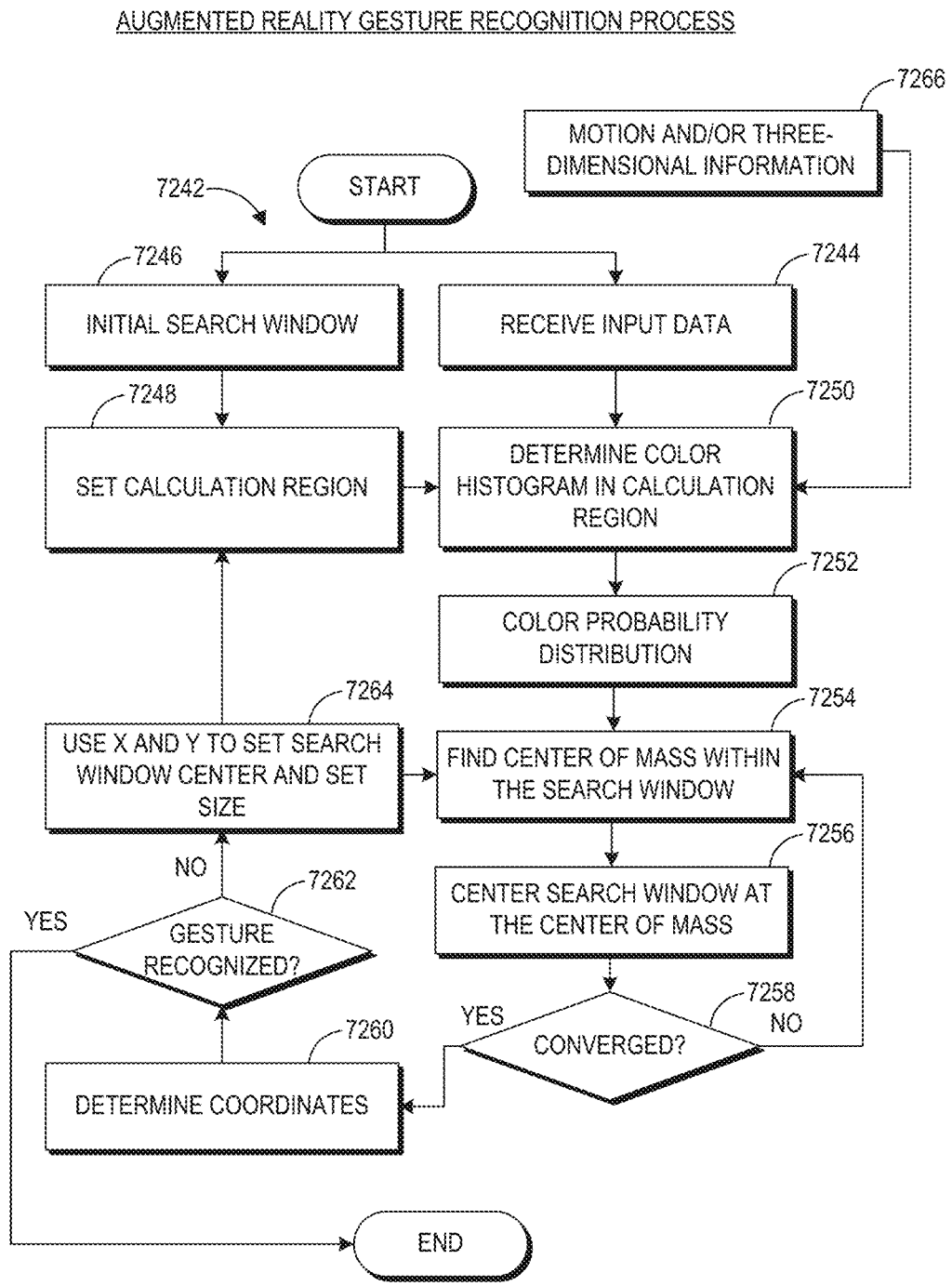
FIG. 72I illustrates an example of an augmented reality gesture recognition process.

FIG. 72I depicts an example augmented reality gesture recognition process 7242. The process 7242 illustrates an example mode of operation of the environment 7202 of FIG. 72A and may be implemented by the various components shown in the environment 7202, such as the augmented reality device 7200 or by an augmented reality server separate from the augmented reality device 7200. For convenience, process 7242 is described in the context of the environment 7202 (such as being implemented by the augmented reality system) but may instead be implemented by other systems described herein or other computing systems not shown. Further, the process 7242 provides an example approach by which the augmented reality system performs gesture recognition. The process of FIG. 72I may include fewer or additional blocks or the blocks may be performed in order different than is illustrated. Further, the blocks of the process 7242 may correspond to one or more blocks of the process 7222 of FIG. 72H, such as block 7232.

At block 7244, the augmented reality system receives input data. Example input data includes image or video data. The input data can be received from an input device, such as an input device of an augmented reality device or another device, such as a monitor. The input device can include a camera. The augmented reality system can receive an image or a video and an image (such as a frame) can be extracted from the video.

At block 7246, an initial search window is established. For example, the augmented reality system can have a default search window that starts at a particular coordinate (such as an X and Y coordinate) and has a predefined size. At block 7248, a calculation region is established. For example, the augmented reality system can have a default calculation region that is equal to the whole frame. As the process 7242 proceeds, the calculation region can change over time. The calculation region can be larger than the search window.

At block 7250, a color histogram can be determined in the calculation region. For example, a pixel distribution, such as a histogram back projection, can be determined. The purpose of the color histogram can be to identify a flesh color (such as the color of a hand) in the image. At block 7252, a color probability distribution can be determined. For example, a range of acceptable colors can be used to compute the probability that any given pixel within the calculation region corresponds to a flesh color. The range of acceptable colors can be generated from examples, such as one or more examples of skin color pixels.

At block 7254, the center of mass within the search window can be found. For example, the maximum density of the acceptable range of colors can be determined within the search window. At block 7256, the search window can be centered at the center of the mass. At block 7258, convergence can be checked. For example, the center of mass can be determined once again from the new position of the search window and if it equals the old position then convergence can be determined. If there is no convergence, the process 7242 can return to blocks 7254 and 7256 to continue to move the search window. Convergence can additionally be defined based on a number of iterations or movement of a threshold distance of the search window. Accordingly, a greater concentration of pixels of the target color(s) can be located in the newly positioned search window.

At block 7260, coordinates of the search window can be determined. For example, coordinates such as (X, Y, and Z), pitch, yaw, and/or roll can be determined. At block 7262, a gesture can be recognized. For example, the augmented reality system can determine whether a series of coordinates from multiple iterations of the process 7242 corresponds to a predefined gesture pattern, such as a flick or swipe of the hand. If a gesture is not recognized, the process 7242 proceeds to block 7264 to perform additional iterations.

At block 7264, the determined X and Y coordinates can be used to set the search window center and the size of the search window can be set. For example, the search window can be resized to account for an object moving closer to or farther away from a camera. Thus, the window size can be adapted to the size and orientation of the target. For example, the size of the search window can be adjusted according to the formula: $2*(\text{area of the search window})^{1/2}$. Other calculations can also (or instead) be used to adjust the size of the search window. The process 7242 can proceed in a loop starting at the block 7248 to reset the calculation region and proceed to the blocks 7250 and 7252 to determine color histograms and color probability distributions, and to the blocks 7254, 7256 to center the search window until convergence, and to the blocks 7260 and 7264 to determine coordinates and check for gesture recognition.

At block 7266, the process 7242 can use motion and/or three-dimensional information for gesture recognition. For example, a motion mask can combine color and movement probability distributions for gesture tracking. The motion and/or three-dimensional information can be used to detect three-dimensional motion in real or near time. Pose estimation techniques can be used to determine a three-dimensional position (such as rotation) of an object from an image.

VII. Additional Auxiliary Device Examples

Several additional examples associated with the auxiliary device 2040 will now be described, including authentication features (see FIG. 73), features for controlling devices that send data to the auxiliary device 2040 (see FIGS. 74 and 76), and features for controlling outputs to the auxiliary device 2040 (see FIG. 75).

In general, as described above, the auxiliary device 2040 can provide second screen functionality for the hub 100, PPM 102, or MMS 2004. Further, as described above, the translation module 2005 can be implemented in any device, including the hub 100 or the MMS 2004. Data set by the translation module 2005 (or from another device shown in FIG. 24 or 72A) to the auxiliary device 2040 may be sent in a format suitable for the auxiliary device 2040 to determine how to display it on the display of the auxiliary device 2040. In other words, devices can feed data to the auxiliary device 2040 independent of any specific user interface formatting, and the auxiliary device 2040 can determine how to format and display that data on its display. For example, a software module installed on the auxiliary device 2040 (not shown) can format received data into any desirable user interface format. The data received by the auxiliary device 2040 can be an XML format or another similar format, and software running in a hardware processor of the auxiliary device 2040 parses the XML (or similar) data and generates a display based on the data.

Figure 73:
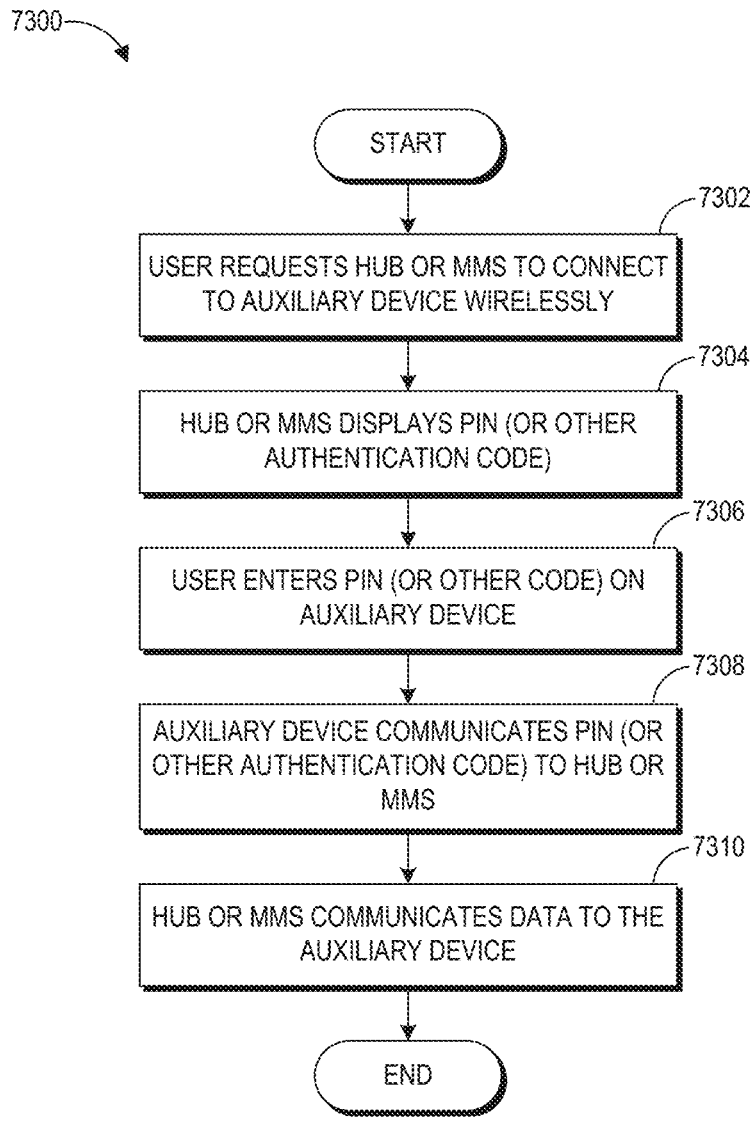
FIG. 73 illustrates an example of an auxiliary device authentication process.

Turning to FIG. 73, an example auxiliary device authentication process 7300 is shown. The process 7300 can be implemented using components of the systems described above with respect to FIGS. 24 and 72A. In general, the process 7300 can be implemented by software or firmware executing on a hardware processor. The process 7300 can enable the auxiliary device 2040 to authenticate to the hub 100, MMS 2004, or PPM 102. (For convenience, the remainder of this disclosure will refer to communications between the auxiliary device 2040 and the hub 100, although it should be understood that any of these communications may also take place between the auxiliary device 2040 and the MMS 2004 or the PPM 102.)

It may be desirable to authenticate the auxiliary device 2040 to the hub 100 so that communications may take place between the two devices. Viewed another way, the process 7300 can be considered a process for pairing the auxiliary device 2040 with the hub 100. Multiple auxiliary devices 2040 can be paired or otherwise authenticated to the hub 100 at one time. This may be useful, for instance so that multiple clinicians can each have a tablet or other auxiliary device 2040, instead of and/or in addition to a TV auxiliary device 2040 being present in the hospital room. Further, the augmented reality device 7200 described above can be an example of one of the auxiliary devices 2040, and multiple clinicians may have augmented reality devices 7200 that they wish to use together with the hub 100 (e.g., so that each one may have a different heads-up display with a set of views customized to that particular clinician).

At block 7302, a user requests the hub 100 (or MMS 2004 etc.) to connect to the auxiliary device 2040 wirelessly (wired connectivity is also possible in other examples). For example, the user can access the settings menu on the hub 100 to begin pairing or authentication of an auxiliary device 2040. At block 7304, the hub 100 displays a PIN number or other authentication code (e.g., a number of alphanumeric digits/letters) on its display. At block 7306, a user enters the PIN or other authentication code on the auxiliary device. At block 7308, the auxiliary device communicates the PIN or other authentication code to the hub or MMS. At block 7310, the hub or MMS communicates data gathered from patient monitors to the auxiliary device. Block 7310 can be implemented either before, during, or after the process 7300.

Figure 74:
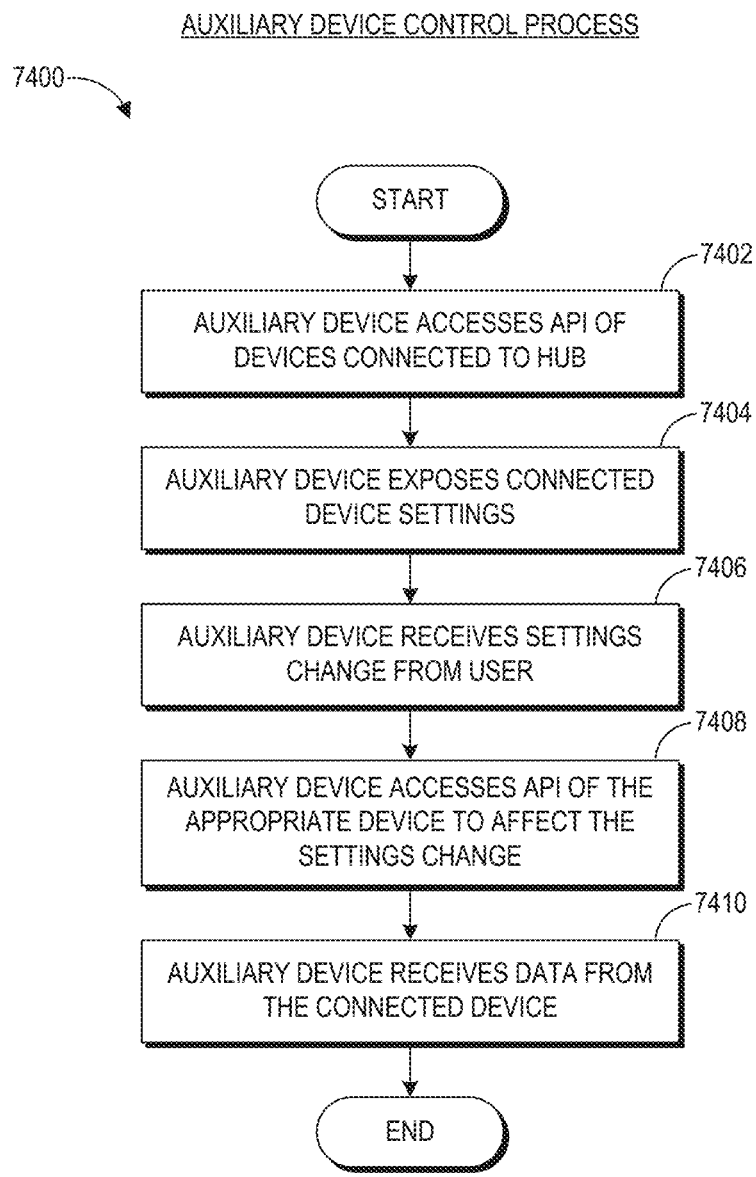
FIG. 74 illustrates an example of an auxiliary device control process.

Turning to FIG. 74, an example auxiliary device control process 7400 is shown. The process 7400 can be implemented using components of the systems described above with respect to FIGS. 24 and 72A. In general, the process 7400 can be implemented by software or firmware executing on a hardware processor. The process 7400 can enable the auxiliary device 2040 to control the hub 100 (and/or MMS 2004, etc.). Thus, for example, the auxiliary device 2040 may not just receive data, but it may also be able to send data to the hub 100 or other devices described above. This data can include control data that enables the auxiliary device 2040 to not just passively receive and display data but also to control the settings of any of the devices described above, including both third-party monitors (e.g., 214-220) connected serially or otherwise to the hub 100 and first party monitors (e.g., 222-226) connected via channels or otherwise to the hub 100.

For example, the auxiliary device 2040 can control any option or setting that is able to be controlled on any of the patient monitors or hub 100. For example, alarms, layouts of user interfaces, settings, etc. may be controlled via the auxiliary device 2040. The auxiliary device 2040 may output a user interface that enables control of these settings. For instance, turning to FIG. 76, an example user interface 7600 is shown that include settings 7610 for controlling an infusion pump, patient bed, and a ventilator, as well as displaying parameter values from multiple devices. Thus, with a single auxiliary device 2040, a clinician can control some or even all devices in a hospital room (e.g., that are in communication with the hub 100 or MMS 2004).

The manufacturer of the hub 100 can provide a software development kit (SDK) for third-party patient monitor manufacturers to use so that an auxiliary device 2040 can communicate with their hardware. Using the SDK, for instance, a third-party monitor manufacturer can install software libraries on a third-party patient monitor (e.g., 214-220) so that the auxiliary device 2040 can communicate changes to settings or other parameters directly to those devices. The software library or libraries may, for instance, include an application programming interface (API) defining routines or functions and associated parameters that the auxiliary device 2040 can call or invoke to set different settings within the third-party devices. A similar library or libraries may be installed on first party devices, such as the channel devices (222-226). The auxiliary device 2040 can include a set of instructions or libraries that it can invoke to send settings changes to the hub 100 (or the MMS 2004), which the hub 100 passes on to the third-party devices or first party devices. The hub 100 may also translate the settings request changes from the auxiliary device 2040 into more complex instructions provided to the individual patient monitors. The manufacturer of the hub 100 can certify medical devices that are capable of control by the auxiliary device 2040. Any of the functions for controlling the third-party and first party devices can also (or instead) be implemented directly by the hub 100 instead of or in addition to by the auxiliary device 2040.

Thus, either the hub 100 or the auxiliary device 2040 can essentially become the monitor itself as it enables full control over a variety of patient monitoring equipment. Thought of another way, auxiliary device 2040 or the hub 100 can include a unified display for managing a plurality of patient devices.

Turning again to FIG. 74, an example process of how the auxiliary device 2040 can perform settings changes for medical devices connected to the hub 100 is shown. At block 7402, and auxiliary device accesses an API of devices connected to the hub, either directly or through the hub itself. At block 7404, the auxiliary device exposes connected device settings, for example on a user interface (see, e.g., FIG. 76) that a user may access. At block 7460, the auxiliary device receives a settings change from a user through the user interface. At block 7408, the auxiliary device accesses the API of the appropriate medical device, either directly or through the hub, to affect the setting change. And at block 7410, the auxiliary device receives data from the connected device. Of course, block 7410 may operate in parallel with the process 7400, such that data is received before, during, and/or after the setting is changed.

Figure 75:
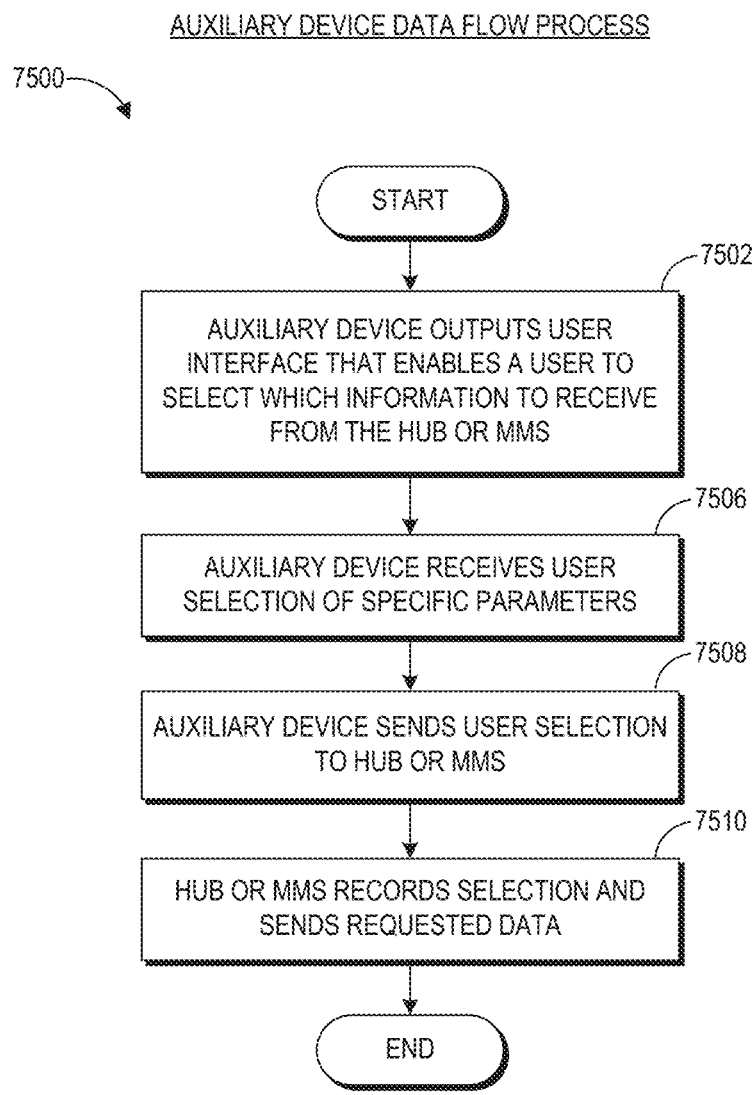
FIG. 75 illustrates an example of an auxiliary device data flow process.
Figure 76:
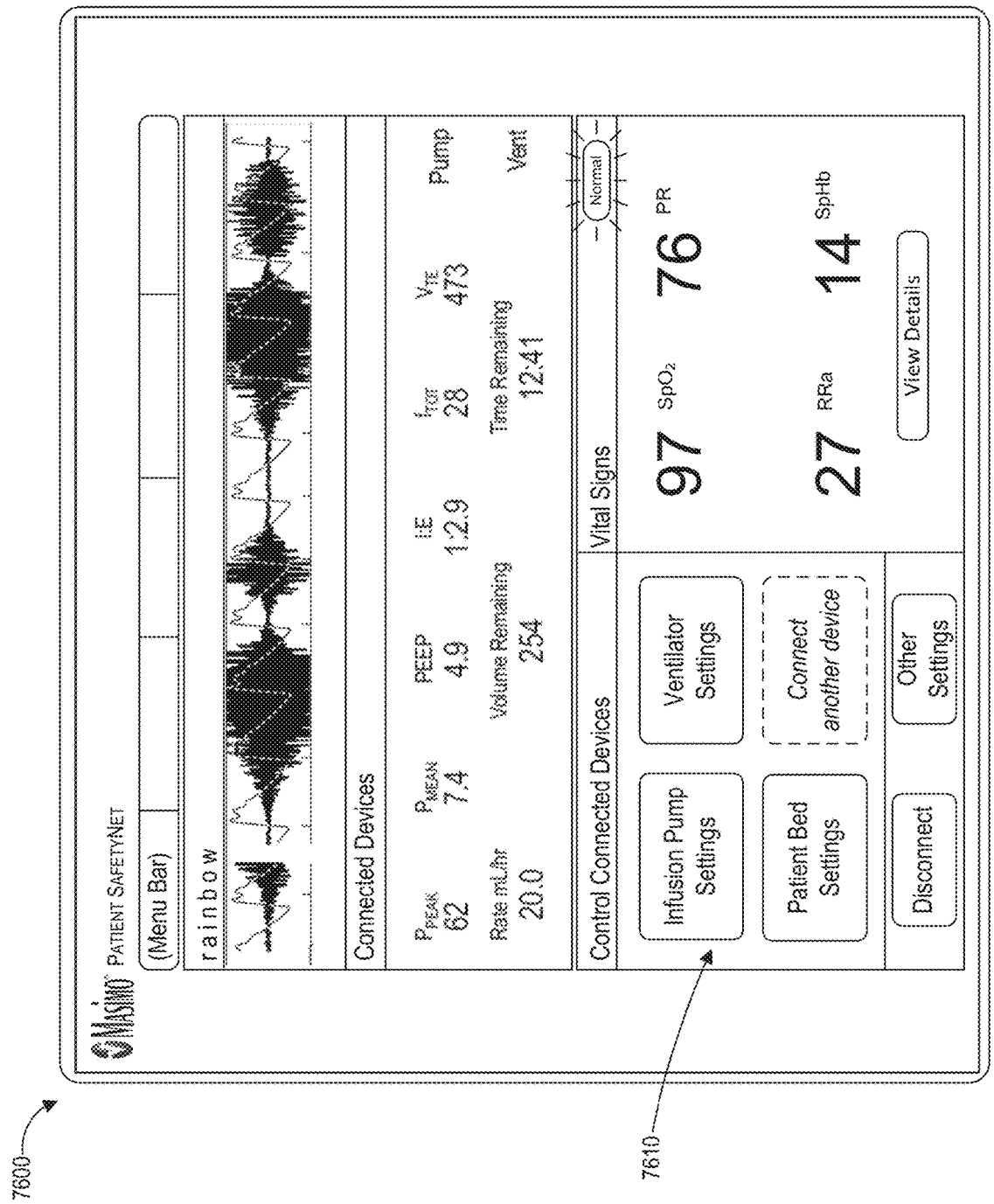
FIG. 76 illustrates an example of a user interface for auxiliary device control.

Turning to FIG. 75, an example auxiliary device data flow process 7500 is shown. The process 7500 can be implemented using components of the systems described above with respect to FIGS. 24 and 72A. In general, the process 7500 can be implemented by software or firmware executing on a hardware processor. The process 7500 can enable the auxiliary device 2040 or the hub 100 to control the flow of data to the auxiliary device 2040.

In some current implementations, the translation module 2005 pushes most or all of the data it receives from most or all the devices connected to the hub 100 on to the auxiliary device 2040. For some auxiliary devices 2040 with lower computing resources (e.g., reduced processing capability, lower memory, lower battery and power capability, lower bandwidth connection, etc.), this can mean that those devices may be overwhelmed with the received data. As a result, these devices may crash or get bad or incomplete results.

One way to solve this problem is to have the auxiliary device 2040 request that the translation module 2005 send data less frequently, for example, by lowering the frequency with which it receives data. Another way is for the auxiliary device 2040 to have a module that reduces the firehose effect of all the data it receives by requesting instead a specific subset of information from the translation module 2005 or hub 100. An example of such a module is shown in FIG. 72A, an IAP (instrument auxiliary protocol) layer 2042. This layer 2042 can automatically request that a subset of information be provided to the auxiliary device 2040. The IAP layer 2042 can expose a user interface on the axillary device 2040 that enables a user to control what data is to be provided to the auxiliary device 2040. Similarly, the layer 2042 may also (or instead) be implemented as a module on the MMS 2004 or directly in the hub 100.

Instead of being fully flexible, the IAP layer 2042 may have a predefined capability for receiving data at the auxiliary device 2040. This capability may be determined, for example, by a level of service paid for by a clinical facility using the auxiliary device 2040, or the like. For instance, greater levels of service can enable a larger number of parameters or different variety of parameters to be provided to the auxiliary device 2040.

Turning specifically to the process 7500 shown in FIG. 75, at block 7502, an auxiliary device outputs a user interface that can enable a user to select which information to receive from the hub or MMS. At block 7506, the auxiliary device receives a user selection of specific parameters from the interface. For instance, the user may request to view ventilator or pump data to the exclusion of other data. At block 7508, the auxiliary device sends the user selection to the hub or MMS. And at block 7510, the hub or MMS records the selection and sends the requested data.

VIII. Terminology

Many other variations than those described herein will be apparent from this disclosure. For example, certain acts, events, or functions of any of the algorithms described herein can be performed in a different sequence, can be added, merged, or left out altogether (e.g., not all described acts or events are necessary for the practice of the algorithms). Moreover, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as may be taught or suggested herein.

The various illustrative logical blocks and modules described in connection with the examples disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another example, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the examples disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. A method for presenting augmented reality data from a medical monitoring device, the method comprising:
under control of a hardware processor,
receiving physiological monitoring data comprising physiological parameter values associated with a patient from a monitoring hub;
receiving hub user interaction data from the monitoring hub, wherein the hub user interaction data comprises a plurality of user interface elements in a first arrangement;
determining a hub user interface configuration from the hub user interaction data;
causing presentation of a user interface on a display of the monitoring hub according to the hub user interface configuration;
accessing user interface configuration data, wherein the user interface configuration data is indicative of the hub user interface configuration;
generating, from the physiological monitoring data, a plurality of augmented reality objects according to the user interface configuration data, wherein each object from the plurality of augmented reality objects corresponds to an element from the plurality of user interface elements;
receiving user interaction data from a user input device of an augmented reality device, wherein the user interaction data comprises an indication of an interaction to virtually pin the plurality of augmented reality objects to a reference object;
determining a reference position based at least in part the user interaction data; and
causing presentation of the plurality of augmented reality objects in an augmented reality display, wherein the plurality of augmented reality objects are presented relative to the reference position in a second arrangement corresponding to the first arrangement.

2. The method of claim 1, further comprising:
identifying, from the user interaction data, the reference object;
determining the reference position for the reference object; and
calculating a positional offset from the reference position, wherein the plurality of augmented reality objects are presented relative to the reference position according to the positional offset.

3. The method of claim 1, further comprising:
determining, from the user interface configuration data, whether to present a direct overlay;
identifying, from the user interface configuration data, the reference object;
calculating the reference position for the reference object, wherein an overlay object of the plurality of augmented reality objects is presented at the reference position.

4. The method of claim 1, wherein the reference object is the patient.

5. The method of claim 1, further comprising:
detecting a gesture from the user interaction data; and
generating the user interface configuration data based at least in part on the gesture.

6. The method of claim 5, wherein the user input device comprises a camera.

7. The method of claim 6, wherein the user input data comprises image data, and wherein detecting the gesture from the user input data further comprises:
determining color histogram data from the image data;
locating a search window in the image data according to the color histogram data; and
identifying a plurality of positions of the search window in the image data.

8. The method of claim 1, further comprising:
receiving second user interaction data from the user input device, the second user interaction data indicating a third arrangement of the plurality of augmented reality objects;
generating second user interface configuration data from the second user interaction data; and
causing presentation, in the augmented reality display, of the plurality of augmented reality objects in the third arrangement according to the second user interface configuration data.

9. The method of claim 1, wherein each element of the plurality of user interface elements comprises a physiological parameter value.

10. The method of claim 1, wherein the hub user interaction data is indicative of at least one addition, removal, or rearrangement of a user interface element.

11. A system configured to present physiological data, the system comprising:
a memory device configured to store instructions; and
a hardware processor configured to execute the instructions to:
receive physiological monitoring data comprising physiological parameter values associated with a patient from a monitoring hub;
receive hub user interaction data from the monitoring hub, wherein the hub user interaction data comprises a plurality of user interface elements in a first arrangement;
determine a hub user interface configuration from the hub user interaction data;
cause presentation of a user interface on a display of the monitoring hub according to the hub user interface configuration;
access user interface configuration data, wherein the user interface configuration data is indicative of the hub user interface configuration;
generate, from the physiological monitoring data, a plurality of augmented reality objects according to the user interface configuration data, wherein each object from the plurality of augmented reality objects corresponds to an element from the plurality of user interface elements;
receive user interaction data from a user input device of an augmented reality device, wherein the user interaction data comprises an indication of an interaction to virtually pin the plurality of augmented reality objects to a reference object;
determining a reference position based at least in part the user interaction data; and
cause presentation of the plurality of augmented reality objects in an augmented reality display, wherein the plurality of augmented reality objects are presented relative to the reference position in a second arrangement corresponding to the first arrangement.

12. The augmented reality device of claim 11, wherein the hardware processor is further configured to:

generate at least part of the user interface configuration data from the user interaction data.

13. The augmented reality device of claim 11, wherein the hardware processor is further configured to:
calculate a positional offset from the reference position, wherein the plurality of augmented reality objects are presented relative to the reference position according to the positional offset.

14. The augmented reality device of claim 11, wherein the hardware processor is further configured to:
determine, from the user interface configuration data, whether to present a direct overlay, wherein an overlay object of the plurality of augmented reality objects is presented at the reference position.

15. The augmented reality device of claim 11, wherein the hardware processor is further configured to:
receive user input data from a user input device;
detect a gesture from the user input data; and
generate the user interface configuration data based at least in part on the gesture.

16. The augmented reality device of claim 15, wherein the user input device comprises a camera.

17. The augmented reality device of claim 15, wherein the user input data comprises image data, and wherein detecting the gesture from the user input data further comprises:
determining color histogram data from the image data;
locating a search window in the image data according to the color histogram data; and
identifying a plurality of positions of the search window in the image data.

18. A system for presenting augmented reality data, the system comprising:
a medical monitoring device comprising a first hardware processor and a first display, the first hardware processor of the medical monitoring device configured to:
receive monitor user interaction data;
determine a monitor user interface configuration from the monitor user interaction data, wherein the monitor user interaction comprises a plurality of user interface elements in a first arrangement; and
cause presentation of a user interface on the first display according to the monitor user interface configuration; and
an augmented reality device comprising a second hardware processor, memory, a second display, and a wireless device configured to communicate with the medical monitoring device in communication with a patient, the second hardware processor of the augmented reality device configured to:
identify a user interaction with the augmented reality device by a clinician wearing the augmented reality device, the user interaction comprising a gesture;
determine that the user interaction is an instruction to virtually pin the user interface of the medical monitoring device to a virtual location separate from the medical monitoring device;
wirelessly obtain patient data depicted in the user interface from the medical monitoring device;
generate, from the patient data, a plurality of augmented reality objects according to the monitor user interface configuration, wherein each object from the plurality of augmented reality objects corresponds to an element from the plurality of user interface elements; and
output for presentation to the clinician, in the second display of the augmented reality device, the plurality of augmented reality objects pinned to the virtual location, wherein the plurality of augmented reality objects are presented in a second arrangement corresponding to the first arrangement.

19. The system of claim 18, wherein the instruction is to virtually pin the user interface outside of and next to a hospital room of the patient so that the clinician can subsequently view the user interface while walking past the hospital room and without entering the hospital room.

20. The system of claim 18, wherein the plurality of augmented reality objects pinned to the virtual location is viewable only when a field of view of the second display includes the virtual location, and wherein the virtual location does not obscure the patient.

21. The system of claim 18, wherein the augmented reality device is further operable to detect that the clinician has moved his or her head away from looking at the medical monitoring device and to reduce a size or content of the plurality of augmented reality objects at the virtual location.

22. The system of claim 21, wherein the augmented reality device further comprises a camera or a movement sensor configured to detect that the clinician has moved his or her head away from looking at the medical monitoring device.

* * * * *